(12) United States Patent
Bock et al.

(10) Patent No.: US 12,247,011 B2
(45) Date of Patent: Mar. 11, 2025

(54) SELECTIVE INHIBITORS OF NLRP3 INFLAMMASOME

(71) Applicant: NodThera Limited, Little Chesterford (GB)

(72) Inventors: Mark G. Bock, Lexington, MA (US); David Harrison, Little Chesterford (GB); Alan Paul Watt, Essex (GB); Roderick Alan Porter, Hertfordshire (GB); Nicolas Felix Pierre Boutard, Cracow (PL); Charles-Henry Robert Yves Fabritius, Poznan (PL); Grzegorz Witold Topolnicki, Piekary Slaskie (PL); Oleksandr Levenets, Cracow (PL)

(73) Assignee: NodThera Limited, Little Chesterford (GB)

( * ) Notice: Subject to any disclaimer, the term of this patent is extended or adjusted under 35 U.S.C. 154(b) by 0 days.

(21) Appl. No.: 16/635,374

(22) PCT Filed: Jul. 31, 2018

(86) PCT No.: PCT/EP2018/070799
§ 371 (c)(1),
(2) Date: Jan. 30, 2020

(87) PCT Pub. No.: WO2019/025467
PCT Pub. Date: Feb. 7, 2019

(65) Prior Publication Data
US 2021/0087147 A1 Mar. 25, 2021

(30) Foreign Application Priority Data
Jul. 31, 2017 (GB) .................................. 1712282

(51) Int. Cl.
*C07D 231/12* (2006.01)
*A61P 37/06* (2006.01)
*C07C 45/68* (2006.01)
*C07C 201/14* (2006.01)
*C07C 209/36* (2006.01)
*C07C 263/10* (2006.01)
*C07C 271/28* (2006.01)
*C07C 271/30* (2006.01)
*C07D 213/55* (2006.01)
*C07D 231/14* (2006.01)
*C07D 233/60* (2006.01)
(Continued)

(52) U.S. Cl.
CPC ............ *C07D 231/12* (2013.01); *A61P 37/06* (2018.01); *C07C 45/68* (2013.01); *C07C 201/14* (2013.01); *C07C 209/36* (2013.01); *C07C 263/10* (2013.01); *C07C 271/28* (2013.01); *C07C 271/30* (2013.01); *C07D 213/55* (2013.01); *C07D 231/14* (2013.01); *C07D 233/60* (2013.01); *C07D 237/08* (2013.01); *C07D 239/26* (2013.01); *C07D 241/12* (2013.01); *C07D 241/24* (2013.01); *C07D 249/08* (2013.01); *C07D 307/79* (2013.01); *C07D 309/12* (2013.01); *C07D 409/12* (2013.01); *C07D 493/04* (2013.01)

(58) Field of Classification Search
CPC .. C07D 231/12; C07D 213/55; C07D 231/14; C07D 233/60; C07D 237/08; C07D 239/26; C07D 241/12; C07D 241/24; C07D 249/08; C07D 307/79; C07D 309/12; C07D 409/12; C07D 493/04; C07C 271/28; C07C 271/30
See application file for complete search history.

(56) References Cited

U.S. PATENT DOCUMENTS 4,522,811 A 6/1985 Eppstein et al.
4,761,175 A 8/1988 Schirmer et al.
(Continued)

FOREIGN PATENT DOCUMENTS

CH 281646 A 3/1952
CH 281649 A 3/1952
(Continued)

OTHER PUBLICATIONS

Finkbeiner, Herman. Journal of the American Chemical Society, 87:20, Oct. 20, 1965.*
(Continued)

*Primary Examiner* — Alicia L Otton
(74) *Attorney, Agent, or Firm* — COOLEY LLP; Heidi A. Erlacher; Christine E. Dunne

(57) ABSTRACT

The present disclosure relates to compounds of Formula (I):

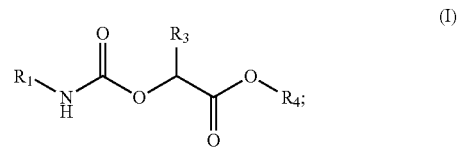

and to their pharmaceutically acceptable salts, pharmaceutical compositions, methods of use, and methods for their preparation. The compounds disclosed herein are useful for inhibiting the maturation of cytokines of the IL-1 family by inhibiting inflammasomes and may be used in the treatment of disorders in which inflammasome activity is implicated, such as autoinflammatory and autoimmune diseases and cancers.

18 Claims, No Drawings

(51) Int. Cl.

| | |
|---|---|
| *C07D 237/08* | (2006.01) |
| *C07D 239/26* | (2006.01) |
| *C07D 241/12* | (2006.01) |
| *C07D 241/24* | (2006.01) |
| *C07D 249/08* | (2006.01) |
| *C07D 307/79* | (2006.01) |
| *C07D 309/12* | (2006.01) |
| *C07D 409/12* | (2006.01) |
| *C07D 493/04* | (2006.01) |

(56) References Cited

U.S. PATENT DOCUMENTS

| | | |
|---|---|---|
| 4,818,899 A | 4/1989 | Tiers |
| 4,983,751 A | 1/1991 | Hirai et al. |
| 5,223,499 A | 6/1993 | Geenlee et al. |
| 5,436,267 A | 7/1995 | Komyoji et al. |
| 5,614,498 A | 3/1997 | Ishikawa et al. |
| 5,763,263 A | 6/1998 | Dehlinger |
| 6,096,758 A | 8/2000 | Grundler et al. |
| 6,921,763 B2 | 7/2005 | Hirst et al. |
| 7,956,061 B2 | 6/2011 | Ashton et al. |
| 8,420,698 B2 | 4/2013 | Lan-Hargest et al. |
| 9,029,548 B2 | 5/2015 | Milne et al. |
| 9,458,145 B2 | 10/2016 | Aktoudianakis et al. |
| 2003/0207876 A1 | 11/2003 | Banks et al. |
| 2004/0038858 A1 | 2/2004 | Dorsch et al. |
| 2006/0135515 A1 | 6/2006 | Dorsch et al. |
| 2012/0177632 A1 | 7/2012 | Shinohara et al. |
| 2012/0258967 A1 | 10/2012 | Qiao et al. |
| 2015/0175623 A1 | 6/2015 | Kotschy et al. |
| 2016/0175287 A1 | 6/2016 | Weibel et al. |
| 2016/0376261 A1 | 12/2016 | Aktoudianakis et al. |
| 2017/0001953 A1 | 1/2017 | Nguyen |
| 2022/0098159 A1 | 3/2022 | Bock et al. |

FOREIGN PATENT DOCUMENTS

| | | |
|---|---|---|
| CN | 104725397 A | 6/2015 |
| CN | 105705484 A | 6/2016 |
| CN | 106458912 A | 2/2017 |
| DE | 1953431 A1 | 6/1970 |
| EP | 0271251 A1 | 6/1988 |
| EP | 0520336 A2 | 12/1992 |
| EP | 0555537 A2 | 8/1993 |
| EP | 1212327 B1 | 8/2003 |
| GB | 789445 A | 1/1958 |
| GB | 1241917 A | 8/1971 |
| GB | 1333209 A | 10/1973 |
| JP | S5424870 A | 2/1979 |
| JP | S568356 A | 1/1981 |
| JP | S63163828 A | 7/1988 |
| JP | H0285269 A | 3/1990 |
| JP | H05163221 A | 6/1993 |
| JP | 2004515538 A | 5/2004 |
| JP | 2006510604 A | 3/2006 |
| JP | 2017501978 A | 1/2017 |
| WO | WO 96/11927 A1 | 4/1996 |
| WO | WO-9912534 A1 | 3/1999 |
| WO | WO 00/64866 A1 | 11/2000 |
| WO | WO 01/16093 A1 | 3/2001 |
| WO | WO 02/48099 A1 | 6/2002 |
| WO | WO 2004/035039 A1 | 4/2004 |
| WO | WO 2005/079300 A2 | 9/2005 |
| WO | WO 2006/037468 A1 | 4/2006 |
| WO | WO 2008/075077 A1 | 6/2008 |
| WO | WO 2014/081856 A2 | 5/2014 |
| WO | WO 2015/077451 A1 | 5/2015 |
| WO | WO 2016/131098 A1 | 8/2016 |
| WO | WO-2016123229 A1 | 8/2016 |
| WO | WO 2018/167468 A1 | 9/2018 |
| WO | WO 2018/225018 A1 | 12/2018 |
| WO | WO 2019/025467 A1 | 2/2019 |
| WO | WO 2020/152361 A1 | 7/2020 |

OTHER PUBLICATIONS

STN Registry database entry for CAS RN 2002505-90-8, entry date Sep. 30, 201; Accessed Dec. 16, 2021.*
STN Registry database entry for CAS RN 855634-67-2, entry date Jul. 18, 2005; Accessed Apr. 22, 2022.*
STN Registry database entry for CAS RN 1782932-86-8, entry date Jun. 17, 2015; Accessed Apr. 22, 2022.*
PubChem CID 53838198 (Create Date Dec. 4, 2011), Accessed Dec. 3, 2022.*
Ito et al. in Cancer Science 94(1), 3-8 (2003).*
STN Registry database entry for CAS RN 10319-68-3, Entered STN Nov. 16, 1984, accessed Jun. 3, 2023.*
STN Registry entry for CAS RN 2088327-68-6, Entered STN Mar. 28, 2017, Accessed via STNext Sep. 29, 2023.*
Das, U.N. (Journal of Inflammation Research, 2010:3, pp. 143-170).*
Hartung, H., et al., "What do we know about the mechanism of action of disease-modifying treatments in MS?" J. Neurol., vol. 251(suppl. 5), pp. V/12-V/29 (2004).*
Wang et al., J. Immunol. 2007, 179, pp. 5958-5965, See Introduction.*
Aggarwal, B.B. et al. (2009) "Targeting inflammatory pathways for prevention and therapy of cancer: short-term friend, long-term foe" Clinical Cancer Research, 15(2):425-430.
Ahmad, I. et al. (2013) "Thymoquinone suppresses metastasis of melanoma cells by inhibition of NLRP3 inflammasome" Toxicology and Applied Pharmacology, 270(1):70-76.
Amieva, M. and R.M. Peek (2016) "Pathobiology of Helicobacter pylori-Induced Gastric Cancer" Gastroenterology, 150(1):64-78.
Antonov, V.K. et al. (1965) "Activation of the Amide Group By Acylation. III. Hydroxyacyl Insertion In the N-Hydroxyacyllactam Series" J General Chemistry USSR, 35:1385-1393.
Apte, R.N. et al. (2006) "The involvement of IL-1 in tumorigenesis, tumor invasiveness, metastasis and tumor-host interactions" Cancer and Metastasis Reviews, 25(3):387-408.
Basso, D. et al. (1996) "Helicobacter pylori infection enhances mucosal interleukin-1β, interleukin-6, and the soluble receptor of interleukin-2" Int J Clin Lab Res, 26:207-210.
Bernstein, C.N. et al. (2001) "Cancer risk in patients with inflammatory bowel disease: a population-based study" Cancer, 91(4):854-862.
Bruchard, M. et al. (2013) "Chemotherapy-triggered cathepsin B release in myeloid-derived suppressor cells activates the Nlrp3 inflammasome and promotes tumour growth" Nature Medicine, 19(1):57-64; including "Online Methods", 2 pages.
Buchman, R. and D.N. Hamilton (1981) "Design, Synthesis, and Biological Activity of Rigid Acetanilide Herbicides" J Agr Food Chem, 29(6):1285-1286.
Bundgaard, H. (1992) "Means to Enhance Penetration. (1) Prodrugs as a means to improve the delivery of peptide drugs" Advanced Drug Delivery Reviews, 8:1-38.
Carrascal, M.T. et al. (2003) "Interleukin-18 binding protein reduces B16 melanoma hepatic metastasis by neutralizing adhesiveness and growth factors of sinusoidal endothelium" Cancer Research, 63(2):491-497.
Chae, J.J. et al. (2011) "Gain-of-Function Pyrin Mutations Induce NLRP3 Protein-Independent Interleukin-1β Activation and Severe Autoinflammation in Mice" Immunity, 34:755-768.
Coll, R.C. et al. (2015) "A small-molecule inhibitor of the NLRP3 inflammasome for the treatment of inflammatory diseases" Nature Medicine, 21(3):248-255; indluding "Online Methods", 2 pages.
Deady, L.W. (1977) "Ring Nitrogen Oxidation of Amino Substituted Nitrogen Heterocycles with m-Chloroperbenzoic Acid" Syn Comm, 7:509-514.
Dinarello, C.A. (2004) "Unraveling the NALP-3/IL-1β inflammasome: a big lesson from a small mutation" Immunity, 20(3):243-244.
Dinarello, C.A. et al. (2010) "Role of IL-1β in type 2 diabetes" Curr Opin Endocrinol Diabetes Obes, 17(4):314-321.
Elaraj, D.M. et al. (2006) "The role of interleukin 1 in growth and metastasis of human cancer xenografts" Clinical Cancer Research, 12(4):1088-1096.

(56) References Cited

OTHER PUBLICATIONS

Fujinami, A. et al. (1971) "Studies on Biological Activity of Cyclic Imide Compounds. Part I. Antimicrobial Activity of 3-Phenyloxazolidine-2, 4-diones and Related Compounds" Agricultural and Biological Chemistry, 35(11):1707-1719.
Gabay, C. and I.B. McInnes (2009) "The biological and clinical importance of the 'new generation' cytokines in rheumatic diseases" Arthritis Research & Therapy, 11(3):230, 14 pages.
Gasse, P. et al. (2009) "Uric acid is a danger signal activating NALP3 inflammasome in lung injury inflammation and fibrosis" Am J Respir Crit Care Med, 179(10):903-913.
George, D.K. et al. (1954) ""Relative Herbicidal and Growth-Modifying Activity of Several Esters of N-(3-Chlorophenyl)-carbamic Acid"" Agricultural and Food Chemistry, 2(19):990-995.
Grivennikov, S.I. et al. (2010) "Immunity, inflammation, and cancer" Cell, 140(6):883-899.
Halle, A. et al. (2008) "The NALP3 inflammasome is involved in the innate immune response to amyloid-beta" Nat Immunol, 9(8):857-865.
Harada, K. et al. (2012) "Identification of oxazolidinediones and thiazolidinediones as potent 17β-hydroxysteroid dehydrogenase type 3 inhibitors" Bioorg & Med Chem Lett, 22(1):504-507.
Heneke, M.T. et al. (2013) "NLRP3 is activated in Alzheimer's disease and contributes to pathology in APP/PS1 mice" Nature, 493:674-678.
Hoffman, H.M. et al. (2001) "Mutation of a new gene encoding a putative pyrin-like protein causes familial cold autoinflammatory syndrome and Muckle-Wells syndrome" Nat Genet, 29(3):301-305.
Hoffman, H.M. al. (2005) "Periodic Fever Disorders" Reumatología, 21(3):96-100.
Holen, I. et al. (2016) "IL-1 drives breast cancer growth and bone metastasis in vivo" Oncotarget, 7(46): 75571-75584.
Jee, C.D. et al. (2005) "Loss of caspase-1 gene expression in human gastric carcinomas and cell lines" Int J Oncol, 26:1265-1271.
Kagan, J. and Horng, T. (2013) "NLRP3 inflammasome activation: CD36 serves double duty" Nature Immunology, 14(8):772-774.
Kakeya, N. et al. (1984) "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid" Chem. Pharm. Bull., 32(2):692-698.
Kim, J.M. (2011) "Inflammatory Bowel Diseases and Inflammasome" Korean J Gastroenterol, vol. 58 No. 6, pp. 300-310 (Korean, English Abstract on p. 300).
Latz, E. et al. (2013) "Activation and regulation of the inflammasomes" Nat Rev Immunol, 13(6):397-411.
Lázár-Molnár, E. et al. (2000) "Autocrine and paracrine regulation by cytokines and growth factors in melanoma" Cytokine, 12(6):547-554.
Lewis, A.M. et al. (2006) "Interleukin-1 and cancer progression: the emerging role of interleukin-1 receptor antagonist as a novel therapeutic agent in cancer treatment" Journal of Translational Medicine, 4:48; 12 pages.
Li, L. and Liu, Y. (2015) "Aging-related gene signature regulated by Nlrp3 predicts glioma progression" American Journal of Cancer Research, 5(1):442-449.
Martinon, F. et al. (2009) "The inflammasomes: guardians of the body" Annu Rev Immunol, 27:229-265.
Masters, S.L. et al. (2009) "Horror Autoinflammaticus: The Molecular Pathophysiology of Autoinflammatory Disease" Annu Rev Immunol, 27:621-668.
Mortaz, E. et al. (2011) "Identification of Novel Therapeutic Targets in COPD" Tanaffos, 10(2):9-14.
Nath, A. et al. (2015) "Elevated free fatty acid uptake via CD36 promotes epithelial-mesenchymal transition in hepatocellular carcinoma" Scientific Reports, 5:14752; 19 pages.
Nielsen, N.M. and H. Bundgaard (1988) "Glycolamide Esters as Biolabile Prodrugs of Carboxylic Acid Agents: Synthesis, Stability, Bioconversion, and Physicochemical Properties" Journal of Pharmaceutical Sciences, 77(4):285-296.
Pascual, G. et al. (2017) "Targeting metastasis-initiating cells through the fatty acid receptor CD36" Nature, 541(7635):41-45; including Supplementary Information, 20 pages.
Patani, G.A. and E. J. Lavoie (1996) "Bioisosterism: A Rational Approach in Drug Design" Chem Rev, 96:3147-3176.
Perregaux, D.G. et al. (2001) "Identification and characterization of a novel class of interleukin-1 post-translational processing inhibitors" J Pharmacol Exp Ther, 299(1):187-197.
Saresella, M. et al. (2016) "The NLRP3 and NLRP1 inflammasomes are activated in Alzheimer's disease" Mol Neurodegener, 11:23; 14 pages.
Schett, G. et al. (2016) "Interleukin-1 function and role in rheumatic disease" Nat Rev Rheumatol, 12(1):14-24.
Sims, J. and Smith, D.E. (2010) "The IL-1 family: regulators of immunity" Nature Reviews Immunology, 10:89-102.
Thompson, H.E. et al. (1946) "New Growth-Regulating Compounds. I. Summary of Growth-Inhibitory Activities of Some Organic Compounds As Determined By Three Tests" Botanical Gazette, 107:476-507.
Uray, G. et al. (1998) "Diphenylethanediamine derivatives as chiral selectors VIII. Influence of the second amido function on the high-performance liquid chromatographic enantioseparation characteristics of (N-3,5-dinitrobenzoyl)-dipenylethanediamine based chiral stationary phases" J Chromatography, 799(1-2):67-81.
Von Geldern, T.W. et al. (1996) "Azole Endothelin Antagonists. 3. Using Δ log P as a Tool To Improve Absorption" J Med Chem, 39:982-991.
Voronov, E. et al. (2003) "IL-1 is required for tumor invasiveness and angiogenesis" Proceedings of the National Academy of Sciences USA, 100(5):2645-2650.
Wang, P. et al. (2006) "Association of interleukin-1 gene polymorphisms with gastric cancer: a meta-analysis" Int J Cancer, 120:552-562.
Wang, Y. et al. (2005) "Dipeptidyl aspartyl fluoromethylketones as potent caspase inhibitors: peptidomimetric replacement of the P2 α-amino acid by a α-hyroxy acid" Bioorg & Med Chem Lett, 15(5):1379-1383.
Xu, Y. et al. (2013) "Mycoplasma hyorhinis Activates the NLRP3 Inflammasome and Promotes Migration and Invasion of Gastric Cancer Cells" PLoS ONE, 8(11):e77955, 14 pages.
Zhang, B. et al. (2004) "IL-18 increases invasiveness of HL-60 myeloid leukemia cells: up-regulation of matrix metalloproteinases-9 (MMP-9) expression" Leukemia Research, 28(1):91-95.
International Search Report and Written Opinion issued in International Patent Application No. PCT/EP2018/070799, mailed Jan. 2, 2019; 22 pages.
Chen, L., et al., "Blockage of the NLRP3 inflammasome by MCC950 improves anti-tumor immune responses in head and neck squamous cell carcinoma," Cellular and Molecular Life Sciences, 74:2405-2058, https://doi.org/10.1007/s00018-017-2720-9 (2018).
Cuisset, L., et al., "Genetic Linkage of the Muckle-Wells Syndrome to Chromosome 1 q44," Am. J. Hum. Genet., 65:1054-1059 (1999).
Feldmann, J., et al., "Chronic Infantile Neurological Cutaneous and Articular Syndrome Is Caused by Mutations in CIAS1, a Gene Highly Expressed in Polymorphonuclear Cells and Chondrocytes," Am. J. Hum. Genet. 71:198-203 (2002).
Hoffman, H. M. et al., "Familial cold autoinflammatory syndrome: Phenotype and genotype of an autosomal dominant periodic fever," J Allegy Clin Immunol, vol. 108, No. 4, pp. 615-620, doi:10.1067/mai.2001.118790 (Oct. 2001).
Ising, et al., "NLRP3 inflammasome activation drives tau pathology," Nature, doi:10.1067/mai.2001.118790 (Nov. 2019).
Shen, H-H., et al., "NLRP3: A promising therapeutic target for autoimmune diseases," Autoimmunity Reviews, 17, 694-702 (2018).
Stancu, I.-C., et al., "Aggregated Tau activates NLRP3-ASC inflammasome exacerbating exogenously seeded and non-exgenously seeded Tau pathology in vivo," Acta Neuropathologica, 137:599-617 (2019).
Thi, et al., "Inflammasome as a Therapeutic Target for Cancer Prevention and Treatment," Journal of Cancer Prevention, vol. 22, No. 2, pp. 62-73, https://doi.org/10.15430/JCP.2017.22.2.62 (Jun. 2017).

(56) References Cited

OTHER PUBLICATIONS

STN database document, disclosing RN Nos. 2028047-16-5, entry date Nov. 9, 2016; 2007828-65-9, entry date Oct. 7, 2016; 2006793-78-6, entry date Oct. 6, 2016; 2004483- 87-6, entry date Oct. 3, 2016; 107520-53-6, entry date Apr. 11, 1987; 101878-32-4, entry date May 4, 1986; 6328-37-6, entry date Nov. 16, 1984; cited in Office Action dated Oct. 28, 2022 for counterpart Chinese Application No. 201880063698.8 (4 total pages).
RN 1998532-01-6 Registry, Database Registry [Online]; Retrieved from STN, Sep. 23, 2016, Retrieved on: Jun. 22, 2020.
RN 1998532-72-1 Registry, Database Registry [Online]; Retrieved from STN, Sep. 23, 2016.
RN 2002521-33-5 Registry, Database Registry [Online]; Retrieved from STN, Sep. 30, 2016, Retrieved on: Jun. 22, 2020.
RN 2004483-87-6 Registry, Database Registry [Online]; Retrieved from STN, Oct. 3, 2016, Retrieved on: Jun. 22, 2020.
RN 2006793-78-6 Registry, Database Registry [Online]; Retrieved from STN, Oct. 6, 2016, Retrieved on: Jun. 22, 2020.
RN 2007828-65-9 Registry, Database Registry [Online]; Retrieved from STN, Oct. 7, 2016, Retrieved on: Jun. 22, 2020.
RN 2028047-16-5 Registry, Database Registry [Online]; Retrieved from STN, Nov. 9, 2016, Retrieved on: Jun. 22, 2020.
Shapiro, Seymour L. et al., Pyridyloxazolidinediones and related compounds, Journal of Organic Chemistry, 1959, vol. 24, p. 1606-1607.
CAS Registry No. 1998892-55-9; date entered STN: Sep. 25, 2016; (2S)-2-[[(Bicyclo[2.2.1]hept-2-ylamino)carbonyl]oxy]propanoic acid (1 page).
CAS Registry No. 1998920-26-5; date entered STN: Sep. 25, 2016; (2R)-2-[[(Bicyclo[2.2.1]hept-2-ylamino)carbonyl]oxy]propanoic acid (1 page).
CAS Registry No. 2002274-78-2; date entered STN: Sep. 29, 2016; 2-[[(Bicyclo[2.2.1]hept-2-ylamino)carbonyl]oxy]propanoic acid (1 page).
CAS Registry No. 2008346-39-0; date entered STN: Oct. 9, 2016; 2-[[(Bicyclo[2.2.1]hept-2-ylamino)carbonyl]oxy]acetic acid (1 page).
CAS Registry No. 2015192-44-4; date entered STN: Oct. 19, 2016; (2S)-2-[[[(2-Fluorophenyl)amino]carbonyl]oxy]propanoic acid (1 page).
Patton, T.L., "Reactions of Isocyanates with Cyanohydrins. The Synthesis of 2,4-Oxazolidinediones and 1,3-Disubstituted Parabanic Acids", Journal of Organic Chemistry (1967), 32(2), 383-388.
CAS Registry No. 117403-13-1, date entered Nov. 12, 1988; Propanoic acid, 2-[[[(4-cyanophenyl)amino]carbonyl]oxy]-, ethyl ester, 2 pages.
CAS Registry No. 27605-07-8; date entered Nov. 16, 1984; Acetic acid, 2-[[[(3,5-dichlorophenyl)amino]carbonyl]oxy]-, 2 pages.
CAS Registry No. 874531-30-3; date entered STN: Feb. 17, 2006; Acetic acid, 2-[[[(7-hydroxy-1-naphthalenyl)amino]carbonyl]oxy]-, 2 pages.
CAS Registry No. RN 1787254-87-8, date entered Jun. 23, 2015; Benzeneacetic acid, α-[[[(2-chlorophenyl)amino]carbonyl]oxy]-, ethyl ester, 1 page.
CAS Registry No. RN 1787254-94-7, date entered Jun. 23, 2015; Benzeneacetic acid, α-[[[(2-methylphenyl)amino]carbonyl]oxy)-, methyl ester, 1 page.
CAS Registry No. RN 849737-15-1, date entered May 4, 2005; Butanoic acid, 2-[[[(2,6-dichlorophenyl]amino]carbonyl]oxy]-3-methyl-, (2S)-, 1 page.

* cited by examiner

SELECTIVE INHIBITORS OF NLRP3 INFLAMMASOME

RELATED APPLICATION

This application is a U.S. National Phase application, filed under U.S.C. § 371 (c), of International Application No. PCT/EP2018/070799, filed Jul. 31, 2018, which claims priority to United Kingdom Patent Application No. 1712282.1, filed Jul. 31, 2017, the entire contents of each of which are incorporated herein by reference in their entireties.

FIELD OF THE DISCLOSURE

The present disclosure concerns particular novel compounds and directly related prodrugs, or pharmaceutically acceptable salt(s) thereof, which possess inflammasome inhibitory activity and are accordingly useful in methods of treatment of the human or animal body. The present disclosure also relates to processes for the preparation of these compounds, to pharmaceutical compositions comprising them and to their use in the treatment of disorders in which inflammasome activity is implicated, such as autoinflammatory and autoimmune and oncological diseases.

BACKGROUND

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation including NLRP1, NLRP3, NLRP6, NLRP7, NLRP12 and NLRC4 (IPAF).

Although inflammasome activation appears to have evolved as an important component of host immunity to pathogens, the NLRP3 inflammasome is unique in its ability activate in response to endogenous or exogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1 and IL-18 being implicated in a diverse range of pathophysiological indications including metabolic, physiologic, inflammatory, hematologic and immunologic disorders.

The disclosure arises from a need to provide novel compounds for the specific modulation of NLRP3-dependent cellular processes. In particular, compounds with improved physicochemical, pharmacological and pharmaceutical properties to existing compounds are desirable.

SUMMARY

In some aspects, the present disclosure provides, inter alia, a compound of Formula (I):

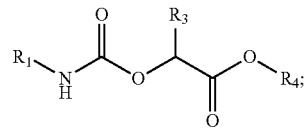

or a prodrug, hydrate, solvate, or pharmaceutically acceptable salt thereof, wherein:

$R_1$ is $C_3$-$C_7$ monocyclic cycloalkyl, polycyclic cycloalkyl, $C_5$-$C_{10}$ aryl, 8- to 12-membered heterocycloalkyl, or 5- to 6-membered heteroaryl, wherein the $C_3$-$C_7$ monocyclic cycloalkyl, polycyclic cycloalkyl, $C_5$-$C_6$ aryl, 8- to 12-membered heterocycloalkyl, or 5- to 6-membered heteroaryl is optionally substituted by one or more $R_6$;

$R_3$ is H or $C_1$-$C_4$ alkyl optionally substituted with one or more $R_7$;

$R_4$ is H, $C_1$-$C_6$ alkyl, —$(CH_2)_{0-3}$—($C_3$-$C_6$ cycloalkyl), or —$(CH_2)_{0-3}$—$C_5$-$C_6$ aryl;

$R_6$ is $C_1$-$C_6$ alkyl, $C_2$-$C_6$ alkenyl, $C_1$-$C_6$ alkoxy, $C_3$-$C_8$ cycloalkyl, halo, oxo, —OH, —CN, —$NH_2$, —NH($C_1$-$C_6$ alkyl), —N($C_1$-$C_6$ alkyl)$_2$, —$CH_2F$, —$CHF_2$, or —$CF_3$;

$R_7$ is —$OR_8$, $C_5$-$C_{10}$ aryl, or 5- to 10-membered heteroaryl, wherein the $C_5$-$C_{10}$ aryl or 5- to 10-membered heteroaryl is optionally substituted by one or more $R_{7S}$, wherein each $R_{7S}$ is independently $C_1$-$C_6$ alkyl, $C_1$-$C_6$ alkoxy, 5- to 10-membered heteroaryl, halo, —OH, —CN, —$(CH_2)_{0-3}$—$NH_2$, —$(CH_2)_{0-3}$—NH($C_1$-$C_6$ alkyl), —$(CH_2)_{0-3}$—N($C_1$-$C_6$ alkyl)$_2$, —$CH_2F$, —$CHF_2$, or —$CF_3$; and $R_8$ is $C_1$-$C_6$ alkyl or 5- to 7-membered heterocycloalkyl, wherein the $C_1$-$C_6$ alkyl or 5- to 7-membered heterocycloalkyl is optionally substituted by one or more $R_{7S}$.

In some aspects, the present disclosure provides a compound obtainable by, or obtained by, a method for preparing a compound as described herein (e.g., a method comprising one or more steps described in Schemes 1-5).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-126).

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutical salt thereof for use in inhibiting inflammasome (e.g., the NLRP3 inflammasome) activity (e.g., in vitro or in vivo).

In some aspects, the present disclosure provides a compound of the present disclosure or a pharmaceutical salt thereof for use in treating or preventing a disease or disorder disclosed herein.

In some aspects, the present disclosure provides use of a compound of the present disclosure or a pharmaceutical salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutical salt thereof in the manufacture of a medicament for treating or preventing a disease or disorder disclosed herein.

In some aspects, the present disclosure provides a method of preparing a compound of the present disclosure.

In some aspects, the present disclosure provides a method of a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

Cytokines from the IL-1 family are highly active and, as important mediators of inflammation, primarily associated with acute and chronic inflammation (Sims J. et al. Nature Reviews Immunology 10, 89-102 (February 2010)). The overproduction of IL-1 is considered to be a mediator of some autoimmune and autoinflammatory diseases. Autoinflammatory diseases are characterised by recurrent and unprovoked inflammation in the absence of autoantibodies, infection, or antigen-specific T lymphocytes.

Proinflammatory cytokines of the IL-1 superfamily include IL-1a, IL-1β, IL-18, and IL-36α, β, λ and are produced in response to pathogens and other cellular stressors as part of a host innate immune response. Unlike many other secreted cytokines, which are processed and released via the standard cellular secretory apparatus consisting of the endoplasmic reticulum and Golgi apparatus, IL-1 family members lack leader sequences required for endoplasmic reticulum entry and thus are retained intracellularly following translation. In addition, IL-1β, IL-18, and IL-36α, β, λ are synthesised as procytokines that require proteolytic activation to become optimal ligands for binding to their cognate receptors on target cells.

In the case of IL-1α, IL-1β and IL-18, it is now appreciated that a multimeric protein complex known as an inflammasome is responsible for activating the proforms of IL-1β and IL-18 and for release of these cytokines extracellularly. An inflammasome complex typically consists of a sensor molecule, such as an NLR (Nucleotide-Oligerimisation Domain (NOD)-like receptor), an adaptor molecule ASC (Apoptosis-associated speck-like protein containing a CARD (Caspase Recruitment Domain)) and procaspase-1. In response to a variety of "danger signals", including pathogen-associated molecule patterns (PAMPs) and danger associated molecular patterns (DAMPs), subunits of an inflammasome oligomerise to form a supramolecular structure within the cell. PAMPs include molecules such as peptidoglycan, viral DNA or RNA and bacterial DNA or RNA. DAMPs, on the other hand, consist of a wide range of endogenous or exogenous sterile triggers including monosodium urate crystals, silica, alum, asbestos, fatty acids, ceramides, cholesterol crystals and aggregates of beta-amyloid peptide. Assembly of an inflammasome platform facilitates autocatalysis of procaspase-1 yielding a highly active cysteine protease responsible for activation and release of pro-IL-1β and pro-IL-18. Thus, release of these highly inflammatory cytokines is achieved only in response to inflammasome sensors detecting and responding to specific molecular danger signals.

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation including NLRP1, NLRP3, NLRP6, NLRP7, NLRP12 and NLRC4 (IPAF).

Two other structurally distinct inflammasome structures containing a PYHIN domain (pyrin and HIN domain containing protein) namely Absent in Melanoma 2 (AIM2) and IFNλ-inducible protein 16 (IFI16) (Latz et al., Nat Rev Immunol 2013 13(6) 397-311) serve as intracellular DNA sensors. Pyrin (encoded by the MEFV gene) represents another type of inflammasome platform associated with proIL-1β activation (Chae et al., Immunity 34, 755-768, 2011).

Requiring assembly of an inflammasome platform to achieve activation and release of IL-1β and IL-18 from monocytes and macrophages ensures their production is carefully orchestrated via a 2-step process. First, the cell must encounter a priming ligand (such as the TLR4 receptor ligand LPS, or an inflammatory cytokine such as TNFα) which leads to NFkB dependent transcription of NLRP3, pro-IL-1β and pro-IL-18. The newly translated procytokines remain intracellular and inactive unless producing cells encounter a second signal leading to activation of an inflammasome scaffold and maturation of procaspase-1.

In addition to proteolytic activation of pro-IL-1β and pro-IL-18, active caspase-1 also triggers a form of inflammatory cell death known as pyroptosis through cleavage of gasdermin-D. Pyroptosis allows the mature forms of IL-1β and IL-18 to be externalized along with release of alarmin molecules (compounds that promote inflammation and activate innate and adaptive immunity) such as high mobility group box 1 protein (HMGB1), IL-33, and IL-1α.

Although inflammasome activation appears to have evolved as an important component of host immunity to pathogens, the NLRP3 inflammasome is unique in its ability activate in response to endogenous and exogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1β and IL-18 being implicated in a diverse range of pathophysiological indications including metabolic, physiologic, inflammatory, hematologic and immunologic disorders.

A link to human disease is best exemplified by discovery that mutations in the NLRP3 gene which lead to gain-of-function confer a range of autoinflammatory conditions collectively known as cryopyrin-associated periodic syndromes (CAPS) including familial cold autoinflammatory syndrome (FCAS), Muckle-Wells syndrome (MWS) and Neonatal onset multisystem inflammatory disease (NOMID) (Hoffman et al., Nat Genet. 29(3) (2001) 301-305). Likewise, sterile mediator-induced activation of NLRP3 has been implicated in a wide range of disorders including joint degeneration (gout, rheumatoid arthritis, osteoarthritis), cardiometabolic (type 2 diabetes, atherosclerosis, hypertension), Central Nervous System (Alzheimer's Disease, Parkinson's disease, multiple sclerosis), gastrointestinal (Crohn's disease, ulcerative colitis), lung (chronic obstructive pulmonary disease, asthma) and fibrosis (non-alcoholic fatty liver disease, non-alcoholic hepatosteatosis, idiopathic pulmonary fibrosis). It is further believed that NLRP3 activation promotes kidney inflammation and thus contributes to chronic kidney disease (CKD).

Current treatment options for diseases where IL-1 is implicated as a contributor to pathogenesis include the IL-1 receptor antagonist anakinra, an Fc-containing fusion construct of the extracellular domains of the IL-1 receptor and IL-1 receptor accessory protein (rilonacept) and the anti-IL-1β monoclonal antibody canakinumab. For example, canakinumab is licensed for CAPS, Tumor Necrosis Factor Receptor Associated Periodic Syndrome (TRAPS), Hyperimmunoglobulin D Syndrome (HIDS)/Mevalonate Kinase Deficiency (MKD), Familial Mediterranean Fever (FMF) and gout.

Some small molecules have been reported to inhibit function of the NLRP3 inflammasome. Glyburide, for example, is a specific inhibitor of NLRP3 activation, albeit at micromolar concentrations which are unlikely attainable in vivo. Non-specific agents such as parthenolide, Bay 11-7082, and 3,4-methylenedioxy-β-nitrostyrene are reported to impair NLRP3 activation but are expected to possess limited therapeutic utility due to their sharing of a common structural feature consisting of an olefin activated by substitution with an electron withdrawing group; this can lead to undesirable formation of covalent adducts with protein-bearing thiol groups. A number of natural products, for example β-hydroxybutyrate, sulforaphane, quercetin, and salvianolic acid, also are reported to suppress NLRP3 activation. Likewise, numerous effectors/modulators of other molecular targets have been reported to impair NLRP3 activation including agonists of the G-protein coupled receptor TGR5, an inhibitor of sodium-glucose co-transport epigliflozin, the dopamine receptor antagonist A-68930, the serotonin reuptake inhibitor fluoxetine, fenamate non-steroidal anti-inflammatory drugs, and the β-adrenergic receptor blocker nebivolol. Utility of these molecules as therapeutics for the chronic treatment of NLRP3-dependent inflammatory disorders remains to be established. A series of sulfonylurea-containing molecules was previously identified as potent and selective inhibitors of post-translational processing of pro-IL-1β (Perregaux et al., J Pharmacol. Exp. Ther. 299, 187-197, 2001). The exemplar molecule CP-456, 773 from this work was recently characterised as a specific inhibitor of NLRP3 activation (Coll et al., Nat Med 21.3 (2015): 248-255.).

The disclosure relates to compounds useful for the specific modulation of NLRP3-dependent cellular processes. In particular, compounds with improved physicochemical, pharmacological and pharmaceutical properties to existing NLRP3-modulating compounds are desired.

Definitions

Unless otherwise stated, the following terms used in the specification and claims have the following meanings set out below.

It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In some embodiments, the cycloalkyl is hexahydroindacenyl.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1] heptanyl, 2-oxa-6-azaspiro[3.3]heptanyl, 2,6-diazaspiro [3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5] decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo [3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d] pyrimidinyl, 2-azaspiro[3.3]heptanyl, 2-methyl-2-azaspiro [3.3]heptanyl, 2-azaspiro[3.5]nonanyl, 2-methyl-2-azaspiro [3.5]nonanyl, 2-azaspiro[4.5]decanyl, 2-methyl-2-azaspiro [4.5]decanyl, 2-oxa-azaspiro[3.4]octanyl, 2-oxa-azaspiro [3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and S(O)$_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O⁻.

As used herein, the term "halo" or "halogen" refers to fluoro, chloro, bromo and iodo.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. *Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having an imprinting disorder. A subject in need thereof can also be one who has (e.g., is suffering from) an imprinting disorder. Alternatively, a subject in need thereof can be one who has an increased risk of developing such disorder relative to the population at large (i.e., a subject who is predisposed to developing such disorder relative to the population at large). A subject in need thereof can have a refractory or resistant imprinting disorder (i.e., an imprinting disorder that doesn't respond or hasn't yet responded to treatment). The subject may be resistant at start of treatment or may become resistant during treatment. In some embodiments, the subject in need thereof received and failed all known effective therapies for an imprinting disorder. In some embodiments, the subject in need thereof received at least one prior therapy. In a preferred embodiment, the subject has an imprinting disorder.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., imprinting disorders, and the like) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is an imprinting disorder.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the imprinting disorder and also preferably causing complete regression of the imprinting disorder. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the present disclosure" refers to those compounds which are disclosed herein, both generically and specifically.

Compounds of the Present Disclosure

In some aspects, the present disclosure relates to a compound of Formula (I):

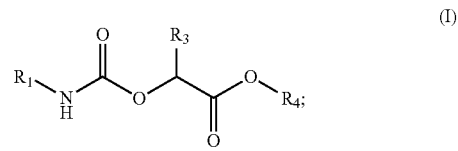

or a prodrug, hydrate, solvate, or pharmaceutically acceptable salt thereof, wherein:

$R_1$ is $C_3$-$C_7$ monocyclic cycloalkyl, polycyclic cycloalkyl, $C_5$-$C_{10}$ aryl, 8- to 12-membered heterocycloalkyl, or 5- to 6-membered heteroaryl, wherein the $C_3$-$C_7$ monocyclic cycloalkyl, polycyclic cycloalkyl, 8- to 12-membered heterocycloalkyl, or 5- to 6-membered heteroaryl is optionally substituted by one or more $R_6$;

$R_3$ is H or $C_1$-$C_4$ alkyl optionally substituted with one or more $R_7$;

$R_4$ is H, $C_1$-$C_6$ alkyl, —$(CH_2)_{0-3}$—($C_3$-$C_6$ cycloalkyl), or —$(CH_2)_{0-3}$—$C_5$-$C_6$ aryl;

$R_6$ is $C_1$-$C_6$ alkyl, $C_2$-$C_6$ alkenyl, $C_1$-$C_6$ alkoxy, $C_3$-$C_8$ cycloalkyl, halo, oxo, —OH, —CN, —$NH_2$, —$NH(C_1$-$C_6$ alkyl), —$N(C_1$-$C_6$ alkyl)$_2$, —$CH_2F$, —$CHF_2$, or —$CF_3$;

$R_7$ is —$OR_8$, $C_5$-$C_{10}$ aryl, or 5- to 10-membered heteroaryl, wherein the $C_5$-$C_{10}$ aryl or 5- to 10-membered heteroaryl is optionally substituted by one or more $R_{7S}$, wherein each $R_{7S}$ is independently $C_1$-$C_6$ alkyl, $C_1$-$C_6$ alkoxy, 5- to 10-membered heteroaryl, halo, —OH, —CN, —$(CH_2)_{0-3}$—$NH_2$, —$(CH_2)_{0-3}$—$NH(C_1$-$C_6$ alkyl), —$(CH_2)_{0-3}$—$N(C_1$-$C_6$ alkyl)$_2$, —$CH_2F$, —$CHF_2$, or —$CF_3$; and $R_8$ is $C_1$-$C_6$ alkyl or 5- to 7-membered heterocycloalkyl, wherein the $C_1$-$C_6$ alkyl or 5- to 7-membered heterocycloalkyl is optionally substituted by one or more $R_{7S}$.

It is understood that, for a compound of Formula (I), $R_1$, $R_3$, $R_4$, $R_6$, $R_7$, $R_{7S}$, and $R_8$ can each be, where applicable, selected from the groups described herein, and any group described herein for any of $R_1$, $R_3$, $R_4$, $R_6$, $R_7$, Res, and $R_8$ can be combined, where applicable, with any group described herein for one or more of the remainder of $R_1$, $R_3$, $R^4$, $R_6$, $R_7$, $R_{7S}$, and $R_8$.

In some embodiments, $R_1$ is $C_3$-$C_7$ monocyclic cycloalkyl, $C_8$-$C_{16}$ polycyclic cycloalkyl, $C_5$-$C_{10}$ aryl, 8- to 12-membered heterocycloalkyl, or 5- to 6-membered heteroaryl, wherein the $C_3$-$C_7$ monocyclic cycloalkyl, $C_8$-$C_{16}$ polycyclic cycloalkyl, 8- to 12-membered heterocycloalkyl, or 5- to 6-membered heteroaryl is optionally substituted by one or more $R_6$.

In some embodiments, $R_1$ is $C_3$-$C_7$ monocyclic cycloalkyl, $C_9$-$C_{10}$ bicyclic cycloalkyl, $C_{12}$-$C_{16}$ tricyclic cycloalkyl, $C_5$-$C_{10}$ aryl, 8- to 12-membered heterocycloalkyl, or 5- to 6-membered heteroaryl, wherein the $C_3$-$C_7$ monocyclic cycloalkyl, $C_9$-$C_{10}$ bicyclic cycloalkyl, $C_{12}$-$C_{16}$ tricyclic cycloalkyl, 8- to 12-membered heterocycloalkyl, or 5- to 6-membered heteroaryl is optionally substituted by one or more $R_6$.

In some embodiments, $R_1$ is $C_3$-$C_7$ monocyclic cycloalkyl, polycyclic cycloalkyl, or $C_5$-$C_{10}$ aryl, wherein the $C_3$-$C_7$ monocyclic cycloalkyl, polycyclic cycloalkyl, or $C_5$-$C_6$ aryl is optionally substituted by one or more $R_6$.

In some embodiments, $R_1$ is $C_3$-$C_7$ monocyclic cycloalkyl, $C_8$-$C_{16}$ polycyclic cycloalkyl, or $C_5$-$C_{10}$ aryl, wherein the $C_3$-$C_7$ monocyclic cycloalkyl, $C_8$-$C_{16}$ polycyclic cycloalkyl, or $C_5$-$C_6$ aryl is optionally substituted by one or more $R_6$.

In some embodiments, $R_1$ is $C_3$-$C_7$ monocyclic cycloalkyl, $C_9$-$C_{10}$ bicyclic cycloalkyl, $C_{12}$-$C_{16}$ tricyclic cycloalkyl, or $C_5$-$C_{10}$ aryl, wherein the $C_3$-$C_7$ monocyclic cycloalkyl, $C_9$-$C_{10}$ bicyclic cycloalkyl, $C_{12}$-$C_{16}$ tricyclic cycloalkyl, or $C_5$-$C_{10}$ aryl, is optionally substituted by one or more $R_6$.

In some embodiments, $R_1$ is $C_3$-$C_7$ monocyclic cycloalkyl, $C_9$-$C_{10}$ bicyclic cycloalkyl, or $C_{12}$-$C_{16}$ tricyclic cycloalkyl, wherein the $C_3$-$C_7$ monocyclic cycloalkyl, $C_9$-$C_{10}$ bicyclic cycloalkyl, or $C_{12}$-$C_{16}$ tricyclic cycloalkyl is optionally substituted by one or more $R_6$.

In some embodiments, $R_1$ is $C_3$-$C_7$ monocyclic cycloalkyl optionally substituted by one or more $R_6$.

In some embodiments, $R_1$ is $C_9$-$C_{10}$ bicyclic cycloalkyl optionally substituted by one or more $R_6$.

In some embodiments, $R_1$ is $C_9$-$C_{10}$ bicyclic cycloalkyl saturated cycloalkyl optionally substituted by one or more $R_6$.

In some embodiments, $R_1$ is $C_9$-$C_{10}$ bicyclic cycloalkyl partially saturated cycloalkyl optionally substituted by one or more $R_6$.

In some embodiments, $R_1$ is $C_{12}$-$C_{16}$ tricyclic cycloalkyl optionally substituted by one or more $R_6$.

In some embodiments, $R_1$ is $C_{12}$-$C_{16}$ tricyclic saturated cycloalkyl optionally substituted by one or more $R_6$.

In some embodiments, $R_1$ is $C_{12}$-$C_{16}$ tricyclic partially unsaturated cycloalkyl optionally substituted by one or more $R_6$.

In some embodiments, $R_1$ is cyclopentyl, cyclohexyl, or cycloheptyl, wherein the cyclopentyl, cyclohexyl, or cycloheptyl is optionally substituted by one or more $R_6$.

In some embodiments, $R_1$ is cyclopentyl, cyclohexyl, or cycloheptyl.

In some embodiments, $R_1$ is

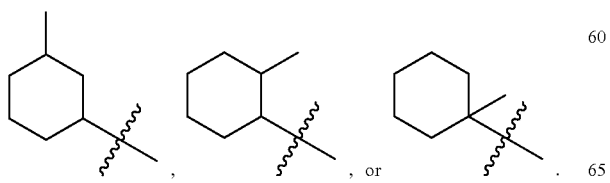

In some embodiments, $R_1$ is

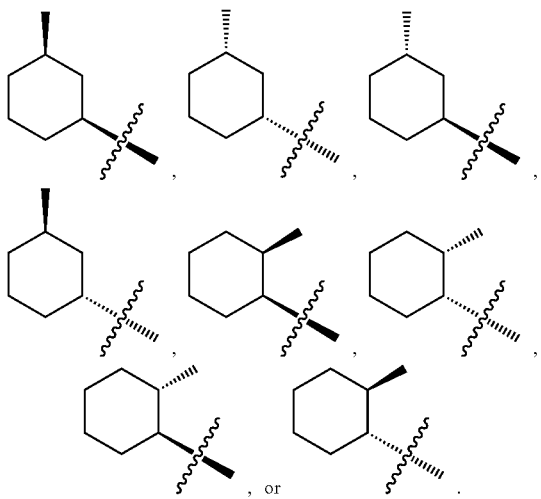

, or .

In some embodiments, $R_1$ is $C_8$-$C_{16}$ polycyclic cycloalkyl substituted by one or more $R_6$.

In some embodiments, $R_1$ is adamantly, norbornyl, or bicyclo[2.2.2]octanyl, wherein the adamantly, norbornyl, or bicyclo[2.2.2]octanyl is optionally substituted by one or more $R_6$.

In some embodiments, $R_1$ is adamantly, norbornyl, or bicyclo[2.2.2]octanyl.

In some embodiments, $R_1$ is

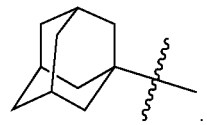 [SMILES: *C12CC3CC(CC(C3)C1)C2]

In some embodiments, $R_1$ is

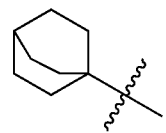

In some embodiments, $R_1$ is hexahydroindacenyl optionally substituted by one or more $R_6$.

In some embodiments, $R_1$ is hexahydroindacenyl.

In some embodiments, $R_1$ is

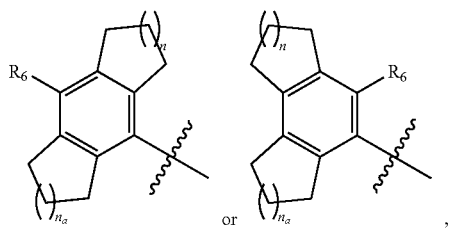

wherein n and $n_a$ each independently are 0, 1, 2, or 3.

In some embodiments, R₁ is

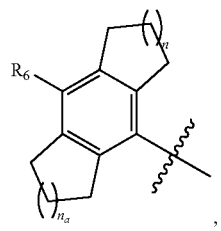

wherein n and n$_a$ each independently are 0, 1, 2, or 3.

In some embodiments, R₁ is

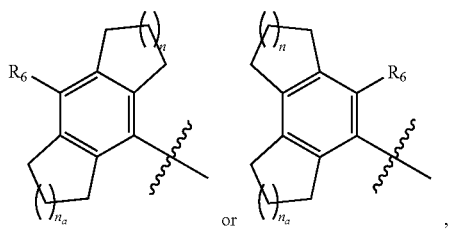

wherein n and n$_a$ each independently are 0, 1, 2, or 3, and wherein R₆ is C₁-C₆ alkyl, C₁-C₆ alkoxy, halo, oxo, —OH, or —CF₃.

In some embodiments, R₁ is

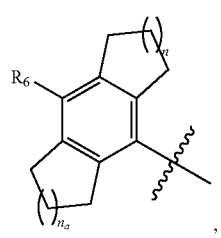

wherein n and n$_a$ each independently are 0, 1, 2, or 3, and wherein R₆ is C₁-C₆ alkyl, C₁-C₆ alkoxy, halo, oxo, —OH, or —CF₃.

In some embodiments, R₁ is

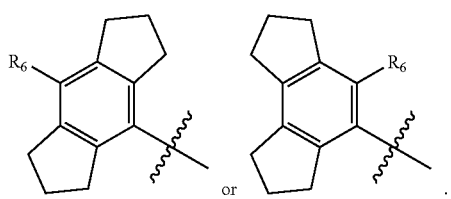

In some embodiments, R₁ is

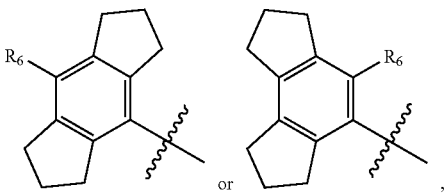

wherein R₆ is C₁-C₆ alkyl, C₁-C₆ alkoxy, halo, oxo, —OH, or —CF₃.

In some embodiments, R₁ is

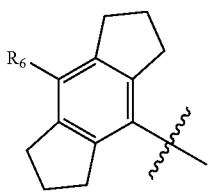

In some embodiments, R₁ is

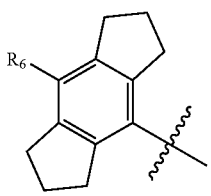

wherein R₆ is C₁-C₆ alkyl, C₁-C₆ alkoxy, halo, oxo, —OH, or —CF₃.

In some embodiments, R₁ is hexahydroindacenyl optionally substituted by one, two, three, or four substituents independently selected from C₁-C₄ alkyl, C₁-C₆ alkoxy, halo, oxo, —OH, and —CF₃.

In some embodiments, R₁ is unsubstituted hexahydroindacenyl.

In some embodiments, R₁ is

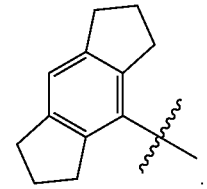 [SMILES: *c1c2c(cc3c1CCC3)CCC2]

In some embodiments, R₁ is C₅-C₁₀ aryl optionally substituted by one or more R₆.

In some embodiments, R₁ is C₅-C₁₀ aryl substituted by one or more R₆.

In some embodiments, R₁ is C₅-C₆ monocyclic aryl optionally substituted by one or more R₆.

In some embodiments, R₁ is C₅-C₆ monocyclic aryl substituted by one or more R₆.

In some embodiments, R₁ is phenyl optionally substituted by one or more R₆.

In some embodiments, R₁ is phenyl substituted by one or more R₆.

In some embodiments, R₁ is phenyl substituted by one R₆.

In some embodiments, $R_1$ is

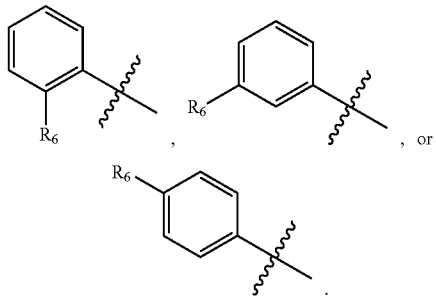

In some embodiments, $R_1$ is phenyl substituted by two $R_6$.
In some embodiments, $R_1$ is

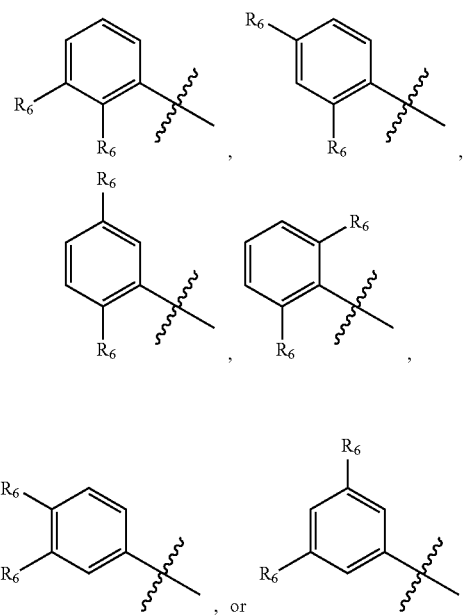

In some embodiments, $R_1$ is phenyl substituted by three $R_6$.
In some embodiments, $R_1$ is

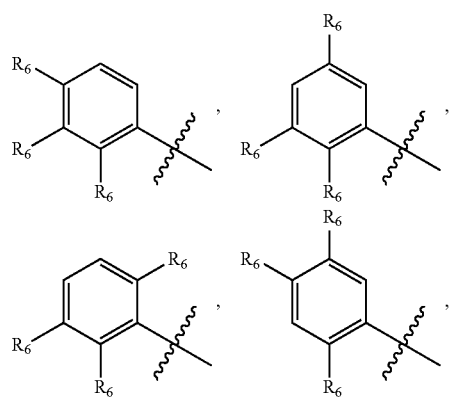

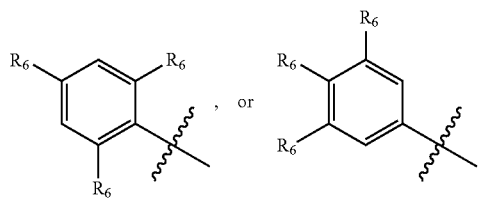

In some embodiments, $R_1$ is

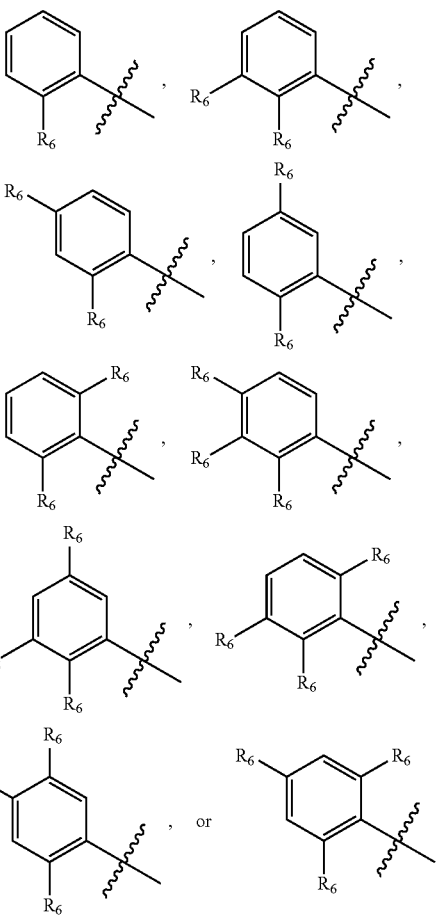

In some embodiments, $R_1$ is phenyl substituted by one or more substituents independently selected from $C_1$-$C_4$ alkyl, halo, —CN, and —$CF_3$.

In some embodiments, $R_1$ is phenyl optionally substituted by one, two, or three substituents independently selected from $C_1$ and F.

In some embodiments, $R_1$ is

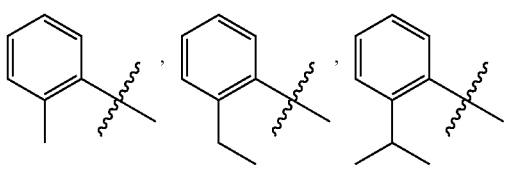

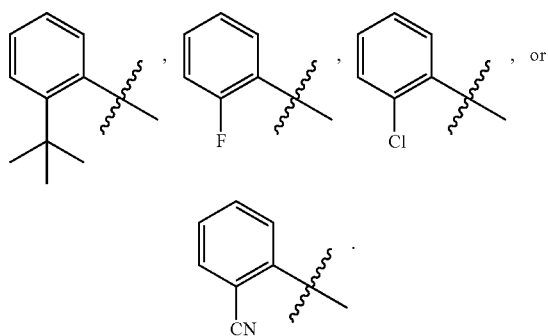
In some embodiments, $R_1$ is
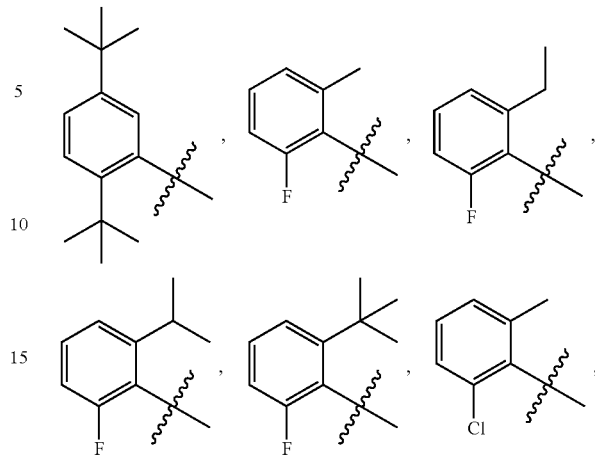
In some embodiments, $R_1$ is
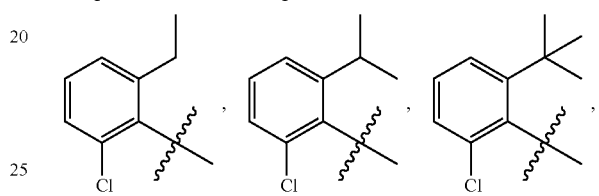
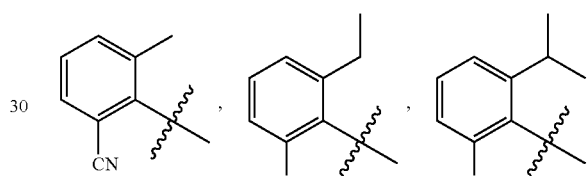
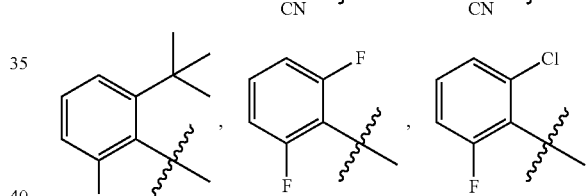
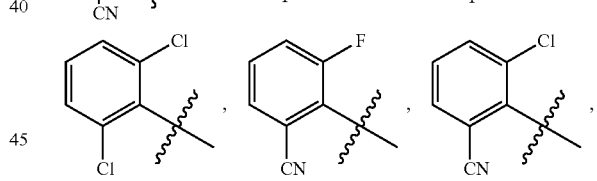
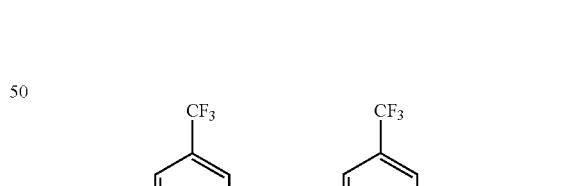
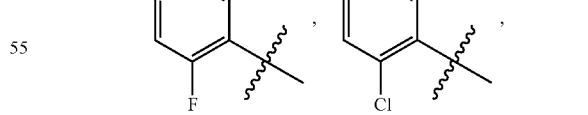
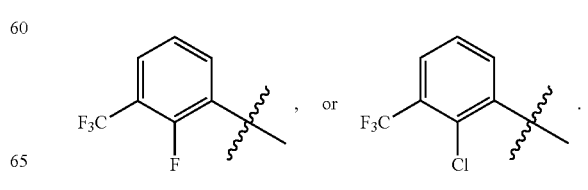

In some embodiments, R₁ is
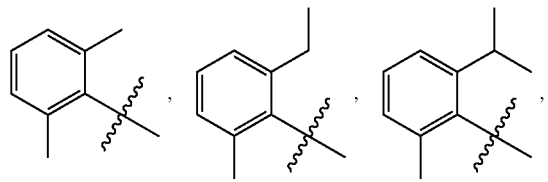
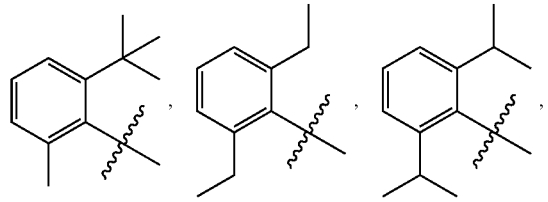
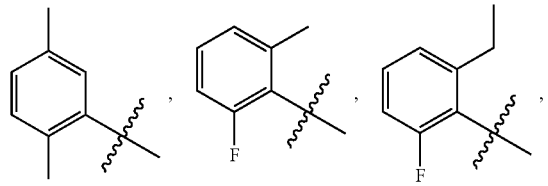
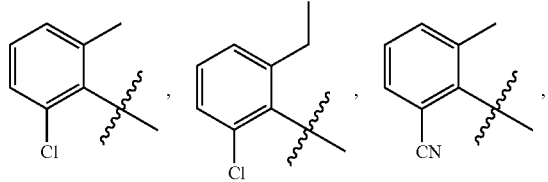
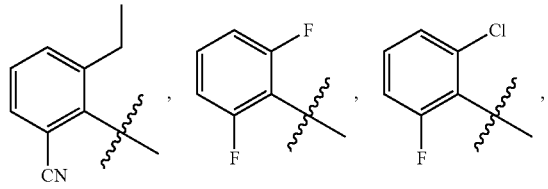
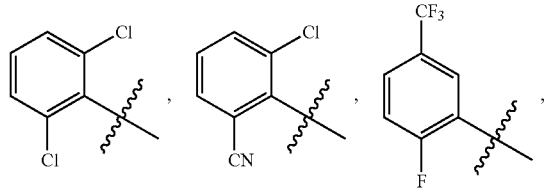
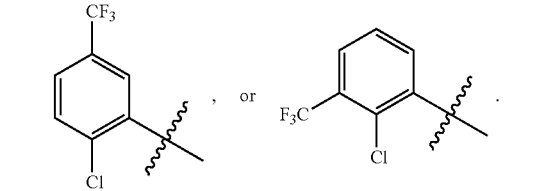
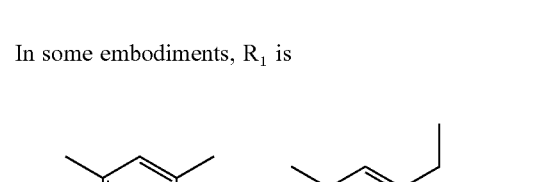
In some embodiments, R₁ is
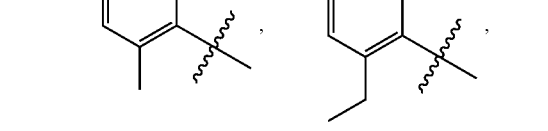
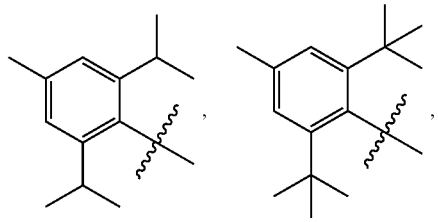
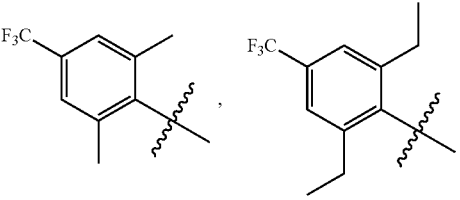
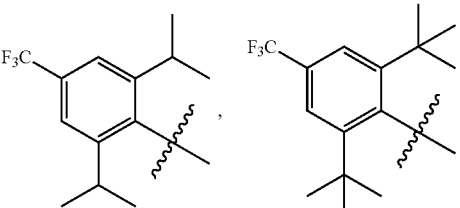
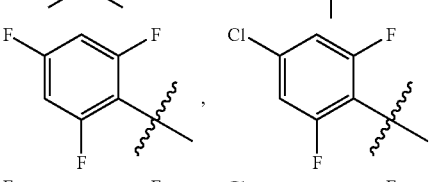
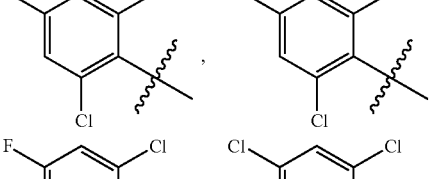
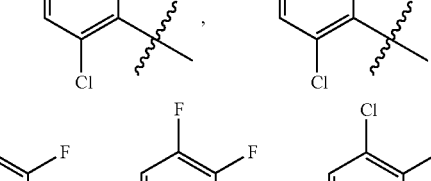
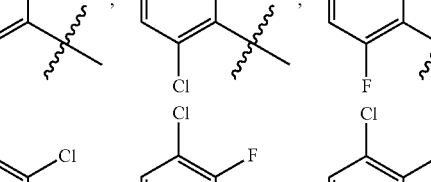
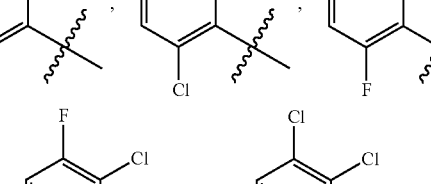
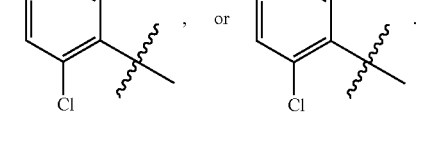

In some embodiments, $R_1$ is

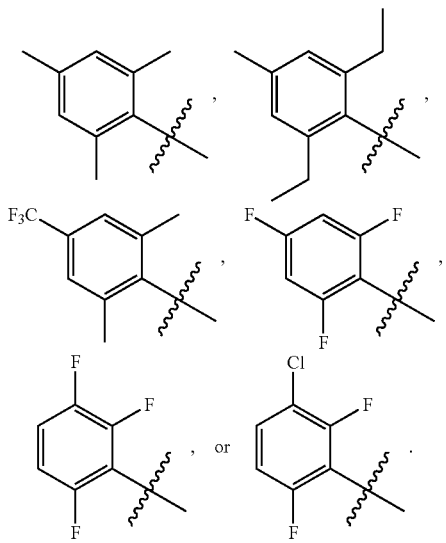

In some embodiments, $R_1$ is naphthalenyl optionally substituted by one or more $R_6$.

In some embodiments, $R_1$ is unsubstituted naphthalenyl.

In some embodiments, $R_1$ is

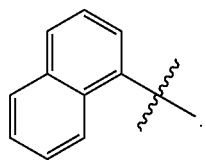 [SMILES: *c1cccc2ccccc12]

In some embodiments, $R_1$ is

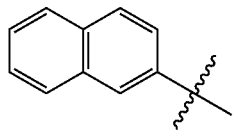

In some embodiments, $R_1$ is 8- to 12-membered heterocycloalkyl optionally substituted by one or more $R_6$.

In some embodiments, $R_1$ is benzofuranyl or dihydrobenzofuranyl, wherein the benzofuranyl or dihydrobenzofuranyl is optionally substituted by one or more $R_6$.

In some embodiments, $R_1$ is benzofuranyl optionally substituted by one or more $R_6$.

In some embodiments, $R_1$ is dihydrobenzofuranyl optionally substituted by one or more $R_6$.

In some embodiments, $R_1$ is

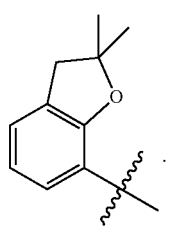 [SMILES: *c1cccc2c1OC(C)(C)C2]

In some embodiments, $R_1$ is

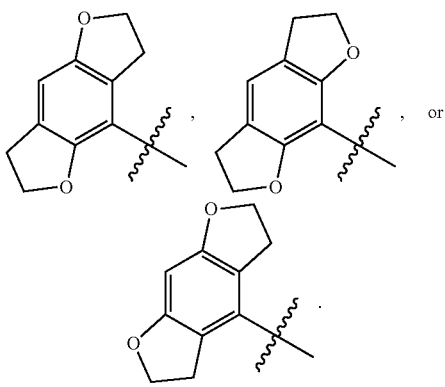

In some embodiments, $R_1$ is 5- to 6-membered heteroaryl optionally substituted by one or more $R_6$.

In some embodiments, $R_1$ is thiophenyl optionally substituted by one or more $R_6$.

In some embodiments, $R_1$ is thiophenyl substituted by one or more $R_6$.

In some embodiments, $R_1$ is

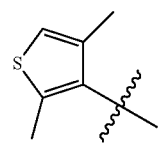

In some embodiments, $R_3$ is H.

In some embodiments, $R_3$ is not H.

In some embodiments, $R_3$ is $C_1$-$C_4$ alkyl optionally substituted with one or more $R_7$.

In some embodiments, $R_3$ is $C_1$-$C_4$ alkyl.

In some embodiments, $R_3$ is methyl.

In some embodiments, $R_3$ is ethyl.

In some embodiments, $R_3$ is $C_1$-$C_4$ alkyl substituted with one or more $R_7$.

In some embodiments, $R_3$ is methyl substituted with one or more $R_7$.

In some embodiments, $R_3$ is methyl substituted with one or more $C_1$-$C_6$ alkoxy, wherein the $C_1$-$C_6$ alkoxy is optionally substituted with one or more $C_1$-$C_6$ alkoxy.

In some embodiments, $R_3$ is methyl substituted with one or more methoxy.

In some embodiments, $R_3$ is

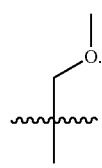

In some embodiments, $R_3$ is methyl substituted with one or more ethoxy.

In some embodiments, $R_3$ is

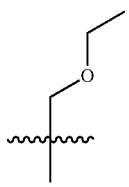

In some embodiments, $R_3$ is methyl substituted with one or more ethoxy, wherein the ethoxy is substituted with one or more methoxy.

In some embodiments, $R_3$ is

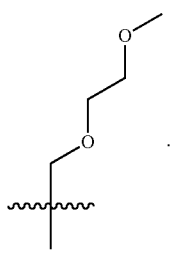 [SMILES: *COCCOC]

In some embodiments, $R_3$ is methyl substituted with one or more propoxy (e.g., i-propoxy).

In some embodiments, $R_3$ is

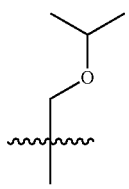

In some embodiments, $R_3$ is methyl substituted with one or more —O-(5- to 7-membered heterocycloalkyl).

In some embodiments, $R_3$ is

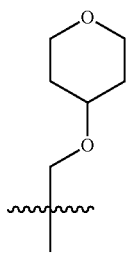

In some embodiments, $R_3$ is methyl with one or more $C_5$-$C_{10}$ aryl, wherein the $C_5$-$C_{10}$ aryl is optionally substituted with one or more 5- to 10-membered heteroaryl or —CN.

In some embodiments, $R_3$ is methyl with one or more phenyl, wherein the phenyl is optionally substituted with one or more 5- to 10-membered heteroaryl or —CN.

In some embodiments, $R_3$ is

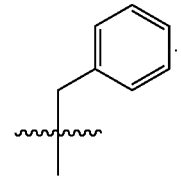 [SMILES: *Cc1ccccc1]

In some embodiments, $R_3$ is methyl with one or more phenyl, wherein the phenyl is optionally substituted with one or more 5- to 10-membered heteroaryl (e.g., pyrazolyl).

In some embodiments, $R_3$ is

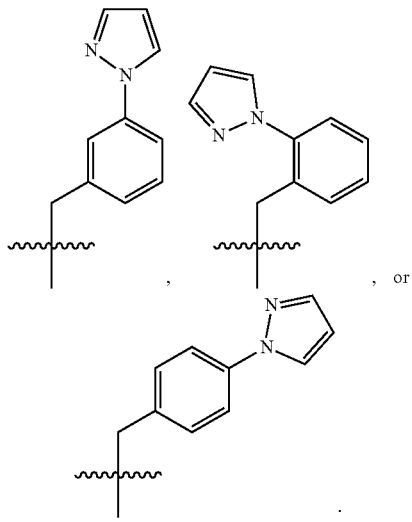

, or

In some embodiments, $R_3$ is methyl with one or more phenyl, wherein the phenyl is optionally substituted with one or more —CN.

In some embodiments, $R_3$ is

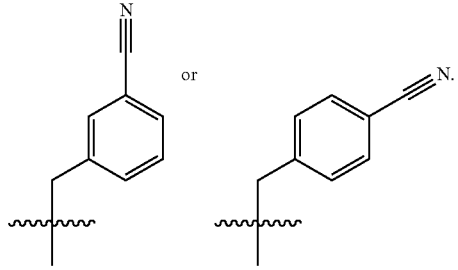 [SMILES: *Cc1cccc(C#N)c1 ; *Cc1ccc(C#N)cc1]

In some embodiments, $R_3$ is methyl substituted with one or more 5- to 10-membered heteroaryl, wherein the 5- to 10-membered heteroaryl is optionally substituted with one or more $C_1$-$C_6$ alkyl, $C_1$-$C_6$ alkoxy, halo, —CN, —(CH$_2$)$_{0-3}$—N(C$_1$-C$_6$ alkyl)$_2$, or —CF$_3$.

In some embodiments, $R_3$ is methyl substituted with one or more pyridinyl, pyrazolyl, imidazolyl, pyridazinyl, pyrimidinyl, pyrazinyl, triazolyl, wherein the pyridinyl, pyrazolyl, imidazolyl, pyridazinyl, pyrimidinyl, pyrazinyl, triazolyl is optionally substituted with one or more $C_1$-$C_6$ alkyl, $C_1$-$C_6$ alkoxy, halo, —CN, —(CH$_2$)$_{0-3}$—N(C$_1$-C$_6$ alkyl)$_2$, or —CF$_3$.

In some embodiments, $R_3$ is methyl substituted with one or more pyridinyl, wherein the pyridinyl is optionally substituted with one or more $C_1$-$C_6$ alkyl, $C_1$-$C_6$ alkoxy, halo, —CN, —(CH$_2$)$_{0-3}$—N(C$_1$-C$_6$ alkyl)$_2$, or —CF$_3$.

In some embodiments, R$_3$ is methyl substituted with one or more pyridinyl.

In some embodiments, R$_3$ is

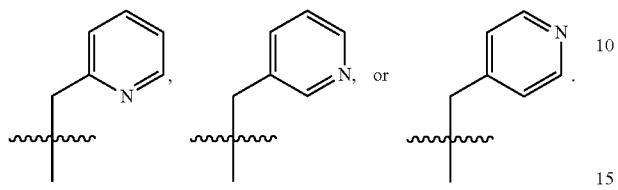

In some embodiments, R$_3$ is methyl substituted with one or more pyrazolyl, wherein the pyrazolyl is optionally substituted with one or more C$_1$-C$_6$ alkyl, C$_1$-C$_6$ alkoxy, halo, —CN, —(CH$_2$)$_{0-3}$—N(C$_1$-C$_6$ alkyl)$_2$, or —CF$_3$.

In some embodiments, R$_3$ is methyl substituted with one or more pyrazolyl, wherein the pyrazolyl is optionally substituted with one or more methyl, methoxy, F, Cl, —CN, —CH$_2$—N(CH$_3$)$_2$, or —CF$_3$.

In some embodiments, R$_3$ is methyl substituted with one or more pyrazolyl.

In some embodiments, R$_3$ is

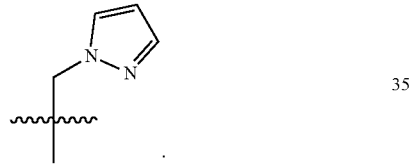

In some embodiments, R$_3$ is methyl substituted with one or more pyrazolyl, wherein the pyrazolyl is substituted with one or more methyl, methoxy, F, Cl, —CN, —CH$_2$—N(CH$_3$)$_2$, or —CF$_3$.

In some embodiments, R$_3$ is

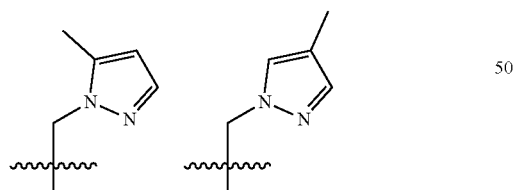

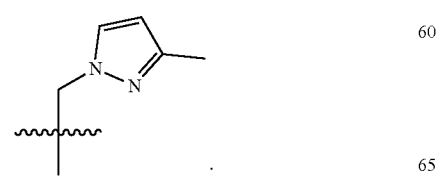

In some embodiments, R$_3$ is

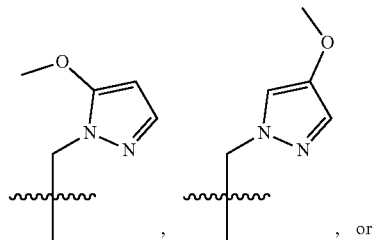

In some embodiments, R$_3$ is

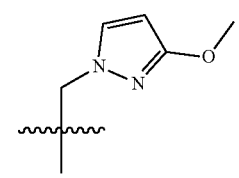

In some embodiments, R$_3$ is

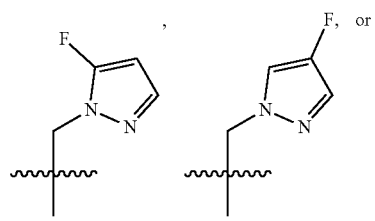

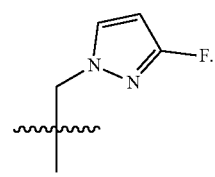

In some embodiments, R$_3$ is

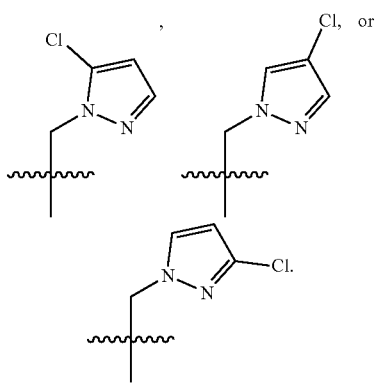

In some embodiments, $R_3$ is

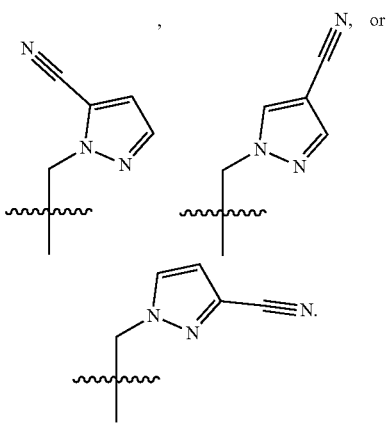

In some embodiments, $R_3$ is

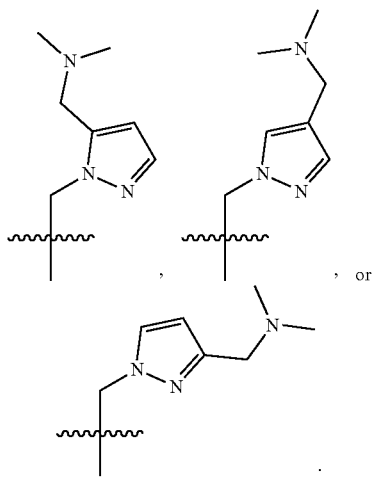

In some embodiments, $R_3$ is

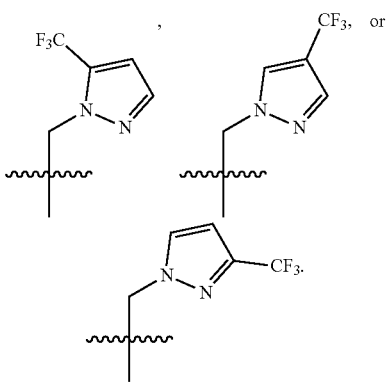

In some embodiments, $R_3$ is methyl substituted with one or more imidazolyl, wherein the imidazolyl is optionally substituted with one or more $C_1$-$C_6$ alkyl, $C_1$-$C_6$ alkoxy, halo, —CN, —$(CH_2)_{0-3}$—$N(C_1$-$C_6$ alkyl$)_2$, or —$CF_3$.

In some embodiments, $R_3$ is methyl substituted with one or more imidazolyl.

In some embodiments, $R_3$ is

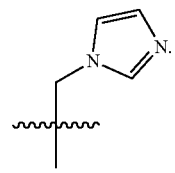 [SMILES: *Cn1ccnc1]

In some embodiments, $R_3$ is methyl substituted with one or more imidazolyl, wherein the imidazolyl is substituted with one or more methyl or —CN.

In some embodiments, $R_3$ is

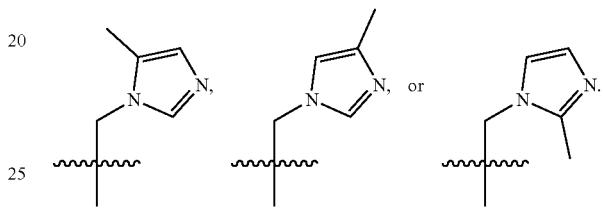

In some embodiments, $R_3$ is

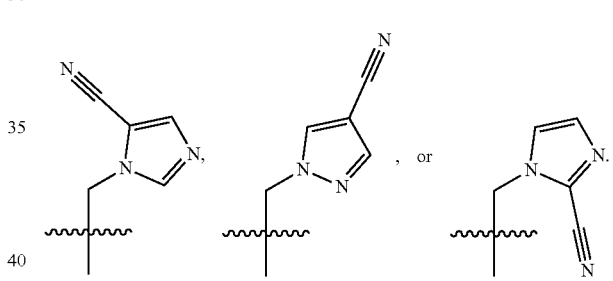

In some embodiments, $R_3$ is methyl substituted with one or more pyridazinyl, wherein the pyridazinyl is optionally substituted with one or more $C_1$-$C_6$ alkyl, $C_1$-$C_6$ alkoxy, halo, —CN, —$(CH_2)_{0-3}$—$N(C_1$-$C_6$ alkyl$)_2$, or —$CF_3$.

In some embodiments, $R_3$ is methyl substituted with one or more pyridazinyl.

In some embodiments, $R_3$ is

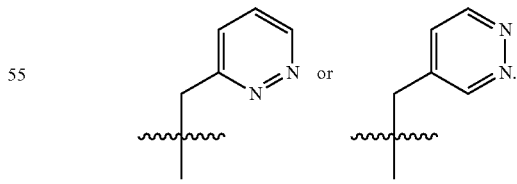

In some embodiments, $R_3$ is methyl substituted with one or more pyrimidinyl, wherein the pyrimidinyl is optionally substituted with one or more $C_1$-$C_6$ alkyl, $C_1$-$C_6$ alkoxy, halo, —CN, —$(CH_2)_{0-3}$—$N(C_1$-$C_6$ alkyl$)_2$, or —$CF_3$.

In some embodiments, $R_3$ is methyl substituted with one or more pyrimidinyl.

In some embodiments, R₃ is

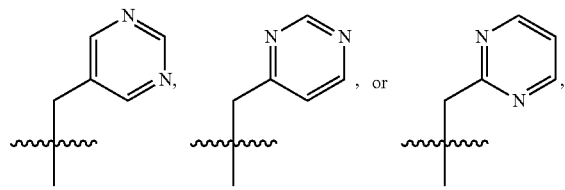 [SMILES: *Cc1cncnc1 ; *Cc1ccncn1 ; *Cc1ncccn1]

In some embodiments, R₃ is methyl substituted with one or more pyrimidinyl, wherein the pyrimidinyl is substituted with one or more methyl or —CN.

In some embodiments, R₃ is


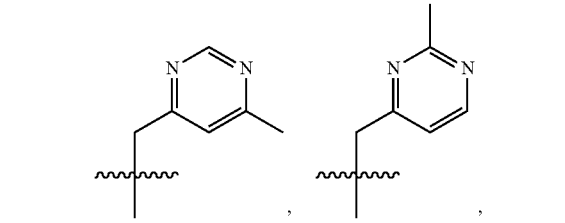

In some embodiments, R₃ is

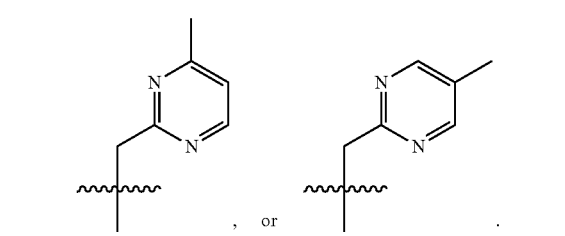

In some embodiments, R₃ is

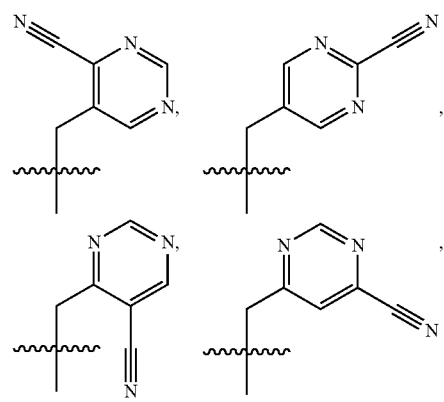

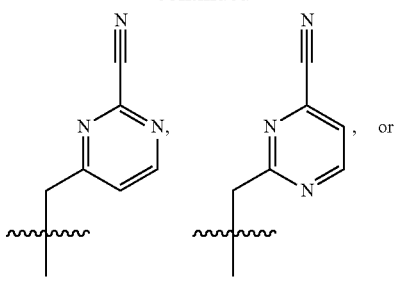

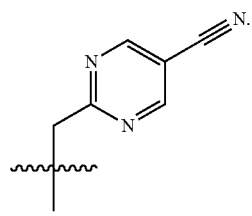

In some embodiments, R₃ is methyl substituted with one or more pyrazinyl, wherein the pyrazinyl is optionally substituted with one or more C₁-C₆ alkyl, C₁-C₆ alkoxy, halo, —CN, —(CH₂)₀₋₃—N(C₁-C₆ alkyl)₂, or —CF₃.

In some embodiments, R₃ is methyl substituted with one or more pyrazinyl.

In some embodiments, R₃ is

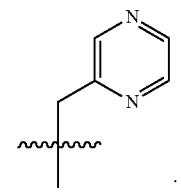 [SMILES: *Cc1cnccn1]

In some embodiments, R₃ is methyl substituted with one or more pyrazinyl, wherein the pyrazinyl is substituted with one or more methyl or —CN.

In some embodiments, R₃ is

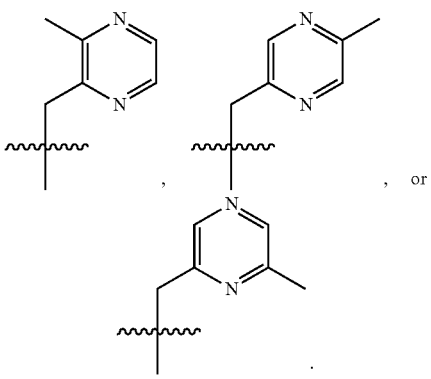

In some embodiments, R₃ is

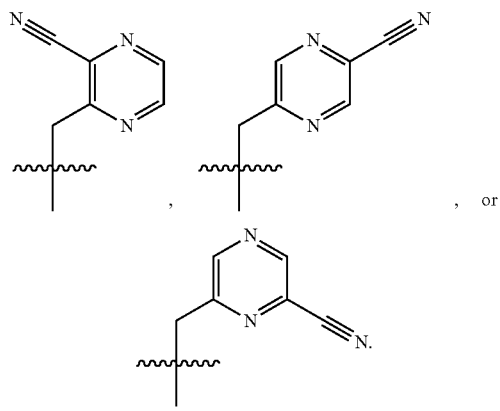

,   , or

In some embodiments, R₃ is methyl substituted with one or more triazolyl, wherein the triazolyl is optionally substituted with one or more $C_1$-$C_6$ alkyl, $C_1$-$C_6$ alkoxy, halo, —CN, —(CH₂)₀₋₃—N($C_1$-$C_6$ alkyl)₂, or —CF₃.

In some embodiments, R₃ is methyl substituted with one or more triazolyl.

In some embodiments, R₃ is

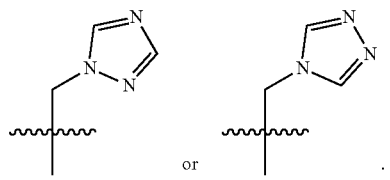 [SMILES: *Cn1cncn1 ; *Cn1cnnc1]

or   .

In some embodiments, R₃ is methyl substituted with one or more triazolyl, wherein the triazolyl is substituted with one or more methyl or —CN.

In some embodiments, R₃ is

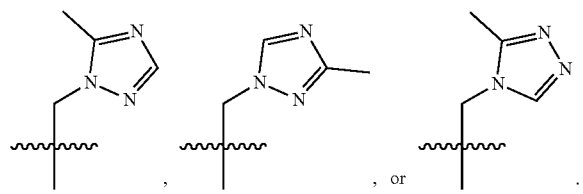

,   , or   .

In some embodiments, R₃ is

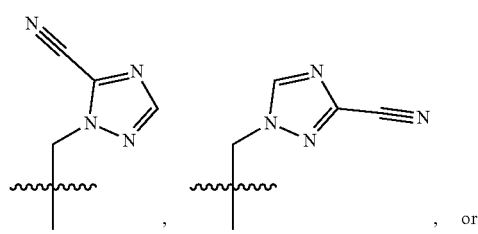

,   , or

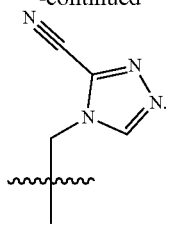

In some embodiments, R₃ is ethyl substituted with one or more R₇.

In some embodiments, R₃ is ethyl substituted with one or more $C_5$-$C_{10}$ aryl.

In some embodiments, R₃ is ethyl substituted with one or more phenyl.

In some embodiments, R₃ is

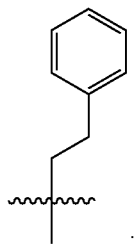 [SMILES: *CCc1ccccc1]

In some embodiments, R₄ is H.

In some embodiments, R₄ is $C_1$-$C_6$ alkyl, —(CH₂)₀₋₃—($C_3$-$C_6$ cycloalkyl), or —(CH₂)₀₋₃—$C_5$-$C_6$ aryl.

In some embodiments, R₄ is $C_1$-$C_6$ alkyl.

In some embodiments, R₄ is methyl, ethyl, propyl, butyl.

In some embodiments, R₄ is methyl.

In some embodiments, R₄ is ethyl.

In some embodiments, R₄ is propyl. In some embodiments, R₄ is

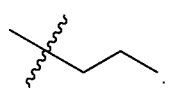 [SMILES: *CCC]

In some embodiments, R₄ is

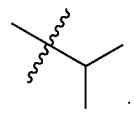 [SMILES: *C(C)C]

In some embodiments, R₄ is butyl. In some embodiments, R₄ is

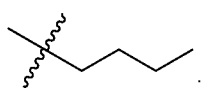 [SMILES: *CCCC]

In some embodiments, $R_4$ is

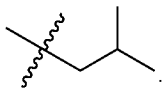 [SMILES: *CC(C)C]

In some embodiments, $R_4$ is

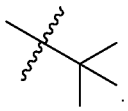 [SMILES: *C(C)(C)C]

In some embodiments, $R_4$ is —$(CH_2)_{0-3}$—($C_3$-$C_6$ cycloalkyl).

In some embodiments, $R_4$ is $C_3$-$C_6$ cycloalkyl. In some embodiments, $R_4$ is

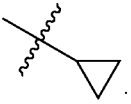

In some embodiments, $R_4$ is

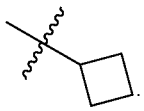

In some embodiments, $R_4$ is

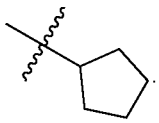

In some embodiments, $R_4$ is

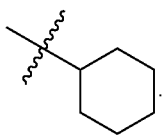 [SMILES: *C1CCCCC1]

In some embodiments, $R_4$ is —$(CH_2)_{1-3}$—($C_3$-$C_6$ cycloalkyl). In some embodiments, $R_4$ is —$CH_2$—($C_3$-$C_6$ cycloalkyl). In some embodiments, $R_4$ is —$(CH_2)_2$—($C_3$-$C_6$ cycloalkyl). In some embodiments, $R_4$ is —$(CH_2)_3$—($C_3$-$C_6$ cycloalkyl).

In some embodiments, $R_4$ is

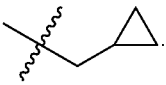 [SMILES: *CC1CC1]

In some embodiments, $R_4$ is

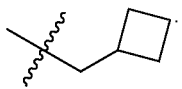 [SMILES: *CC1CCC1]

In some embodiments, $R_4$ is

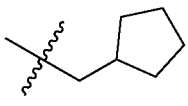

In some embodiments, $R_4$ is

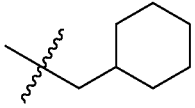

In some embodiments, $R_4$ is —$(CH_2)_{0-3}$—$C_5$-$C_6$ aryl.

In some embodiments, $R_4$ is $C_5$-$C_6$ aryl. In some embodiments, $R_4$ is

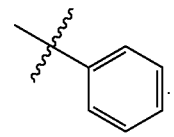 [SMILES: *c1ccccc1]

In some embodiments, $R_4$ is —$(CH_2)_{1-3}$—$C_5$-$C_6$ aryl. In some embodiments, $R_4$ is —$CH_2$—$C_5$-$C_6$ aryl. In some embodiments, $R_4$ is —$(CH_2)_2$—$C_5$-$C_6$ aryl. In some embodiments, $R_4$ is —$(CH_2)_3$—$C_5$-$C_6$ aryl.

In some embodiments, $R_4$ is —$(CH_2)_{1-3}$-phenyl. In some embodiments, $R_4$ is

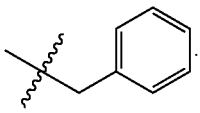

In some embodiments, at least one $R_6$ is $C_1$-$C_6$ alkyl, $C_2$-$C_6$ alkenyl, $C_1$-$C_6$ alkoxy, or $C_3$-$C_8$ cycloalkyl.

In some embodiments, at least one $R_6$ is $C_1$-$C_6$ alkyl. In some embodiments, at least one $R_6$ is methyl. In some embodiments, at least one $R_6$ is ethyl. In some embodiments, at least one $R_6$ is propyl. In some embodiments, at least one $R_6$ is butyl. In some embodiments, at least one $R_6$ is pentyl. In some embodiments, at least one $R_6$ is hexyl.

In some embodiments, at least one $R_6$ is $C_2$-$C_6$ alkenyl. In some embodiments, at least one $R_6$ is ethenyl. In some embodiments, at least one $R_6$ is propenyl. In some embodiments, at least one $R_6$ is butenyl. In some embodiments, at least one $R_6$ is pentenyl. In some embodiments, at least one $R_6$ is hexenyl.

In some embodiments, at least one $R_6$ is $C_1$-$C_6$ alkoxy. In some embodiments, at least one $R_6$ is methoxy. In some embodiments, at least one $R_6$ is ethoxy. In some embodiments, at least one $R_6$ is propoxy. In some embodiments, at least one $R_6$ is butoxy. In some embodiments, at least one $R_6$ is pentoxy. In some embodiments, at least one $R_6$ is hexoxy.

In some embodiments, at least one $R_6$ is $C_3$-$C_8$ cycloalkyl. In some embodiments, at least one $R_6$ is cyclopropyl. In some embodiments, at least one $R_6$ is cyclobutyl. In some embodiments, at least one $R_6$ is cyclopentyl. In some embodiments, at least one $R_6$ is cyclohexyl. In some embodiments, at least one $R_6$ is cycloheptyl. In some embodiments, at least one $R_6$ is cyclooctyl.

In some embodiments, at least one $R_6$ is halo, oxo, —OH, —CN, —NH$_2$, —NH(C$_1$-C$_6$ alkyl), —N(C$_1$-C$_6$ alkyl)$_2$, —CH$_2$F, —CHF$_2$, or —CF$_3$.

In some embodiments, at least one $R_6$ is halo. In some embodiments, at least one $R_6$ is F, C$_1$, or Br. In some embodiments, at least one $R_6$ is F or C$_1$. In some embodiments, at least one $R_6$ is F. In some embodiments, at least one $R_6$ is Cl.

In some embodiments, at least one $R_6$ is oxo. In some embodiments, at least one $R_6$ is —OH. In some embodiments, at least one $R_6$ is —CN. In some embodiments, at least one $R_6$ is —NH$_2$. In some embodiments, at least one $R_6$ is —NH(C$_1$-C$_6$ alkyl). In some embodiments, at least one $R_6$ is —N(C$_1$-C$_6$ alkyl)$_2$. In some embodiments, at least one $R_6$ is —CH$_2$F. In some embodiments, at least one $R_6$ is —CHF$_2$. In some embodiments, at least one $R_6$ is —CF$_3$.

In some embodiments, at least one $R_7$ is —OR$_8$.

In some embodiments, at least one $R_7$ is C$_1$-C$_6$ alkoxy optionally substituted by one or more $R_{7S}$. In some embodiments, at least one $R_7$ is methoxy optionally substituted by one or more $R_{7S}$. In some embodiments, at least one $R_7$ is ethoxy optionally substituted by one or more $R_{7S}$. In some embodiments, at least one $R_7$ is propoxy optionally substituted by one or more $R_{7S}$. In some embodiments, at least one $R_7$ is butoxy optionally substituted by one or more $R_{7S}$. In some embodiments, at least one $R_7$ is pentoxy optionally substituted by one or more $R_{7S}$. In some embodiments, at least one $R_7$ is hexoxy optionally substituted by one or more $R_{7S}$.

In some embodiments, at least one $R_7$ is —O-(5- to 7-membered heterocycloalkyl) optionally substituted with one or more $R_{7S}$. In some embodiments, at least one $R_7$ is —O-pyrrolidinyl optionally substituted with one or more $R_{7S}$. In some embodiments, at least one $R_7$ is —O-tetrahydrofuranyl optionally substituted with one or more Res. In some embodiments, at least one $R_7$ is —O-pyrazolidinyl optionally substituted with one or more $R_{7S}$. In some embodiments, at least one $R_7$ is —O-imidazolidinyl optionally substituted with one or more $R_{7S}$. In some embodiments, at least one $R_7$ is —O-oxazolidinyl optionally substituted with one or more $R_{7S}$. In some embodiments, at least one $R_7$ is —O-isoxazolidinyl optionally substituted with one or more $R_{7S}$. In some embodiments, at least one $R_7$ is —O-dioxolanyl optionally substituted with one or more $R_{7S}$. In some embodiments, at least one $R_7$ is —O-piperidinyl optionally substituted with one or more $R_{7S}$. In some embodiments, at least one $R_7$ is —O-tetrahydropyranyl optionally substituted with one or more $R_{7S}$. In some embodiments, at least one $R_7$ is —O-piperazinyl optionally substituted with one or more $R_{7S}$. In some embodiments, at least one $R_7$ is —O-morpholinyl optionally substituted with one or more $R_{7S}$. In some embodiments, at least one $R_7$ is —O-dioxanyl optionally substituted with one or more $R_{7S}$. In some embodiments, at least one $R_7$ is —O-triazinyl optionally substituted with one or more $R_{7S}$. In some embodiments, at least one $R_7$ is —O-trioxanyl optionally substituted with one or more $R_{7S}$. In some embodiments, at least one $R_7$ is —O-azepanyl optionally substituted with one or more $R_{7S}$. In some embodiments, at least one $R_7$ is —O-diazepanyl optionally substituted with one or more $R_{7S}$.

In some embodiments, at least one $R_7$ is $C_5$-$C_{10}$ aryl optionally substituted by one or more $R_{7S}$. In some embodiments, at least one $R_7$ is phenyl optionally substituted by one or more $R_{7S}$.

In some embodiments, at least one $R_7$ is 5- to 10-membered heteroaryl optionally substituted by one or more $R_{7S}$.

In some embodiments, at least one $R_7$ is 5- to 6-membered heteroaryl optionally substituted by one or more $R_{7S}$.

In some embodiments, at least one $R_7$ is 5-membered heteroaryl optionally substituted by one or more $R_{7S}$. In some embodiments, at least one $R_7$ is pyrrolyl optionally substituted by one or more $R_{7S}$. In some embodiments, at least one $R_7$ is pyrazolyl optionally substituted by one or more $R_{7S}$. In some embodiments, at least one $R_7$ is imidazolyl optionally substituted by one or more $R_{7S}$. In some embodiments, at least one $R_7$ is triazolyl optionally substituted by one or more $R_{7S}$.

In some embodiments, at least one $R_7$ is 6-membered heteroaryl optionally substituted by one or more $R_{7S}$. In some embodiments, at least one $R_7$ is pyridinyl optionally substituted by one or more $R_{7S}$. In some embodiments, at least one $R_7$ is diazinyl optionally substituted by one or more $R_{7S}$. In some embodiments, at least one $R_7$ is pyridazinyl optionally substituted by one or more $R_{7S}$. In some embodiments, at least one $R_7$ is pyrimidinyl optionally substituted by one or more $R_{7S}$. In some embodiments, at least one $R_7$ is pyrazinyl optionally substituted by one or more $R_{7S}$. In some embodiments, at least one $R_7$ is triazinyl optionally substituted by one or more $R_{7S}$. In some embodiments, at least one $R_7$ is tetrazinyl optionally substituted by one $R_{7S}$. In some embodiments, at least one $R_7$ is pentazinyl.

In some embodiments, at least one $R_{7S}$ is C$_1$-C$_6$ alkyl, C$_1$-C$_6$ alkoxy, or 5- to 10-membered heteroaryl.

In some embodiments, at least one $R_{7S}$ is C$_1$-C$_6$ alkyl. In some embodiments, at least one $R_{7S}$ is methyl. In some embodiments, at least one $R_{7S}$ is ethyl. In some embodiments, at least one $R_{7S}$ is propyl. In some embodiments, at least one $R_{7S}$ is butyl. In some embodiments, at least one $R_{7S}$ is pentyl. In some embodiments, at least one $R_{7S}$ is hexyl.

In some embodiments, at least one $R_{7S}$ is C$_1$-C$_6$ alkoxy. In some embodiments, at least one $R_{7S}$ is methoxy. In some embodiments, at least one $R_{7S}$ is ethoxy. In some embodiments, at least one $R_{7S}$ is propoxy. In some embodiments, at least one $R_{7S}$ is butoxy. In some embodiments, at least one $R_{7S}$ is pentoxy. In some embodiments, at least one $R_{7S}$ is hexoxy.

In some embodiments, at least one $R_{7S}$ is 5- to 10-membered heteroaryl. In some embodiments, at least one $R_{7S}$ is 5- to 6-membered heteroaryl.

In some embodiments, at least one $R_{7S}$ is 5-membered heteroaryl. In some embodiments, at least one $R_{7S}$ is pyrrolyl. In some embodiments, at least one $R_{7S}$ is pyrazolyl. In some embodiments, at least one $R_{7S}$ is imidazolyl. In some embodiments, at least one $R_{7S}$ is triazolyl.

In some embodiments, at least one $R_{7S}$ is 6-membered heteroaryl. In some embodiments, at least one $R_{7S}$ is pyridinyl. In some embodiments, at least one $R_{7S}$ is diazinyl. In some embodiments, at least one $R_{7S}$ is pyridazinyl. In some embodiments, at least one $R_{7S}$ is pyrimidinyl. In some embodiments, at least one $R_{7S}$ is pyrazinyl. In some embodiments, at least one $R_{7S}$ is triazinyl. In some embodiments, at least one $R_{7S}$ is tetrazinyl. In some embodiments, at least one $R_{7S}$ is pentazinyl.

In some embodiments, at least one $R_{7S}$ is halo, —OH, —CN, —(CH$_2$)$_{0-3}$—NH$_2$, —(CH$_2$)$_{0-3}$—NH(C$_1$-C$_6$ alkyl), —(CH$_2$)$_{0-3}$—N(C$_1$-C$_6$ alkyl)$_2$, —CH$_2$F, —CHF$_2$, or —CF$_3$.

In some embodiments, at least one $R_{7S}$ is halo. In some embodiments, at least one $R_{7S}$ is F, Cl, or Br. In some embodiments, at least one $R_{7S}$ is F or Cl. In some embodiments, at least one $R_{7S}$ is F. In some embodiments, at least one $R_{7S}$ is Cl. In some embodiments, at least one $R_{7S}$ is —OH. In some embodiments, at least one $R_{7S}$ is —CN.

In some embodiments, at least one $R_{7S}$ is —(CH$_2$)$_{0-3}$—NH$_2$, —(CH$_2$)$_{0-3}$—NH(C$_1$-C$_6$ alkyl), or —(CH$_2$)$_{0-3}$—N(C$_1$-C$_6$ alkyl)$_2$.

In some embodiments, at least one $R_{7S}$ is —(CH$_2$)$_{0-3}$—NH$_2$. In some embodiments, at least one $R_{7S}$ is —NH$_2$. In some embodiments, at least one $R_{7S}$ is —(CH$_2$)$_{1-3}$—NH$_2$. In some embodiments, at least one $R_{7S}$ is —CH$_2$—NH$_2$. In some embodiments, at least one $R_{7S}$ is —(CH$_2$)$_2$—NH$_2$. In some embodiments, at least one $R_{7S}$ is —(CH$_2$)$_3$—NH$_2$.

In some embodiments, at least one $R_{7S}$ is —(CH$_2$)$_{0-3}$—NH(C$_1$-C$_6$ alkyl). In some embodiments, at least one $R_{7S}$ is —NH(C$_1$-C$_6$ alkyl). In some embodiments, at least one $R_{7S}$ is —NH(CH$_3$). In some embodiments, at least one $R_{7S}$ is —(CH$_2$)$_{1-3}$—NH(C$_1$-C$_6$ alkyl). In some embodiments, at least one $R_{7S}$ is —(CH$_2$)$_{1-3}$—NH(CH$_3$). In some embodiments, at least one $R_{7S}$ is —CH$_2$—NH(C$_1$-C$_6$ alkyl). In some embodiments, at least one $R_{7S}$ is —CH$_2$—NH(CH$_3$). In some embodiments, at least one $R_{7S}$ is —(CH$_2$)$_2$—NH(C$_1$-C$_6$ alkyl). In some embodiments, at least one $R_{7S}$ is —(CH$_2$)$_2$—NH(CH$_3$). In some embodiments, at least one $R_{7S}$ is —(CH$_2$)$_3$—NH(C$_1$-C$_6$ alkyl). In some embodiments, at least one $R_{7S}$ is —(CH$_2$)$_3$—NH(CH$_3$)

In some embodiments, at least one $R_{7S}$ is —(CH$_2$)$_{0-3}$—N(C$_1$-C$_6$ alkyl)$_2$. In some embodiments, at least one $R_{7S}$ is —N(C$_1$-C$_6$ alkyl)$_2$. In some embodiments, at least one $R_{7S}$ is N(CH$_3$)$_2$. In some embodiments, at least one $R_{7S}$ is —(CH$_2$)$_{1-3}$—N(C$_1$-C$_6$ alkyl)$_2$. In some embodiments, at least one $R_{7S}$ is —(CH$_2$)$_{1-3}$—N(CH$_3$)$_2$. In some embodiments, at least one $R_{7S}$ is —CH$_2$—N(C$_1$-C$_6$ alkyl)$_2$. In some embodiments, at least one $R_{7S}$ is —CH$_2$—N(CH$_3$)$_2$. In some embodiments, at least one $R_{7S}$ is —(CH$_2$)$_2$—N(C$_1$-C$_6$ alkyl)$_2$. In some embodiments, at least one $R_{7S}$ is —(CH$_2$)$_2$—N(CH$_3$)$_2$. In some embodiments, at least one $R_{7S}$ is —(CH$_2$)$_3$—N(C$_1$-C$_6$ alkyl)$_2$. In some embodiments, at least one $R_{7S}$ is —(CH$_2$)$_3$—N(CH$_3$)$_2$.

In some embodiments, at least one $R_{7S}$ is —CH$_2$F. In some embodiments, at least one $R_{7S}$ is —CHF$_2$. In some embodiments, at least one $R_{7S}$ is —CF$_3$.

In some embodiments, $R_8$ is $C_1$-$C_6$ alkyl optionally substituted by one or more $R_{7S}$. In some embodiments, $R_8$ is methyl optionally substituted by one or more $R_{7S}$. In some embodiments, $R_8$ is ethyl optionally substituted by one or more $R_{7S}$. In some embodiments, $R_8$ is propyl optionally substituted by one or more $R_{7S}$. In some embodiments, $R_8$ is butyl optionally substituted by one or more $R_{7S}$. In some embodiments, $R_8$ is pentyl optionally substituted by one or more $R_{7S}$. In some embodiments, $R_8$ is hexyl optionally substituted by one or more $R_{7S}$.

In some embodiments, $R_8$ is 5- to 7-membered heterocycloalkyl optionally substituted with one or more $R_{7S}$. In some embodiments, $R_8$ is pyrrolidinyl optionally substituted with one or more $R_{7S}$. In some embodiments, $R_8$ is tetrahydrofuranyl optionally substituted with one or more $R_{7S}$. In some embodiments, $R_8$ is pyrazolidinyl optionally substituted with one or more $R_{7S}$. In some embodiments, $R_8$ is imidazolidinyl optionally substituted with one or more $R_{7S}$. In some embodiments, $R_8$ is oxazolidinyl optionally substituted with one or more $R_{7S}$. In some embodiments, $R_8$ is isoxazolidinyl optionally substituted with one or more $R_{7S}$. In some embodiments, $R_8$ is dioxolanyl optionally substituted with one or more $R_{7S}$. In some embodiments, $R_8$ is piperidinyl optionally substituted with one or more $R_{7S}$. In some embodiments, $R_8$ is tetrahydropyranyl optionally substituted with one or more $R_{7S}$. In some embodiments, $R_8$ is piperazinyl optionally substituted with one or more $R_{7S}$. In some embodiments, $R_8$ is morpholinyl optionally substituted with one or more $R_{7S}$. In some embodiments, $R_8$ is dioxanyl optionally substituted with one or more $R_{7S}$. In some embodiments, $R_8$ is triazinyl optionally substituted with one or more $R_{7S}$. In some embodiments, $R_8$ is trioxanyl optionally substituted with one or more $R_{7S}$. In some embodiments, $R_8$ is azepanyl optionally substituted with one or more $R_{7S}$. In some embodiments, $R_8$ is diazepanyl optionally substituted with one or more $R_{7S}$.

In some embodiments, the compound is of Formula (Ia) or (Ib):

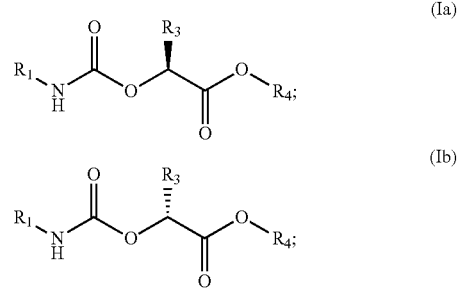

or a prodrug, hydrate, solvate, or pharmaceutically acceptable salt thereof.

In some embodiments, the compound is of any one of Formulae (II), (IIa), and (IIb):

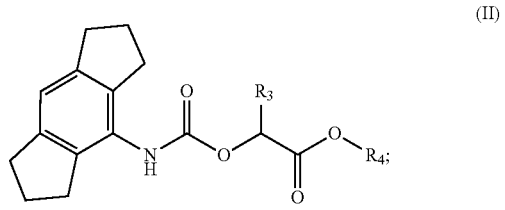

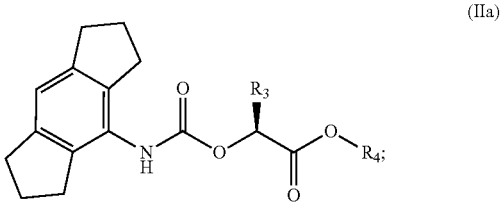

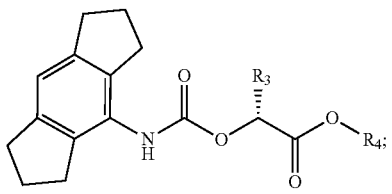

or a prodrug, hydrate, solvate, or pharmaceutically acceptable salt thereof.

In some embodiments, the compound is of any one of Formulae (III), (IIIa), and (IIIb):

(III)
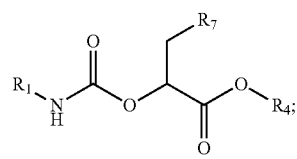

(IIIa)
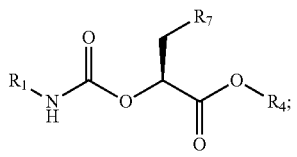

(IIIb)
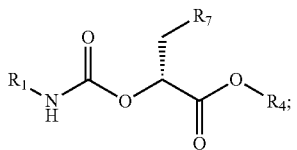

or a prodrug, hydrate, solvate, or pharmaceutically acceptable salt thereof.

In some embodiments, the compound is of any one of Formulae (IV), (IVa), and (IVb):

(IV)
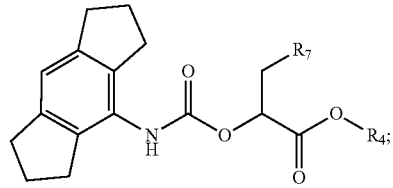

(IVa)
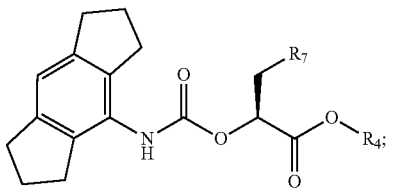

(IVb)
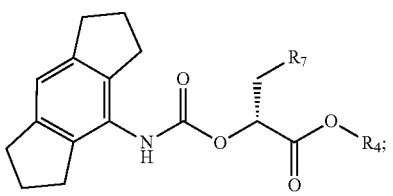

or a prodrug, hydrate, solvate, or pharmaceutically acceptable salt thereof.

In some embodiments, the compound is of any one of Formulae (V), (Va), (Vb), (VI), (VIa), and (VIb):

(V)
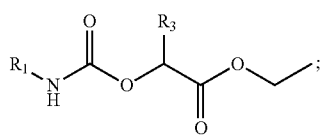

(Va)
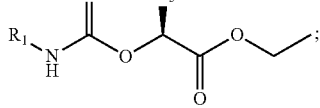

(Vb)
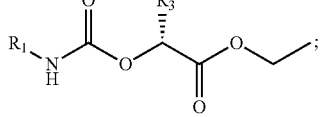

(VI)
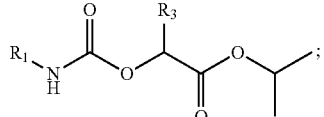

(VIa)
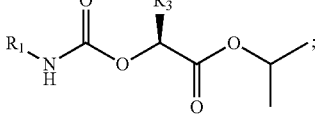

(VIb)
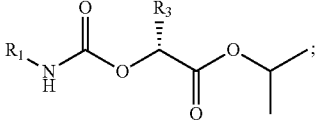

or a prodrug, hydrate, solvate, or pharmaceutically acceptable salt thereof.

In some embodiments, the compound is of any one of Formulae (VII), (VIIa), (VIIb), (VIII), (VIIIa), and (VIIIb):

(VII)
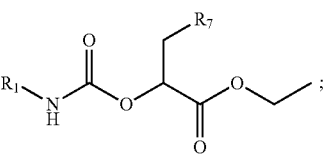

(VIIa)
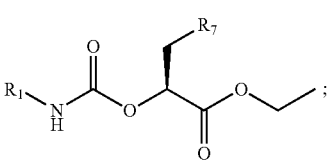

(VIIb)
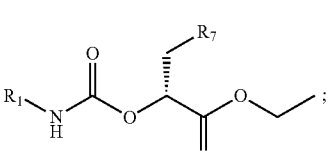

(VIII)
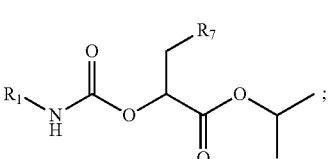

49

-continued (VIIIa)

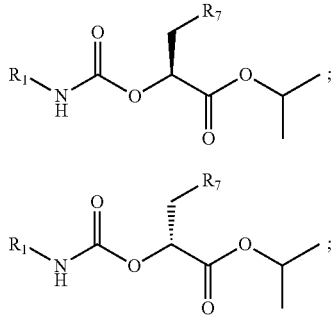

(VIIIb)

or a prodrug, hydrate, solvate, or pharmaceutically acceptable salt thereof.

In some embodiments, the compound is of any one of Formulae (IX), (IXa), (IXb), (X), (Xa), and (Xb):

(IX)

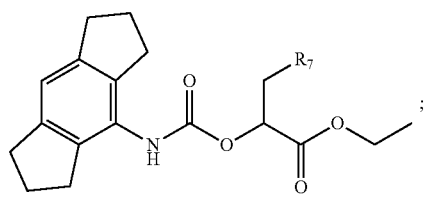

(IXa)

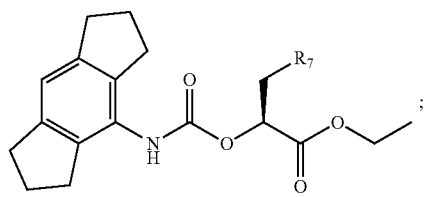

(IXb)


50

-continued (X)

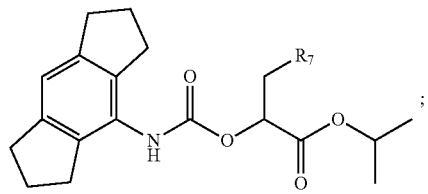

(Xa)

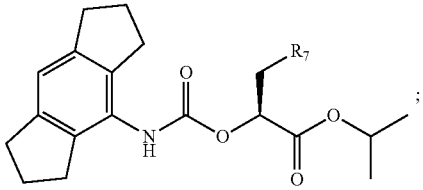

(Xb)

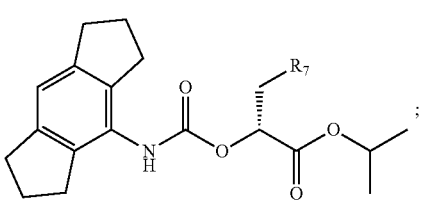

or a prodrug, hydrate, solvate, or pharmaceutically acceptable salt thereof.

It is understood that, for a compound of any one of Formulae (I)-(X), (Ia)-(Xa), and (Ib)-(Xb), $R_1$, $R_3$, $R_4$, $R_6$, $R_7$, $R_{7S}$, and $R_8$ can each be, where applicable, selected from the groups described herein, and any group described herein for any of $R_1$, $R_3$, $R_4$, $R_6$, $R_7$, $R_{7S}$, and $R_8$ can be combined, where applicable, with any group described herein for one or more of the remainder of $R_1$, $R_3$, $R_4$, $R_6$, $R_7$, $R_{7S}$, and $R_8$.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the compounds described in Table 1.

TABLE 1

| Compound No. | Structure | Name |
| --- | --- | --- |
| 1 | 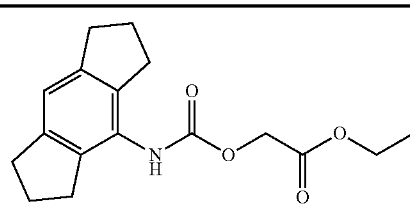 | Ethyl 2-{[(1,2,3,5,6,7-hexahydro-s-indacen-4-yl)-carbamoyl]oxy}acetate |
| 2 | 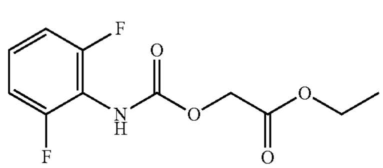 [SMILES: CCOC(=O)COC(=O)Nc1c(F)cccc1F] | Ethyl 2-{[(2,6-difluorophenyl)-carbamoyl]oxy}acetate |

TABLE 1-continued

| Compound No. | Structure | Name |
|---|---|---|
| 3 | 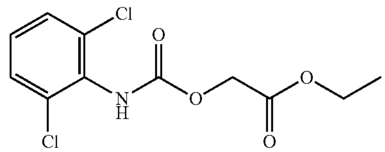 [SMILES: CCOC(=O)COC(=O)Nc1c(Cl)cccc1Cl] | Ethyl 2-{[(2,6-dichlorophenyl)-carbamoyl]oxy}acetate |
| 4 | 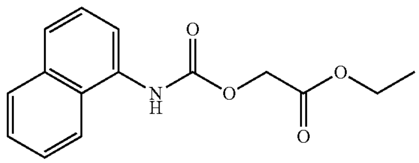 [SMILES: CCOC(=O)COC(=O)Nc1cccc2ccccc12] | Ethyl 2-{[(naphthalen-1-yl)-carbamoyl]oxy}acetate |
| 5 | 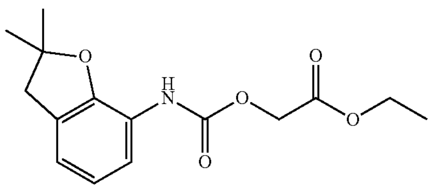 [SMILES: CCOC(=O)COC(=O)Nc1cccc2c1OC(C)(C)C2] | Ethyl 2-{[(2,2-dimethyl-2,3-dihydro-1-benzofuran-7-yl)-carbamoyl]oxy}acetate |
| 6 | 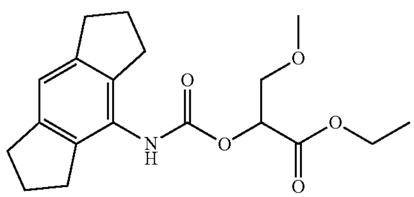 [SMILES: CCOC(=O)C(COC)OC(=O)Nc1c2c(cc3c1CCC3)CCC2] | Ethyl 2-{[(1,2,3,5,6,7-hexahydro-s-indacen-4-yl)-carbamoyl]oxy}-3-methoxypropanoate |
| 7 | 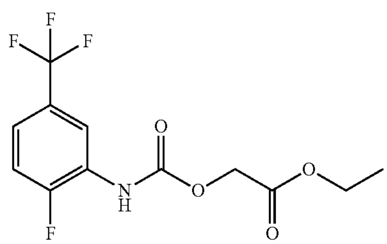 [SMILES: CCOC(=O)COC(=O)Nc1cc(C(F)(F)F)ccc1F] | Ethyl 2-({[2-fluoro-5-(trifluoromethyl)phenyl]-carbamoyl}oxy)acetate |
| 8 | 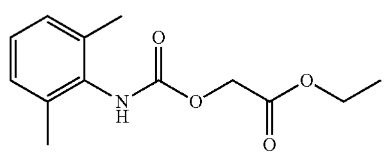 [SMILES: CCOC(=O)COC(=O)Nc1c(C)cccc1C] | Ethyl 2-{[(2,6-dimethylphenyl)carbamoyl]oxy}-acetate |
| 9 | 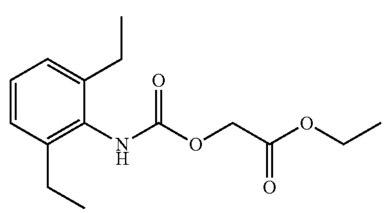 [SMILES: CCOC(=O)COC(=O)Nc1c(CC)cccc1CC] | Ethyl 2-{[(2,6-diethylphenyl)-carbamoyl]oxy}acetate |
| 10 | 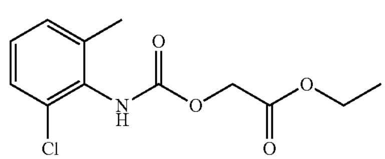 [SMILES: CCOC(=O)COC(=O)Nc1c(C)cccc1Cl] | Ethyl 2-({[2-(chloro-6-methylphenyl)carbamoyl]oxy}acetate |

TABLE 1-continued

| Compound No. | Structure | Name |
|---|---|---|
| 11 | 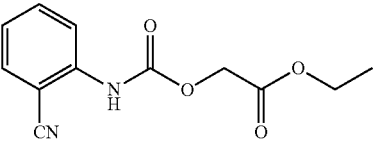 [SMILES: CCOC(=O)COC(=O)Nc1ccccc1C#N] | Ethyl 2-{[(2-cyanophenyl)-carbamoyl]oxy}acetate |
| 12 | 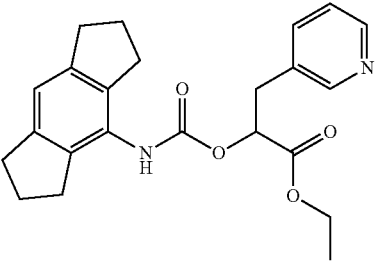 [SMILES: CCOC(=O)C(Cc1cccnc1)OC(=O)Nc1c2c(cc3c1CCC3)CCC2] | Ethyl 2-{[(1,2,3,5,6,7-hexahydro-s-indacen-4-yl)-carbamoyl]oxy}-3-(pyridin-3-yl)propanoate |
| 13 | 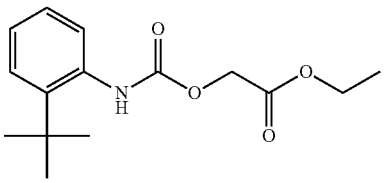 [SMILES: CCOC(=O)COC(=O)Nc1ccccc1C(C)(C)C] | Ethyl 2-{[(2-tert-butylphenyl)-carbamoyl]oxy}acetate |
| 14 | 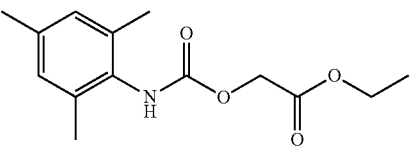 [SMILES: CCOC(=O)COC(=O)Nc1c(C)cc(C)cc1C] | Ethyl 2-((mesitylcarbamoyl)-oxy)acetate |
| 15 | 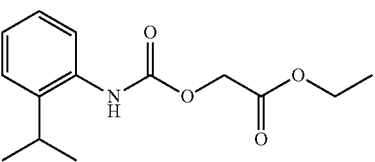 [SMILES: CCOC(=O)COC(=O)Nc1ccccc1C(C)C] | Ethyl 2-(((2-isopropylphenyl)-carbamoyl)oxy)acetate |
| 16 | 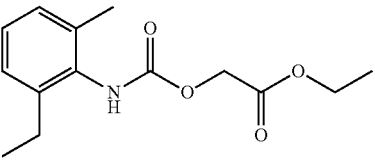 [SMILES: CCOC(=O)COC(=O)Nc1c(C)cccc1CC] | Ethyl 2-(((2-ethyl-6-methylphenyl)carbamoyl)oxy)acetate |
| 17 | 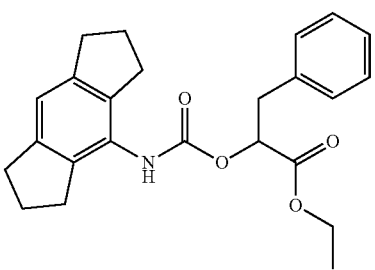 [SMILES: CCOC(=O)C(Cc1ccccc1)OC(=O)Nc1c2c(cc3c1CCC3)CCC2] | Ethyl 2-(((1,2,3,5,6,7-hexahydro-s-indacen-4-yl)-carbamoyl)oxy)-3-phenylpropanoate |

TABLE 1-continued

| Compound No. | Structure | Name |
|---|---|---|
| 18 | 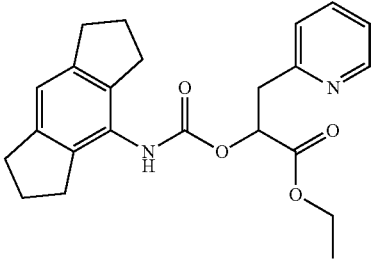 [SMILES: CCOC(=O)C(Cc1ccccn1)OC(=O)Nc1c2c(cc3c1CCC3)CCC2] | Ethyl 2-(((1,2,3,5,6,7-hexa-hydro-s-indacen-4-yl)-carbamoyl)oxy)-3-(pyridin-2-yl)propanoate |
| 19 | 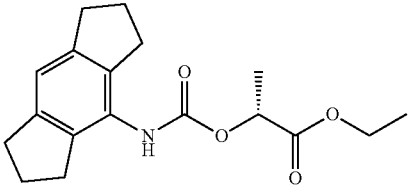 [SMILES: CCOC(=O)[C@@H](C)OC(=O)Nc1c2c(cc3c1CCC3)CCC2] | Ethyl (2R)-2-{[(1,2,3,5,6,7-hexahydro-s-indacen-4-yl)-carbamoyl]oxy}propanoate |
| 20 | 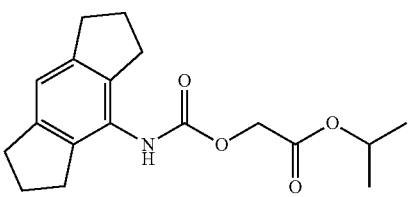 [SMILES: CC(C)OC(=O)COC(=O)Nc1c2c(cc3c1CCC3)CCC2] | Propan-2-yl 2-{[(1,2,3,5,6,7-hexahydro-s-indacen-4-yl)-carbamoyl]oxy}acetate |
| 21 | 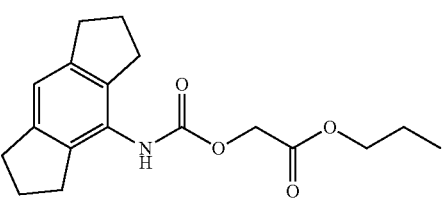 [SMILES: CCCOC(=O)COC(=O)Nc1c2c(cc3c1CCC3)CCC2] | 2-{[(1,2,3,5,6,7-Hexahydro-s-indacen-4-yl)carbamoyl]oxy}-acetate |
| 22 | 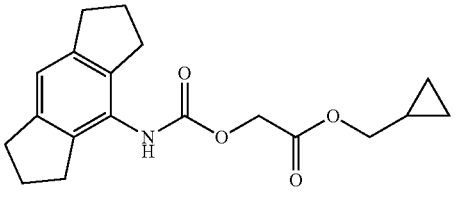 [SMILES: O=C(COC(=O)Nc1c2c(cc3c1CCC3)CCC2)OCC1CC1] | Cyclopropylmethyl 2-{[(1,2,3,5,6,7-hexahydro-s-indacen-4-yl)carbamoyl]oxy}-acetate |
| 23 | 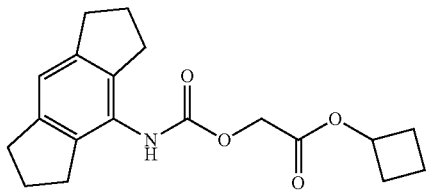 [SMILES: O=C(COC(=O)Nc1c2c(cc3c1CCC3)CCC2)OC1CCC1] | Cyclobutyl 2-{[(1,2,3,5,6,7-hexahydro-s-indacen-4-yl)-carbamoyl]oxy}acetate |
| 24 | 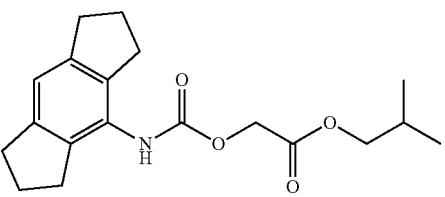 [SMILES: CC(C)COC(=O)COC(=O)Nc1c2c(cc3c1CCC3)CCC2] | 2-methylpropyl 2-{[(1,2,3,5,6,7-hexahydro-s-indacen-4-yl)carbamoyl]-oxy}acetate |

TABLE 1-continued

| Compound No. | Structure | Name |
|---|---|---|
| 25 | 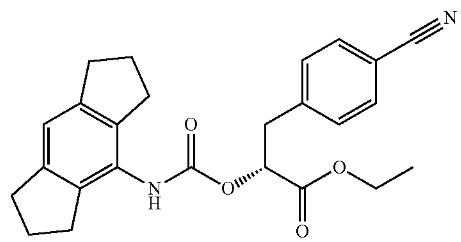 [SMILES: CCOC(=O)[C@@H](Cc1ccc(C#N)cc1)OC(=O)Nc1c2c(cc3c1CCC3)CCC2] | Ethyl 3-(4-cyanophenyl)-2-{[(1,2,3,5,6,7-hexahydro-s-indacen-4-yl)carbamoyl]-oxy}propanoate |
| 26 | 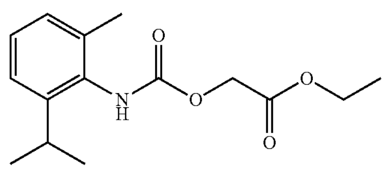 [SMILES: CCOC(=O)COC(=O)Nc1c(C)cccc1C(C)C] | Ethyl 2-({[2-methyl-6-(propan-2-yl)phenyl]carbamoyl}oxy)-acetate |
| 27 | 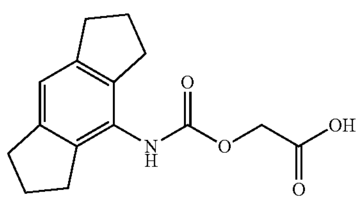 [SMILES: O=C(O)COC(=O)Nc1c2c(cc3c1CCC3)CCC2] | 2-{[(1,2,3,5,6,7-Hexahydro-s-indacen-4-yl)carbamoyl]oxy}-acetic acid |
| 28 | 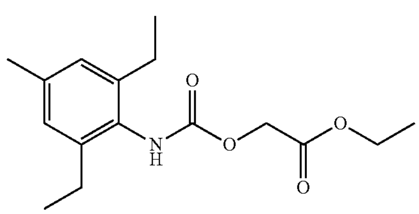 [SMILES: CCOC(=O)COC(=O)Nc1c(CC)cc(C)cc1CC] | Ethyl 2-{[(2,6-diethyl-4-methylphenyl)carbamoyl]-oxy}acetate |
| 29 | 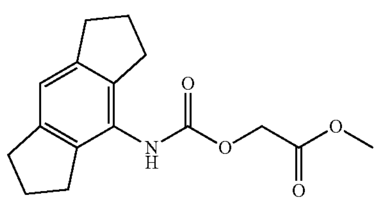 [SMILES: COC(=O)COC(=O)Nc1c2c(cc3c1CCC3)CCC2] | Methyl 2-{[(1,2,3,5,6,7-hexahydro-s-indacen-4-yl)-carbamoyl]oxy}acetate |
| 30 | 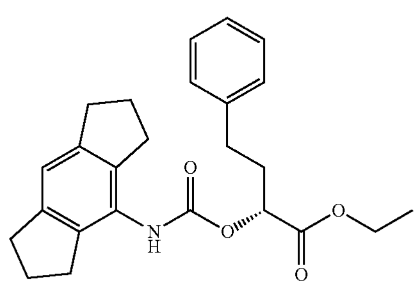 [SMILES: CCOC(=O)[C@@H](CCc1ccccc1)OC(=O)Nc1c2c(cc3c1CCC3)CCC2] | Ethyl (2R)-2-{[(1,2,3,5,6,7-hexahydro-s-indacen-4-yl)-carbamoyl]oxy}-4-phenyl-butanoate |
| 31 | 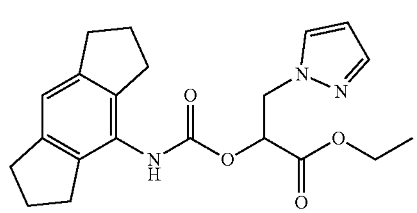 [SMILES: CCOC(=O)C(Cn1cccn1)OC(=O)Nc1c2c(cc3c1CCC3)CCC2] | Ethyl 2-{[(1,2,3,5,6,7-hexahydro-s-indacen-4-yl)-carbamoyl]oxy}-3-(1H-pyrazol-1-yl)propanoate |

TABLE 1-continued

| Compound No. | Structure | Name |
|---|---|---|
| 32 | 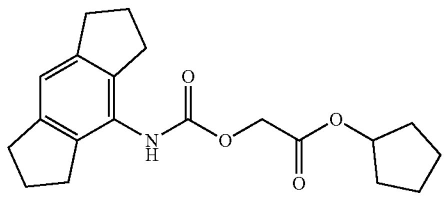 [SMILES: O=C(COC(=O)Nc1c2c(cc3c1CCC3)CCC2)OC1CCCC1] | Cyclopentyl 2-{[(1,2,3,5,6,7-hexahydro-s-indacen-4-yl)-carbamoyl]oxy}acetate |
| 33 | 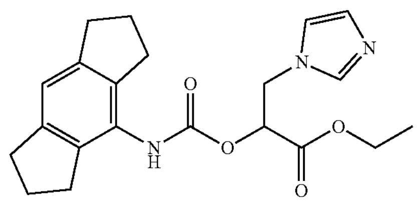 [SMILES: CCOC(=O)C(Cn1ccnc1)OC(=O)Nc1c2c(cc3c1CCC3)CCC2] | Ethyl 2-{[(1,2,3,5,6,7-hexahydro-s-indacen-4-yl)-carbamoyl]oxy}-3-(1H-imidazol-1-yl)propanoate |
| 34 | 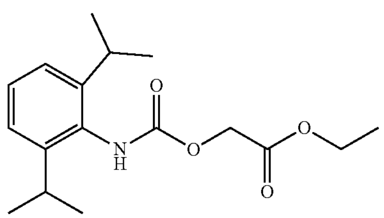 [SMILES: CCOC(=O)COC(=O)Nc1c(C(C)C)cccc1C(C)C] | Ethyl 2-({[2,6-bis(propan-2-yl)phenyl]carbamoyl}oxy)-acetate |
| 35 | 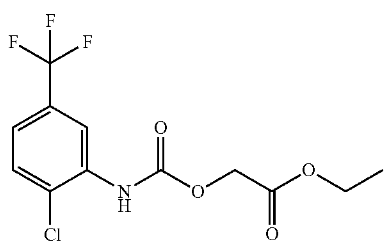 [SMILES: CCOC(=O)COC(=O)Nc1cc(C(F)(F)F)ccc1Cl] | Ethyl 2-({[2-chloro-5-(trifluoromethyl)phenyl]carbamoyl}oxy)acetate |
| 36 | 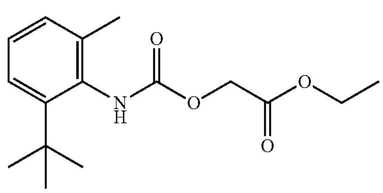 [SMILES: CCOC(=O)COC(=O)Nc1c(C)cccc1C(C)(C)C] | Ethyl 2-{[(2-tert-butyl-6-methylphenyl)carbamoyl]-oxy}acetate |
| 37 | 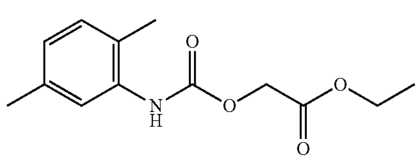 [SMILES: CCOC(=O)COC(=O)Nc1cc(C)ccc1C] | Ethyl 2-{[(2,5-dimethylphenyl)carbamoyl]oxy}acetate |
| 38 | 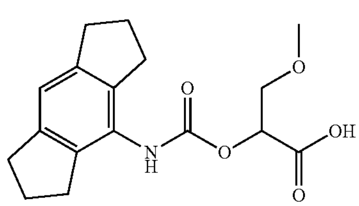 [SMILES: COCC(OC(=O)Nc1c2c(cc3c1CCC3)CCC2)C(=O)O] | 2-{[(1,2,3,5,6,7-hexahydro-s-indacen-4-yl)carbamoyl]oxy}-3-methoxypropanoic acid |

TABLE 1-continued

| Compound No. | Structure | Name |
|---|---|---|
| 39 | 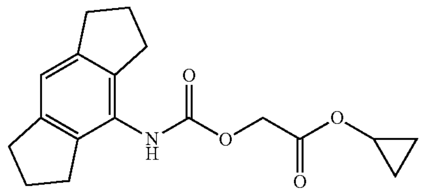 [SMILES: O=C(COC(=O)Nc1c2c(cc3c1CCC3)CCC2)OC1CC1] | cyclopropyl 2-{[(1,2,3,5,6,7-hexahydro-s-indacen-4-yl)-carbamoyl]oxy}acetate |
| 40 | 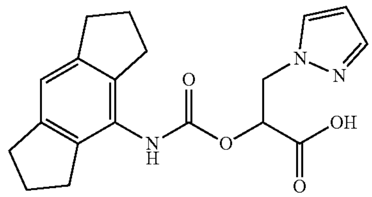 | 2-{[(1,2,3,5,6,7-hexahydro-s-indacen-4-yl)carbamoyl]oxy}-3-(1H-pyrazol-1-yl)propanoic acid |
| 41 | 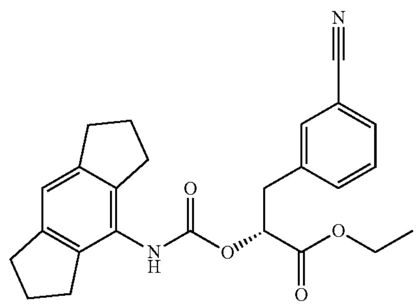 [SMILES: CCOC(=O)[C@@H](Cc1cccc(C#N)c1)OC(=O)Nc1c2c(cc3c1CCC3)CCC2] | Ethyl (2R)-3-(3-cyanophenyl)-2-{[(1,2,3,5,6,7-hexahydro-s-indacen-4-yl)carbamoyl]oxy}-propanoate |
| 42 | 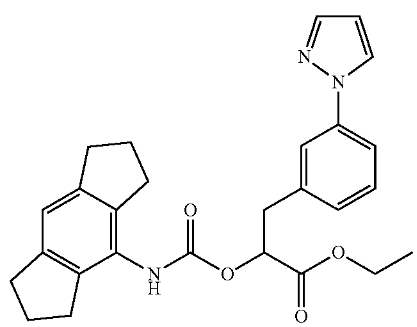 [SMILES: CCOC(=O)C(Cc1cccc(-n2cccn2)c1)OC(=O)Nc1c2c(cc3c1CCC3)CCC2] | Ethyl 2-{[(1,2,3,5,6,7-hexa-hydro-s-indacen-4-yl)-carbamoyl]oxy}-3-[3-(1H-pyrazol-1-yl)phenyl]propanoate |
| 43 | 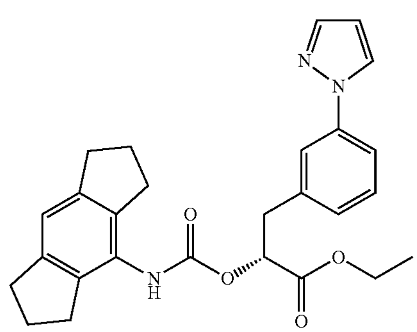 [SMILES: CCOC(=O)[C@@H](Cc1cccc(-n2cccn2)c1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-[3-(1H-pyrazol-1-yl)phenyl]propanoate |
| 44 | 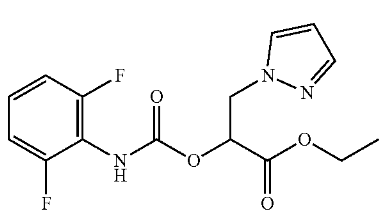 | Ethyl 2-{[(2,6-difluorophenyl)-carbamoyl]oxy}-3-1H-pyrazol-1-yl)propanoate |

TABLE 1-continued

| Compound No. | Structure | Name |
|---|---|---|
| 45 | 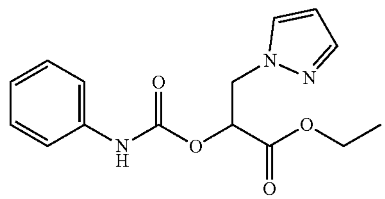 [SMILES: CCOC(=O)C(Cn1cccn1)OC(=O)Nc1ccccc1] | Ethyl 2-[(phenylcarbamoyl)-oxy]-3-(1H-pyrazol-1-yl)-propanoate |
| 46 | 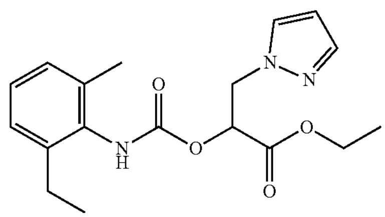 [SMILES: CCOC(=O)C(Cn1cccn1)OC(=O)Nc1c(C)cccc1CC] | Ethyl 2-{[(2-ethyl-6-methyl-phenyl)carbamoyl]oxy}-3-(1H-pyrazol-1-yl)propanoate |
| 47 | 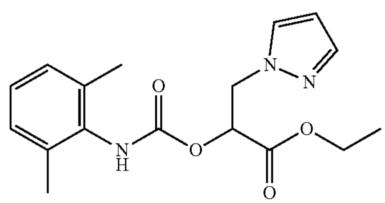 | Ethyl 2-{[(2,6-dimethyl-phenyl)carbamoyl]oxy}-3-(1H-pyrazol-1-yl)propanoate |
| 48 | 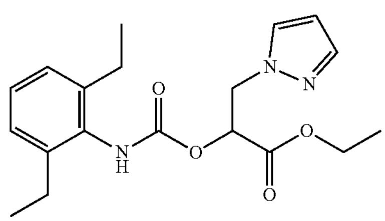 [SMILES: CCOC(=O)C(Cn1cccn1)OC(=O)Nc1c(CC)cccc1CC] | Ethyl 2-{[(2,6-diethylphenyl)-carbamoyl]oxy}-3-(1H-pyrazol-1-yl)propanoate |
| 49 | 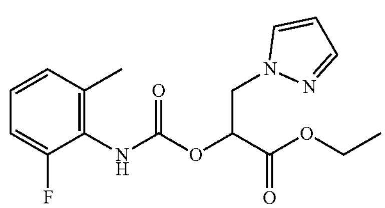 [SMILES: CCOC(=O)C(Cn1cccn1)OC(=O)Nc1c(C)cccc1F] | Ethyl 2-{[(2-fluoro-6-methyl-phenyl)carbamoyl]oxy}-3-(1H-pyrazol-1-yl)propanoate |
| 50 | 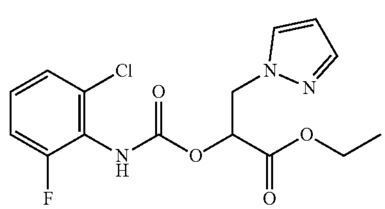 | Ethyl 2-{[(2-chloro-6-fluoro-phenyl)carbamoyl]oxy}-3-(1H-pyrazol-1-yl)propanoate |
| 51 | 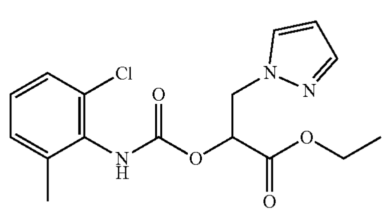 [SMILES: CCOC(=O)C(Cn1cccn1)OC(=O)Nc1c(C)cccc1Cl] | Ethyl 2-{[(2-chloro-6-methyl-phenyl)carbamoyl]oxy}-3-(1H-pyrazol-1-yl)propanoate |

TABLE 1-continued

| Compound No. | Structure | Name |
|---|---|---|
| 52 | 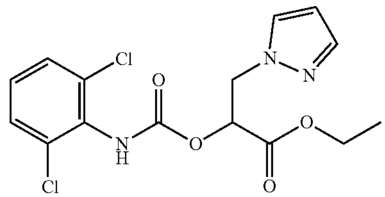 | Ethyl 2-{[(2,6-dichlorophenyl)-carbamoyl]oxy}-3-(1H-pyrazol-1-yl)propanoate |
| 53 | 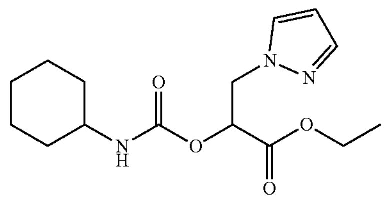 [SMILES: CCOC(=O)C(Cn1cccn1)OC(=O)NC1CCCCC1] | ethyl 2-[(cyclohexyl-carbamoyl)oxy]-3-(1H-pyrazol-1-yl)-propanoate |
| 54 | 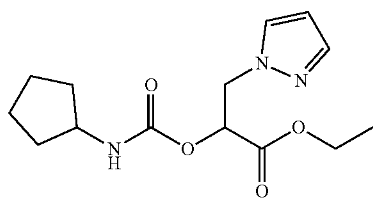 [SMILES: CCOC(=O)C(Cn1cccn1)OC(=O)NC1CCCC1] | Ethyl 2-[(cyclopentyl-carbamoyl)oxy]-3-(1H-pyrazol-1-yl)propanoate |
| 55 | 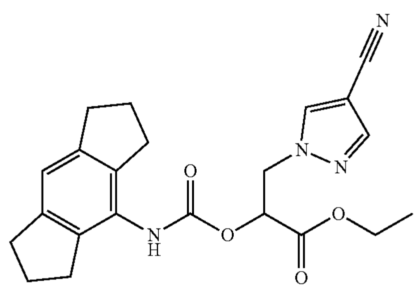 [SMILES: CCOC(=O)C(Cn1cc(C#N)cn1)OC(=O)Nc1c2c(cc3c1CCC3)CCC2] | Ethyl 3-(4-cyano-1H-pyrazol-1-yl)-2-{[(1,2,3,5,6,7-hexahydro-s-indacen-4-yl)-carbamoyl]oxy}propanoate |
| 56 | 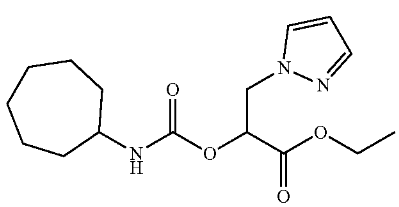 [SMILES: CCOC(=O)C(Cn1cccn1)OC(=O)NC1CCCCCC1] | Ethyl 2-[(cycloheptyl-carbamoyl)oxy]-3-(1H-pyrazol-1-yl)propanoate |
| 57 | 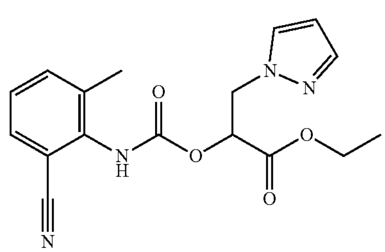 [SMILES: CCOC(=O)C(Cn1cccn1)OC(=O)Nc1c(C)cccc1C#N] | Ethyl 2-{[(2-cyano-6-methylphenyl)carbamoyl]-oxy}-3-(1H-pyrazol-1-yl)-propanoate |

TABLE 1-continued

| Compound No. | Structure | Name |
|---|---|---|
| 58 | 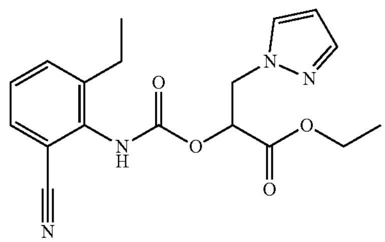 [SMILES: CCOC(=O)C(Cn1cccn1)OC(=O)Nc1c(C#N)cccc1CC] | Ethyl 2-{[(2-cyano-6-ethylphenyl)carbamoyl]oxy}-3-(1H-pyrazol-1-yl)propanoate |
| 59 | 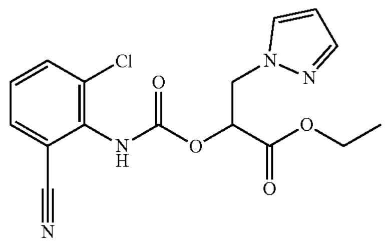 [SMILES: CCOC(=O)C(Cn1cccn1)OC(=O)Nc1c(Cl)cccc1C#N] | Ethyl 2-{[(2-chloro-6-cyanophenyl)carbamoyl]oxy}-3-(1H-pyrazol-1-yl)propanoate |
| 60 | 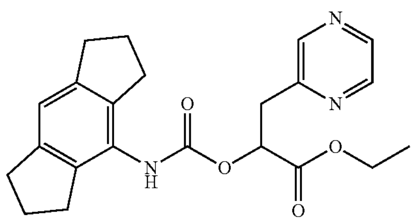 [SMILES: CCOC(=O)C(Cc1cnccn1)OC(=O)Nc1c2c(cc3c1CCC3)CCC2] | Ethyl 2-{[(1,2,3,5,6,7-hexahydro-s-indacen-4-yl)-carbamoyl]oxy}-3-(pyrazin-2-yl)propanoate |
| 61 | 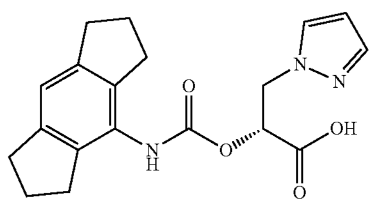 [SMILES: O=C(Nc1c2c(cc3c1CCC3)CCC2)O[C@H](Cn1cccn1)C(=O)O] | (2R)-2-{[(1,2,3,5,6,7-hexahydro-s-indacen-4-yl)-carbamoyl]oxy}-3-(1H-pyrazol-1-yl)propanoic acid |
| 62 | 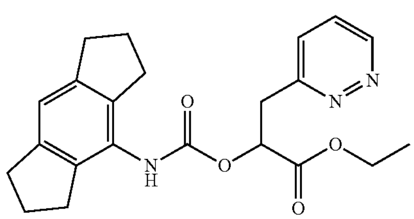 [SMILES: CCOC(=O)C(Cc1cccnn1)OC(=O)Nc1c2c(cc3c1CCC3)CCC2] | Ethyl 2-{[(1,2,3,5,6,7-hexahydro-s-indacen-4-yl)-carbamoyl]oxy}-3-(pyridazin-3-yl)propanoate |
| 63 | 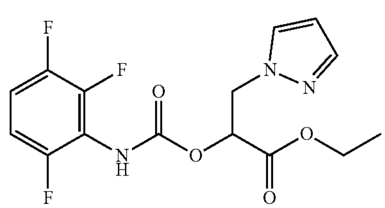 [SMILES: CCOC(=O)C(Cn1cccn1)OC(=O)Nc1c(F)ccc(F)c1F] | Ethyl 3-(1H-pyrazol-1-yl)-2-{[(2,3,6-trifluorophenyl)-carbamoyl]oxy}propanoate |
| 64 | 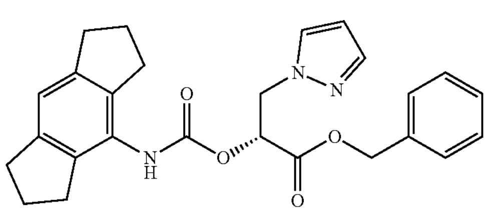 [SMILES: O=C(Nc1c2c(cc3c1CCC3)CCC2)O[C@H](Cn1cccn1)C(=O)OCc1ccccc1] | Benzyl (2R)-2-{[(1,2,3,5,6,7-hexahydro-s-indacen-4-yl)-carbamoyl]oxy}-3-(1H-pyrazol-1-yl)propanoate |

TABLE 1-continued

| Compound No. | Structure | Name |
|---|---|---|
| 65 | 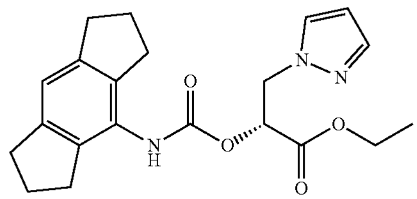 | Ethyl (2R)-2-{[(1,2,3,5,6,7-hexahydro-s-indacen-4-yl)-carbamoyl]oxy}-3-(1H-pyrazol-1-yl)propanoate |
| 66 | 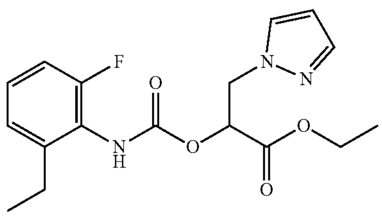 [SMILES: CCOC(=O)C(Cn1cccn1)OC(=O)Nc1c(F)cccc1CC] | Ethyl 2-{[(2-ethyl-6-fluoro-phenyl)carbamoyl]oxy}-3-(1H-pyrazol-1-yl)propanoate |
| 67 | 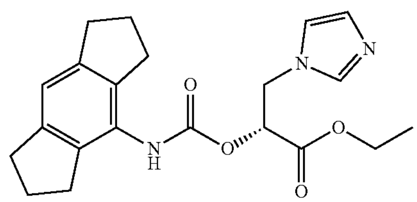 [SMILES: CCOC(=O)[C@@H](Cn1ccnc1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(1H-imidazol-1-yl)propanoate |
| 68 | 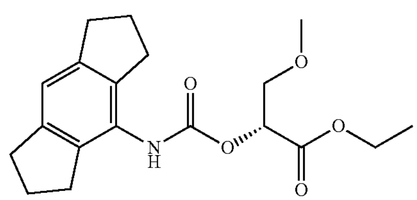 [SMILES: CCOC(=O)[C@@H](COC)OC(=O)Nc1c2c(cc3c1CCC3)CCC2] | Ethyl (2R)-2-{[(1,2,3,5,6,7-hexahydro-indacen-4-yl)-carbamoyl]oxy}-3-methoxy-propanoate |
| 69 | 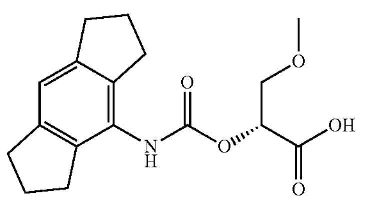 [SMILES: COC[C@@H](OC(=O)Nc1c2c(cc3c1CCC3)CCC2)C(=O)O] | (2R)-2-{[(1,2,3,5,6,7-hexahydro-s-indacen-4-yl)-carbamoyl]oxy}-3-methoxy-propanoic acid |
| 70 | 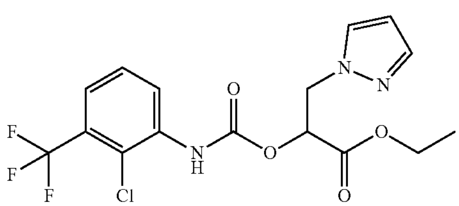 [SMILES: CCOC(=O)C(Cn1cccn1)OC(=O)Nc1cccc(C(F)(F)F)c1Cl] | Ethyl 2-({[2-chloro-3-(trifluoromethyl)phenyl]-carbamoyl}oxy)-3-(1H-pyrazol-1-yl)propanoate |
| 71 | 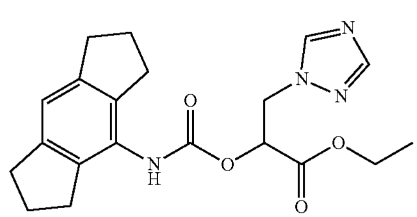 [SMILES: CCOC(=O)C(Cn1cncn1)OC(=O)Nc1c2c(cc3c1CCC3)CCC2] | Ethyl 2-{[(1,2,3,5,6,7-hexahydro-s-indacen-4-yl)-carbamoyl]oxy}-3-(1H-1,2,4-triazol-1-yl)propanoate |

TABLE 1-continued

| Compound No. | Structure | Name |
|---|---|---|
| 72 | 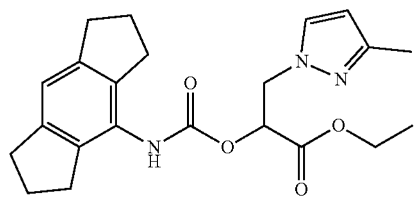 [SMILES: CCOC(=O)C(Cn1ccc(C)n1)OC(=O)Nc1c2c(cc3c1CCC3)CCC2] | Ethyl 2-{[(1,2,3,5,6,7-hexahydro-s-indacen-4-yl)-carbamoyl]oxy}-3-(3-methyl-1H-pyrazol-1-yl)propanoate |
| 73 | 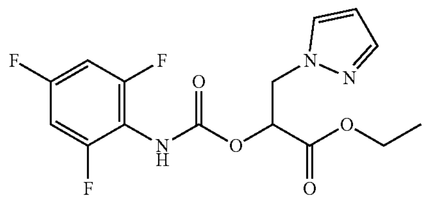 [SMILES: CCOC(=O)C(Cn1cccn1)OC(=O)Nc1c(F)cc(F)cc1F] | Ethyl 3-(1H-pyrazol-1-yl)-2-{[(2,4,6-trifluorophenyl)-carbamoyl]oxy}propanoate |
| 74 | 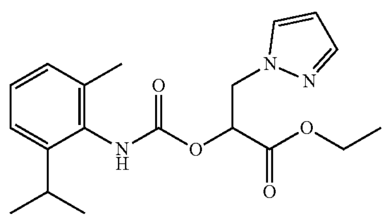 [SMILES: CCOC(=O)C(Cn1cccn1)OC(=O)Nc1c(C)cccc1C(C)C] | Ethyl 2-({[2-methyl-6-(propan-2-yl)phenyl]-carbamoyl}oxy)-3-(1H-pyrazol-1-yl)propanoate |
| 75 | 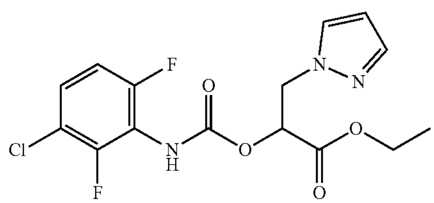 [SMILES: CCOC(=O)C(Cn1cccn1)OC(=O)Nc1c(F)ccc(Cl)c1F] | Ethyl 2-{[(3-chloro-2,6-difluorophenyl)carbamoyl]-oxy}-3-(1H-pyrazol-1-yl)-propanoate |
| 76 | 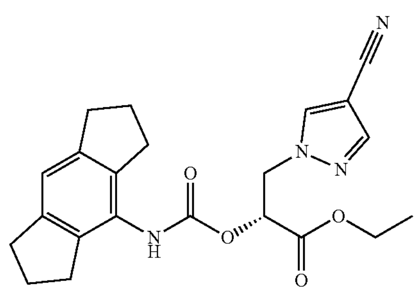 [SMILES: CCOC(=O)[C@@H](Cn1cc(C#N)cn1)OC(=O)Nc1c2c(cc3c1CCC3)CCC2] | Ethyl (2R)-3-(4-cyano-1H-pyrazol-1-yl)-2-{[(1,2,3,5,6,7-hexahydro-s-indacen-4-yl)-carbamoyl]oxy}propanoate |
| 77 | 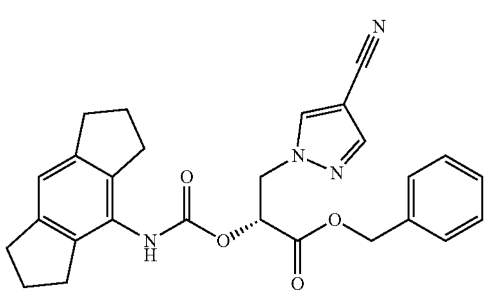 [SMILES: N#Cc1cnn(C[C@@H](OC(=O)Nc2c3c(cc4c2CCC4)CCC3)C(=O)OCc2ccccc2)c1] | Benzyl (2R)-3-(4-cyano-1H-pyrazol-1-yl)-2-{[(1,2,3,5,6,7-hexahydro-s-indacen-4-yl)-carbamoyl]oxy}propanoate |

TABLE 1-continued

| Compound No. | Structure | Name |
| --- | --- | --- |
| 78 | 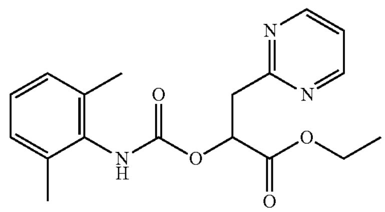 [SMILES: CCOC(=O)C(Cc1ncccn1)OC(=O)Nc1c(C)cccc1C] | Ethyl 2-{[(2,6-dimethylphenyl)-carbamoyl]oxy}-3-(pyrimidin-2-yl)propanoate |
| 79 | 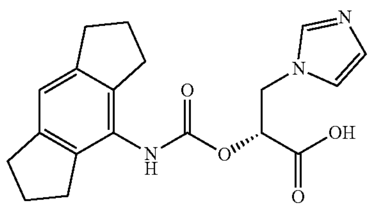 [SMILES: O=C(Nc1c2c(cc3c1CCC3)CCC2)O[C@H](Cn1ccnc1)C(=O)O] | (2R)-2-{[(1,2,3,5,6,7-hexahydro-s-indacen-4-yl)-carbamoyl]oxy}-3-(1H-imidazol-1-yl)propanoic acid |
| 80 | 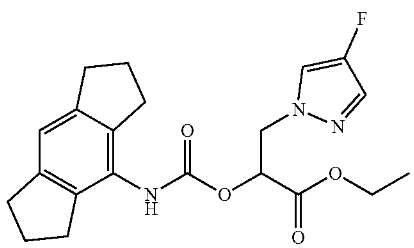 [SMILES: CCOC(=O)C(Cn1cc(F)cn1)OC(=O)Nc1c2c(cc3c1CCC3)CCC2] | Ethyl 3-(4-fluoro-1H-pyrazol-1-yl)-2-{[(1,2,3,5,6,7-hexahydro-s-indacen-4-yl)-carbamoyl]oxy}propanoate |
| 81 | 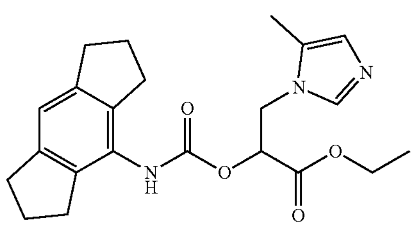 [SMILES: CCOC(=O)C(Cn1cncc1C)OC(=O)Nc1c2c(cc3c1CCC3)CCC2] | Ethyl 2-{[(1,2,3,5,6,7-hexahydro-s-indacen-4-yl)-carbamoyl]oxy}-3-(5-methyl-1H-imidazol-1-yl)propanoate |
| 82 | 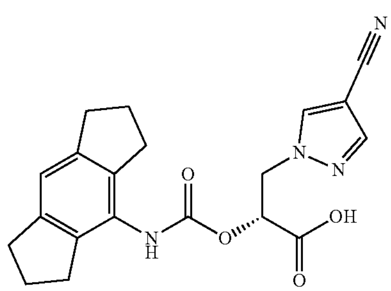 [SMILES: N#Cc1cnn(C[C@@H](OC(=O)Nc2c3c(cc4c2CCC4)CCC3)C(=O)O)c1] | (2R)-3-(4-cyano-1H-pyrazol-1-yl)-2-{[(1,2,3,5,6,7-hexahydro-s-indacen-4-yl)-carbamoyl]oxy}propanoic acid |
| 83 | 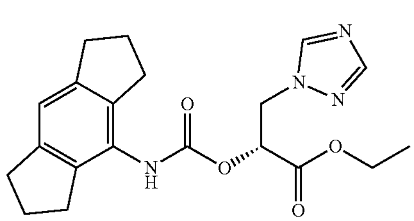 | Ethyl (2R)-2-{[(1,2,3,5,6,7-hexahydro-s-indacen-4-yl)-carbamoyl]oxy}-3-(1H-1,2,4-triazol-1-yl)propanoate |

TABLE 1-continued

| Compound No. | Structure | Name |
|---|---|---|
| 84 | 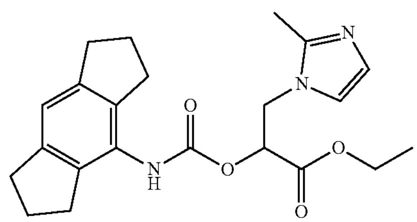 [SMILES: CCOC(=O)C(Cn1ccnc1C)OC(=O)Nc1c2c(cc3c1CCC3)CCC2] | Ethyl 2-{[(1,2,3,5,6,7-hexahydro-s-indacen-4-yl)-carbamoyl]oxy}-3-(2-methyl-1H-imidazol-1-yl)propanoate |
| 85 | 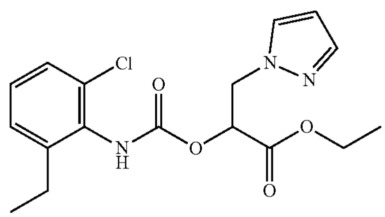 [SMILES: CCOC(=O)C(Cn1cccn1)OC(=O)Nc1c(Cl)cccc1CC] | Ethyl 2-{[(2-chloro-6-ethylphenyl)carbamoyl]oxy}-3-(1H-pyrazol-1-yl)propanoate |
| 86 | 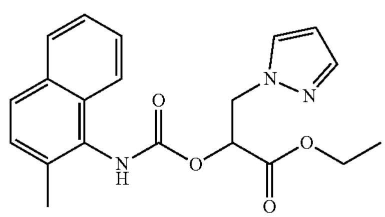 [SMILES: CCOC(=O)C(Cn1cccn1)OC(=O)Nc1c(C)ccc2ccccc12] | Ethyl 2-{[(2-methylnaphthalen-1-yl)carbamoyl]oxy}-3-(1H-pyrazol-1-yl)propanoate |
| 87 | 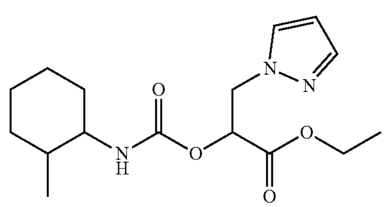 [SMILES: CCOC(=O)C(Cn1cccn1)OC(=O)NC1CCCCC1C] | Ethyl 2-{[(2-methylcyclohexyl)carbamoyl]oxy}-3-(1H-pyrazol-1-yl)propanoate |
| 88 | 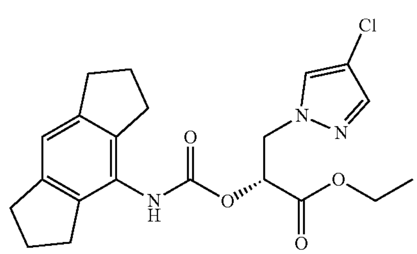 [SMILES: CCOC(=O)[C@@H](Cn1cc(Cl)cn1)OC(=O)Nc1c2c(cc3c1CCC3)CCC2] | Ethyl (2R)-3-(4-chloro-1H-pyrazol-1-yl)-2-{[(1,2,3,5,6,7-hexahydro-s-indacen-4-yl)-carbamoyl]oxy}propanoate |
| 89 | 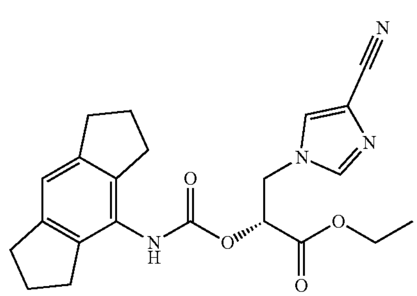 [SMILES: CCOC(=O)[C@@H](Cn1cnc(C#N)c1)OC(=O)Nc1c2c(cc3c1CCC3)CCC2] | Ethyl (2R)-3-(4-cyano-1H-imidazol-1-yl)-2-{[(1,2,3,5,6,7-hexahydro-s-indacen-4-yl)-carbamoyl]oxy}propanoate |

TABLE 1-continued

| Compound No. | Structure | Name |
| --- | --- | --- |
| 90 | 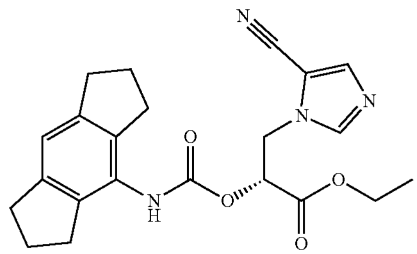 [SMILES: CCOC(=O)[C@@H](Cn1cncc1C#N)OC(=O)Nc1c2c(cc3c1CCC3)CCC2] | Ethyl (2R)-3-(5-cyano-1H-imidazol-1-yl)-2-{[(1,2,3,5,6,7-hexahydro-s-indacen-4-yl)-carbamoyl]oxy}propanoate |
| 91 | 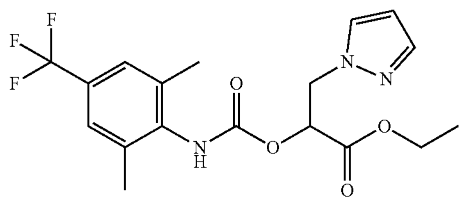 [SMILES: CCOC(=O)C(Cn1cccn1)OC(=O)Nc1c(C)cc(C(F)(F)F)cc1C] | Ethyl 2-({[2,6-dimethyl-4-(trifluoromethyl)phenyl]-carbamoyl}oxy)-3-(1H-pyrazol-1-yl)propanoate |
| 92 | 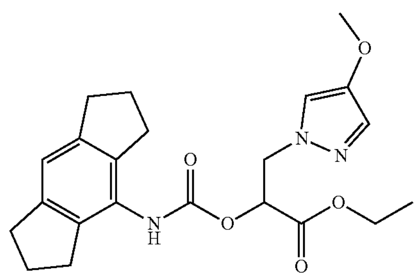 [SMILES: CCOC(=O)C(Cn1cc(OC)cn1)OC(=O)Nc1c2c(cc3c1CCC3)CCC2] | Ethyl 2-{[(1,2,3,5,6,7-hexahydro-s-indacen-4-yl)carbamoyl]oxy}-3-(4-methoxy-1H-pyrazol-1-yl)propanoate |
| 93 | 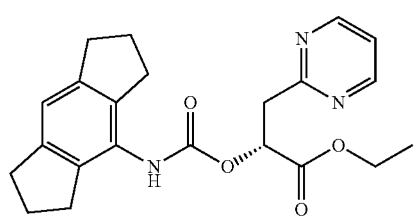 | Ethyl (2R)-2-{[(1,2,3,5,6,7-hexahydro-s-indacen-4-yl)-carbamoyl]oxy}-3-(pyrimidin-2-yl)propanoate |
| 94 | 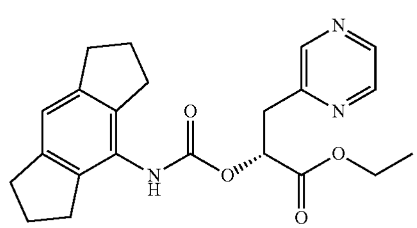 [SMILES: CCOC(=O)[C@@H](Cc1cnccn1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(pyrazin-2-yl)propanoate |
| 95 | 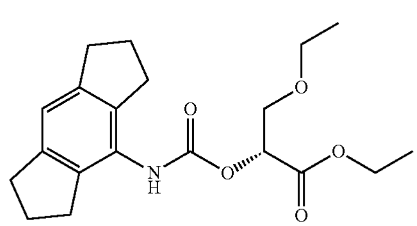 [SMILES: CCOC[C@@H](OC(=O)Nc1c2c(cc3c1CCC3)CCC2)C(=O)OCC] | Ethyl (2R)-3-ethoxy-2-{[(1,2,3,5,6,7-hexahydro-s-indacen-4-yl)carbamoyl]oxy}-propanoate |

TABLE 1-continued

| Compound No. | Structure | Name |
|---|---|---|
| 96 | 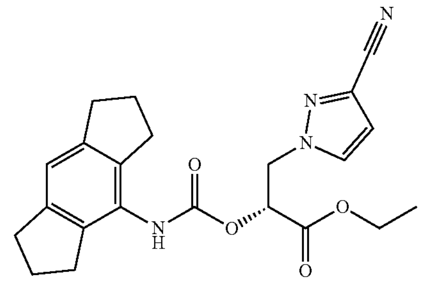 [SMILES: CCOC(=O)[C@@H](Cn1ccc(C#N)n1)OC(=O)Nc1c2c(cc3c1CCC3)CCC2] | Ethyl (2R)-3-(3-cyano-1H-pyrazol-1-yl)-2-{[(1,2,3,5,6,7-hexahydro-s-indacen-4-yl)-carbamoyl]oxy}propanoate |
| 97 | 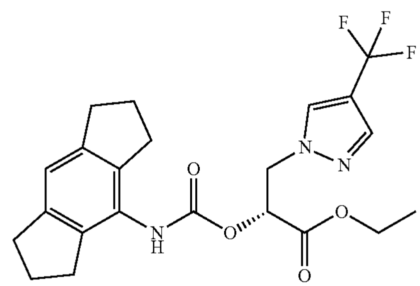 [SMILES: CCOC(=O)[C@@H](Cn1cc(C(F)(F)F)cn1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-[4-(trifluoromethyl)-1H-pyrazol-1-yl]propanoate |
| 98 | 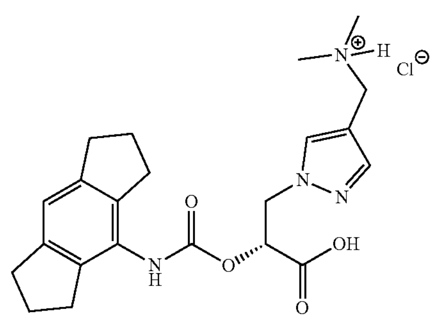 [SMILES: C[NH+](C)Cc1cnn(C[C@@H](OC(=O)Nc2c3c(cc4c2CCC4)CCC3)C(=O)O)c1 ; [Cl-]] | (2R)-3-{4-[(dimethylamino)-methyl]-1H-pyrazol-1-yl}-2-{[(1,2,3,5,6,7-hexahydro-s-indacen-4-yl)carbamoyl]oxy}-propanoic acid hydrochloride |
| 99 | 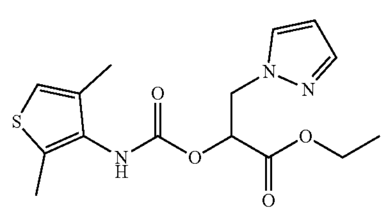 [SMILES: CCOC(=O)C(Cn1cccn1)OC(=O)Nc1c(C)csc1C] | Ethyl 2-{[(2,4-dimethyl-thiophen-3-yl)carbamoyl]-oxy}-3-(1H-pyrazol-1-yl)-propanoate |
| 100 | 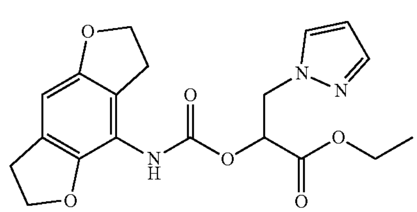 [SMILES: CCOC(=O)C(Cn1cccn1)OC(=O)Nc1c2c(cc3c1OCC3)OCC2] | Ethyl 2-[({4,10-dioxatricyclo-[7.3.0.0$^{3,7}$]dodeca-1,3(7),8-trien-2-yl}carbamoyl)oxy]-3-(1H-pyrazol-1-yl)propanoate |
| 101 | 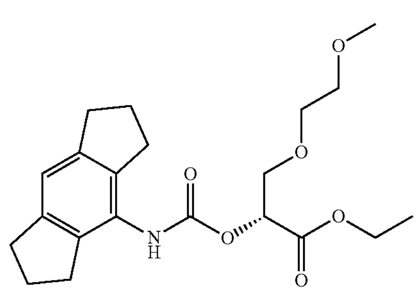 [SMILES: CCOC(=O)[C@@H](COCCOC)OC(=O)Nc1c2c(cc3c1CCC3)CCC2] | Ethyl (2R)-2-{[(1,2,3,5,6,7-hexahydro-indacen-4-yl)-carbamoyl]oxy}-3-(2-methoxyethoxy)propanoate |

TABLE 1-continued

| Compound No. | Structure | Name |
|---|---|---|
| 102 | 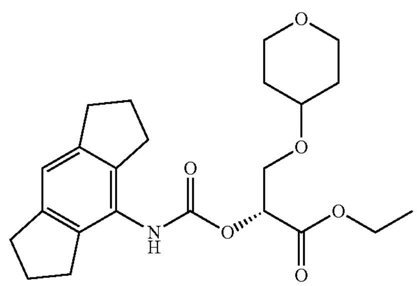 [SMILES: CCOC(=O)[C@@H](COC1CCOCC1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(oxan-4-yloxy)propanoate |
| 103 | 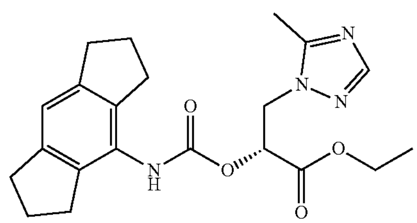 [SMILES: CCOC(=O)[C@@H](Cn1ncnc1C)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(5-methyl-1H-1,2,4-triazol-1-yl)-propanoate |
| 104 | 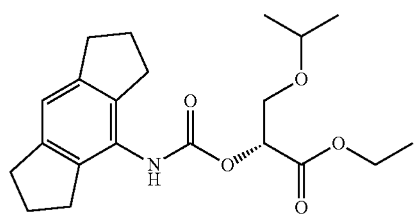 [SMILES: CCOC(=O)[C@@H](COC(C)C)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(propan-2-yloxy)propanoate |
| 105 | 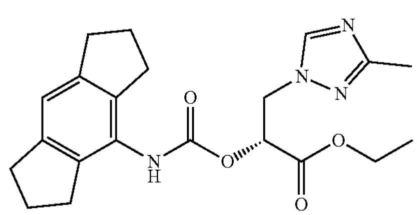 [SMILES: CCOC(=O)[C@@H](Cn1cnc(C)n1)OC(=O)Nc1c2c(cc3c1CCC3)CCC2] | Ethyl (2R)-2-{[(1,2,3,5,6,7-hexahydro-s-indacen-4-yl)-carbamoyl]oxy}-3-(3-methyl-1H-1,2,4-triazol-1-yl)propanoate |
| 106 | 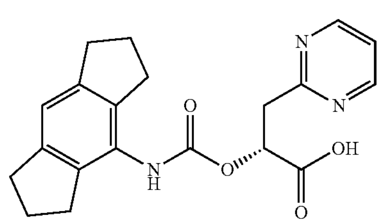 [SMILES: O=C(Nc1c2c(cc3c1CCC3)CCC2)O[C@H](Cc1ncccn1)C(=O)O] | (2R)-2-{[(1,2,3,5,6,7-hexahydro-s-indacen-4-yl)-carbamoyl]oxy}-3-(pyrimidin-2-yl)propanoic acid |
| 107 | 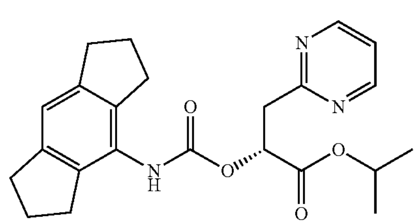 [SMILES: CC(C)OC(=O)[C@@H](Cc1ncccn1)OC(=O)Nc1c2c(cc3c1CCC3)CCC2] | Propan-2-yl (2R)-2-{[(1,2,3,5,6,7-hexahydro-s-indacen-4-yl)carbamoyl]oxy}-3-(pyrimidin-2-yl)propanoate |

TABLE 1-continued

| Compound No. | Structure | Name |
|---|---|---|
| 108 | 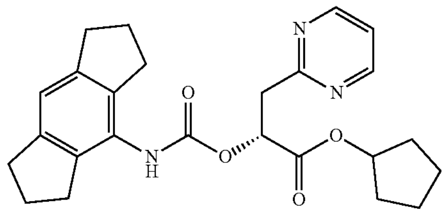 [SMILES: O=C(Nc1c2c(cc3c1CCC3)CCC2)O[C@H](Cc1ncccn1)C(=O)OC1CCCC1] | Cyclopentyl (2R)-2-{[(1,2,3,5,6,7-hexahydro-s-indacen-4-yl)carbamoyl]oxy}-3-(pyrimidin-2-yl)propanoate |
| 109 | 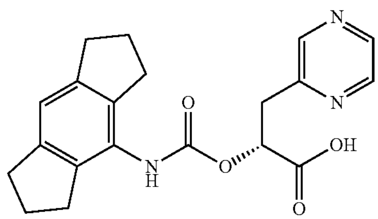 [SMILES: O=C(Nc1c2c(cc3c1CCC3)CCC2)O[C@H](Cc1cnccn1)C(=O)O] | (2R)-2-{[(1,2,3,5,6,7-hexahydro-s-indacen-4-yl)-carbamoyl]oxy}-3-(pyrazin-2-yl)propanoic acid |
| 110 | 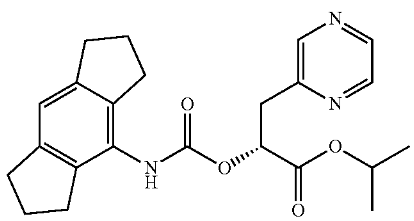 [SMILES: CC(C)OC(=O)[C@@H](Cc1cnccn1)OC(=O)Nc1c2c(cc3c1CCC3)CCC2] | Propan-2-yl (2R)-2-{[(1,2,3,5,6,7-hexahydro-s-indacen-4-yl)carbamoyl]oxy}-3-(pyrazin-2-yl)propanoate |
| 111 | 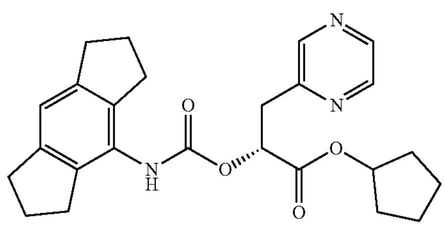 [SMILES: O=C(Nc1c2c(cc3c1CCC3)CCC2)O[C@H](Cc1cnccn1)C(=O)OC1CCCC1] | Cyclopentyl (2R)-2-{[(1,2,3,5,6,7-hexahydro-s-indacen-4-yl)carbamoyl]oxy}-3-(pyrazin-2-yl)propanoate |
| 112 | 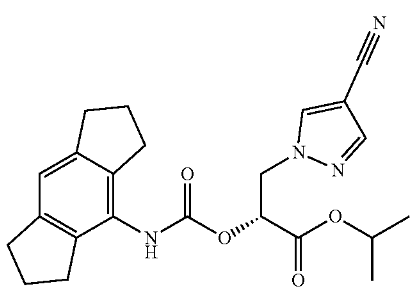 [SMILES: CC(C)OC(=O)[C@@H](Cn1cc(C#N)cn1)OC(=O)Nc1c2c(cc3c1CCC3)CCC2] | Propan-2-yl (2R)-3-(4-cyano-1H-pyrazol-1-yl)-2-{[(1,2,3,5,6,7-hexahydro-s-indacen-4-yl)carbamoyl]oxy}-propanoate |
| 113 | 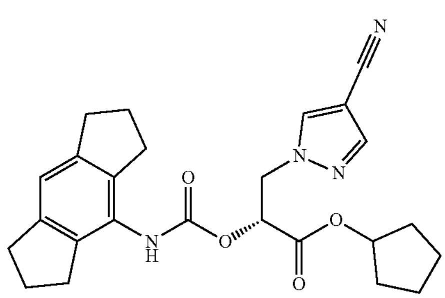 [SMILES: N#Cc1cnn(C[C@@H](OC(=O)Nc2c3c(cc4c2CCC4)CCC3)C(=O)OC2CCCC2)c1] | Cyclopentyl (2R)-3-(4-cyano-1H-pyrazol-1-yl)-2-{[(1,2,3,5,6,7-hexahydro-s-indacen-4-yl)carbamoyl]-oxy}propanoate |

TABLE 1-continued

| Compound No. | Structure | Name |
|---|---|---|
| 114 | 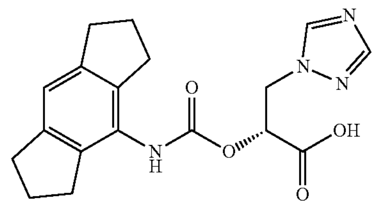 [SMILES: O=C(Nc1c2c(cc3c1CCC3)CCC2)O[C@H](Cn1cncn1)C(=O)O] | (2R)-2-{[(1,2,3,5,6,7-hexahydro-s-indacen-4-yl)-carbamoyl]oxy}-3-(1H-1,2,4-triazol-1-yl)propanoic acid |
| 115 | 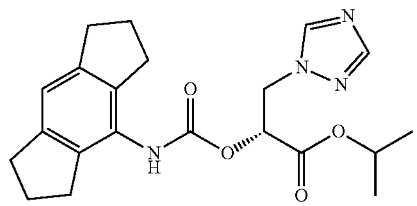 [SMILES: CC(C)OC(=O)[C@@H](Cn1cncn1)OC(=O)Nc1c2c(cc3c1CCC3)CCC2] | Propan-2-yl (2R)-2-{[(1,2,3,5,6,7-hexahydro-s-indacen-4-yl)carbamoyl]-oxy}-3-(1H-1,2,4-triazol-1-yl)propanoate |
| 116 | 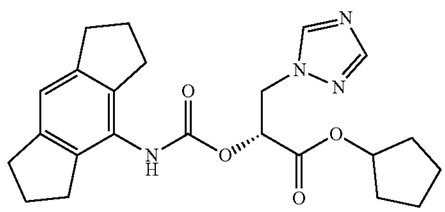 [SMILES: O=C(Nc1c2c(cc3c1CCC3)CCC2)O[C@H](Cn1cncn1)C(=O)OC1CCCC1] | Cyclopentyl (2R)-2-{[(1,2,3,5,6,7-hexahydro-s-indacen-4-yl)carbamoyl]oxy}-3-(1H-1,2,4-triazol-1-yl)-propanoate |
| 117 | 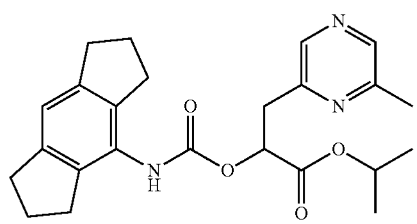 [SMILES: Cc1cncc(CC(OC(=O)Nc2c3c(cc4c2CCC4)CCC3)C(=O)OC(C)C)n1] | Propan-2-yl 2-{[(1,2,3,5,6,7-hexahydro-s-indacen-4-yl)-carbamoyl]oxy}-3-(6-methyl-pyrazin-2-yl)propanoate |
| 118 | 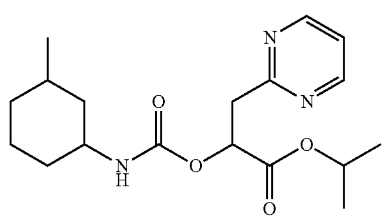 [SMILES: CC1CCCC(NC(=O)OC(Cc2ncccn2)C(=O)OC(C)C)C1] | Propan-2-yl 2-{[(3-methyl-cyclohexyl)carbamoyl]oxy}-3-(pyrimidin-2-yl)propanoate |
| 119 | 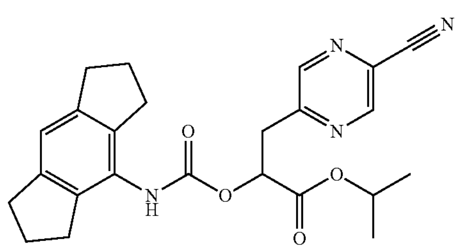 [SMILES: CC(C)OC(=O)C(Cc1cnc(C#N)cn1)OC(=O)Nc1c2c(cc3c1CCC3)CCC2] | Propan-2-yl 3-(5-cyano-pyrazin-2-yl)-2-{[(1,2,3,5,6,7-hexahydro-s-indacen-4-yl)-carbamoyl]oxy}propanoate |
| 120 | 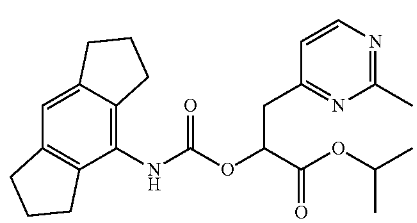 [SMILES: Cc1nccc(CC(OC(=O)Nc2c3c(cc4c2CCC4)CCC3)C(=O)OC(C)C)n1] | Propan-2-yl 2-{[(1,2,3,5,6,7-hexahydro-s-indacen-4-yl)-carbamoyl]oxy}-3-(2-methyl-pyrimidin-4-yl)propanoate |

TABLE 1-continued

| Compound No. | Structure | Name |
|---|---|---|
| 121 | 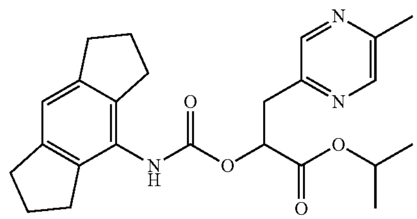 [SMILES: Cc1cnc(CC(OC(=O)Nc2c3c(cc4c2CCC4)CCC3)C(=O)OC(C)C)cn1] | Propan-2-yl 2-{[(1,2,3,5,6,7-hexahydro-s-indacen-4-yl)-carbamoyl]oxy}-3-(5-methyl-pyrazin-2-yl)propanoate |
| 122 | 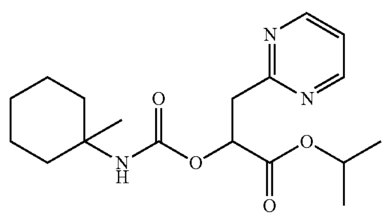 [SMILES: CC(C)OC(=O)C(Cc1ncccn1)OC(=O)NC1(C)CCCCC1] | Propan-2-yl 2-{[(1-methyl-cyclohexyl)carbamoyl]oxy}-3-(pyrimidin-2-yl)propanoate |
| 123 | 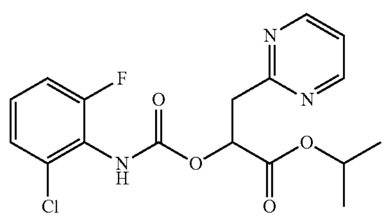 [SMILES: CC(C)OC(=O)C(Cc1ncccn1)OC(=O)Nc1c(F)cccc1Cl] | Propan-2-yl 2-{[(2-chloro-6-fluorophenyl)carbamoyl]oxy}-3-(pyrimidin-2-yl)propanoate |
| 124 | 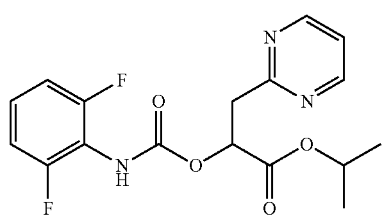 [SMILES: CC(C)OC(=O)C(Cc1ncccn1)OC(=O)Nc1c(F)cccc1F] | Propan-2-yl 2-{[(2,6-difluoro-phenyl)carbamoyl]oxy}-3-(pyrimidin-2-yl)propanoate |
| 125 | 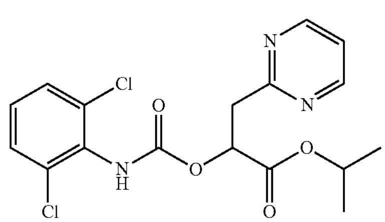 [SMILES: CC(C)OC(=O)C(Cc1ncccn1)OC(=O)Nc1c(Cl)cccc1Cl] | Propan-2-yl 2-{[(2,6-dichloro-phenyl)carbamoyl]oxy}-3-(pyrimidin-2-yl)propanoate |
| 126 | 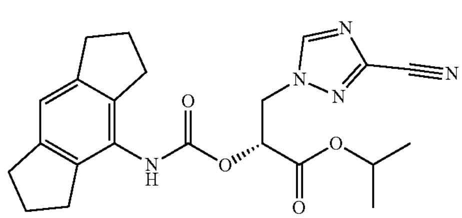 [SMILES: CC(C)OC(=O)[C@@H](Cn1cnc(C#N)n1)OC(=O)Nc1c2c(cc3c1CCC3)CCC2] | Propan-2-yl (2R)-3-(3-cyano-1H-1,2,4-triazol-1-yl)-2-{[(1,2,3,5,6,7-hexahydro-s-indacen-4-yl)carbamoyl]oxy}-propanoate |
| 127 | 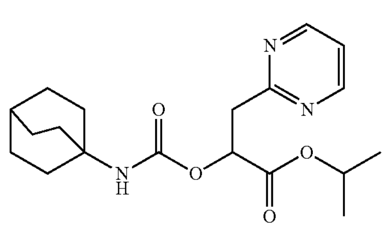 [SMILES: CC(C)OC(=O)C(Cc1ncccn1)OC(=O)NC12CCC(CC1)CC2] | Propan-2-yl 2-[({bicyclo-[2.2.2]octan-1-yl}carbamoyl)-oxy]-3-(pyrimidin-2-yl)-propanoate |

TABLE 1-continued

| Compound No. | Structure | Name |
|---|---|---|
| 128 | 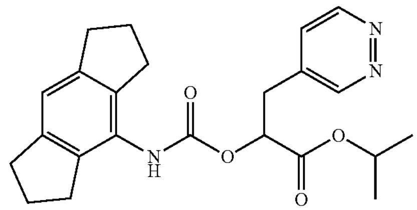 [SMILES: CC(C)OC(=O)C(Cc1ccnnc1)OC(=O)Nc1c2c(cc3c1CCC3)CCC2] | Propan-2-yl 2-{[(1,2,3,5,6,7-hexahydro-s-indacen-4-yl)-carbamoyl]oxy}-3-(pyridazin-4-yl)propanoate |
| 129 | 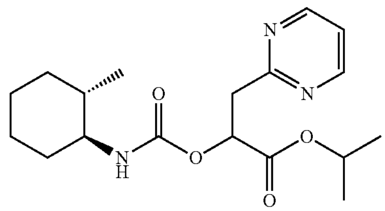 [SMILES: CC(C)OC(=O)C(Cc1ncccn1)OC(=O)N[C@H]1CCCC[C@@H]1C] | Propan-2-yl 2-{[(trans-2-methyl-cyclohexyl)carbamoyl]oxy}-3-(pyrimidin-2-yl)propanoate |
| 130 | 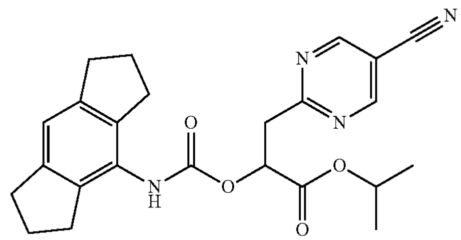 [SMILES: CC(C)OC(=O)C(Cc1ncc(C#N)cn1)OC(=O)Nc1c2c(cc3c1CCC3)CCC2] | Propan-2-yl 3-(5-cyano-pyrimidin-2-yl)-2-{[(1,2,3,5,6,7-hexahydro-s-indacen-4-yl)carbamoyl]oxy}-propanoate |

In some embodiments, the compound is selected from the group consisting of:
Ethyl 2-{[(1,2,3,5,6,7-hexahydro-s-indacen-4-yl)carbamoyl]oxy}acetate
Ethyl 2-{[(2,6-difluorophenyl)carbamoyl]oxy}acetate
Ethyl 2-{[(2,6-dichlorophenyl)carbamoyl]oxy}acetate
Ethyl 2-{[(naphthalen-1-yl)carbamoyl]oxy}acetate
Ethyl 2-{[(2,2-dimethyl-2,3-dihydro-1-benzofuran-7-yl)carbamoyl]oxy}acetate
Ethyl 2-{[(1,2,3,5,6,7-hexahydro-s-indacen-4-yl)carbamoyl]oxy}-3-methoxypropanoate
Ethyl 2-({[2-fluoro-5-(trifluoromethyl)phenyl]carbamoyl}oxy)acetate
Ethyl 2-{[(2,6-dimethylphenyl)carbamoyl]oxy}acetate
Ethyl 2-{[(2,6-diethylphenyl)carbamoyl]oxy}acetate
Ethyl 2-({[2-(chloro-6-methylphenyl)carbamoyl]oxy}acetate
Ethyl 2-{[(2-cyanophenyl)carbamoyl]oxy}acetate
Ethyl 2-{[(1,2,3,5,6,7-hexahydro-s-indacen-4-yl)carbamoyl]oxy}-3-(pyridin-3-yl)propanoate
Ethyl 2-{[(2-tert-butylphenyl)carbamoyl]oxy}acetate
Ethyl 2-((mesitylcarbamoyl)oxy)acetate
Ethyl 2-(((2-isopropylphenyl)carbamoyl)oxy)acetate
Ethyl 2-(((2-ethyl-6-methylphenyl)carbamoyl)oxy)acetate
Ethyl 2-(((1,2,3,5,6,7-hexahydro-s-indacen-4-yl)carbamoyl)oxy)-3-phenylpropanoate
Ethyl 2-(((1,2,3,5,6,7-hexahydro-s-indacen-4-yl)carbamoyl)oxy)-3-(pyridin-2-yl)propanoate
Ethyl (2R)-2-{[(1,2,3,5,6,7-hexahydro-s-indacen-4-yl)carbamoyl]oxy}propanoate
Propan-2-yl 2-{[(1,2,3,5,6,7-hexahydro-s-indacen-4-yl)carbamoyl]oxy}acetate
2-{[(1,2,3,5,6,7-Hexahydro-s-indacen-4-yl)carbamoyl]oxy}acetate
Cyclopropylmethyl 2-{[(1,2,3,5,6,7-hexahydro-s-indacen-4-yl)carbamoyl]oxy}acetate
Cyclobutyl 2-{[(1,2,3,5,6,7-hexahydro-s-indacen-4-yl)carbamoyl]oxy}acetate
2-methylpropyl 2-{[(1,2,3,5,6,7-hexahydro-s-indacen-4-yl)carbamoyl]oxy}acetate
Ethyl 3-(4-cyanophenyl)-2-{[(1,2,3,5,6,7-hexahydro-s-indacen-4-yl)carbamoyl]oxy}propanoate
Ethyl 2-({[2-methyl-6-(propan-2-yl)phenyl]carbamoyl}oxy)acetate
2-{[(1,2,3,5,6,7-Hexahydro-s-indacen-4-yl)carbamoyl]oxy}acetic acid
Ethyl 2-{[(2,6-diethyl-4-methylphenyl)carbamoyl]oxy}acetate
Methyl 2-{[(1,2,3,5,6,7-hexahydro-s-indacen-4-yl)carbamoyl]oxy}acetate
Ethyl (2R)-2-{[(1,2,3,5,6,7-hexahydro-s-indacen-4-yl)carbamoyl]oxy}-4-phenylbutanoate
Ethyl 2-{[(1,2,3,5,6,7-hexahydro-s-indacen-4-yl)carbamoyl]oxy}-3-(1H-pyrazol-1-yl)propanoate
Cyclopentyl 2-{[(1,2,3,5,6,7-hexahydro-s-indacen-4-yl)carbamoyl]oxy}acetate; and
Ethyl 2-{[(1,2,3,5,6,7-hexahydro-s-indacen-4-yl)carbamoyl]oxy}-3-(1H-imidazol-1-yl)propanoate.

In some embodiments, the compound is not any one of

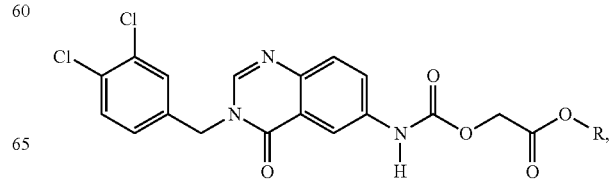

-continued

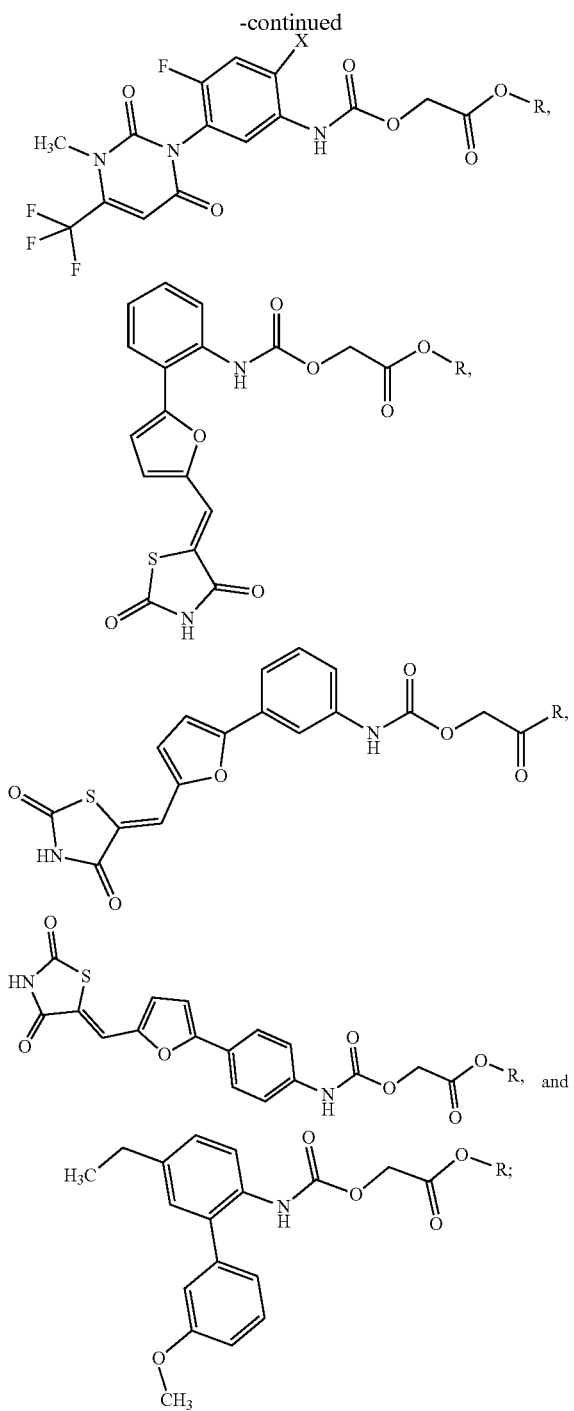

wherein X is CN, Cl, or Br, and R is H, $C_1$-$C_6$ alkyl, —$(CH_2)_{0-3}$—($C_3$-$C_6$ cycloalkyl), or —$(CH_2)_{0-3}$—$C_5$-$C_6$ aryl.

In some aspects, the present disclosure provides a compound being an isotopic derivative (e.g., isotopically labeled compound) of any one of the compounds of formulae (I)-(X), (Ia)-(Xa), and (Ib)-(Xb).

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of the compounds described in Table 1.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of formulae (I)-(X), (Ia)-(Xa), and (Ib)-(Xb).

In some embodiments, the compound is a deuterium labeled compound of any one of the compounds described in Table 1 and prodrugs and pharmaceutically acceptable salts thereof.

In some embodiments, the compound is a deuterium labeled compound of any one of the compounds described in Table 1 and pharmaceutically acceptable salts thereof.

In some embodiments, the compound is a deuterium labeled compound of any one of the compounds described in Table 1.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognised techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with heavier deuterium (i.e., $^2$H) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

Particular compounds of the disclosure include, for example, compounds of any one of Formulae (I)-(X), (Ia)-(Xa), and (Ib)-(Xb), or pharmaceutically acceptable salt thereof, wherein, unless otherwise stated, each of $R_1$, $R_3$, $R_4$ and any associated substituent groups has any of the meanings defined hereinbefore.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

It will be understood that the compounds of any one of Formulae (I)-(X), (Ia)-(Xa), and (Ib)-(Xb) and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

It is also to be understood that certain compounds of any one of Formulae (I)-(X), (Ia)-(Xa), and (Ib)-(Xb) may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of Formulae (I)-(X), (Ia)-(Xa), and (Ib)-(Xb) may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of Formulae (I)-(X), (Ia)-(Xa), and (Ib)-(Xb) may exist in a number of different tautomeric forms and references to compounds of the formula I include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

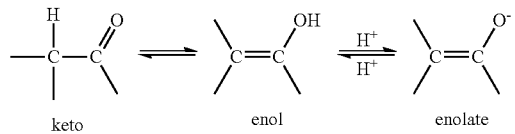

Compounds of any one of Formulae (I)-(X), (Ia)-(Xa), and (Ib)-(Xb) containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of any one of Formulae (I)-(X), (Ia)-(Xa), and (Ib)-(Xb) may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include in vivo cleavable ester derivatives that may be formed at a carboxy group or a hydroxy group in a compound of the any one of Formulae (I)-(X), (Ia)-(Xa), and (Ib)-(Xb) and in vivo cleavable amide derivatives that may be formed at a carboxy group or an amino group in a compound of any one of Formulae (I)-(X), (Ia)-(Xa), and (Ib)-(Xb).

Accordingly, the present disclosure includes those compounds of any one of Formulae (I)-(X), (Ia)-(Xa), and (Ib)-(Xb) as defined hereinbefore when made available by organic synthesis and when made available within the human or animal body by way of cleavage of a prodrug thereof. Accordingly, the present disclosure includes those compounds of any one of Formulae (I)-(X), (Ia)-(Xa), and (Ib)-(Xb) that are produced by organic synthetic means and also such compounds that are produced in the human or animal body by way of metabolism of a precursor compound, that is a compound of any one of Formulae (I)-(X), (Ia)-(Xa), and (Ib)-(Xb) may be a synthetically-produced compound or a metabolically-produced compound.

A suitable pharmaceutically acceptable prodrug of a compound of any one of Formulae (I)-(X), (Ia)-(Xa), and (Ib)-(Xb) is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Prodrugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of Formulae (I)-(X), (Ia)-(Xa), and (Ib)-(Xb) that possesses a carboxy group is, for example, an in vivo cleavable ester thereof. An in vivo cleavable ester of a compound of any one of Formulae (I)-(X), (Ia)-(Xa), and (Ib)-(Xb) containing a carboxy group is, for example, a pharmaceutically acceptable ester which is cleaved in the human or animal body to produce the parent acid. Suitable pharmaceutically acceptable esters for carboxy include $C_1$-$C_6$ alkyl esters such as methyl, ethyl and tert-butyl, $C_1$-$C_6$ alkoxymethyl esters such as methoxymethyl esters, $C_1$-$C_6$ alkanoyloxymethyl esters such as pivaloyloxymethyl esters, 3-phthalidyl esters, $C_3$-$C_8$ cycloalkylcarbonyloxy-$C_1$-$C_6$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_1$-$C_6$ alkoxycarbonyloxy-$C_{1-6}$alkyl esters such as methoxycarbonyloxymethyl and 1-methoxycarbonyloxyethyl esters.

A suitable pharmaceutically acceptable prodrug of a compound of any one of Formulae (I)-(X), (Ia)-(Xa), and (Ib)-(Xb) that possesses a hydroxy group is, for example, an in vivo cleavable ester or ether thereof. An in vivo cleavable ester or ether of a compound of any one of Formulae (I)-(X), (Ia)-(Xa), and (Ib)-(Xb) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N-($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of Formulae (I)-(X), (Ia)-(Xa), and (Ib)-(Xb) that possesses a carboxy group is, for example, an in vivo cleavable amide thereof, for example an amide formed with an amine such as ammonia, a $C_1$-4alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of Formulae (I)-(X), (Ia)-(Xa), and (Ib)-(Xb) that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of Formulae (I)-(X), (Ia)-(Xa), and (Ib)-(Xb) may be exerted in part by one or more metabolites that are formed within the human or animal body after administration of a compound of any one of Formulae (I)-(X), (Ia)-(Xa), and (Ib)-(Xb). As stated hereinbefore, the in vivo effects of a compound of any one of Formulae (I)-(X), (Ia)-(Xa), and (Ib)-(Xb) may also be exerted by way of metabolism of a precursor compound (a prodrug).

Though the present disclosure may relate to any compound or particular group of compounds defined herein by way of optional, preferred or suitable features or otherwise in terms of particular embodiments, the present disclosure may also relate to any compound or particular group of compounds that specifically excludes said optional, preferred or suitable features or particular embodiments. A feature of the disclosure concerns particular structural groups at $R_1$, which is relevant to the scope of the claims, as defined herein. In some cases, specific groups define structures that are not relevant to the present invention and thus may be disclaimed. Such structures may be disclaimed where $R_1$ corresponds to a phenyl directly substituted with at least 2 groups including: 1 halogen group and 1 methyl group; 2 or more halogen groups; or 2 methyl groups.

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-5 herein.

Compound 1a is reacted with Compound 1b in the presence of a base (e.g., triethylamine) in a solvent (e.g., acetonitrile) and, optionally, at an elevated temperature to yield Compound 1C.

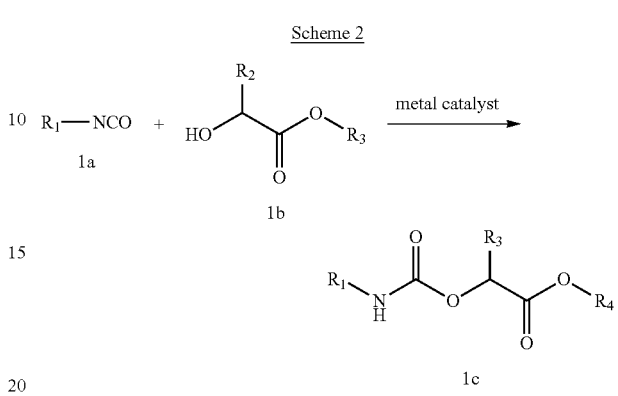

Compound 1a is reacted with Compound 1b in the presence of a metal catalyst (e.g., copper chloride) in a solvent (e.g., dimethylformamide) and, optionally, at an elevated temperature to yield Compound 1c.

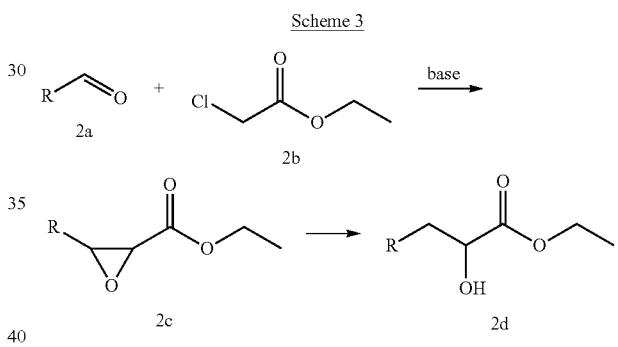

Compound 2a is reacted with Compound 2b in the presence of a base (e.g., sodium bis(trimethylsilyl)amide) in a solvent (e.g., tetrahydrofuran) and, optionally, at a reduced temperature (e.g., −78° C.), to yield Compound 2c. Compound 2c is reacted in the presence of a metal catalyst for hydrogenation (e.g., 10% Pd/C) in a solvent (e.g., ethyl acetate) and, optionally, at an elevated temperature, to yield Compound 2d.

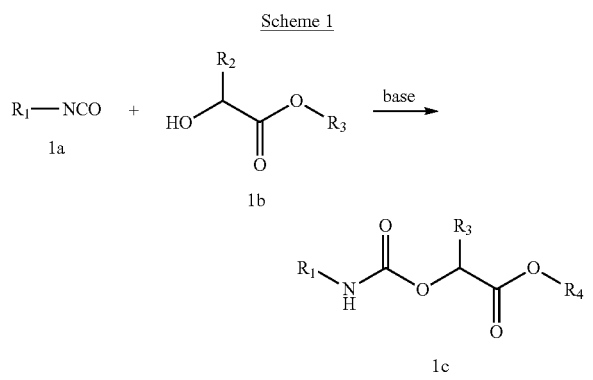

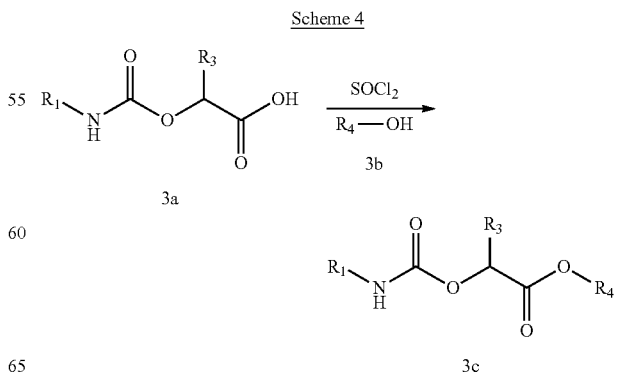

Compound 3a is reacted with Compound 3b in the presence of thionyl chloride and, optionally, at a reduced temperature (e.g., 0° C.), to yield Compound 3c.

It should be understood that in the description and formulae shown above, the various groups, such as $R_1$-$R_4$ and R, are as defined herein, except where otherwise indicated. Furthermore, for synthetic purposes, the compounds in the Schemes are mere representatives with elected substituents to illustrate the general synthetic methodology of a compound disclosed herein.

Biological Assays

Compounds designed, selected and/or optimised by methods described above, once produced, can be characterized using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthio late, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

The size of the dose for therapeutic or prophylactic purposes of a compound of the Formula I will naturally vary according to the nature and severity of the conditions, the age and sex of the animal or patient and the route of administration, according to well-known principles of medicine.

Methods of Use

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is associated with an implicated inflammasome activity. In some embodiments, the disease or disorder is a disease or disorder in which inflammasome activity is implicated.

In some embodiments, the disease or disorder is an autoinflammatory disorder, an autoimmune disorder, a neurodegenerative disease, or cancer.

In some embodiments, the disease or disorder is an autoinflammatory disorder and/or an autoimmune disorder.

In some embodiments, the disease or disorder is selected from cryopyrin-associated autoinflammatory syndrome (CAPS; e.g., familial cold autoinflammatory syndrome (FCAS)), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), non-alcoholic steatohepatitis (NASH), gout, rheumatoid arthritis, osteoarthritis, Crohn's disease, Cchronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases).

In some embodiments, the disease or disorder is a neurodegenerative disease.

In some embodiments, the disease or disorder is Parkinson's disease or Alzheimer's disease.

In some embodiments, the disease or disorder is cancer.

In some embodiments, the cancer is metastasising cancer, gastrointestinal cancer, skin cancer, non-small-cell lung carcinoma, or colorectal adenocarcinoma.

In some aspects, the present disclosure provides a method of treating or preventing an autoinflammatory disorder, an autoimmune disorder, a neurodegenerative disease or cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing an autoinflammatory disorder and/or an autoimmune disorder selected from cryopyrin-associated autoinflammatory syndrome (CAPS; e.g., familial cold autoinflammatory syndrome (FCAS)), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), nonalcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disease (e.g., Parkinson's disease or Alzheimer's disease) in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cancer in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutical salt thereof for use in inhibiting inflammasome (e.g., the NLRP3 inflammasome) activity (e.g., in vitro or in vivo).

In some aspects, the present disclosure provides a compound of the present disclosure or a pharmaceutical salt thereof for use in treating or preventing a disease or disorder disclosed herein.

In some aspects, the present disclosure provides a compound of the present disclosure or a pharmaceutical salt thereof for use in treating or preventing an autoinflammatory disorder, an autoimmune disorder, a neurodegenerative disease or cancer in a subject in need thereof.

In some aspects, the present disclosure provides a compound of the present disclosure or a pharmaceutical salt thereof for use in treating or preventing an autoinflammatory disorder and/or an autoimmune disorder selected from cryopyrin-associated autoinflammatory syndrome (CAPS; e.g., familial cold autoinflammatory syndrome (FCAS)), Muckle-Wells syndrome (MWS), chronic infantile neurological cutaneous and articular (CINCA) syndrome/neonatal-onset multisystem inflammatory disease (NOMID), familial Mediterranean fever and nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof.

In some aspects, the present disclosure provides a compound of the present disclosure or a pharmaceutical salt thereof for use in treating or preventing a neurodegenerative disease (e.g., Parkinson's disease or Alzheimer's disease) in a subject in need thereof.

In some aspects, the present disclosure provides a compound of the present disclosure or a pharmaceutical salt thereof for use in treating or preventing cancer in a subject in need thereof.

In some aspects, the present disclosure provides use of a compound of the present disclosure or a pharmaceutical salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutical salt thereof in the manufacture of a medicament for treating or preventing a disease or disorder disclosed herein.

In some aspects, the present disclosure provides use of a compound of the present disclosure or a pharmaceutical salt thereof in the manufacture of a medicament for treating or preventing an autoinflammatory disorder, an autoimmune disorder, a neurodegenerative disease or cancer in a subject in need thereof.

In some aspects, the present disclosure provides use of a compound of the present disclosure or a pharmaceutical salt thereof in the manufacture of a medicament for treating or preventing an autoinflammatory disorder and/or an autoimmune disorder selected from cryopyrin-associated autoinflammatory syndrome (CAPS; e.g., familial cold autoinflammatory syndrome (FCAS)), Muckle-Wells syndrome (MWS), chronic infantile neurological cutaneous and articular (CINCA) syndrome/neonatal-onset multisystem inflammatory disease (NOMID), familial Mediterranean fever and nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof.

In some aspects, the present disclosure provides use of a compound of the present disclosure or a pharmaceutical salt thereof in the manufacture of a medicament for treating or preventing a neurodegenerative disease (e.g., Parkinson's disease or Alzheimer's disease) in a subject in need thereof.

In some aspects, the present disclosure provides use of a compound of the present disclosure or a pharmaceutical salt thereof in the manufacture of a medicament for treating or preventing cancer in a subject in need thereof.

The present disclosure provides compounds that function as inhibitors of inflammasome activity. The present disclosure therefore provides a method of inhibiting inflammasome activity in vitro or in vivo, said method comprising contacting a cell with an effective amount of a compound, or a pharmaceutically acceptable salt thereof, as defined herein.

Effectiveness of compounds of the disclosure can be determined by industry-accepted assays/disease models according to standard practices of elucidating the same as described in the art and are found in the current general knowledge.

The present disclosure also provides a method of treating a disease or disorder in which inflammasome activity is implicated in a patient in need of such treatment, said method comprising administering to said patient a therapeutically effective amount of a compound, or a pharmaceutically acceptable salt thereof, or a pharmaceutical composition as defined herein.

On a general level, the compounds of the present disclosure, which inhibit the maturation of cytokines of the IL-1 family, are effective in all therapeutic indications that are mediated or associated with elevated levels of active forms of cytokines belonging to IL-1 family of cytokines (Sims J. et al. Nature Reviews Immunology 10, 89-102 (February 2010).

Exemplary diseases and the corresponding references will be given in the following: autoinflammatory and autoimmune diseases like CAPS (Dinarello C A. Immunity. 2004

March; 20(3):243-4; Hoffman H M. al. Reumatologia 2005; 21(3)), gout, rheumatoid arthritis (Gabay C et al. Arthritis Research & Therapy 2009, 11:230; Schett G. et al. Nat Rev Rheumatol. 2016 January; 12(1):14-24.), Crohn's disease (Jung Mogg Kim Korean J Gastroenterol Vol. 58 No. 6, 300-310), COPD (Mortaz E. et al. Tanaffos. 2011; 10(2): 9-14.), fibrosis (Gasse P. et al. Am J Respir Crit Care Med. 2009 May 15; 179(10):903-13), obesity, type 2 diabetes ((Dinarello C A. et al. Curr Opin Endocrinol Diabetes Obes. 2010 August; 17(4):314-21)) multiple sclerosis (see EAE-model in Coll R C. et al. Nat Med. 2015 March; 21(3):248-55) and many others (Martinon F. et al. Immunol. 2009. 27:229-65) like Parkinson disease or Alzheimer disease (Michael T. et al. Nature 493, 674-678 (31 Jan. 2013); Halle A. et al., Nat Immunol. 2008 August; 9(8):857-65; Saresella M. et al. Mol Neurodegener. 2016 Mar. 3; 11:23) and even some oncological disorders.

Suitably, the compounds according to the present disclosure can be used for the treatment of a disease selected from the group consisting of an autoinflammatory disease, an autoimmune disease, a neurodegenerative disease and cancer. Said autoinflammatory and autoimmune disease is suitably selected from the group consisting of a cryopyrin-associated autoinflammatory syndrome (CAPS) such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID), familial Mediterranean fever and nonalcoholic fatty liver disease (NAFLD), gout, rheumatoid arthritis, Crohn's disease, COPD, fibrosis, obesity, type 2 diabetes, multiple sclerosis and neuroinflammation occurring in protein misfolding diseases, such as Prion diseases. Said neurodegenerative disease is suitably selected from Parkinson's disease and Alzheimer's disease.

Accordingly, the compounds of the present disclosure can be used for the treatment of a disease selected from the group consisting of cryopyrin-associated autoinflammatory syndrome (CAPS) such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID), familial Mediterranean fever, gout, rheumatoid arthritis, Crohn's disease, COPD, fibrosis, obesity, type 2 diabetes, multiple sclerosis, neuroinflammation occurring in protein misfolding diseases, such as Prion diseases, Parkinson's disease, Alzheimer's disease and oncological disorders.

Treatment in Cancer; Links with Inflammasome

Chronic inflammation responses have long been observed to be associated with various types of cancer. During malignant transformation or cancer therapy inflammasomes may become activated in response to danger signals and this activation may be both beneficial and detrimental in cancer.

IL-1β expression is elevated in a variety of cancers (including breast, prostate, colon, lung, head and neck cancers and melanomas) and patients with IL-1β producing tumours generally have a worse prognosis (Lewis, Anne M., et al. "Interleukin-1 and cancer progression: the emerging role of interleukin-1 receptor antagonist as a novel therapeutic agent in cancer treatment." Journal of translational medicine 4.1 (2006): 48).

Cancers derived from epithelial cells (carcinoma) or epithelium in glands (adenocarcinoma) are heterogeneous; consisting of many different cell types. This may include fibroblasts, immune cells, adipocytes, endothelial cells and pericytes amongst others, all of which may be cytokine/chemokine secreting (Grivennikov, Sergei I., Florian R. Greten, and Michael Karin. "Immunity, inflammation, and cancer." Cell 140.6 (2010): 883-899). This can lead to cancer-associated inflammation through the immune cell infiltration. The presence of leukocytes in tumours is known but it has only recently become evident that an inflammatory microenvironment is an essential component of all tumours. Most tumours (>90%) are the result of somatic mutations or environmental factors rather than germline mutations and many environmental causes of cancer are associated with chronic inflammation (20% of cancers are related to chronic infection, 30% to smoking/inhaled pollutants and 35% to dietary factors (20% of all cancers are linked to obesity)) (Aggarwal, Bharat B., R. V. Vijayalekshmi, and Bokyung Sung. "Targeting inflammatory pathways for prevention and therapy of cancer: short-term friend, long-term foe." Clinical Cancer Research 15.2 (2009): 425-430).

GI Cancer

Cancers of the gastrointestinal (GI) tract are frequently associated with chronic inflammation. For example, *H. pylori* infection is associated with gastric cancer (Amieva, Manuel, and Richard M. Peek. "Pathobiology of *Helicobacter pylori*-Induced Gastric Cancer." Gastroenterology 150.1 (2016): 64-78). Colorectal cancer is associated with inflammatory bowel disease (Bernstein, Charles N., et al. "Cancer risk in patients with inflammatory bowel disease." Cancer 91.4 (2001): 854-862). Chronic inflammation in stomach leads to the upregulation of IL-1 and other cytokines (Basso D, et al., (1996) *Helicobacter pylori* infection enhances mucosal interleukin-1 beta, interleukin-6, and the soluble receptor of interleukin-2 Int J Clin Lab Res 26:207-210) and polymorphisms in IL-1β gene can increase risk of gastric cancer (Wang P, et al., (2007) Association of interleukin-1 gene polymorphisms with gastric cancer: a meta-analysis. Int J Cancer 120:552-562).

In 19% of gastric cancer cases, caspase-1 expression is decreased which correlates with stage, lymph node metastasis and survival (Jee et al., 2005). Mycoplasma hyorhinis is associated with the development of gastric cancer its activation of the NLRP3 inflammasome may be associated with its promotion of gastric cancer metastasis (Xu et al., 2013).

Skin Cancers

Ultraviolet radiation is the greatest environmental risk for skin cancer which is promoted by causing DNA damage, immunosuppression and inflammation. The most malignant skin cancer, melanoma, is characterised by the upregulation of inflammatory cytokines, all of which can be regulated by IL-1β (Lazar-Molnar, Eszter, et al. "Autocrine and paracrine regulation by cytokines and growth factors in melanoma." Cytokine 12.6 (2000): 547-554). Systemic inflammation induces an enhancement of melanoma cell metastasis and growth by IL-1-dependent mechanisms in vivo. Using thymoquinone inhibition of metastasis in a B16F10 mouse melanoma model was shown to be dependent on inhibition of the NLRP3 inflammasome (Ahmad, Israr, et al. "Thymoquinone suppresses metastasis of melanoma cells by inhibition of NLRP3 inflammasome." Toxicology and applied pharmacology 270.1 (2013): 70-76).

Glioblastoma

NLRP3 contributes to radiotherapy resistance in glioma. Ionising radiation can induce NLRP3 expression whereas NLRP3 inhibition reduced tumour growth and prolonged mouse survival following radiation therapy. NLRP3 inflammasome inhibition can therefore provide a therapeutic strategy for radiation-resistant glioma (Li, Lianling, and Yuguang Liu. "Aging-related gene signature regulated by Nlrp3 predicts glioma progression." American journal of cancer research 5.1 (2015): 442).

Metastasis

More widely, NLRP3 is considered by the applicants to be involved in the promotion of metastasis and consequently modulation of NLRP3 should plausibly block this. IL-1 is involved in tumour genesis, tumour invasiveness, metastasis, tumour host interactions (Apte, Ron N., et al. "The involvement of IL-1 in tumorigenesis, tumor invasiveness, metastasis and tumor-host interactions." Cancer and Metastasis Reviews 25.3 (2006): 387-408) and angiogenesis (Voronov, Elena, et al. "IL-1 is required for tumor invasiveness and angiogenesis." Proceedings of the National Academy of Sciences 100.5 (2003): 2645-2650).

The IL-1 gene is frequently expressed in metastases from patients with several types of human cancers. For example, IL-1mRNA was highly expressed in more than half of all tested metastatic human tumour specimens including specifically non-small-cell lung carcinoma, colorectal adenocarcinoma, and melanoma tumour samples (Elaraj, Dina M., et al. "The role of interleukin 1 in growth and metastasis of human cancer xenografts." Clinical Cancer Research 12.4 (2006): 1088-1096) and IL-1RA inhibits xenograft growth in IL-1 producing tumours but without anti-proliferative effects in vitro.

Further, IL-1 signalling is a biomarker for predicting breast cancer patients at increased risk for developing bone metastasis. In mouse models IL-10 and its receptor are upregulated in breast cancer cells that metastasise to bone compared with cells that do not. In a mouse model the IL-1 receptor antagonist anakinra reduced proliferation and angiogenesis in addition to exerting significant effects on the tumour environment reducing bone turnover markers, IL-10 and TNF alpha (Holen, Ingunn, et al. "IL-1 drives breast cancer growth and bone metastasis in vivo." Oncotarget (2016).

IL-18 induced the production of MMP-9 in the human leukaemia cell line HL-60, thus favouring degradation of the extracellular matrix and the migration and invasiveness of cancer cells (Zhang, Bin, et al. "IL-18 increases invasiveness of HL-60 myeloid leukemia cells: upregulation of matrix metalloproteinases-9 (MMP-9) expression." Leukemia research 28.1 (2004): 91-95). Additionally IL-18 can support the development of tumour metastasis in the liver by inducing expression of VCAM-1 on hepatic sinusoidal endothelium (Carrascal, Maria Teresa, et al. "Interleukin-18 binding protein reduces b16 melanoma hepatic metastasis by neutralizing adhesiveness and growth factors of sinusoidal endothelium." Cancer Research 63.2 (2003): 491-497).

CD36

The fatty acid scavenger receptor CD36 serves a dual role in priming gene transcription of pro-IL-10 and inducing assembly of the NLRP3 inflammasome complex. CD36 and the TLR4-TLR6 heterodimer recognize oxLDL, which initiates a signaling pathway leading to transcriptional upregulation of NLRP3 and pro-IL-1β (signal 1). CD36 also mediates the internalisation of oxLDL into the lysosomal compartment, where crystals are formed that induce lysosomal rupture and activation of the NLRP3 inflammasome (signal 2) (Kagan, J. and Horng T., "NLRP3 inflammasome activation: CD36 serves double duty." Nature Immunology 14.8 (2013): 772-774).

A subpopulation of human oral carcinoma cells express high levels of the fatty acid scavenger receptor CD36 and are unique in their ability to initiate metastasis. Palmitic acid or a high fat diet boosted the metastatic potential of the CD36+ cells. Neutralising anti-CD36 antibodies blocked metastasis in orthotopic mouse models of human oral cancer. The presence of CD36+ metastasis-initiating cells correlates with a poor prognosis for numerous types of carcinomas. It is suggested that dietary lipids may promote metastasis (Pasqual, G, Avgustinova, A., Mejetta, S, Martin, M, Castellanos, A, Attolini, CS-O, Berenguer, A., Prats, N, Toll, A, Hueto, JA, Bescos, C, Di Croce, L, and Benitah, S A. 2017 "Targeting metastasis-initiating cells through the fatty acid receptor CD36" Nature 541:41-45).

In hepatocellular carcinoma exogenous palmitic acid activated an epithelial-mesenchymal transition (EMT)-like program and induced migration that was decreased by the CD36 inhibitor, sulfo-N-succinimidyl oleate (Nath, Aritro, et al. "Elevated free fatty acid uptake via CD36 promotes epithelial-mesenchymal transition in hepatocellular carcinoma." Scientific reports 5 (2015). Body mass index was not associated with the degree of EMT highlighting that it is actually CD36 and free fatty acids that are important.

Cancer stems cells (CSCs) use CD36 to promote their maintenance. Oxidised phospholipids, ligands of CD36, were present in glioblastoma and the proliferation of CSCs but not non-CSCs increased with exposure to oxidised LDL. CD36 also correlated with patient prognosis.

Chemotherapy Resistance

In addition to direct cytotoxic effects, chemotherapeutic agents harness the host immune system which contributes to anti-tumour activity. However, gemcitabine and 5-FU were shown to activate NLRP3 in myeloid-derived suppressor cells leading to production of IL-1β which curtails anti-tumour efficacy. Mechanistically these agents destabilised the lysosome to release cathepsin B to activate NLRP3. IL-1β drove the production of IL-17 from CD4+ T cells which in turn blunted the efficacy of the chemotherapy. Higher anti-tumoral effects for both gemcitabine and 5-FU were observed when tumours were established in NLRP3$^{-/-}$ or Caps1$^{-/-}$ mice, or WT mice treated with IL-1RA. Myeloid-derived suppressor cell NLRP3 activation therefore limits the anti-tumour efficacy of gemcitabine and 5-FU (Bruchard, Melanie, et al. "Chemotherapy-triggered cathepsin B release in myeloid-derived suppressor cells activates the Nlrp3 inflammasome and promotes tumor growth." Nature medicine 19.1 (2013): 57-64.). Compounds of the present disclosure may therefore be useful in chemotherapy to treat a range of cancers.

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e., by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure may need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardisation of in vitro and in vivo test systems for the evaluation of the effects of inhibitors of inflammasome in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

Routes of Administration

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The disclosure having been described, the following examples are offered by way of illustration and not limitation.

EXAMPLES

Abbreviations

ACN Acetonitrile
aq. Aqueous
AP atmospheric pressure
Ar Argon
DCM Dichloromethane
DMF N,N-dimethylformamide
DMSO-d6 Hexadeuterodimethylsulfoxide
eq. Equivalents
MS ES+ Positive electrospray ionization mass spectroscopy
EtOAc ethyl acetate
FCC flash column chromatography
HPLC high performance liquid chromatography
Min Minutes
NaHMDS Sodium hexamethyldisilylazide
RM reaction mixture
rt room temperature
sat. Saturated
SM starting material
TEA Triethylamine
TFA trifluoroacetic acid
THF Tetrahydrofuran
TLC thin layer chromatography
Y Yield General Procedure A

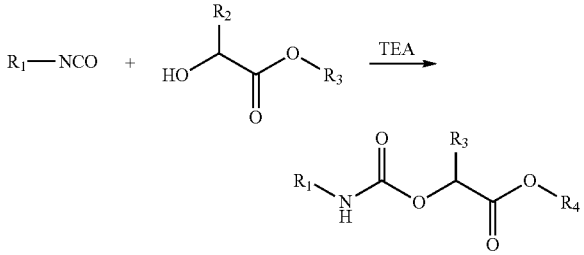

The α-hydroxy ester or α-hydroxy acid (1 eq.) was dissolved in ACN (2 ml/mmol of α-hydroxy ester or α-hydroxy acid) and the solution was cooled down to 0° C. TEA (1 eq.) was added followed by dropwise addition of the isocyanate (1.2 eq.). The reaction mixture was allowed to warm up to room temperature and stirring was continued for 15 h under Ar. The reaction mixture was diluted with DCM and the solution was washed with 1M HCl. The aqueous layer was extracted twice with DCM and the combined organic layers were dried over anhydrous sodium sulfate and concentrated under reduced pressure. The crude product was purified by FCC (DCM or EtOAc gradient in hexane) or by preparative reverse-phase HPLC (ACN water, 0.1% formic acid buffer).

General Procedure B

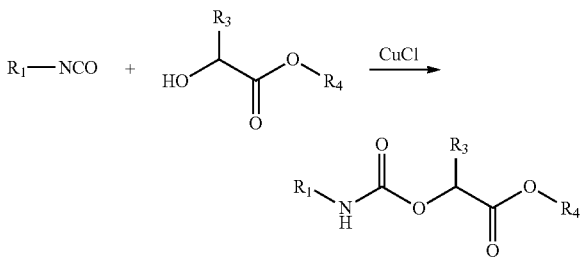

The α-hydroxy ester (1 eq.), isocyanate (1.1 eq.), CuCl (1 eq.), DMF (4 ml/mmol of α-hydroxy ester, degassed beforehand by bubbling Ar for 20 minutes) were mixed and stirred at room temperature for 15 h under Ar. The mixture was then poured into water, and the resulting precipitate was filtered off and washed with water. It was re-dissolved in MeOH and the solution was evaporated. The residue was dissolved in DCM, dried over anhydrous sodium sulfate and filtered on a pad of alumina. The filtering bed was washed with EtOAc and the filtrate evaporated. The residue was purified by FCC (DCM or EtOAc gradient in hexane) to give the desired product.

General Procedure C

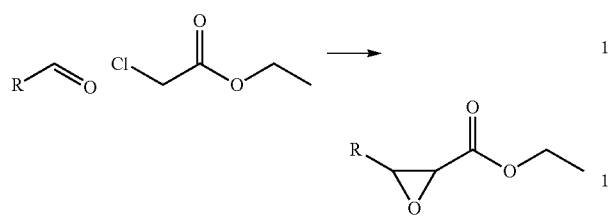

A solution of 1.0 M NaHMDS in THF (1 eq.) was added dropwise to a stirred solution of aldehyde (1 eq.) and ethyl chloroacetate (1 eq.) in dry THF (3 ml/mmol of aldehyde) under argon atmosphere at −78° C. The reaction was stirred at −78° C. for 30 min, warmed to 0° C., quenched with water and concentrated. The residue was partitioned between diethyl ether and water and the aqueous layer was extracted twice with diethyl ether. The combined organic fractions were washed with brine, dried over anhydrous sodium sulfate and concentrated. The crude product was used in the next step without further purification.

General Procedure D

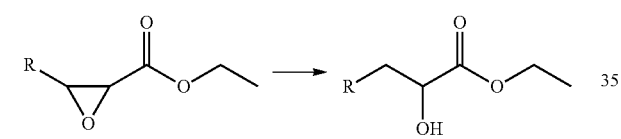

The oxirane (1 eq.) was dissolved in EtOAc (10 ml/mmol of oxirane) and 10% Pd/C (10% by weight relative to the oxirane) was added. The reaction mixture was stirred at rt under hydrogen atmosphere (AP) overnight. The reaction mixture was filtered through a Celite pad, the filtering bed was washed with EtOAc and the filtrate was concentrated under reduced pressure. The crude product was used in next step without further purification.

General Procedure E

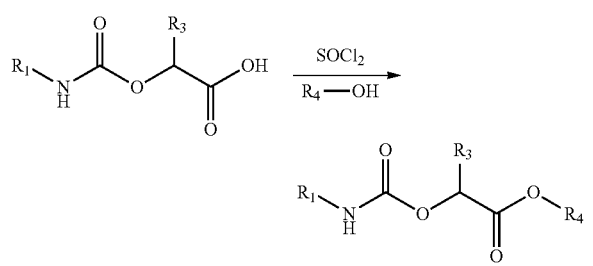

The carboxylic acid (1 eq.) was dissolved in the alcohol $R^3$—OH (6 ml/mmol of acid) and the solution was cooled to 0° C. under Ar. Thionyl chloride (1.5 eq.) was added dropwise at 0° C. and the reaction mixture was stirred at room temperature for 15 h under Ar. It was then evaporated to dryness and co-evaporated with cyclohexane (twice). The residue was purified by trituration in Et2O/hexane or by FCC (0 to 20% EtOAc in hexane).

Example 1. Synthesis of Intermediates

4-Isocyanato-1,2,3,5,6,7-hexahydro-s-indacene (Intermediate A)

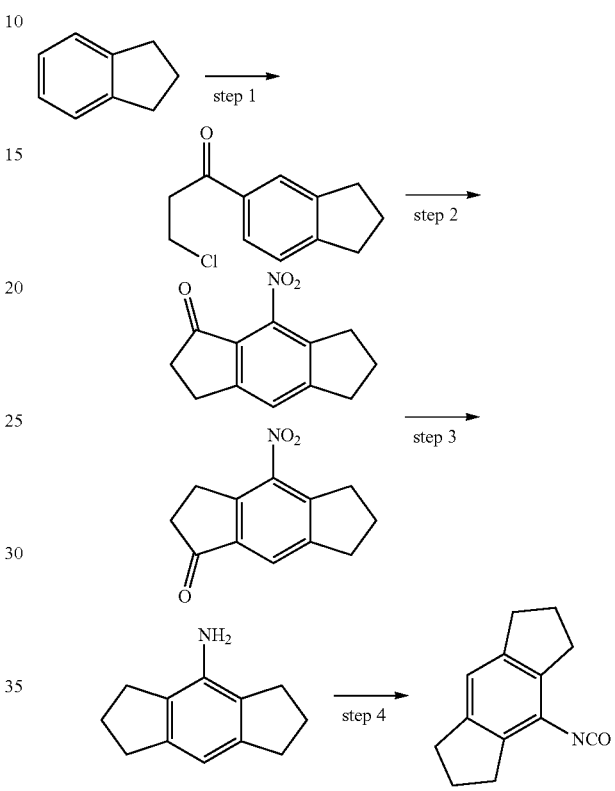

Step 1. 3-Chloro-1-(2,3-dihydro-1H-inden-5-yl)propan-1-one. A suspension of aluminium chloride (12.4 g, 93 mmol, 1 eq.) in DCM (50 ml) under an argon atmosphere was cooled to −10° C. with vigorous stirring. To this was added a solution of 3-chloropropionyl chloride (11 g, 93 mmol 1 eq.) and indane (10 g, 85 mmol, 0.9 eq.) in DCM (15 ml), dropwise over 0.5 h, keeping the temperature between −15° C. and −5° C. The reaction was allowed to warm to rt and stirred overnight. The reaction mixture was added dropwise to cold (0° C.) 2 M HCl over 30 min maintaining the temperature between 0° C. and 10° C. The layers were separated and the aqueous phase was extracted with DCM (3×30 ml). The combined organic layers were washed sequentially with water, saturated sodium bicarbonate and brine. The organic phase was dried over $Na_2SO_4$, filtered and evaporated under reduced pressure to around 30 ml. Hexane (50 ml) was added and the evaporation continued, the procedure was repeated twice. After further addition of hexane (50 ml) the slurry was filtered and dried to provide 3-chloro-1-(2,3-dihydro-1H-inden-5-yl)propan-1-one as a tan solid. Y=81%. $^1$H NMR (400 MHz, DMSO-$d_6$) δ 7.84 (d, 1H), 7.78-7.76 (m, 1H), 7.37 (d, J=8 Hz, 1H), 3.92 (t, J=6 Hz, 2H), 3.51 (t, J=6 Hz, 2H), 2.92 (t, J=8 Hz, 4H), 2.09-2.01 (m, 2H).

Step 2. 8-nitro-1,2,3,5,6,7-hexahydro-s-indacen-1-one and 4-nitro-1,2,3,5,6,7-hexahydro-s-indacen-1-one. 3-Chloro-1-(2,3-dihydro-1H-inden-5-yl)propan-1-one (82 g, 0.39 mol, 1 eq.) was added portion wise to concentrated sulfuric acid (71 ml, 1.34 mol, 3.4 eq.). The resulting mixture was heated to 60° C. for 2 days. The RM was cooled to 0° C. and a mixture of nitric acid (26 ml, 0.59 mol, 1.5 q.) and concentrated sulfuric acid (26 ml, 0.49 mol, 1.25 eq.) was added dropwise. The RM was stirred for 1 h, maintaining temperature between 0° C. and 5° C. The RM was slowly added to a mixture of water and DCM with ice bath cooling. The layers were separated and the aqueous layer was extracted with DCM. The combined organic layers were washed sequentially with brine and saturated sodium bicarbonate. The organic layers were dried over $Na_2SO_4$ and filtered. The crude mixture was purified by FCC (hexane/ethyl acetate). The desired products were further purified by crystallisation from MeOH. 8-Nitro-1,2,3,5,6,7-hexahydro-s-indacen-1-one: Y=36%. MS ES$^+$: 218. $^1$H NMR (400 MHz, DMSO-d$_6$) δ 7.67 (s, 1H), 3.15-3.08 (m, 2H), 3.04 (t, J=8 Hz, 2H), 2.90 (t, J=8 Hz, 2H), 2.77-2.71 (m, 2H), 2.17-2.10 (m, 2H). 4-Nitro-1,2,3,5,6,7-hexahydro-s-indacen-1-one: Y=5%. MS ES$^+$: 218. $^1$H NMR (400 MHz, DMSO-d$_6$) δ 7.82 (s, 1H), 3.41-3.36 (m, 2H), 3.34-3.29 (m, 3H), 3.02 (t, J=8 Hz, 2H), 2.77-2.69 (m, 2H), 2.17-2.10 (m, 2H).

Step 3. 1,2,3,5,6,7-Hexahydro-s-indacen-4-amine. A mixture of 8-nitro-1,2,3,5,6,7-hexahydro-s-indacen-1-one and 4-nitro-1,2,3,5,6,7-hexahydro-s-indacen-1-one (7.00 g, 32 mmol, 1 eq.) was suspended in MeOH (70 ml). The solution was treated with 20% palladium hydroxide on carbon (50% water wet. 1.72 g, 12 mmol, 0.4 eq.) and methanesulfonic acid (3.41 g, 35 mmol, 1.1 eq.). The mixture was hydrogenated at 35 psi for 5 h. The catalyst was removed by filtration over a pad of Celite and the filtering bed was washed with MeOH. The filtrate was diluted with water (350 ml) and the pH adjusted to 11 with 2 M NaOH. The resulting slurry was filtered and the crude solid was recrystallised from MeOH/water (9:1) to afford of 1,2,3,5,6,7-hexahydro-s-indacen-4-amine as colourless needles. Y=73%. MS ES$^+$: 174.1. $^1$H NMR (400 MHz, DMSO-d$_6$) δ 6.35 (s, 1H), 4.52 (s, 2H), 2.72 (t, J=7 Hz, 4H), 2.59 (t, J=7 Hz, 4H), 2.00-1.93 (m, 4H).

Step 4. 4-Isocyanato-1,2,3,5,6,7-hexahydro-s-indacene (Intermediate A). To a stirred solution of 1,2,3,5,6,7-hexahydro-s-indacen-4-amine (1.1 g, 6.35 mmol, 1 eq.) and TEA (0.973 ml, 6.98 mmol, 1.1 eq.) in THF (20 ml) was added triphosgene (0.64 g, 2.16 mmol, 3 eq.) in one portion. The mixture was heated to reflux for 4 h and cooled to rt. The THF was evaporated and the residue was taken up in pentane and filtered through a plug of silica gel. Evaporation of the solvent in vacuo afforded 4-isocyanato-1,2,3,5,6,7-hexahydro-s-indacene as a white solid. Y=71%. $^1$H NMR (400 MHz, Chloroform-d) δ 6.96 (s, 1H), 2.94-2.89 (m, 8H), 2.22-2.03 (m, 4H).

2-{[(1,2,3,5,6,7-Hexahydro-s-indacen-4-yl)carbamoyl]oxy}acetic acid (Intermediate B)

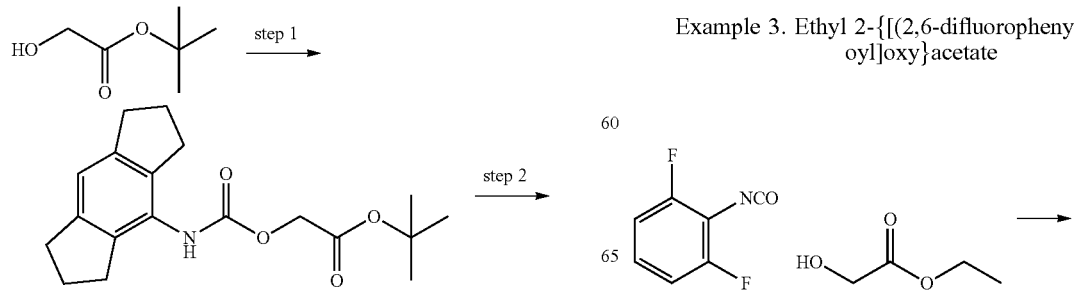

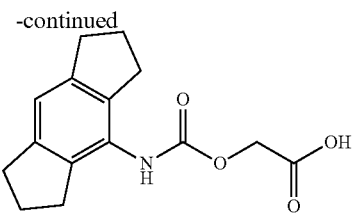

Step 1: tert-butyl 2-{[(1,2,3,5,6,7-hexahydro-s-indacen-4-yl)carbamoyl]oxy}acetate The title compound was prepared according to the General procedure A using tert-butyl glycolate and intermediate A as starting materials. The crude product was purified by FCC (0 to 100% DCM in hexane). Y=65%. MS ES$^+$ ([M+Na]$^+$): 354.4. $^1$H NMR (400 MHz, DMSO-d$_6$) δ 9.13 (s, 1H), 6.95 (s, 1H), 4.48 (s, 2H), 2.81 (t, J=7 Hz, 4H), 2.72 (t, J=7 Hz, 4H), 2.03-1.91 (m, 4H), 1.43 (s, 9H).

Step 2: 2-{[(1,2,3,5,6,7-hexahydro-s-indacen-4-yl)carbamoyl]oxy}acetic acid. Tert-butyl 2-{[(1,2,3,5,6,7-hexahydro-s-indacen-4-yl)carbamoyl]oxy}acetate (1.75 g, 5.28 mmol) was dissolved in a 20% solution of TFA in DCM (100 ml). The reaction mixture was stirred at rt for 2 h and evaporated to dryness. The residue was co-evaporated twice with cyclohexane and triturated with hexane. The resulting white powder was filtered off, washed with hexane and dried under vacuum. Y=96%. MS ES$^+$: 276.1. $^1$H NMR (300 MHz, DMSO-d$_6$) δ 12.88 (s, 1H), 9.09 (s, 1H), 6.95 (s, 1H), 4.52 (s, 2H), 2.81 (t, J=7 Hz, 4H), 2.71 (t, J=7 Hz, 4H), 2.04-1.89 (m, 4H).

Example 2. Ethyl 2-{[(1,2,3,5,6,7-hexahydro-s-indacen-4-yl)carbamoyl]oxy}acetate

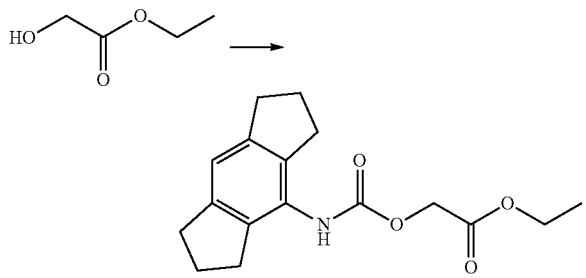

The title compound was prepared according to the General procedure A using ethyl 2-hydroxyacetate and Intermediate A as starting materials. The crude product was purified by FCC (0 to 100% DCM in hexane). Y=40%. MS ES$^+$ ([M+Na]$^+$): 326.2. $^1$H NMR (300 MHz, DMSO-d$_6$) δ 9.19 (s, 1H), 6.95 (s, 1H), 4.62 (s, 2H), 4.18-4.11 (m, 2H), 2.80 (t, J=7 Hz, 4H), 2.70 (t, J=7 Hz, 4H), 2.05-1.88 (m, 4H), 1.21 (t, J=7 Hz, 3H).

Example 3. Ethyl 2-{[(2,6-difluorophenyl)carbamoyl]oxy}acetate

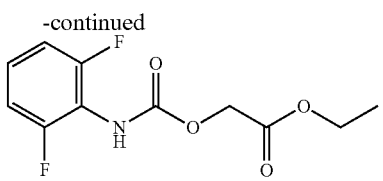

The title compound was prepared according to the General procedure A using ethyl 2-hydroxyacetate and 1,3-difluoro-2-isocyanatobenzene as starting materials. The crude product was purified by FCC (0 to 100% DCM in hexane). Y=28%. MS ES⁺ ([M+Na]⁺): 282.0. ¹H NMR (400 MHz, Chloroform-d) δ 7.28-7.19 (m, 1H), 7.03-6.94 (m, 2H), 6.34 (s, 1H), 4.72 (s, 2H), 4.30-4.25 (m, 2H), 1.32 (t, J=7 Hz, 3H).

Example 4. Ethyl 2-{[(2,6-dichlorophenyl)carbamoyl]oxy}acetate

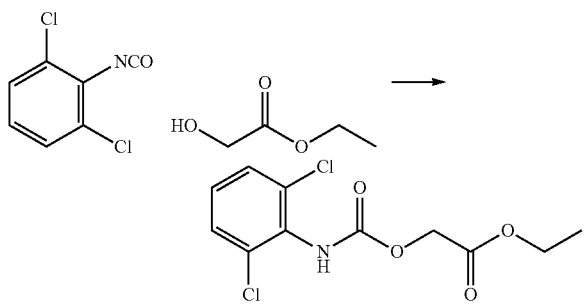

The title compound was prepared according to the General procedure A using ethyl 2-hydroxyacetate and 1,3-dichloro-2-isocyanatobenzene as starting materials. The crude product was purified by FCC (0 to 25% EtOAc in hexane). Y=65%. MS ES⁺ ([M+Na]⁺): 314.5. ¹H NMR (400 MHz, Chloroform-d) δ 7.40 (d, J=8 Hz, 2H), 7.21 (t, J=7 Hz, 1H), 6.54 (s, 1H), 4.72 (s, 2H), 4.30-4.25 (m, 2H), 1.32 (t, J=7 Hz, 3H).

Example 5. Ethyl 2-{[(naphthalen-1-yl)carbamoyl]oxy}acetate

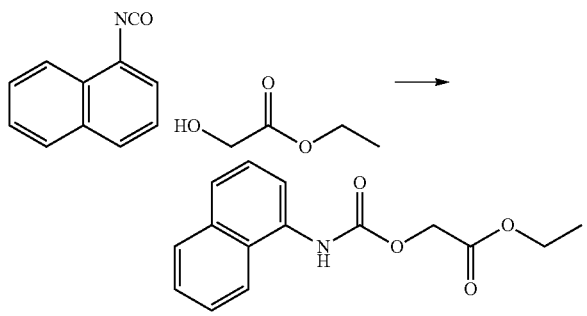

The title compound was prepared according to the General procedure A using ethyl 2-hydroxyacetate and 1-isocyanatonaphthalene as starting materials. The crude product was purified by FCC (0 to 25% EtOAc in hexane). Y=96%. MS ES⁺ ([M+Na]⁺): 296.1. ¹H NMR (400 MHz, Chloroform-d) δ 7.95 (d, J=8 Hz, 1H), 7.92-7.83 (m, 2H), 7.73 (d, J=8 Hz, 1H), 7.61-7.47 (m, 3H), 7.15 (s, 1H), 4.76 (s, 2H), 4.33-4.28 (m, 2H), 1.34 (t, J=7 Hz, 3H).

Example 6. Ethyl 2-{[(2,2-dimethyl-2,3-dihydro-1-benzofuran-7-yl)carbamoyl]oxy}acetate

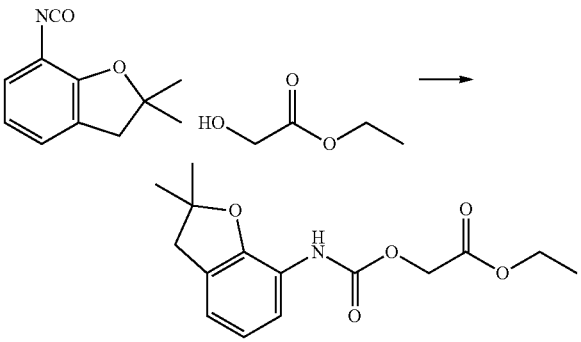

The title compound was prepared according to the General procedure A using ethyl 2-hydroxyacetate and 7-isocyanato-2,2-dimethyl-2,3-dihydro-1-benzofuran as starting materials. The crude product was purified by FCC (0 to 20% EtOAc in hexane). Y=74%. MS ES⁺ ([M+Na]⁺): 316.2. ¹H NMR (400 MHz, DMSO-d₆) δ 8.98 (s, 1H), 7.21 (d, J=8 Hz, 1H), 6.99-6.94 (m, 1H), 6.75 (t, J=8 Hz, 1H), 4.63 (s, 2H), 4.18-4.12 (m, 2H), 3.02 (s, 2H), 1.43 (s, 6H), 1.21 (t, J=7 Hz, 3H).

Example 7. Ethyl 2-{[(1,2,3,5,6,7-hexahydro-s-indacen-4-yl)carbamoyl]oxy}-3-methoxypropanoate

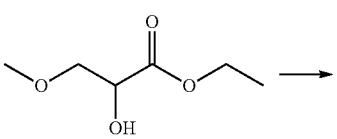

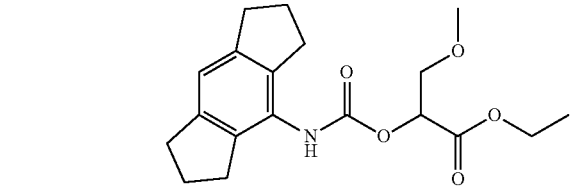

The title compound was prepared according to the General procedure A using ethyl 2-hydroxy-3-methoxypropanoate and intermediate A as starting materials. The crude product was purified by FCC (0 to 25% EtOAc in hexane). Y=54%. MS ES⁺ ([M+Na]⁺): 370.6 ¹H NMR (400 MHz, DMSO-d₆) δ 9.26 (s, 1H), 6.95 (s, 1H), 5.15-5.00 (m, 1H), 4.22-4.09 (m, 2H), 3.87-3.62 (m, 2H), 3.31 (d, J=4 Hz, 3H), 2.81 (t, J=7 Hz, 4H), 2.71 (t, J=7 Hz, 4H), 2.03-1.92 (m, 4H), 1.21 (t, J=7 Hz, 3H).

Example 8. Ethyl 2-({[2-fluoro-5-(trifluoromethyl)phenyl]carbamoyl}oxy)acetate

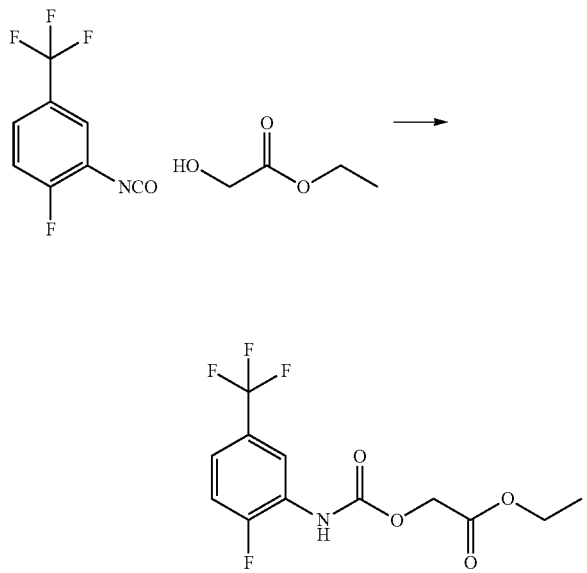

The title compound was prepared according to the General procedure A using ethyl 2-hydroxyacetate and 2-fluoro-5-(trifluoromethyl)phenyl isocyanate as starting materials. The crude product was purified by preparative TLC (20% EtOAc in hexane). Y=14%. MS ES$^+$ ([M+Na]$^+$): 332.5. $^1$H NMR (400 MHz, DMSO-d$_6$) δ 10.12 (s, 1H), 8.11-8.09 (m, 1H), 7.68-7.38 (m, 2H), 4.74 (s, 2H), 4.20-4.15 (m, 2H), 1.22 (t, J=7 Hz, 3H).

Example 9. Ethyl 2-{[(2,6-dimethylphenyl)carbamoyl]oxy}acetate

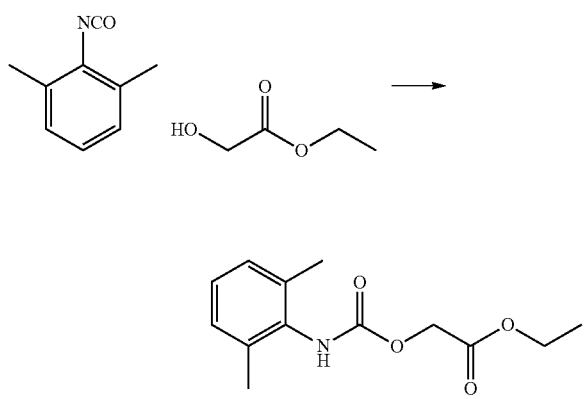

The title compound was prepared according to the General procedure A using ethyl 2-hydroxyacetate and 2,6-dimethylphenyl isocyanate as starting materials. The crude product was purified by FCC (0 to 20% EtOAc in hexane). Y=38%. MS ES$^+$ ([M+Na]$^+$): 274.1 $^1$H NMR (400 MHz, Chloroform-d) δ 7.11 (s, 3H), 6.26 (s, 1H), 4.70 (s, 2H), 4.30-4.25 (m, 2H), 2.32 (s, 6H), 1.32 (t, J=7 Hz, 3H).

Example 10. Ethyl 2-{[(2,6-diethylphenyl)carbamoyl]oxy}acetate

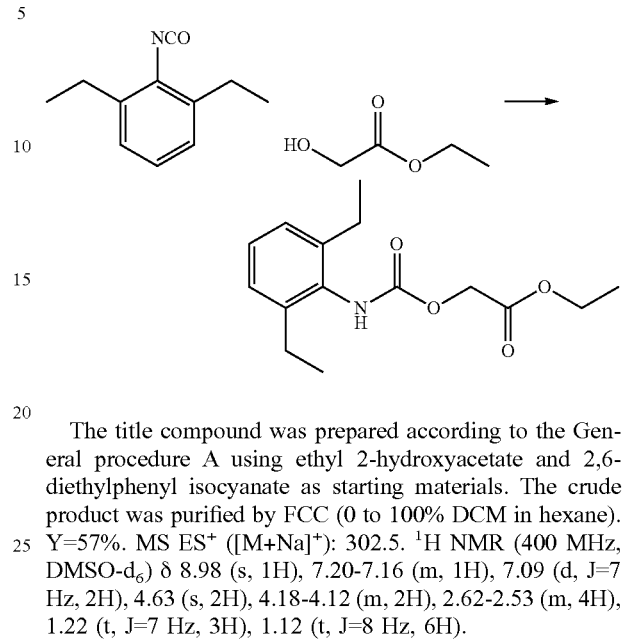

The title compound was prepared according to the General procedure A using ethyl 2-hydroxyacetate and 2,6-diethylphenyl isocyanate as starting materials. The crude product was purified by FCC (0 to 100% DCM in hexane). Y=57%. MS ES$^+$ ([M+Na]$^+$): 302.5. $^1$H NMR (400 MHz, DMSO-d$_6$) δ 8.98 (s, 1H), 7.20-7.16 (m, 1H), 7.09 (d, J=7 Hz, 2H), 4.63 (s, 2H), 4.18-4.12 (m, 2H), 2.62-2.53 (m, 4H), 1.22 (t, J=7 Hz, 3H), 1.12 (t, J=8 Hz, 6H).

Example 11. Ethyl 2-({[2-(chloro-6-methylphenyl)carbamoyl]oxy}acetate

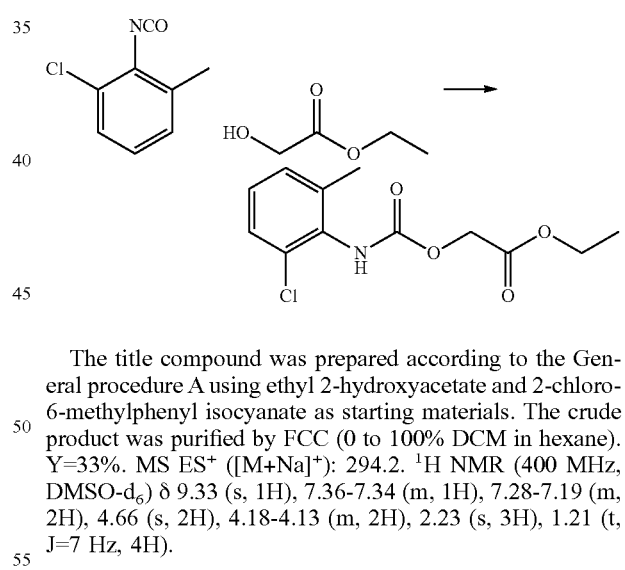

The title compound was prepared according to the General procedure A using ethyl 2-hydroxyacetate and 2-chloro-6-methylphenyl isocyanate as starting materials. The crude product was purified by FCC (0 to 100% DCM in hexane). Y=33%. MS ES$^+$ ([M+Na]$^+$): 294.2. $^1$H NMR (400 MHz, DMSO-d$_6$) δ 9.33 (s, 1H), 7.36-7.34 (m, 1H), 7.28-7.19 (m, 2H), 4.66 (s, 2H), 4.18-4.13 (m, 2H), 2.23 (s, 3H), 1.21 (t, J=7 Hz, 4H).

Example 12. Ethyl 2-{[(2-cyanophenyl)carbamoyl]oxy}acetate

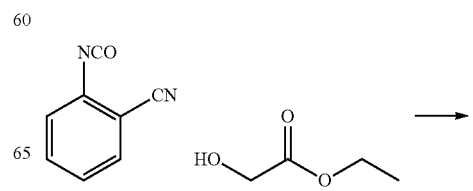

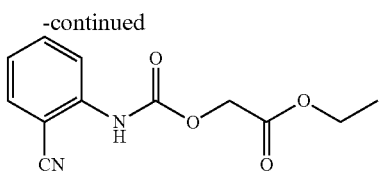

The title compound was prepared according to the General procedure A using ethyl 2-hydroxyacetate and 2-isocyanatobenzonitrile as starting materials. The crude product was purified by FCC (0 to 30% EtOAc in hexane). Y=21%. MS ES+ ([M+Na]+): 271.0. $^1$H NMR (400 MHz, Chloroform-d) δ 8.25 (d, J=8 Hz, 1H), 7.63-7.59 (m, 2H), 7.36 (s, 1H), 7.18 (t, J=8 Hz, 1H), 4.74 (s, 2H), 4.33-4.27 (m, 2H), 1.34 (t, J=7 Hz, 3H).

Example 13. Ethyl 2-{[(1,2,3,5,6,7-hexahydro-s-indacen-4-yl)carbamoyl]oxy}-3-(pyridin-3-yl)propanoate

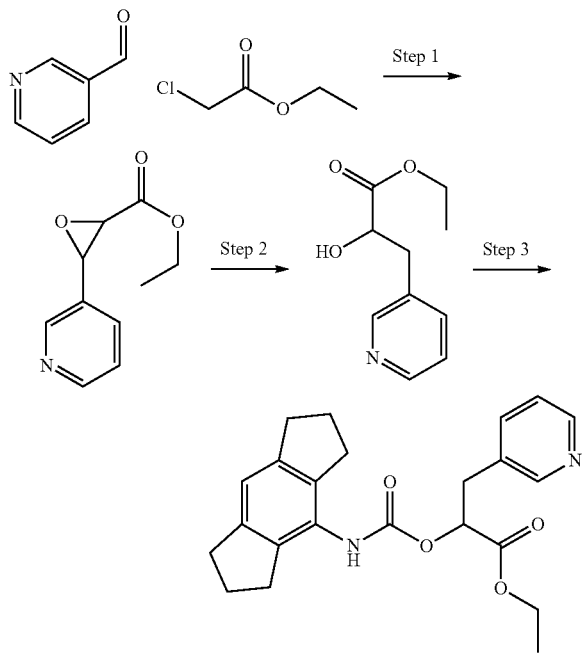

Step 1: Ethyl 3-(pyridin-3-yl)oxirane-2-carboxylate. The title compound was prepared according to the General procedure C using 3-pyridinecarboxaldehyde as starting material. Y=41%. MS ES+: 194.1. $^1$H NMR (300 MHz, Chloroform-d) δ 8.67-8.59 (m, 2H), 7.63-7.54 (m, 1H), 7.39-7.28 (m, 1H), 4.44-4.24 (m, 2H), 4.16 (d, J=2 Hz, 1H), 3.55 (d, J=2 Hz, 1H), 1.36 (t, J=7 Hz, 3H).

Step 2: Ethyl 2-hydroxy-3-(pyridin-3-yl)propanoate. The title compound was prepared according to the General procedure D using ethyl 3-(pyridin-3-yl)oxirane-2-carboxylate as starting material. Y=70%. MS ES+: 196.2. $^1$H NMR (300 MHz, Chloroform-d) δ 8.50 (d, J=6 Hz, 2H), 7.62 (d, J=8 Hz, 1H), 7.36-7.16 (m, 1H), 4.52-4.39 (m, 1H), 4.29-4.23 (m, 2H), 3.18-3.10 (m, 1H), 3.03-2.96 (m, 1H), 1.31 (t, J=7 Hz, 3H).

Step 3: Ethyl 2-{[(1,2,3,5,6,7-hexahydro-s-indacen-4-yl)carbamoyl]oxy}-3-(pyridin-3-yl)propanoate. The title compound was prepared according to the General procedure A using ethyl 2-hydroxy-3-(pyridin-3-yl)propanoate and Intermediate A as starting materials. The crude product was purified by reverse-phase preparative HPLC. Y=5%. MS ES+: 395.4. $^1$H NMR (300 MHz, DMSO-d$_6$) δ 9.15 (s, 1H), 8.52 (s, 1H), 8.46 (s, 1H), 7.75 (s, 1H), 7.36 (s, 1H), 6.95 (s, 1H), 5.31-5.05 (m, 1H), 4.13-4.06 (m, 2H), 3.24-3.08 (m, 2H), 2.80 (t, J=7 Hz, 4H), 2.71-2.56 (m, 4H), 2.09-1.78 (m, 4H), 1.14 (t, J=7 Hz, 3H).

Example 14. Ethyl 2-{[(2-tert-butylphenyl)carbamoyl]oxy}acetate

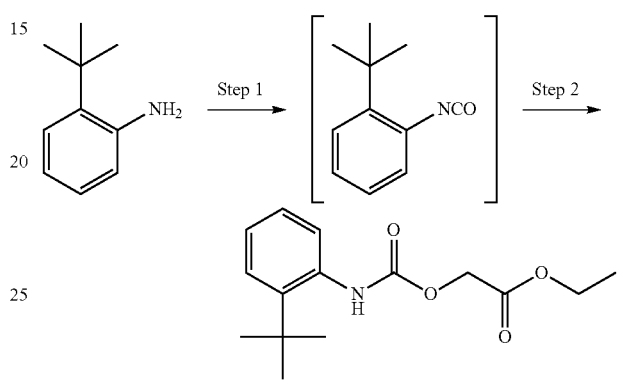

2-tert-Butylaniline (200 mg, 1.34 mmol, 1 eq.) was dissolved in anhydrous THF (10 ml) and TEA (0.224 ml, 1.61 mmol, 1.2 eq.) was added. The solution was treated with triphosgene (0.159 mg, 0.54 mmol, 0.4 eq.) and the resulting mixture was stirred at 60° C. for 4 h. The reaction mixture was cooled to 0° C. and ethyl glycolate (0.167 ml, 1.61 mmol, 1.2 eq.) and TEA (0.163 mg, 1.61 mmol, 1.2 eq.) were added. The reaction mixture was stirred at rt for 15 h, filtered through Celite and the filtering bed was washed with EtOAc. The filtrate was concentrated under reduced pressure and the residue was purified by FCC (0 to 20% EtOAc in hexane). Y=47%. MS ES+ ([M+Na]+): 302.6. $^1$H NMR (300 MHz, DMSO-d$_6$) δ 8.94 (s, 1H), 7.42-7.37 (m, 1H), 7.26-7.15 (m, 2H), 7.13-6.97 (m, 1H), 4.62 (s, 2H), 4.18-4.12 (m, 2H), 1.34 (s, 9H), 1.21 (t, J=7 Hz, 3H).

Example 15. Ethyl 2-((mesitylcarbamoyl)oxy)acetate

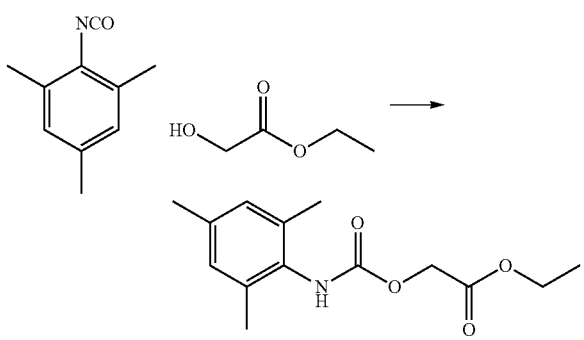

The title compound was prepared according to the General procedure A using ethyl glycolate and 2,4,6-trimethylphenyl isocyanate as starting materials. The crude product was purified by preparative TLC (20% EtOAc in hexane) and FCC (0 to 100% DCM in hexane). Y=57%. MS ES⁺ ([M+Na]⁺): 288.1. ¹H NMR (400 MHz, Chloroform-d) δ 6.92 (s, 2H), 6.19 (s, 1H), 4.70 (s, 2H), 4.30-4.24 (m, 2H), 2.29 (s, 9H), 1.32 (t, J=7 Hz, 3H).

Example 16. Ethyl 2-(((2-isopropylphenyl)carbamoyl)oxy)acetate

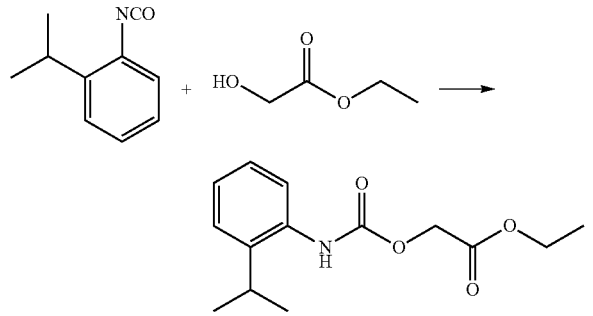

The title compound was prepared according to the General procedure A using ethyl glycolate and 2-isopropylphenyl isocyanate as starting materials. The crude product was purified by FCC (0 to 20% EtOAc in hexane). Y=49%. MS ES⁺ ([M+Na]⁺): 288.2. ¹H NMR (400 MHz, Chloroform-d) δ 7.73-7.63 (m, 1H), 7.32-7.29 (m, 1H), 7.25-7.17 (m, 2H), 6.64 (s, 1H), 4.71 (s, 2H), 4.31-4.25 (m, 2H), 3.17-3.03 (m, 1H), 1.33 (t, J=7 Hz, 3H), 1.28 (d, J=7 Hz, 6H)

Example 17. Ethyl 2-(((2-ethyl-6-methylphenyl)carbamoyl)oxy)acetate

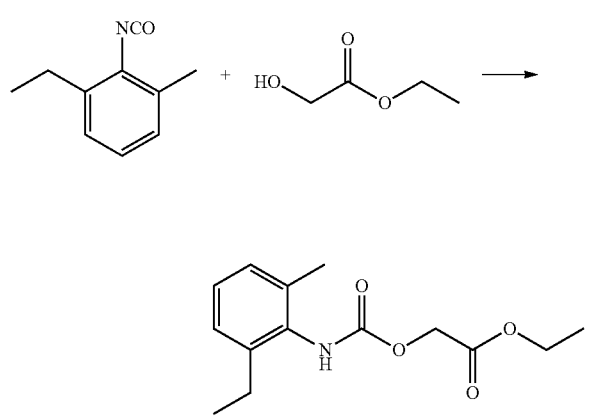

The title compound was prepared according to General procedure A using ethyl glycolate and 2-ethyl-6-methylphenyl isocyanate as starting materials. The crude product was purified by FCC (0 to 20% EtOAc in hexane) followed by preparative TLC (100% DCM). Y=35%. MS ES⁺ ([M+Na]⁺): 288.2. ¹H NMR (400 MHz, DMSO-d₆) major conformer: δ 9.00 (s, 1H), 7.16-7.10 (m, 1H), 7.10-7.06 (m, 2H), 4.64 (s, 2H), 4.18-4.12 (m, 2H), 2.59-2.52 (m, 2H), 2.17 (s, 3H), 1.21 (t, J=7 Hz, 3H), 1.11 (t, J=7 Hz, 3H).

Example 18. Ethyl 2-(((1,2,3,5,6,7-hexahydro-s-indacen-4-yl)carbamoyl)oxy)-3-phenylpropanoate

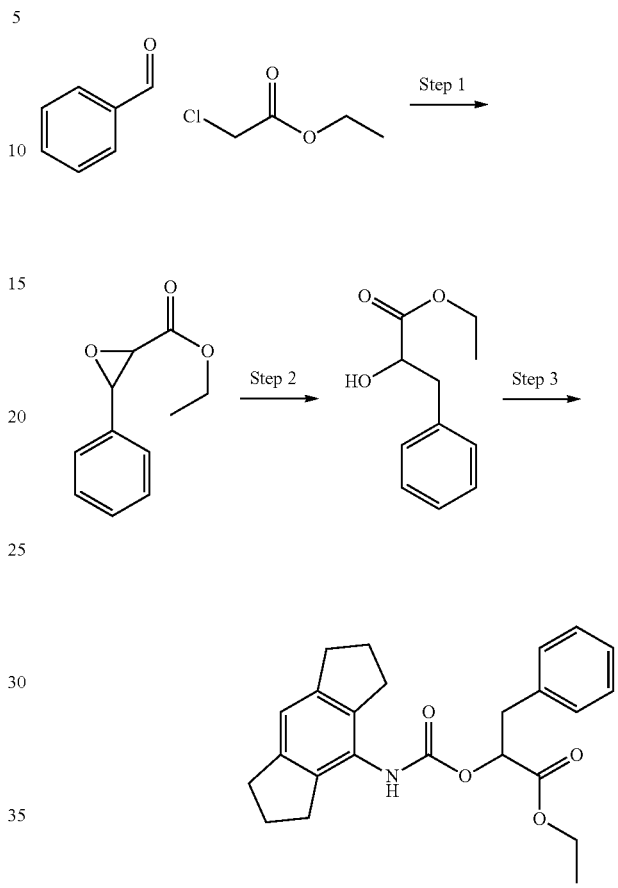

Step 1: Ethyl 3-phenyloxirane-2-carboxylate. The title compound was prepared according to the General procedure C using ethyl chloroacetate and benzaldehyde as starting materials. The crude product was purified by FCC (0 to 10% EtOAc in hexane). Y=45%. MS ES⁺ ([M+Na]⁺): 234.1. ¹H NMR (400 MHz, DMSO-d₆) δ 7.38 (s, 5H), 4.24-4.18 (m, 2H), 4.16 (d, J=2 Hz, 1H), 3.81 (d, J=2 Hz, 1H), 1.25 (t, J=7 Hz, 3H).

Step 2: Ethyl 2-hydroxy-3-phenylpropanoate. The title compound was prepared according to the General procedure D using ethyl 3-phenyloxirane-2-carboxylate as a starting material. Y=96%. MS ES⁻¹: 195.2. ¹H NMR (400 MHz, DMSO-d₆) δ 7.30-7.24 (m, 2H), 7.24-7.17 (m, 3H), 5.53 (d, J=6 Hz, 1H), 4.26-4.19 (m, 1H), 4.09-4.03 (m, 2H), 2.98-2.90 (m, 1H), 2.87-2.79 (m, 1H), 1.14 (t, J=7 Hz, 3H).

Step 3: Ethyl 2-(((1,2,3,5,6,7-hexahydro-s-indacen-4-yl)carbamoyl)oxy)-3-phenylpropanoate. The title compound was prepared according to the General procedure A using ethyl 2-hydroxy-3-phenylpropanoate and Intermediate A as starting materials. The crude was purified by two consecutive FCC purifications (0 to 100% DCM in hexane and 0 to 20% EtOAc in hexane). Y=21%. MS ES⁺ ([M+Na]⁺): 416.8. ¹H NMR (400 MHz, methanol-d₄) δ 7.40-7.03 (m, 5H), 6.97 (s, 1H), 5.26-5.09 (m, 1H), 4.21-4.15 (m, 2H), 3.28-3.09 (m, 2H), 2.97-2.82 (m, 4H), 2.80-2.53 (m, 4H), 2.12-1.94 (m, 4H), 1.23 (t, J=7 Hz, 3H).

Example 19. Ethyl 2-(((1,2,3,5,6,7-hexahydro-s-indacen-4-yl)carbamoyl)oxy)-3-(pyridin-2-yl)propanoate

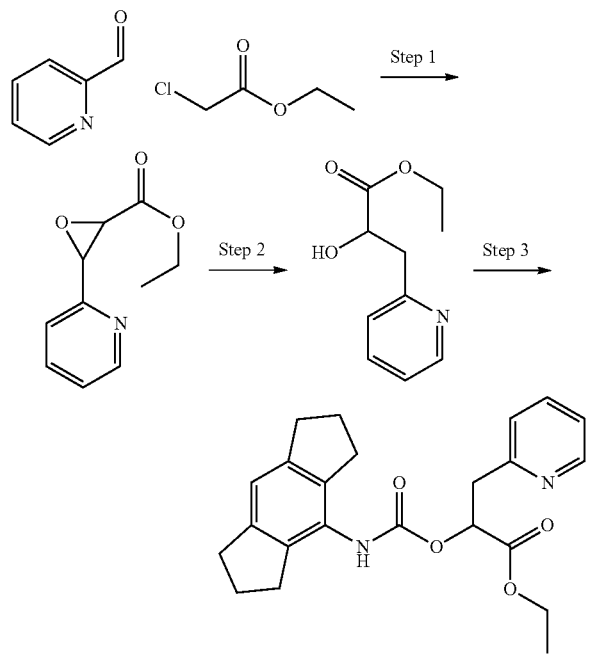

Step 1: ethyl 3-(pyridin-2-yl)oxirane-2-carboxylate. The title compound was prepared according to the General procedure C using ethyl chloroacetate and 2-pyridine carbaldehyde as starting materials. The crude product was purified by FCC (0 to 50% EtOAc gradient in hexane). Y=67%, mixture of diastereoisomers (75/25). MS ES+: 194.1. Diastereoisomer 1 (major): $^1$H NMR (400 MHz, DMSO-d$_6$) δ 8.59-8.56 (m, 1H), 7.88-7.83 (m, 1H), 7.50-7.45 (m, 1H), 7.44-7.39 (m, 1H), 4.25-4.18 (m, 3H), 3.98-3.96 (m, 1H), 1.25 (t, J=7 Hz, 3H). Diastereoisomer 2 (minor): $^1$H NMR (400 MHz, DMSO-d$_6$) δ 8.54-8.51 (m, 1H), 7.82-7.78 (m, 1H), 7.39-7.33 (m, 2H), 4.40 (d, J=5 Hz, 1H), 4.10 (d, J=5 Hz, 1H), 3.95-3.92 (m, 2H), 0.95 (t, J=7 Hz, 3H).

Step 2: Ethyl 2-hydroxy-3-(pyridin-2-yl)propanoate. The title compound was prepared according to the General procedure D using ethyl 3-(pyridin-2-yl)oxirane-2-carboxylate (mixture of both diastereoisomers) as starting material. Y=85%. MS ES+: 196.1. $^1$H NMR (400 MHz, DMSO-d$_6$) δ 8.51-8.46 (m, 1H), 7.71-7.67 (m, 1H), 7.26 (d, J=8 Hz, 1H), 7.24-7.20 (m, 1H), 5.60-5.54 (m, 1H), 4.49-4.41 (m, 1H), 4.10-4.04 (m, 2H), 3.10-3.05 (m, 1H), 2.99-2.94 (m, 1H), 1.14 (t, J=7 Hz, 3H).

Step 3: ethyl 2-(((1,2,3,5,6,7-hexahydro-s-indacen-4-yl)carbamoyl)oxy)-3-(pyridin-2-yl)propanoate. The title compound was prepared according to General procedure A using ethyl 2-hydroxy-3-(pyridin-2-yl)propanoate and Intermediate A as starting materials. The crude product was purified by FCC (0 to 20% EtOAc in hexane). Y=16%. MS ES+: 395.4. $^1$H NMR (400 MHz, DMSO-d$_6$) δ 9.08 (s, 1H), 8.52 (d, J=4 Hz, 1H), 7.81-7.69 (m, 1H), 7.42-7.33 (m, 1H), 7.31-7.24 (m, 1H), 6.93 (s, 1H), 5.41-5.33 (m, 1H), 4.14-4.09 (m, 2H), 3.31-3.20 (m, 2H), 2.78 (t, J=7 Hz, 4H), 2.67-2.55 (m, 4H), 2.01-1.83 (m, 4H), 1.15 (t, J=7 Hz, 3H).

Example 20. Ethyl (2R)-2-{[(1,2,3,5,6,7-hexahydro-s-indacen-4-yl)carbamoyl]oxy}-propanoate

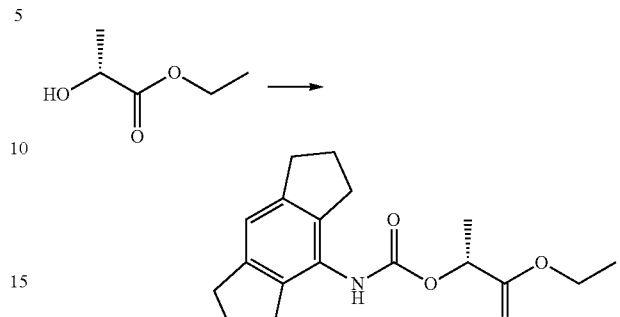

The title compound was prepared according to the General procedure A using ethyl (2R)-2 hydroxypropanoate and Intermediate A as starting materials. The crude product was purified by FCC (0 to 20% EtOAc in hexane). Y=24%. MS ES+ ([M+Na]+): 340.3. $^1$H NMR (400 MHz, DMSO-d$_6$) δ 9.13 (s, 1H), 6.95 (s, 1H), 4.94-4.89 (m, 1H), 4.16-4.11 (m, 2H), 2.81 (t, J=7 Hz, 4H), 2.70 (t, J=7 Hz, 4H), 2.02-1.91 (m, 4H), 1.43 (d, J=5 Hz, 3H), 1.21 (t, J=7 Hz, 3H).

Example 21. Propan-2-yl 2-{[(1,2,3,5,6,7-hexahydro-s-indacen-4-yl)carbamoyl]oxy}acetate

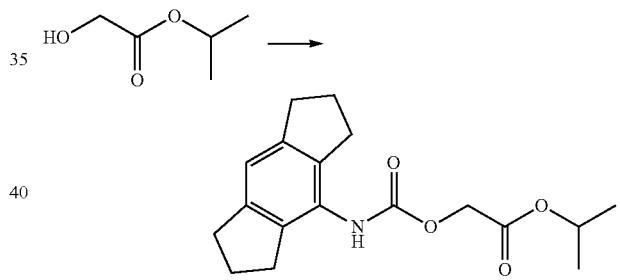

The title compound was prepared according to the General procedure A using propan-2-yl 2-hydroxyacetate and Intermediate A as starting materials. The crude product was purified by FCC (0 to 100% DCM in hexane). Y=56%. MS ES+ ([M+Na]+): 340.3. $^1$H NMR (400 MHz, DMSO-d$_6$) δ 9.16 (s, 1H), 6.95 (s, 1H), 5.04-4.91 (m, 1H), 4.58 (s, 2H), 2.81 (t, J=7 Hz, 4H), 2.76-2.66 (m, 4H), 2.11-1.86 (m, 4H), 1.21 (d, J=6 Hz, 6H).

Example 22. 2-{[(1,2,3,5,6,7-Hexahydro-s-indacen-4-yl)carbamoyl]oxy}acetate

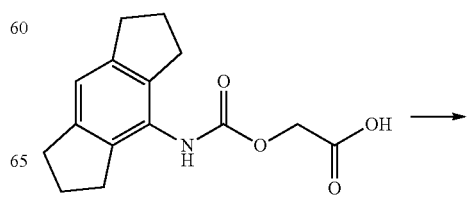

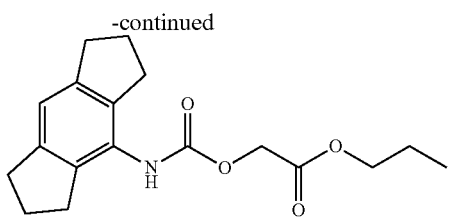

2-{[(1,2,3,5,6,7-Hexahydro-s-indacen-4-yl)carbamoyl]oxy}acetic acid (Intermediate B, 200 mg, 0.73 mmol, 1 eq.) was suspended in acetone (2 ml) and TEA (152 μl, 1.09 mmol, 1.5 eq.) was added. 1-Iodopropane (78 μl, 0.8 mmol, 1.1 eq.) was added to the resulting solution and the RM was stirred at rt under Ar for 15 h. The RM was diluted with DCM and the solution was washed with 1 M HCl. The aqueous layer was extracted twice with DCM. The combined organic layers were dried over anhydrous sodium sulfate and concentrated under reduced pressure. The crude product was purified by trituration in hexane to give the title compound. Y=15%. MS ES$^+$ ([M+Na]$^+$): 340.4. $^1$H NMR (400 MHz, DMSO-d$_6$) δ 9.17 (s, 1H), 6.95 (s, 1H), 4.63 (s, 2H), 4.07 (t, J=7 Hz, 2H), 2.81 (t, J=6 Hz, 4H), 2.71 (t, J=7 Hz, 4H), 2.06-1.89 (m, 4H), 1.66-1.55 (m, 2H), 0.90 (t, J=7 Hz, 3H).

Example 23. Cyclopropylmethyl 2-{[(1,2,3,5,6,7-hexahydro-s-indacen-4-yl)carbamoyl]oxy}acetate

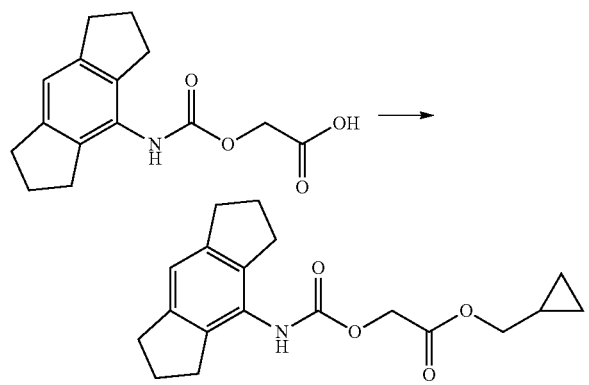

The title compound was prepared according to the General procedure E using Intermediate B and cyclopropylmethanol as starting materials. The crude product was purified by trituration in Et$_2$O/hexane. Y=69%. MS ES$^+$ ([M+Na]$^+$): 352.4. $^1$H NMR (400 MHz, DMSO-d$_6$) δ 9.18 (s, 1H), 6.95 (s, 1H), 4.64 (s, 2H), 3.95 (d, J=7 Hz, 2H), 2.81 (t, J=7 Hz, 4H), 2.77-2.66 (m, 4H), 2.09-1.87 (m, 4H), 1.16-1.03 (m, 1H), 0.56-0.49 (m, 2H), 0.32-0.26 (m, 2H).

Example 24. Cyclobutyl 2-{[(1,2,3,5,6,7-hexahydro-s-indacen-4-yl)carbamoyl]oxy}acetate

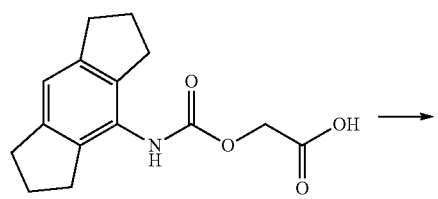

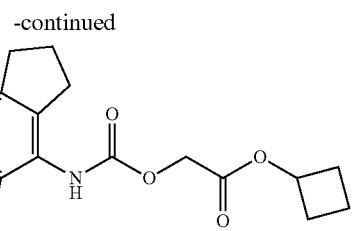

The title compound was prepared according to the General procedure E using Intermediate B and cyclobutanol as starting materials. The crude product was purified by trituration with Et$_2$O/hexane. Y=61%. MS ES$^+$ ([M+Na]$^+$): 352.3. $^1$H NMR (400 MHz, DMSO-d$_6$) δ 9.17 (s, 1H), 6.95 (s, 1H), 5.04-4.92 (m, 1H), 4.60 (s, 2H), 2.81 (t, J=7 Hz, 4H), 2.71 (t, J=7 Hz, 4H), 2.35-2.23 (m, 2H), 2.09-2.00 (m, 2H), 2.00-1.92 (m, 4H), 1.81-1.70 (m, 1H), 1.68-1.54 (m, 1H).

Example 25. 2-methylpropyl 2-{[(1,2,3,5,6,7-hexahydro-s-indacen-4-yl)carbamoyl]oxy}acetate

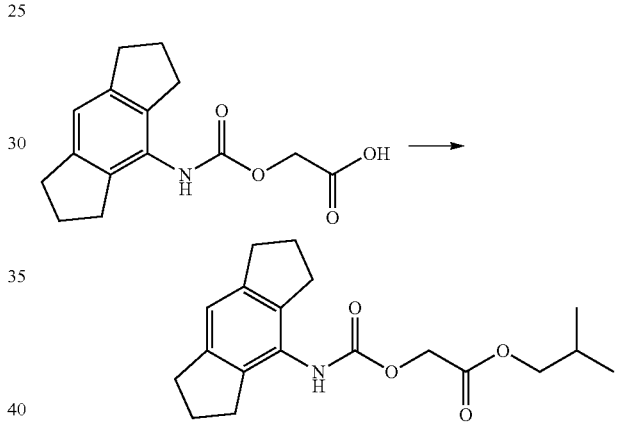

The title compound was prepared according to the General procedure E using Intermediate B and 2-methylpropan-1-ol as starting materials. The crude product was purified by trituration with Et$_2$O/hexane. Y=56%. MS ES$^+$ ([M+Na]$^+$): 354.4. $^1$H NMR (400 MHz, DMSO-d$_6$) δ 9.18 (s, 1H), 6.95 (s, 1H), 4.65 (s, 2H), 3.91 (d, J=7 Hz, 2H), 2.81 (t, J=7 Hz, 4H), 2.77-2.64 (m, 4H), 2.01-1.93 (m, 4H), 1.92-1.83 (m, 1H), 0.90 (d, J=7 Hz, 6H).

Example 26. Ethyl(2R)-3-(4-cyanophenyl)-2-{[(1,2,3,5,6,7-hexahydro-s-indacen-4yl)carbamoyl]oxy}propanoate

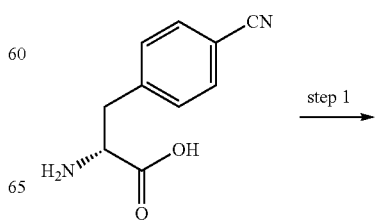

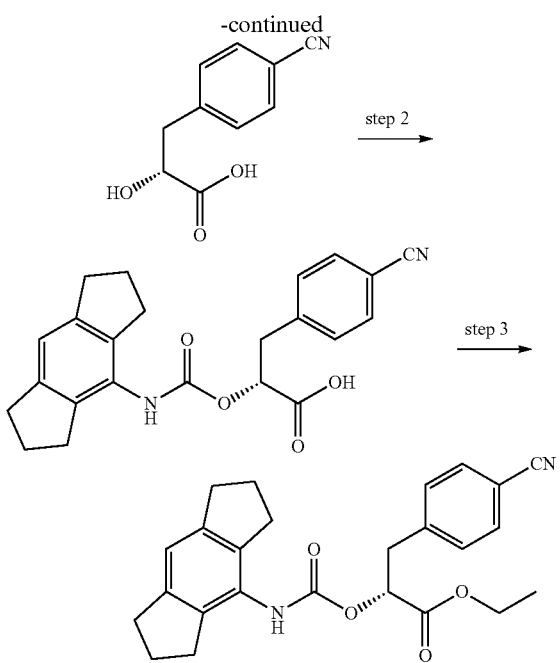

Step 1: (2R)-3-(4-cyanophenyl)-2-hydroxypropanoic acid. (2R)-2-amino-3-(4-cyanophenyl)propanoic acid (500 mg, 2.63 mmol, 1 eq.) was dissolved in 4:1 deionised water:acetic acid (30 ml) and a solution of sodium nitrite (544 mg, 7.89 mmol, 3 eq.) in water (5 ml) was slowly added at 0° C. over a period of 10 min. The RM was warmed to rt and stirred for 15 h. The reaction was quenched with 2 M methylamine in THF (2 ml) and the resulting mixture was evaporated under reduced pressure to about one third of its volume. It was basified to pH 9 with aq. sat. NaHCO$_3$ and washed with EtOAc. The aqueous layer was then acidified to pH 3 with 2 M HCl. The mixture was extracted four times with DCM and the combined organic layers were dried over anhydrous sodium sulfate and evaporated to dryness. The residue was purified by trituration with Et$_2$O/hexane. Y=43%. MS ES$^-$: 190.2. $^1$H NMR (400 MHz, DMSO-d$_6$) δ 12.60 (s, 1H), 7.75 (d, J=8 Hz, 2H), 7.45 (d, J=8 Hz, 2H), 5.41 (s, 1H), 4.20 (m, 1H), 3.06 (m, 1H), 2.88 (m, 1H).

Step 2: (2R)-3-(4-cyanophenyl)-2-{[(1,2,3,5,6,7-hexa-hydro-s-indacen-4-yl)carbamoyl]oxy}propanoic acid. The title compound was prepared according to the General procedure A using (2R)-3-(4-cyanophenyl)-2-hydroxypropanoic acid and intermediate A as starting materials. The crude product was purified by trituration with Et$_2$O. Y=55%. MS ES$^+$: 391.0.

Step 3: ethyl (2R)-3-(4-cyanophenyl)-2-{[(1,2,3,5,6,7-hexahydro-s-indacen-4-yl)carbamoyl]oxy}propanoate. (2R)-3-(4-cyanophenyl)-2-{[(1,2,3,5,6,7-hexahydro-s-indacen-4-yl)carbamoyl]oxy}propanoic acid (200 mg, 0.51 mmol, 1 eq.) was suspended in acetone (2 ml) and treated with TEA (107 μl, 0.77 mmol, 1.5 eq.). Ethyl iodide (49 μl, 0.61 mmol, 1.2 eq.) was added to the resulting solution and the RM was stirred at rt under Ar for 15 h. The reaction mixture was diluted with DCM and the solution was washed with 1 M HCl. The aqueous layer was extracted twice with DCM and the combined organic layers were dried over anhydrous sodium sulfate and concentrated under reduced pressure. The crude product was purified by FCC (0 to 40% EtOAc in hexane). Y=22%. MS ES$^+$ ([M+Na]$^+$): 442.1. $^1$H NMR (400 MHz, DMSO-d$_6$) δ 9.13 (s, 1H), 7.90-7.70 (m, 2H), 7.62-7.42 (m, 2H), 6.94 (s, 1H), 5.31-5.11 (m, 1H), 4.13-4.07 (m, 2H), 3.30-3.10 (m, 2H), 2.80 (t, J=7 Hz, 4H), 2.66-2.57 (m, 4H), 2.00-1.85 (m, 4H), 1.14 (t, J=7 Hz, 3H).

Example 27. Ethyl 2-({[2-methyl-6-(propan-2-yl)phenyl]carbamoyl}oxy)acetate-5Z

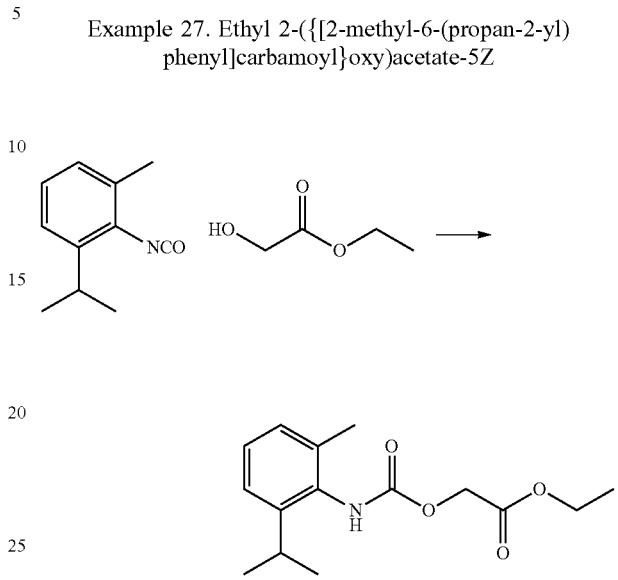

The title compound was prepared according to the General procedure A using ethyl glycolate and 2-isopropyl-6-methylphenyl isocyanate as starting materials. The crude product was purified by FCC (0 to 20% EtOAc gradient in hexane). Y=66%. MS ES$^+$ ([M+Na]$^+$): 302.3. $^1$H NMR (300 MHz, DMSO-d$_6$) δ 8.98 (s, 1H), 7.20-7.12 (m, 2H), 7.11-7.01 (m, 1H), 4.63 (s, 2H), 4.17-4.09 (m, 2H), 3.21-3.09 (m, 1H), 2.16 (s, 3H), 1.20 (t, J=7 Hz, 3H), 1.11 (d, J=7 Hz, 6H).

Example 28. 2-{[(1,2,3,5,6,7-Hexahydro-s-indacen-4-yl)carbamoyl]oxy}acetic acid

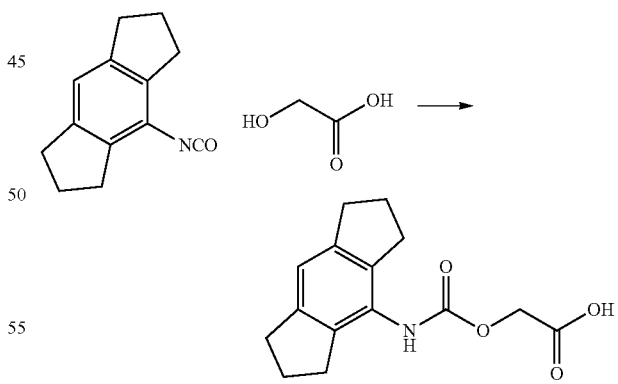

The title compound was prepared according to the General procedure A using glycolic acid and intermediate A as starting materials. The crude product was purified by FCC (0 to 10% MeOH in DCM). Y=17%. MS ES$^+$ ([M+Na]$^+$): 298.3. $^1$H NMR (300 MHz, DMSO-d$_6$) δ 12.88 (s, 1H), 9.09 (s, 1H), 6.95 (s, 1H), 4.52 (s, 2H), 2.81 (t, J=7 Hz, 4H), 2.71 (t, J=7 Hz, 4H), 2.04-1.89 (m, 4H).

Example 29. Ethyl 2-{[(2,6-diethyl-4-methylphenyl)carbamoyl]oxy}acetate

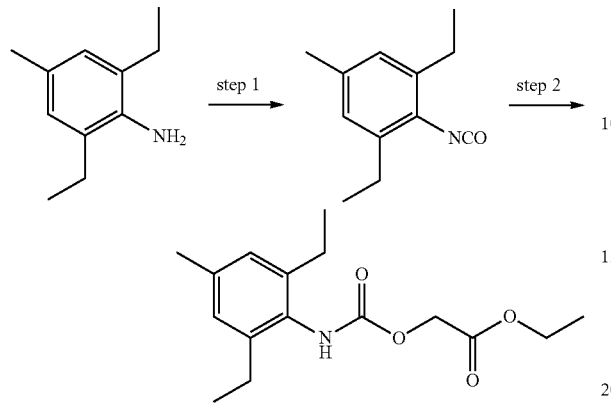

Step 1: 2,6-diethyl-4-methylphenyl isocyanate. A mixture of di-tert-butyl dicarbonate (702 mg, 3.22 mmol, 1.5 eq.) and DMAP (131 mg, 0.11 mmol, 0.5 eq.) in dry ACN (5 ml) was stirred for 5 minutes at rt. A solution of 2,6-diethyl-4-methylaniline (350 mg, 2.14 mmol, 1 eq.) in dry ACN (2 ml) was then added dropwise. After 30 min at rt the mixture was concentrated under reduced pressure, dissolved in dry hexane and filtered through a plug of silica gel. The filtrate was evaporated and the residue was used in the next step without further purification. Y=40%. $^1$H NMR (400 MHz, Chloroform-d) δ 6.90 (s, 2H), 2.70-2.63 (m, 4H), 2.32 (s, 3H), 1.26 (t, J=8 Hz, 6H).

Step 2: ethyl 2-{[(2,6-diethyl-4-methylphenyl)carbamoyl]oxy}acetate. The title compound was prepared according to the General procedure A using ethyl glycolate and 2,6-diethyl-4-methylphenyl isocyanate as starting materials. The crude product was purified by reverse-phase preparative HPLC (0.1% formic acid buffer). Y=50%. MS ES$^+$ ([M+Na]$^+$): 316.3. $^1$H NMR (400 MHz, DMSO-d$_6$) 8.86 (s, 1H), 6.89 (s, 2H), 4.62 (s, 2H), 4.18-4.10 (m, 2H), 2.60-2.44 (m, 4H), 2.26 (s, 3H), 1.21 (t, J=7 Hz, 3H), 1.10 (t, J=7 Hz, 6H).

Example 30. Methyl 2-{[(1,2,3,5,6,7-hexahydro-s-indacen-4-yl)carbamoyl]oxy}acetate

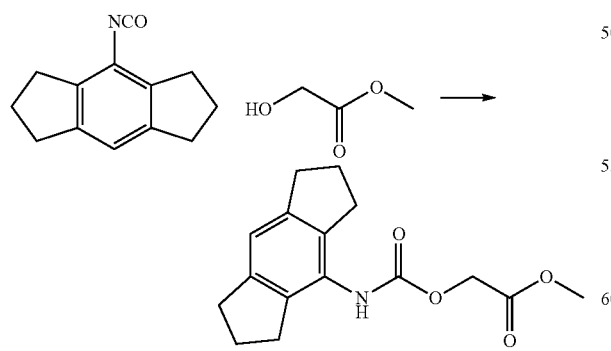

The title compound was prepared according to the General procedure A with methyl glycolate and intermediate A as starting materials, using THF as reaction solvent. Purified by FCC (0 to 25% EtOAc in hexane). Y=66%. MS ES$^+$ ([M+Na]$^+$): 312.3. $^1$H NMR (400 MHz, DMSO-d$_6$) δ 9.17 (s, 1H), 6.95 (s, 1H), 4.64 (s, 2H), 3.69 (s, 3H), 2.81 (t, J=7 Hz, 4H), 2.71 (t, J=7 Hz, 4H), 2.02-1.93 (m, 4H).

Example 31. Ethyl (2R)-2-{[(1,2,3,5,6,7-hexahydro-s-indacen-4-yl)carbamoyl]oxy}-4-phenylbutanoate

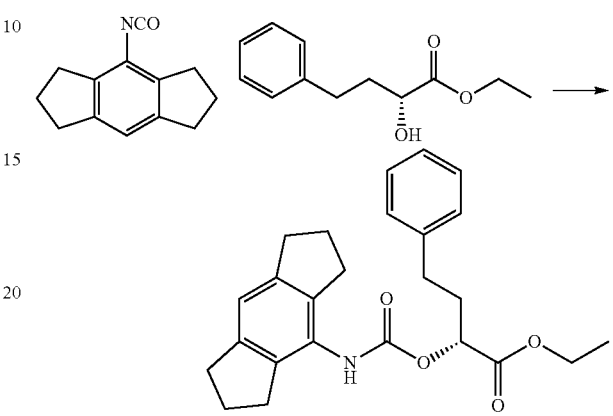

The title compound was prepared according to the General procedure A with ethyl (R)-2-hydroxy-4-phenylbutyrate and intermediate A as starting materials, using THF as reaction solvent. The crude product was purified by preparative TLC (100% DCM). Y=9%. MS ES$^+$ ([M+Na]$^+$): 430.6. $^1$H NMR (400 MHz, DMSO-d$_6$) δ 9.22 (s, 1H), 7.36-7.17 (m, 5H), 6.96 (s, 1H), 4.79-4.72 (m, 1H), 4.17-4.08 (m, 2H), 2.82 (t, J=7 Hz, 4H), 2.86-2.66 (m, 2H), 2.78-2.69 (m, 4H), 2.09-2.07 (m, 2H), 2.03-1.93 (m, 4H), 1.20 (t, J=7 Hz, 3H).

Example 32. Ethyl 2-{[(1,2,3,5,6,7-hexahydro-s-indacen-4-yl)carbamoyl]oxy}-3-(1H-pyrazol-1-yl)propanoate

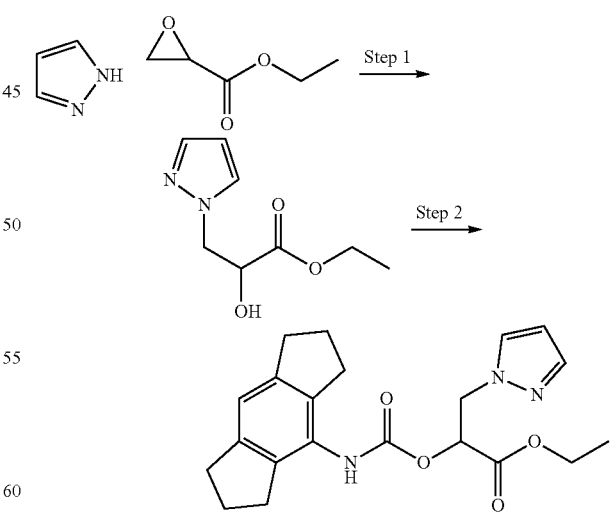

Step 1: Ethyl 2-hydroxy-3-(1H-pyrazol-1-yl)propanoate. A microwave vial was charged with pyrazole (293 mg, 4.30 mmol, 2.5 eq.) and ethyl 2,3-epoxypropanoate (200 mg, 1.72 mmol, 1 eq.). The substrates were dissolved in absolute EtOH (3 ml) under argon atmosphere and the vial was sealed. The reaction was heated for 3 days at 90° C. (oil bath) and monitored by TLC. The solvent was removed in vacuo and the residue was purified by FCC (0 to 15% EtOAc in hexane). Y=96%. MS ES⁺: 185.4. ¹H NMR (400 MHz, DMSO-d₆) δ 7.68-7.65 (m, 1H), 7.45-7.41 (m, 1H), 6.21 (t, J=2 Hz, 1H), 5.85-5.81 (m, 1H), 4.43-4.33 (m, 2H), 4.31-4.23 (m, 1H), 4.13-4.07 (m, 2H), 1.18 (t, J=7 Hz, 3H).

Step 2: Ethyl 2-{[(1,2,3,5,6,7-hexahydro-s-indacen-4-yl)carbamoyl]oxy}-3-(1H-pyrazol-1-yl)propanoate. The title compound was prepared according to the General procedure A using ethyl 2-hydroxy-3-(1H-pyrazol-1-yl)propanoate and intermediate A as starting materials, with THF as reaction solvent. The crude product was purified by preparative TLC (DCM:EtOAc 9:1). Y=18%. MS ES⁺: 384.4. ¹H NMR (400 MHz, DMSO-d₆) δ 9.18 (s, 1H), 7.78 (s, 1H), 7.47 (s, 1H), 6.95 (s, 1H), 6.28 (s, 1H), 5.27 (s, 1H), 4.61 (s, 2H), 4.15-4.10 (m, 2H), 2.80 (t, J=7 Hz, 4H), 2.66 (t, J=8 Hz, 4H), 2.01-1.89 (m, 4H), 1.18 (t, J=7 Hz, 3H).

Example 33. Cyclopentyl 2-{[(1,2,3,5,6,7-hexahydro-s-indacen-4-yl)carbamoyl]oxy}acetate

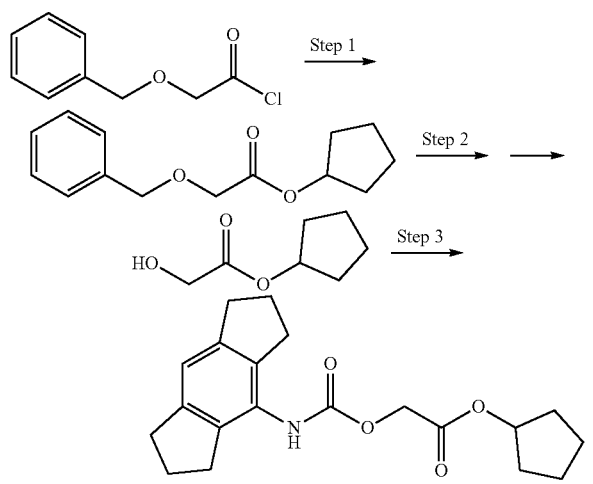

Step 1: cyclopentyl 2-(benzyloxy)acetate. Cyclopentanol (735 mg, 8.53 mmol, 1.05 eq.) was dissolved in anhydrous DCM (8 ml) under Ar and the solution was cooled to 0° C. Anhydrous pyridine (0.723 ml, 8.94 mmol, 1.1 eq.) was added, followed by dropwise addition of benzyloxyacetyl chloride (1.5 mg, 8.12 mmol, 1 eq.). The mixture was left with stirring under Ar at rt for 16 h. The reaction was quenched with water at 0° C. and the layers were separated. The organic layer was washed with aq. sat. NaHCO₃, dried over anhydrous Na₂SO₄ and concentrated. The residue was purified by FCC (0 to 10% EtOAc in hexane). Y=97%. ¹H NMR (400 MHz, Chloroform-d) δ 7.42-7.30 (m, 5H), 5.32-5.26 (m, 1H), 4.65 (s, 2H), 4.08 (s, 2H), 1.97-1.85 (m, 2H), 1.81-1.68 (m, 4H), 1.68-1.56 (m, 2H).

Step 2: cyclopentyl 2-hydroxyacetate. Cyclopentyl 2-(benzyloxy)acetate (1.93 g, 8.25 mmol, 1 eq.) was dissolved in anhydrous MeOH (40 ml). The air was removed using vacuum pump and the flask was purged with argon. Pd/C (10% w/w, 190 mg) was added and the Ar atmosphere was replaced with a H₂ atmosphere. The reaction was stirred at room temperature and atmospheric pressure for 16 h. The reaction mixture was filtered through a pad of Celite, the filtering bed was washed with MeOH and the filtrate was evaporated in vacuo. The crude product was used in the next step without further purification. Y=57%. ¹H NMR (400 MHz, Chloroform-d) δ 5.34-5.27 (m, 1H), 4.12 (s, 2H), 1.99-1.85 (m, 2H), 1.85-1.68 (m, 4H), 1.68-1.53 (m, 2H).

Step 3: cyclopentyl 2-{[(1,2,3,5,6,7-hexahydro-s-indacen-4-yl)carbamoyl]oxy}acetate. The title compound was prepared according to the General procedure A with cyclopentyl 2-hydroxyacetate and Intermediate A as starting materials, using THF as reaction solvent. The crude product was purified by FCC (0 to 80% DCM in hexane). Y=24%. MS ES⁺ ([M+Na]⁺): 366.5. ¹H NMR (400 MHz, DMSO-d₆) δ 9.17 (s, 1H), 6.95 (s, 1H), 5.18-5.12 (m, 1H), 4.57 (s, 2H), 2.81 (t, J=7 Hz, 4H), 2.76-2.66 (m, 4H), 2.02-1.91 (m, 4H), 1.90-1.78 (m, 2H), 1.70-1.49 (m, 6H).

Example 34. Ethyl 2-{[(1,2,3,5,6,7-hexahydro-s-indacen-4-yl)carbamoyl]oxy}-3-(1H-imidazol-1-yl)propanoate

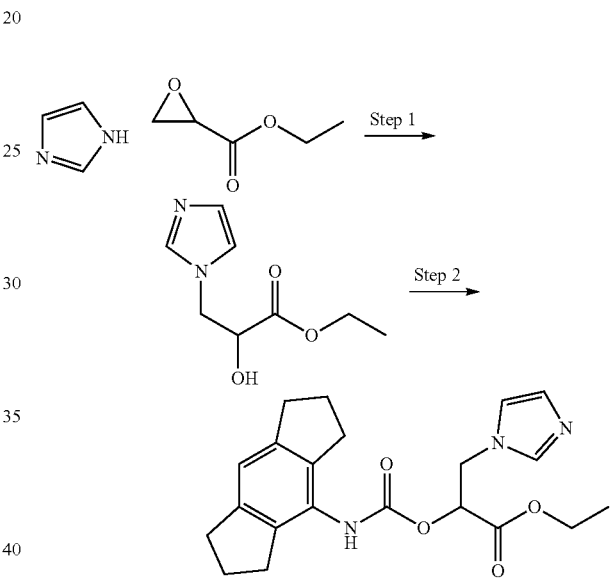

Step 1: ethyl 2-hydroxy-3-(1H-imidazol-1-yl)propanoate. A microwave vial was charged with 1H-imidazole (176 mg, 2.58 mmol, 1 eq.) and ethyl 2,3-epoxypropanoate (300 mg, 2.58 mmol, 1 eq.), and the substrates were dissolved in absolute EtOH (3 ml) under Ar. The tube was sealed and the mixture was heated at 90° C. (oil bath) for 16 h. The solvent was removed in vacuo and the residue was purified by FCC (0 to 10% MeOH in DCM) to give the title compound. Y=33%. MS ES⁺: 185.2. ¹H NMR (300 MHz, DMSO-d₆) δ 7.58-7.53 (m, 1H), 7.15-7.10 (m, 1H), 6.88-6.83 (m, 1H), 5.94 (d, J=6 Hz, 1H), 4.28-4.18 (m, 1H), 4.18-4.06 (m, 4H), 1.19 (t, J=7 Hz, 3H).

Step 2: ethyl 2-{[(1,2,3,5,6,7-hexahydro-s-indacen-4-yl)carbamoyl]oxy}-3-(1H-imidazol-1-yl)propanoate. The title compound was prepared according to the General procedure A with ethyl 2-hydroxy-3-(1H-imidazol-1-yl)propanoate and Intermediate A as starting materials, using THF as reaction solvent. The crude product was purified by reverse-phase preparative HPLC (0.1% formic acid buffer). Y=26%. MS ES⁺: 384.4. ¹H NMR (300 MHz, DMSO-d₆) δ 9.24 (s, 1H), 7.67 (s, 1H), 7.22 (s, 1H), 6.97 (s, 1H), 6.91 (s, 1H), 5.30-5.21 (m, 1H), 4.49 (s, 2H), 4.15-4.08 (m, 2H), 2.81 (t, J=7 Hz, 4H), 2.72-2.60 (m, 4H), 2.03-1.90 (m, 4H), 1.17 (t, J=7 Hz, 3H).

Example 35. Ethyl 2-({[2,6-bis(propan-2-yl)phenyl]carbamoyl}oxy)acetate

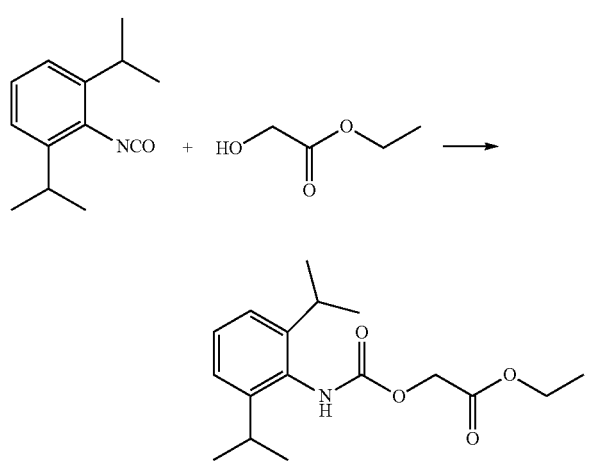

The title compound was prepared according to the general procedure A using ethyl glycolate and 2,6-diisopropylphenyl isocyanate as starting materials. The crude product was purified by FCC (4:1 hexane/EtOAc). Y=42%. MS ES$^+$: 308.3. $^1$H NMR (400 MHz, DMSO-d$_6$) δ 8.96 (s, 1H), 7.32-7.22 (m, 1H), 7.15 (d, J=8 Hz, 2H), 4.63 (s, 2H), 4.17-4.10 (m, 2H), 3.21-3.11 (m, 2H), 1.23-1.20 (m, 3H), 1.18-1.06 (m, 12H).

Example 36. Ethyl 2-({[2-chloro-5-(trifluoromethyl)phenyl]carbamoyl}oxy)acetate

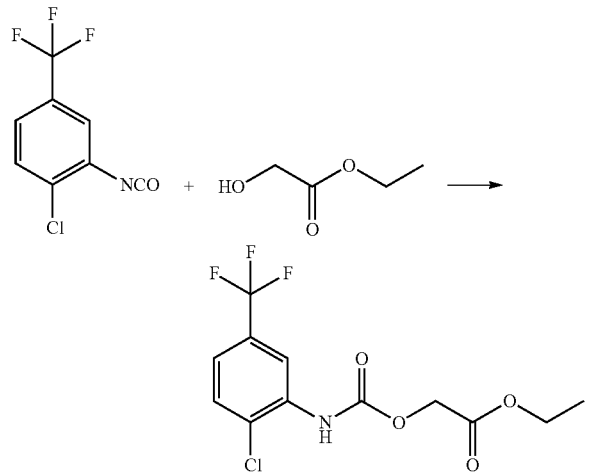

The title compound was prepared according to the general procedure A using ethyl glycolate and 2-chloro-5-(trifluoromethyl)phenyl isocyanate as starting materials. The crude product was purified twice by FCC (hexane/DCM). Y=6%. MS ES$^+$: 348.6. $^1$H NMR (400 MHz, DMSO-d$_6$) δ 9.78 (s, 1H), 7.96 (d, J=2 Hz, 1H), 7.76 (d, J=8 Hz, 1H), 7.57 (dd, J=2, 8 Hz, 1H), 4.73 (s, 2H), 4.17 (q, J=7 Hz, 2H), 1.22 (t, J=7 Hz, 3H).

Example 37. Ethyl 2-{[(2-tert-butyl-6-methylphenyl)carbamoyl]oxy}acetate

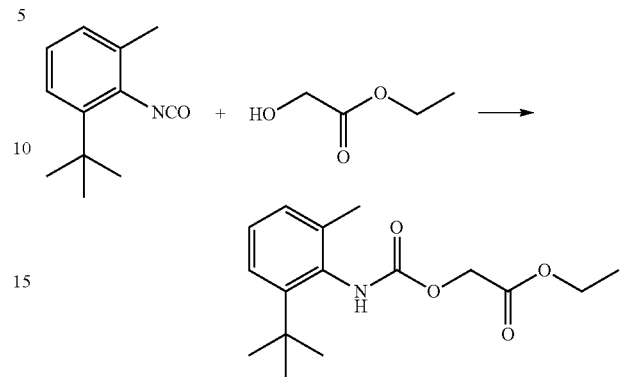

The title compound was prepared according to the general procedure A using ethyl glycolate and 2-tert-butyl-6-methylphenyl isocyanate as starting materials. The crude product was purified by FCC (4:1 hexane/EtOAc). Y=22%. MS ES$^+$316.2 [M+Na]$^+$. $^1$H NMR (400 MHz, chloroform-d) δ 7.33-7.29 (m, 1H), 7.22-7.16 (m, 2H), 6.33 (s, 1H), 4.72 (s, 2H), 4.28 (q, J=7 Hz, 2H), 2.32 (s, 3H), 1.43 (s, 9H), 1.32 (t, J=7 Hz, 3H).

Example 38. Ethyl 2-{[(2,5-dimethylphenyl)carbamoyl]oxy}acetate

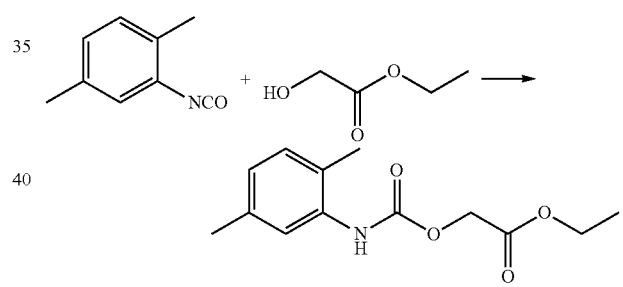

The title compound was prepared according to the general procedure A using ethyl glycolate and 2,5-dimethylphenyl isocyanate as starting materials. The crude product was purified twice by FCC (hexane/EtOAc and then hexane/DCM). Y=22%. MS ES$^+$274.2 [M+Na]$^+$. $^1$H NMR (400 MHz, chloroform-d) δ 7.62 (s, 1H), 7.07 (d, J=8 Hz, 1H), 6.89 (d, J=8 Hz, 1H), 6.56 (s, 1H), 4.70 (s, 2H), 4.29 (q, J=7 Hz, 2H), 2.34 (s, 3H), 2.26 (s, 3H), 1.33 (t, J=7 Hz, 3H).

Example 39. 2-{[(1,2,3,5,6,7-hexahydro-s-indacen-4-yl)carbamoyl]oxy}-3-methoxypropanoic acid

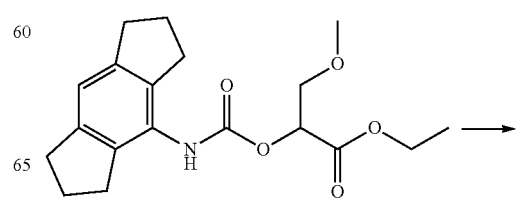

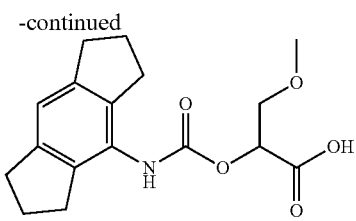

Ethyl 2-{[(1,2,3,5,6,7-hexahydro-s-indacen-4-yl)carbamoyl]oxy}-3-methoxypropanoate (Example 5F) (51 mg, 0.15 mmol) was dissolved in 1:1 THF/water (1.5 ml) and cooled to 0° C. Lithium hydroxide monohydrate (7 mg, 0.16 mmol) was added and the reaction stirred for 30 min. The THF was removed in vacuo. The RM was acidified with 1M HCl to pH 3 and extracted with EtOAc. The organic phase was dried over $Na_2SO_4$ and concentrated. A precipitate appeared which was filtered off and purified by prep TLC eluting with 9:1 DCM/MeOH. The product spot was extracted with THF and evaporated to give the title compound as a white solid. Y=60%. MS ES⁺: 320. ¹H NMR (400 MHz, DMSO-d₆) δ 11.74 (s, 1H), 8.69 (s, 1H), 6.89 (s, 1H), 4.81-4.75 (m, 1H), 3.85-3.73 (m, 1H), 3.73-3.65 (m, 1H), 3.24 (s, 3H), 2.79 (t, J=7 Hz, 4H), 2.72 (t, J=7 Hz, 4H), 2.00-1.88 (m, 4H).

Example 40. Cyclopropyl 2-{[(1,2,3,5,6,7-hexahydro-s-indacen-4-yl)carbamoyl]oxy}acetate

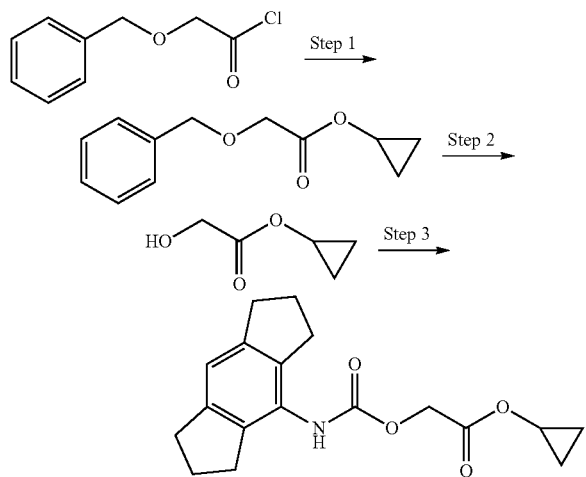

Step 1: cyclopropyl 2-(benzyloxy)acetate. Cyclopropanol (108 μl, 1.71 mmol) was dissolved in dry DCM (8 ml) and cooled to 0° C. Triethylamine (294 μl, 2.11 mmol) was added, followed by 2-benzyloxyacetyl chloride (256 μl, 1.62 mmol) dropwise. The RM was stirred at rt for 18 h then concentrated. A precipitate was filtered off and the filtrate evaporated to dryness to give the title compound as a yellow oil. Y=100%. ¹H NMR (400 MHz, chloroform-d) δ 7.41-7.30 (m, 5H), 4.65 (s, 2H), 4.27-4.21 (m, 1H), 4.09 (s, 2H), 0.81-0.70 (m, 4H).

Step 2: cyclopropyl 2-hydroxyacetate. Cyclopropyl 2-(benzyloxy)acetate (0.375 g, 1.82 mmol) was dissolved in THF (18 ml) and purged with argon. 10% Pd/C (40 mg) was added and the RM purged (argon/vacuum cycles) and then stirred under hydrogen atmosphere for 18 h. The RM was filtered through Celite, washed with ACN and evaporated to dryness to give the title compound. Y=67%. ¹H NMR (300 MHz, DMSO-d₆) δ 5.32 (t, J=7 Hz, 1H), 4.13-4.05 (m, 1H), 3.97 (d, J=7 Hz, 2H), 0.74-0.56 (m, 4H).

Step 3: cyclopropyl 2-{[(1,2,3,5,6,7-hexahydro-s-indacen-4-yl)carbamoyl]oxy}acetate. The title compound was prepared according to the General procedure A using cyclopropyl 2-(benzyloxy)acetate and Intermediate A as starting materials. The crude product was purified by FCC (0 to 15% EtOAc in hexane), then by prep TLC (silica, 100% DCM). Y=2%. MS ES⁺: 315.4. ¹H NMR (400 MHz, DMSO-d₆) δ 9.18 (s, 1H), 6.96 (s, 1H), 4.60 (s, 2H), 4.20-4.12 (m, 1H), 2.81 (t, J=7 Hz, 4H), 2.71 (t, J=8 Hz, 4H), 1.98 (q, J=7 Hz, 4H), 0.76-0.61 (m, 4H).

Example 41. 2-{[(1,2,3,5,6,7-hexahydro-s-indacen-4-yl)carbamoyl]oxy}-3-(1H-pyrazol-1-yl)propanoic acid

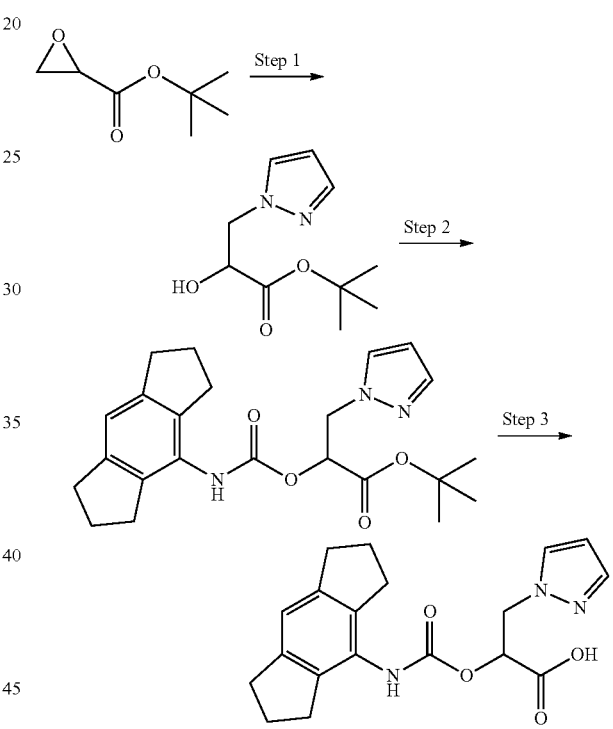

Step 1: tert-butyl 2-hydroxy-3-(1H-pyrazol-1-yl)propanoate. Tert-butyl oxirane-2-carboxylate (10 g, 69.4 mmol) was dissolved in dry absolute EtOH (210 ml). Pyrazole (11.8 g, 174.4 mmol) was added and the reaction heated at 80° C. for 16 h. The reaction was concentrated in vacuo and co-evaporated with toluene twice. The crude was purified by FCC (0-40% EtOAc in DCM) followed by reverse phase FCC (C18, 5-90% ACN in $H_2O$) to give the title compound as a white solid. Y=19%. ¹H NMR (300 MHz, DMSO-d₆) δ 7.66 (dd, J=2, 1 Hz, 1H), 7.43 (dd, J=2, 1 Hz, 1H), 6.21 (t, J=2 Hz, 1H), 5.69-5.65 (m, 1H), 4.37-4.18 (m, 3H), 1.39 (s, 9H).

Step 2: tert-butyl 2-{[(1,2,3,5,6,7-hexahydro-s-indacen-4-yl)carbamoyl]oxy}-3-(1H-pyrazol-1-yl)propanoate. The title compound was prepared according to the General procedure A using Tert-butyl oxirane-2-carboxylate and Intermediate A as starting materials. The crude product was purified by FCC (0 to 40% EtOAc in hexane). Y=22%. MS ES⁺: 412.

Step 3: 2-{[(1,2,3,5,6,7-hexahydro-s-indacen-4-yl)carbamoyl]oxy}-3-(1H-pyrazol-1-yl)propanoic acid. Tert-butyl 2-{[(1,2,3,5,6,7-hexahydro-s-indacen-4-yl)carbamoyl]oxy}-3-(1H-pyrazol-1-yl)propanoate (30 mg, 0.073 mmol) was dissolved in anhydrous 1,4-dioxane (0.3 ml) and cooled to 0° C. 4M HCl (0.5 ml, 2 mmol) was added and the RM stirred at 0° C. for 16 h. The reaction was not complete therefore the solvent was removed in vacuo and 20% TFA in DCM (0.7 ml) was added and the reaction stirred at 0° C. for 16 h. The RM was concentrated, co-evaporated with hexane and then co-evaporated three times with Et$_2$O. The resulting solid was filtered, washed with Et$_2$O and dried to give the title product as a grey solid. Y=46%. MS ES$^+$: 356. $^1$H NMR (300 MHz, DMSO-d$_6$) δ 13.26 (s, 1H), 9.08 (s, 1H), 7.77 (s, 1H), 7.46 (s, 1H), 6.94 (s, 1H), 6.27 (s, 1H), 5.22 (t, J=6 Hz, 1H), 4.58 (s, 2H), 2.80 (t, J=7 Hz, 4H), 2.63 (t, J=7 Hz, 4H), 2.03-1.86 (m, 4H).

Example 41. Ethyl (2R)-3-(3-cyanophenyl)-2-{[(1,2,3,5,6,7-hexahydro-s-indacen-4-yl)carbamoyl]oxy}propanoate

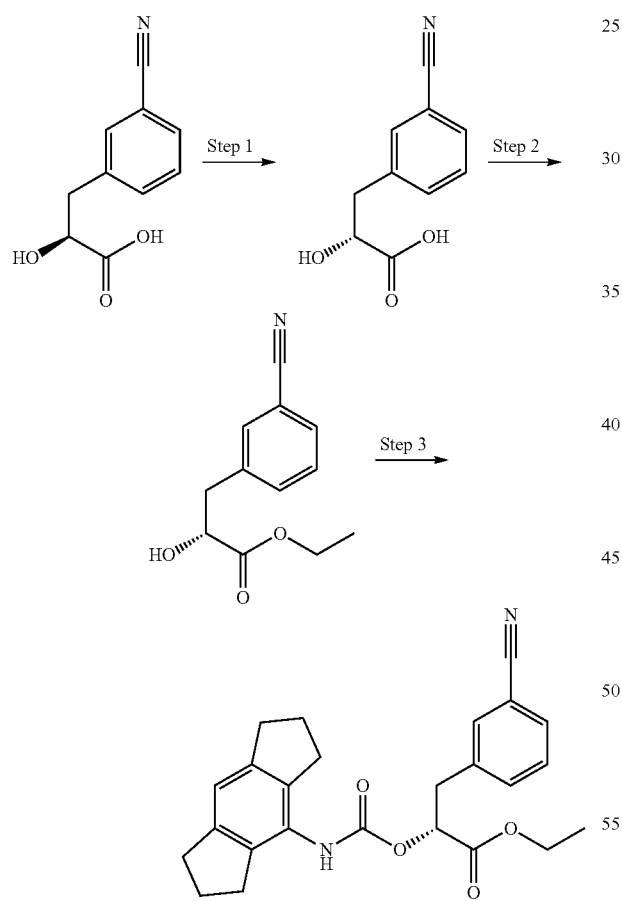

Step 1: (2R)-3-(3-cyanophenyl)-2-hydroxypropanoic acid. A solution of D-3-cyanophenylalanine (0.30 g, 1.58 mmol) was dissolved in water (1.6 ml) and AcOH (0.4 ml) and cooled to 0° C. To this was added slowly 1M sodium nitrite (aq.)(2.4 ml, 3.16 mmol). The RM was allowed to warm to RT and stirred for 16 h. Methylamine (40% in H$_2$O, 0.285 ml, 4.73 mmol) was added to quench the reaction, then it was acidified to pH ~3 with 1M HCl. The mixture was extracted with EtOAc, the organic phase dried (Na$_2$SO$_4$) and concentrated to give an orange liquid. 60% ACN (+0.1% TFA) in water was added and the mixture lyophilised to give the title product. Y=29%. $^1$H NMR (400 MHz, DMSO-d$_6$) δ 12.54 (s, 1H), 7.77-7.64 (m, 2H), 7.60 (d, J=8 Hz, 1H), 7.50 (t, J=8 Hz, 1H), 4.26-4.14 (m, 1H), 3.04 (dd, J=14, 4 Hz, 1H), 2.86 (dd, J=14, 8 Hz, 1H). OH proton not seen.

Step 2: ethyl (2R)-3-(3-cyanophenyl)-2-hydroxypropanoate. To a solution of (2R)-3-(3-cyanophenyl)-2-hydroxypropanoic acid (0.22 g, 1.15 mmol) in EtOH (16 ml) cooled to 0° C. was added dropwise thionyl chloride (48 μl, 1.38 mmol). The RM was stirred at RT for 1 h then evaporated in vacuo. The crude was purified by FCC (silica, hexane/EtOAc) to give the title compound as a pale yellow oil. Y=59%. $^1$H NMR (300 MHz, DMSO-d$_6$) δ 7.72-7.66 (m, 2H), 7.63-7.55 (m, 1H), 7.54-7.45 (m, 1H), 5.63 (d, J=6 Hz, 1H), 4.34-4.22 (m, 1H), 4.08 (q, J=7 Hz, 2H), 3.02 (dd, J=14, 5 Hz, 1H), 2.89 (dd, J=14, 8 Hz, 1H), 1.15 (t, J=7 Hz, 3H).

Step 3: Ethyl (2R)-3-(3-cyanophenyl)-2-{[(1,2,3,5,6,7-hexahydro-s-indacen-4-yl)carbamoyl]oxy}propanoate. The title compound was prepared according to the General procedure B using ethyl (2R)-3-(3-cyanophenyl)-2-hydroxypropanoate and Intermediate A as starting materials. The crude product was purified by FCC (EtOAc in hexane) followed by prep HPLC. Y=30%. MS ES$^+$: 419. $^1$H NMR (300 MHz, DMSO-d$_6$) δ 9.14 (s, 1H), 7.87-7.62 (m, 3H), 7.62-7.29 (m, 1H), 6.95 (s, 1H), 5.21-5.17 (m, 1H), 4.11 (q, J=7 Hz, 2H), 3.25-3.10 (m, 2H), 2.83-2.78 (m, 4H), 2.73-2.51 (m, 4H), 1.99-1.90 (m, 4H), 1.14 (t, J=7 Hz, 3H)

Example 42. Ethyl 2-{[(1,2,3,5,6,7-hexahydro-s-indacen-4-yl)carbamoyl]oxy}-3-[3-(1H-pyrazol-1-yl)phenyl]propanoate

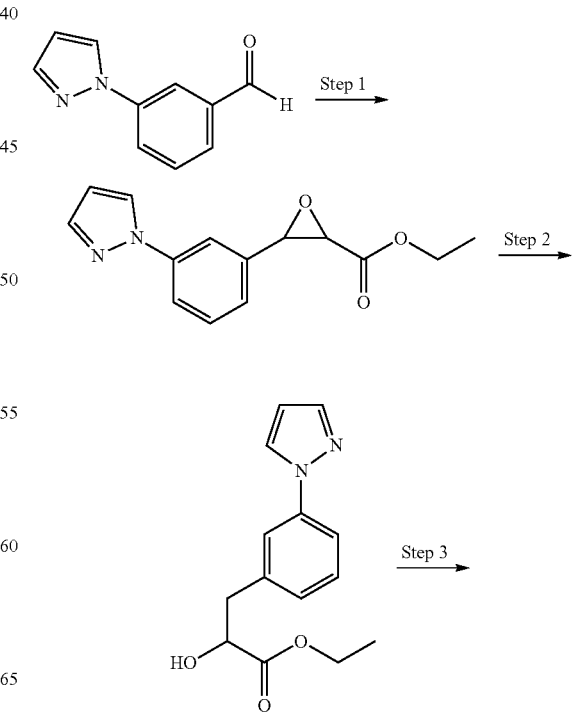

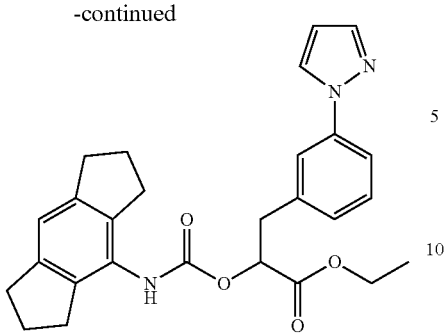

Step 1: ethyl 3-[3-(1H-pyrazol-1-yl)phenyl]oxirane-2-carboxylate. 3-(1H-pyrazol-1-yl)benzaldehyde (0.50 g, 2.90 mmol) and ethyl chloroacetate (0.31 ml, 2.90 mmol) were dissolved in anhydrous THF (12 ml) under argon and cooled to −78° C. To this was added dropwise 1.0 M sodium hexamethyldisilazane in THF (2.90 ml, 2.90 mmol). The RM was stirred at −78° C. for 30 min then warmed to 0° C. and quenched with water. The RM was concentrated, partitioned between water and Et$_2$O and separated. The organic phase was washed with brine, dried over Na$_2$SO$_4$, filtered and concentrated to give the title compound. Y=39%. MS ES$^+$: 259.1.

Step 2: ethyl 2-hydroxy-3-[3-(1H-pyrazol-1-yl)phenyl]propanoate. In a hydrogenation flask a solution of ethyl 3-[3-(1H-pyrazol-1-yl)phenyl]oxirane-2-carboxylate (0.35 g, 1.36 mmol) in EtOAc (15 ml) was treated with 10% Pd on carbon (14 mg). The RM was purged and then stirred under hydrogen atmosphere for 16 h at room temperature and pressure. The RM was filtered through Celite, washed with EtOAc and concentrated to give the title compound as a yellow oil. Y=83%. MS ES$^+$: 261.1.

Step 3: ethyl 2-{[(1,2,3,5,6,7-hexahydro-s-indacen-4-yl)carbamoyl]oxy}-3-[3-(1H-pyrazol-1-yl)phenyl]propanoate. The title compound was prepared according to the General procedure B using ethyl 2-hydroxy-3-[3-(1H-pyrazol-1-yl)phenyl]propanoate and Intermediate A as starting materials. The crude product was purified by FCC (EtOAc in hexane). Y=48%. MS ES$^+$: 460.6. $^1$H NMR (300 MHz, DMSO-d$_6$) δ 9.13 (s, 1H), 8.49 (s, 1H), 7.96-7.63 (m, 3H), 7.43 (s, 1H), 7.25 (s, 1H), 6.92 (s, 1H), 6.65-6.44 (m, 1H), 5.23-5.18 (m, 1H), 4.12 (q, J=7 Hz, 2H), 3.21 (s, 2H), 2.81-2.74 (m, 4H), 2.64-2.58 (m, 4H), 1.94-1.88 (m, 4H), 1.15 (t, J=7 Hz, 3H).

Example 43. Ethyl (2R)-2-{[(1,2,3,5,6,7-hexahydro-s-indacen-4-yl)carbamoyl]oxy}-3-[3-(1H-pyrazol-1-yl)phenyl]propanoate

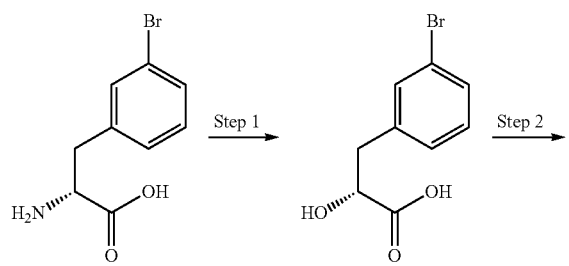

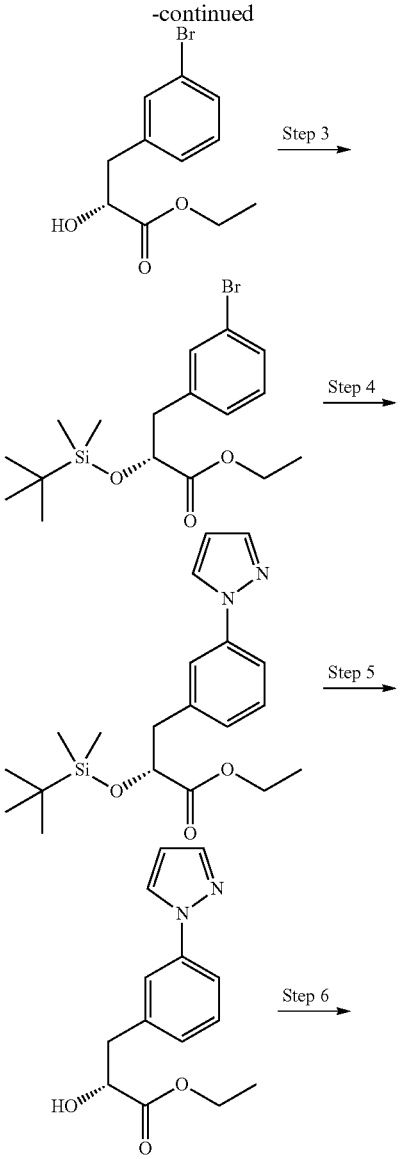

Step 1: (2R)-3-(3-bromophenyl)-2-hydroxypropanoic acid. (2R)-2-amino-3-(3-bromophenyl)propanoic acid (1.0 g, 4.10 mmol) was dissolved in 4:1 water/AcOH (40 ml) and cooled to 0° C. To this was added slowly 1 M sodium nitrite (8.2 ml, 8.2 mmol). The reaction was stirred at RT for 16 h, treated with 40% aqueous methylamine (0.48 ml, 12.3 mmol) and stirred for a further 10 min. The reaction was acidified to pH 3 with 1 M HCl and extracted with EtOAc. The organic phase was dried over Na$_2$SO$_4$ and concentrated to give the title compound as a yellow oil. Y=54%. $^1$H NMR (400 MHz, DMSO-d$_6$) δ 7.54-7.35 (m, 2H), 7.34-7.16 (m, 2H), 5.76 (s, 1H), 4.16 (dd, J=8, 4 Hz, 1H), 2.97 (dd, J=14, 4 Hz, 1H), 2.79 (dd, J=14, 8 Hz, 1H). CO$_2$H proton not seen.

Step 2: ethyl (2R)-3-(3-bromophenyl)-2-hydroxypropanoate. A solution of (2R)-3-(3-bromophenyl)-2-hydroxypropanoic acid (0.93 g, 3.80 mmol) in EtOH (16 ml) was cooled to 0° C. and treated dropwise with thionyl chloride (0.16 ml, 4.55 mmol). The RM was allowed to warm to RT and stirred for 1 h, then evaporated to dryness. The crude was purified by FCC (EtOAc in hexane) to give the title compound as a pale yellow oil. Y=75%. $^1$H NMR (400 MHz, DMSO-d$_6$) δ 7.51-7.35 (m, 2H), 7.24 (d, J=2 Hz, 2H), 5.59 (d, J=6 Hz, 1H), 4.33-4.18 (m, 1H), 4.14-3.97 (m, 2H), 2.95 (dd, J=14, 5 Hz, 1H), 2.83 (dd, J=14, 8 Hz, 1H), 1.15 (t, J=7 Hz, 3H)

Step 3: ethyl (2R)-3-(3-bromophenyl)-2-[(tert-butyldimethylsilyl)oxy]propanoate. A solution of ethyl (2R)-3-(3-bromophenyl)-2-hydroxypropanoate (0.75 g, 3.06 mmol) and imidazole (0.42 g, 6.12 mmol) in DMF (16 ml) was treated with tert-butyldimethylsilyl chloride (0.55 g, 3.67 mmol). The RM was stirred at RT for 16 h, then diluted with water and extracted twice with EtOAc. The combined organics were washed with brine, dried over anhydrous Na$_2$SO$_4$ and concentrated. The crude was purified by FCC (EtOAc in hexane) to give the title compound as a colourless oil. Y=98%. $^1$H NMR (300 MHz, DMSO-d$_6$) δ 7.48-7.38 (m, 2H), 7.28-7.20 (m, 2H), 4.40 (dd, J=9, 4 Hz, 1H), 4.18-4.05 (m, 2H), 3.02 (dd, J=13, 4 Hz, 1H), 2.81 (dd, J=13, 9 Hz, 1H), 1.19 (t, J=7 Hz, 3H), 0.76 (s, 9H), −0.10 (s, 3H), −0.23 (s, 3H)

Step 4: ethyl (2R)-2-[(tert-butyldimethylsilyl)oxy]-3-[3-(1H-pyrazol-1-yl)phenyl]propanoate. A sealed vessel charged with ethyl (2R)-3-(3-bromophenyl)-2-[(tert-butyldimethylsilyl)oxy]propanoate (0.30 g, 0.77 mmol), pyrazole (79 mg, 1.16 mmol), copper(I) iodide (15 mg, 0.077 mmol), (S,S)-(+)-N,N'-dimethyl-1,2-cyclohexanediamine (22 mg, 0.16 mmol) and potassium carbonate (225 mg, 1.63 mmol) in 1,4-dioxane (15 ml) was degassed and back-filled with argon. The reaction was stirred at 100° C. for 16 h. The RM was filtered through Celite, washed with EtOAc and concentrated. The residue was partitioned between water and EtOAc, then the organic phase dried (Na$_2$SO$_4$), filtered and concentrated. The crude was purified by FCC (EtOAc/hexane) to give the title compound as a yellow oil. Y=14%. MS ES$^+$: 375.1

Step 5: ethyl (2R)-2-hydroxy-3-[3-(1H-pyrazol-1-yl)phenyl]propanoate. To a solution of ethyl (2R)-2-[(tert-butyldimethylsilyl)oxy]-3-[3-(1H-pyrazol-1-yl)phenyl]propanoate (0.10 g, 0.27 mmol) in dry THF (1 ml) was added triethylamine trihydrofluoride (0.52 ml, 3.2 mmol). The RM was stirred at RT for 16 h, diluted with EtOAc and washed with dilute sodium bicarbonate solution. The aqueous phase was extracted with EtAOc and the combined organics washed sequentially with water and brine, dried over Na$_2$SO$_4$, filtered and concentrated in vacuo to give the title compound as a yellow oil. Y=57%. MS ES$^+$: 261.3

Step 6: ethyl (2R)-2-{[(1,2,3,5,6,7-hexahydro-s-indacen-4-yl)carbamoyl]oxy}-3-[3-(1H-pyrazol-1-yl)phenyl]propanoate. The title compound was prepared according to the General procedure B using ethyl (2R)-2-hydroxy-3-[3-(1H-pyrazol-1-yl)phenyl]propanoate and Intermediate A as starting materials. The crude product was purified by FCC (EtOAc in hexane). Y=12%. MS ES$^+$: 460.6. $^1$H NMR (300 MHz, DMSO-d$_6$) δ 9.12 (s, 1H), 8.49 (s, 1H), 7.88-7.63 (m, 3H), 7.50-7.34 (m, 1H), 7.29-7.15 (m, 1H), 6.92 (s, 1H), 6.65-6.44 (m, 1H), 5.23-5.18 (m, 1H), 4.12 (q, J=7 Hz, 2H), 3.21 (s, 2H), 2.81-2.74 (m, 4H), 2.64-2.58 (m, 4H), 1.99-1.81 (m, 4H), 1.15 (t, J=7 Hz, 3H).

Example 44. Ethyl 2-{[(2,6-difluorophenyl)carbamoyl]oxy}-3-1H-pyrazol-1-yl)propanoate

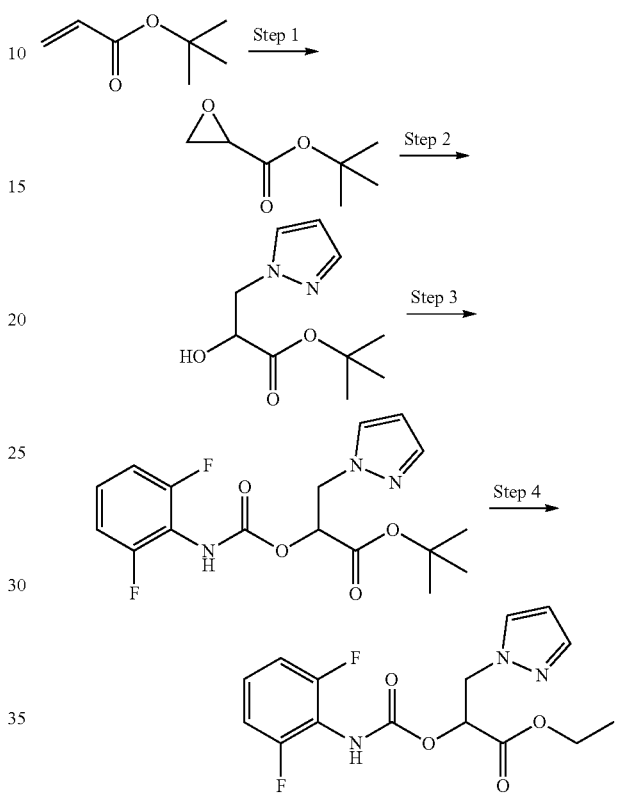

Step 1: tert-butyl oxirane-2-carboxylate. Tert-butyl acrylate (30 g, 234 mmol) was dissolved in DCM (300 ml). A solution of meta-chloroperoxybenzoic acid (50.5 g, 293 mmol) in DCM (420 ml) was added and the RM heated at reflux for 2 days. More meta-chloroperoxybenzoic acid (67 g, 388 mmol) was added and the reaction heated at reflux for a further 4 days. The RM was filtered. The filtrate was cooled over an ice-water bath and sat. Na$_2$S$_2$O$_3$ was added carefully. The layers were separated. The organic phase was filtered, washed with sat. sodium bicarbonate solution and filtered again. The organic phase was washed with brine and filtered. The filtrate was dried over Na$_2$SO$_4$, filtered and concentrated in vacuo. The resulting residue was suspended in hexanes, filtered and the filtrate concentrated in vacuo to give the title compound as a yellow oil. Y=47%. $^1$H NMR (300 MHz, DMSO-d$_6$) δ 3.34 (dd, J=4, 3 Hz, 1H), 2.95-2.87 (m, 2H), 1.52 (s, 9H)

Step 2: tert-butyl 2-hydroxy-3-(1H-pyrazol-1-yl)propanoate. Tert-butyl oxirane-2-carboxylate (10.0 g, 69.4 mmol) was dissolved in anhydrous EtOH (210 ml) and treated with pyrazole (11.8 g, 173 mmol). The RM was heated at 80° C. for 18 h. The solvent was removed in vacuo and then co-evaporated with toluene. Purification by FCC (0-40% EtOAc in DCM) followed by reverse-phase FCC (C18, 5-90% ACN in H$_2$O) gave the title compound as a white solid. Y=19%. $^1$H NMR (300 MHz, DMSO-d$_6$) δ 7.66 (dd, J=2, 1 Hz), 7.43 (dd, J=2, 1 Hz), 6.21 (t, J=2 Hz, 1H), 5.69-5.65 (m, 1H), 4.37-4.18 (m, 3H), 1.39 (s, 9H)

Step 3: tert-butyl 2-{[(2,6-difluorophenyl)carbamoyl]oxy}-3-(1H-pyrazol-1-yl)propanoate. The title compound was prepared according to the General procedure A using tert-butyl 2-hydroxy-3-(1H-pyrazol-1-yl)propanoate and 2,6-difluorophenyl isocyanate as starting materials. The crude product was purified by FCC (0 to 10% MeOH in DCM). Y=69%. MS ES+: 368

Step 4: ethyl 2-{[(2,6-difluorophenyl)carbamoyl]oxy}-3-1H-pyrazol-1-yl)propanoate. A solution of tert-butyl 2-{[(2,6-difluorophenyl)carbamoyl]oxy}-3-(1H-pyrazol-1-yl)propanoate (0.10 g, 0.27 mmol) in EtOH (2.0 ml) was treated with 4 M HCl in dioxane (0.10 ml, 0.4 mmol) and heated to reflux for 3 h. The RM was evaporated to dryness and purified by FCC (0-10% MeOH in DCM) to give the title compound as a white solid. Y=22%. MS ES+: 340.3. ¹H NMR (300 MHz, DMSO-d₆) δ 9.55 (s, 1H), 7.78 (s, 1H), 7.46 (s, 1H), 7.43-7.32 (m, 1H), 7.22-7.12 (m, 2H), 6.27 (s, 1H), 5.29 (s, 1H), 4.62 (s, 2H), 4.12 (q, J=7 Hz, 2H), 1.17 (t, J=7 Hz, 3H)

Example 45. Ethyl 2-[(phenylcarbamoyl)oxy]-3-(1H-pyrazol-1-yl)propanoate

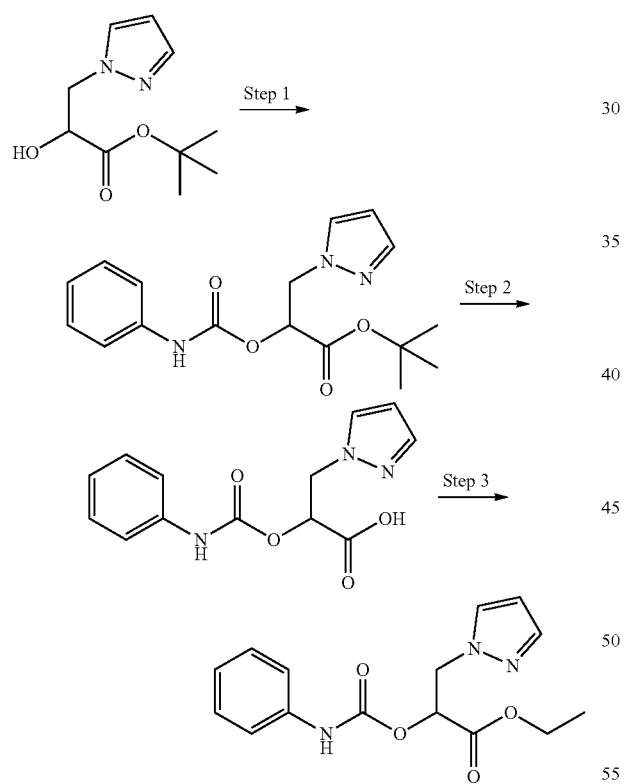

Step 1: tert-butyl 2-[(phenylcarbamoyl)oxy]-3-(1H-pyrazol-1-yl)propanoate. The title compound was prepared according to the General procedure A using tert-butyl 2-hydroxy-3-(1H-pyrazol-1-yl)propanoate and phenyl isocyanate as starting materials. The crude product was purified by FCC (0 to 40% EtOAc in hexane). Y=65%. ¹H NMR (300 MHz, DMSO-d₆) δ 9.89 (s, 1H), 7.79 (dd, J=2, 1 Hz, 1H), 7.47 (dd, J=2, 1 Hz, 1H), 7.46-7.37 (m, 2H), 7.34-7.24 (m, 2H), 7.04-7.00 (m, 1H), 6.28 (t, J=2 Hz, 1H), 5.26-5.21 (m, 1H), 4.63-4.57 (m, 2H), 1.39 (s, 9H)

Step 2: 2-[(phenylcarbamoyl)oxy]-3-(1H-pyrazol-1-yl)propanoic acid. A solution of tert-butyl 2-[(phenylcarbamoyl)oxy]-3-(1H-pyrazol-1-yl)propanoate (218 mg, 0.66 mmol) in 4:1 DCM/TFA (5 ml) was stirred at RT for 12 h. The RM was evaporated and coevaporated with hexane, then purified by reverse phase HPLC to give the title compound as an off-white solid. Y=14%. MS ES+: 276.1

Step 3: ethyl 2-[(phenylcarbamoyl)oxy]-3-(1H-pyrazol-1-yl)propanoate. The title compound was prepared according to General Procedure E using 2-[(phenylcarbamoyl)oxy]-3-(1H-pyrazol-1-yl)propanoic acid and EtOH as starting materials. The crude was purified by FCC (0-40% EtOAc in hexane) followed by prep TLC (40% EtOAc in hexane). Y=18%. MS ES+: 304.3. ¹H NMR (400 MHz, DMSO-d₆) δ 9.94 (s, 1H), 7.78 (d, J=2 Hz, 1H), 7.47 (dd, J=2, 1 Hz, 1H), 7.46-7.37 (m, 2H), 7.33-7.24 (m, 2H), 7.06-6.98 (m, 1H), 6.30-6.26 (m, 1H), 5.37 (t, J=5 Hz, 1H), 4.65-4.62 (m, 2H), 4.18-4.11 (m, 2H), 1.18 (t, J=7 Hz, 3H)

Example 46. Ethyl 2-{[(2-ethyl-6-methylphenyl)carbamoyl]oxy}-3-(1H-pyrazol-1-yl)propanoate

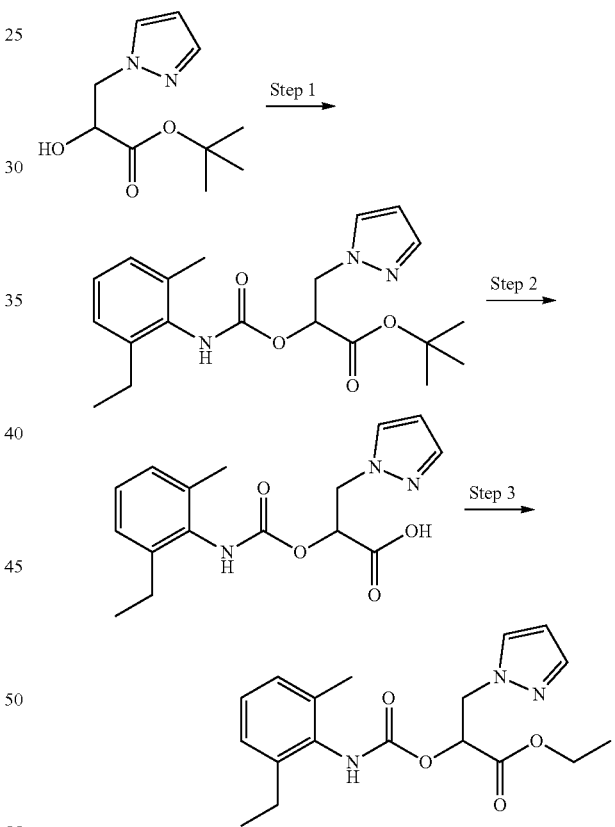

Step 1: tert-butyl 2-{[(2-ethyl-6-methylphenyl)carbamoyl]oxy}-3-(1H-pyrazol-1-yl)propanoate. The title compound was prepared according to the General procedure A using tert-butyl 2-hydroxy-3-(1H-pyrazol-1-yl)propanoate and 1-ethyl-2-isocyanato-3-methylbenzene as starting materials. The crude product was purified by FCC (0 to 40% EtOAc in hexane). Y=50%. ¹H NMR (300 MHz, DMSO-d₆) δ 8.96 (s, 1H), 7.80 (d, J=2 Hz, 1H), 7.48 (d, J=1 Hz, 1H), 7.14-7.02 (m, 3H), 6.29 (t, J=2 Hz, 1H), 5.16 (t, J=6 Hz, 1H), 4.59 (d, J=6 Hz, 2H), 2.12 (s, 3H), 1.40-1.36 (m, 11H), 1.07 (t, J=8 Hz, 3H)

Step 2: 2-{[(2-ethyl-6-methylphenyl)carbamoyl]oxy}-3-(1H-pyrazol-1-yl)propanoic acid. A solution of tert-butyl 2-{[(2-ethyl-6-methylphenyl)carbamoyl]oxy}-3-(1H-pyrazol-1-yl)propanoate (0.22 g, 0.59 mmol) in 4:1 DCM/TFA (5 ml) was stirred at RT for 2 h. The RM was evaporated and co-evaporated with hexane, then purified by reverse phase HPLC to give the title compound as an off-white solid. Y=11%. MS ES+: 318.4

Step 3: ethyl 2-{[(2-ethyl-6-methylphenyl)carbamoyl]oxy}-3-(1H-pyrazol-1-yl)propanoate. The title compound was prepared according to General Procedure E using 2-{[(2-ethyl-6-methylphenyl)carbamoyl]oxy}-3-(1H-pyrazol-1-yl)propanoic acid and EtOH as starting materials. The crude was purified by FCC (0-40% EtOAc in hexane). Y=25%. MS ES+: 346.4. $^1$H NMR (400 MHz, DMSO-$d_6$) δ 9.00 (s, 1H), 7.79 (d, J=2 Hz, 1H), 7.48 (d, J=1 Hz, 1H), 7.14-7.04 (m, 3H), 6.29 (t, J=2 Hz, 1H), 5.31 (t, J=6 Hz, 1H), 4.65-4.62 (m, 2H), 4.17-4.10 (m, 2H), 2.54-2.52 (m, 2H), 2.11 (s, 3H), 1.18 (t, J=7 Hz, 3H), 1.07 (t, J=8 Hz, 3H)

Example 47. Ethyl 2-{[(2,6-dimethylphenyl)carbamoyl]oxy}-3-(1H-pyrazol-1-yl)propanoate Step 2: 2-{[(2,6-dimethylphenyl)carbamoyl]oxy}-3-(1H-pyrazol-1-yl)propanoic acid. A solution of tert-butyl 2-{[(2,6-dimethylphenyl)carbamoyl]oxy}-3-(1H-pyrazol-1-yl)propanoate (0.36 g, 1.00 mmol) in 4:1 DCM/TFA (5 ml) was stirred at RT for 5 h. The RM was evaporated and co-evaporated three times with hexane, then purified by prep TLC (10% MeOH, 2% AcOH, 88% DCM) to give the title compound as an off-white solid. Y=7% MS ES+: 304.2.

Step 3: ethyl 2-{[(2,6-dimethylphenyl)carbamoyl]oxy}-3-(1H-pyrazol-1-yl)propanoate. The title compound was prepared according to General Procedure E using 2-{[(2,6-dimethylphenyl)carbamoyl]oxy}-3-(1H-pyrazol-1-yl)propanoic acid and EtOH as starting materials. The crude was purified by FCC (0-40% EtOAc in hexane). Y=34%. MS ES+: 332.6. $^1$H NMR (400 MHz, DMSO-$d_6$) δ 9.01 (s, 1H), 7.79 (d, J=2 Hz, 1H), 7.48 (d, J=2 Hz, 1H), 7.10-7.03 (m, 3H), 6.29 (t, J=2 Hz, 1H), 5.30 (t, J=6 Hz, 1H), 4.65-4.62 (m, 2H), 4.16-4.09 (m, 2H), 2.12 (s, 6H), 1.18 (t, J=7 Hz, 3H).

Example 48. The following compounds were synthesised according to the scheme below using a synthetic route analogous to Example 47

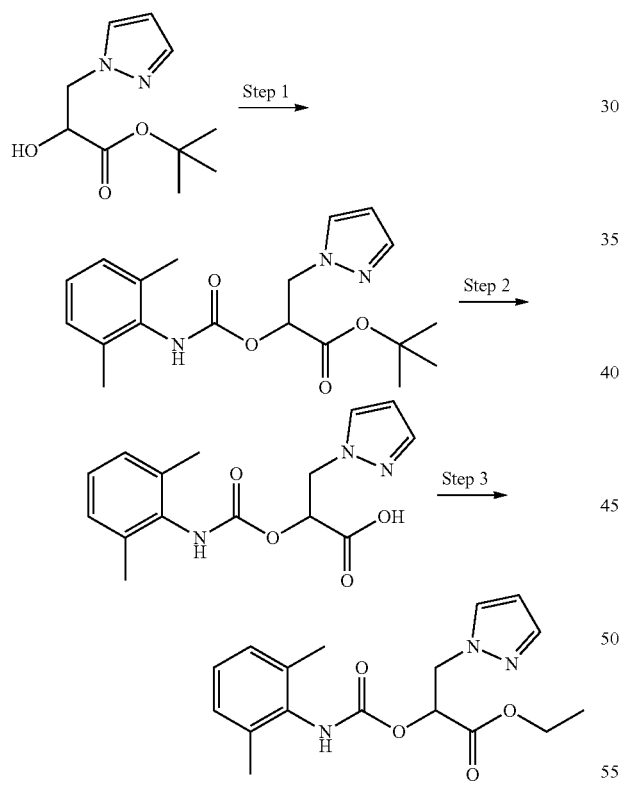

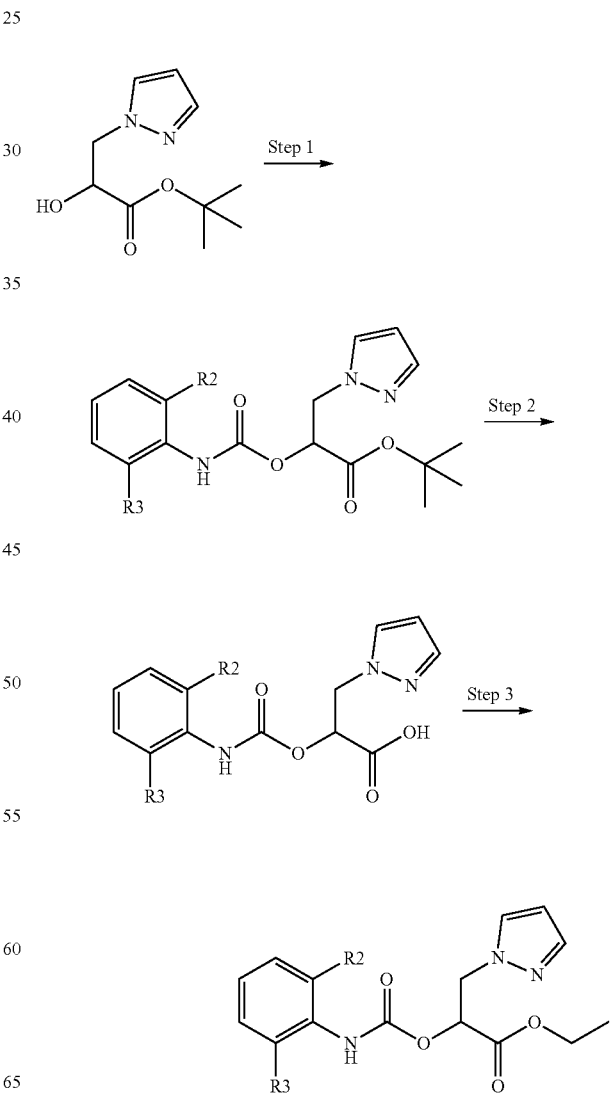

Step 1: tert-butyl 2-{[(2,6-dimethylphenyl)carbamoyl]oxy}-3-(1H-pyrazol-1-yl)propanoate. The title compound was prepared according to the General procedure A using tert-butyl 2-hydroxy-3-(1H-pyrazol-1-yl)propanoate and 2,6-dimethylphenylisocyanate as starting materials. The crude product was purified by FCC (0 to 40% EtOAc in hexane). Y=56%. $^1$H NMR (300 MHz, DMSO-$d_6$) δ 8.98 (s, 1H), 7.80 (d, J=2 Hz, 1H), 7.48 (d, J=2 Hz, 1H), 7.09-7.02 (m, 3H), 6.29 (t, J=2 Hz, 1H), 5.17 (t, J=6 Hz, 1H), 4.60 (d, J=6 Hz, 2H), 2.13 (s, 6H), 1.38 (s, 9H).

151
Ethyl 2-{[(2,6-diethylphenyl)carbamoyl]oxy}-3-(1H-pyrazol-1-yl)propanoate

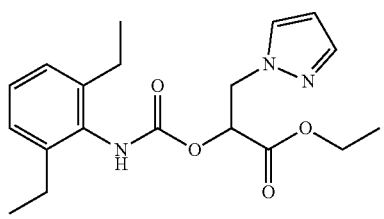 [SMILES: CCOC(=O)C(Cn1cccn1)OC(=O)Nc1c(CC)cccc1CC]

MS ES⁻¹: 360.4. ¹H NMR (400 MHz, DMSO-d₆) δ 8.98 (s, 1H), 7.79 (d, J=2 Hz, 1H), 7.49 (d, J=1 Hz, 1H), 7.13-7.04 (m, 3H), 6.30 (t, J=2 Hz, 1H), 5.31 (t, J=6 Hz, 1H), 4.63 (d, J=6 Hz, 2H), 4.17-4.09 (m, 2H), 2.49-2.43 (m, 4H), 2.12 (s, 6H), 1.18 (t, J=7 Hz, 3H), 1.13-1.03 (m, 6H).

Ethyl 2-{[(2-fluoro-6-methylphenyl)carbamoyl]oxy}-3-(1H-pyrazol-1-yl)propanoate

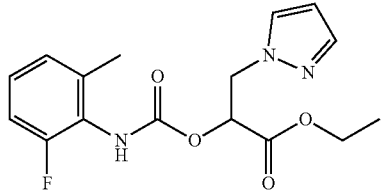 [SMILES: CCOC(=O)C(Cn1cccn1)OC(=O)Nc1c(C)cccc1F]

MS ES⁻¹: 336.5. ¹H NMR (300 MHz, DMSO-d₆) δ 9.24 (s, 1H), 7.78 (s, 1H), 7.47 (s, 1H), 7.29-7.14 (m, 1H), 7.13-6.97 (m, 2H), 6.28 (s, 1H), 5.38-5.20 (m, 1H), 4.75-4.52 (m, 2H), 4.12 (q, J=7 Hz, 2H), 2.17 (s, 3H), 1.17 (t, J=7 Hz, 3H).

Ethyl 2-{[(2-chloro-6-fluorophenyl)carbamoyl]oxy}-3-(1H-pyrazol-1-yl)propanoate

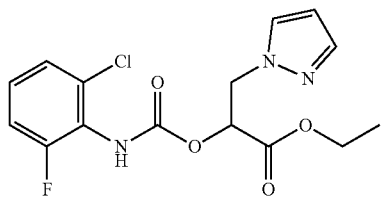

MS ES⁻¹: 356.5. ¹H NMR (400 MHz, DMSO-d₆) δ 9.59 (s, 1H), 7.78 (s, 1H), 7.47 (s, 1H), 7.41-7.24 (m, 3H), 6.28 (s, 1H), 5.29 (s, 1H), 4.63 (s, 2H), 4.12 (q, J=7 Hz, 2H), 1.17 (t, J=7 Hz, 3H).

152
Ethyl 2-{[(2-chloro-6-methylphenyl)carbamoyl]oxy}-3-(1H-pyrazol-1-yl)propanoate

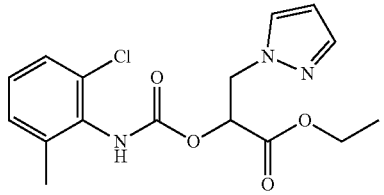 [SMILES: CCOC(=O)C(Cn1cccn1)OC(=O)Nc1c(C)cccc1Cl]

MS ES⁻¹: 352.5. ¹H NMR (300 MHz, DMSO-d₆) δ 9.34 (s, 1H), 7.79 (d, J=2 Hz, 1H), 7.48 (d, J=1 Hz, 1H), 7.36-7.31 (m, 1H), 7.27-7.19 (m, 2H), 6.32-6.26 (m, 1H), 5.31 (t, J=6 Hz, 1H), 4.64 (d, J=5 Hz, 2H), 4.13 (q, J=7 Hz, 2H), 2.18 (s, 3H), 1.18 (t, J=7 Hz, 3H).

Ethyl 2-{[(2,6-dichlorophenyl)carbamoyl]oxy}-3-(1H-pyrazol-1-yl)propanoate

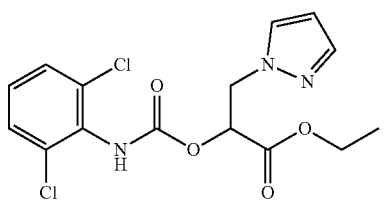 [SMILES: CCOC(=O)C(Cn1cccn1)OC(=O)Nc1c(Cl)cccc1Cl]

MS ES⁺: 372.8. ¹H NMR (300 MHz, chloroform-d) δ 7.54 (s, 1H), 7.42-7.36 (m, 2H), 7.26-7.17 (m, 1H), 6.26 (s, 1H), 5.52-5.44 (m, 1H), 4.74-4.62 (m, 2H), 4.27 (q, J=7 Hz, 2H), 1.30 (t, J=7 Hz, 3H).

Example 49. Ethyl 2-[(cyclohexylcarbamoyl)oxy]-3-(1H-pyrazol-1-yl)propanoate

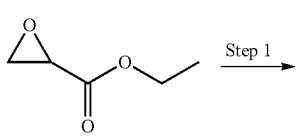

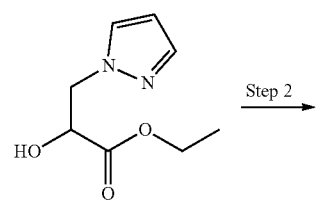

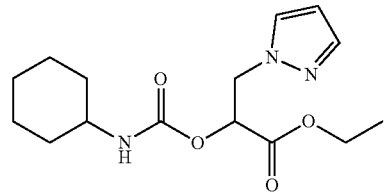

Step 1: ethyl 2-hydroxy-3-(1H-pyrazol-1-yl)propanoate. To a stirred solution of ethyl-2,3-epoxy propanoate (2 g, 17.2 mmol) in ethanol (20 ml) was added pyrazole (1.17 g, 17.2 mmol) at room temperature. The reaction mixture was heated at 80° C. for 16 h. The reaction mixture was allowed to cool to room temperature and concentrated under vacuum. The resulting crude was poured in water (100 ml) and extracted with ethyl acetate (3×70 ml). The combined organic phases were washed with water (5×70 ml) to remove excess of pyrazole. The organic phase was dried over anhydrous Na₂SO₄, filtered and concentrated under vacuum to give the title compound. Y=35%. MS ES⁺: 185.2.

Step 2: ethyl 2-[(cyclohexylcarbamoyl)oxy]-3-(1H-pyrazol-1-yl)propanoate. To a solution of cyclohexyl isocyanate (0.067 g, 0.54 mmol) in DMF (1.5 ml) were added ethyl 2-hydroxy-3-(1H-pyrazol-1-yl)propanoate (0.1 g, 0.54 mmol) and copper(I)chloride (0.058 g 5.90 mmol) at room temperature. The reaction was at stirred room temperature for 10 min. The reaction mixture was poured in water (30 ml) and extracted with ethyl acetate (2×30 mL). The combined organic phases were washed with cold water (5×30 ml) followed by brine (30 ml), dried over anhydrous Na₂SO₄, filtered and concentrated under vacuum. The crude material was purified by FCC (20% ethyl acetate in hexane) to give the title compound as a colorless liquid. Y=55%. MS ES⁺: 310.2. ¹H NMR (400 MHz, DMSO-d₆) δ 7.73-7.72 (m, 1H), 7.44-7.41 (m, 2H), 6.25 (t, J=4 Hz, 1H), 5.16 (t, J=5 Hz, 1H), 4.57-4.51 (m, 2H), 4.10-4.05 (m, 2H), 3.20-3.15 (m, 1H), 1.73-1.51 (m, 5H), 1.28-1.19 (m, 8H).

Example 50. Ethyl 2-[(cyclopentylcarbamoyl)oxy]-3-(1H-pyrazol-1-yl)propanoate

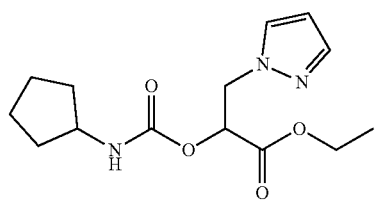 [SMILES: CCOC(=O)C(Cn1cccn1)OC(=O)NC1CCCC1]

Synthesised using a synthetic route analogous to Example 49. MS ES⁺: 296.2. ¹H NMR (400 MHz, DMSO-d₆) δ 7.72 (d, J=2 Hz, 1H), 7.50-7.44 (m, 2H), 6.25 (t, J=2 Hz, 1H), 5.16 (t, J=5 Hz, 1H), 4.56-4.51 (m, 2H), 4.12-4.06 (m, 2H), 3.74-3.69 (m, 1H), 1.77-1.71 (m, 2H), 1.69-1.58 (m, 2H), 1.48-1.38 (m, 4H), 1.30-1.26 (m, 3H).

Example 51. Ethyl 3-(4-cyano-1H-pyrazol-1-yl)-2-{[(1,2,3,5,6,7-hexahydro-s-indacen-4-yl)carbamoyl]oxy}propanoate

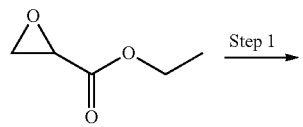

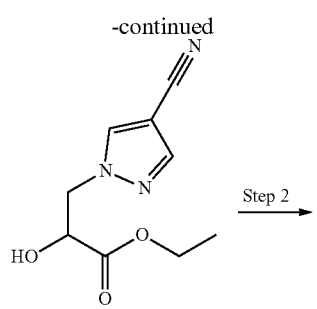

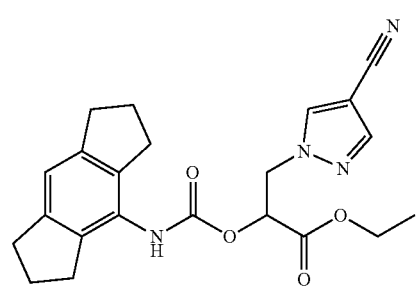

Step 1: ethyl 3-(4-cyano-1H-pyrazol-1-yl)-2-hydroxypropanoate. To a solution of ethyl-2,3-epoxy propanoate (0.75 g, 6.45 mmol) in dry EtOH (5 ml) was added 4-cyanopyrazole (0.30 g, 3.22 mmol). The RM was heated at 90° C. in a sealed tube for 16 h. The RM was evaporated to give the title compound as a yellow liquid, used without further purification. MS ES⁺: 210.1

Step 2: ethyl 3-(4-cyano-1H-pyrazol-1-yl)-2-{[(1,2,3,5,6,7-hexahydro-s-indacen-4-yl)carbamoyl]oxy}propanoate.
The title compound was prepared according to the General procedure B using ethyl 3-(4-cyano-1H-pyrazol-1-yl)-2-hydroxypropanoate and Intermediate A as starting materials. The crude product was purified by FCC (0-30% EtOAc in hexane). Y=10%. MS ES⁺: 409.2. ¹H NMR (300 MHz, DMSO-d₆) δ 9.17 (s, 1H), 8.68-8.61 (m, 1H), 8.10 (s, 1H), 6.96 (s, 1H), 5.35 (br. s, 1H), 4.71 (br. s, 2H), 4.14 (q, J=7 Hz, 2H), 2.89-2.79 (m, 4H), 2.73-2.58 (m, 4H), 2.03-1.89 (m, 4H), 1.19 (t, J=7 Hz, 3H).

Example 52. Ethyl 2-[(cycloheptylcarbamoyl)oxy]-3-(1H-pyrazol-1-yl)propanoate

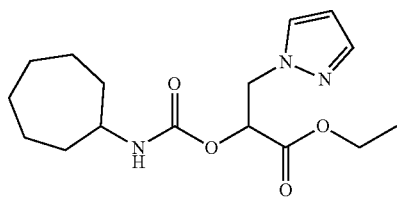 [SMILES: CCOC(=O)C(Cn1cccn1)OC(=O)NC1CCCCCC1]

Synthesised using a synthetic route analogous to Example 49. MS ES⁺: 324.3. ¹H NMR (400 MHz, DMSO-d₆) δ 7.72 (d, J=2 Hz, 1H), 7.46-7.44 (m, 2H), 6.25 (t, J=2 Hz, 1H), 5.15 (t, J=5 Hz, 1H), 4.52-4.51 (m, 2H), 4.11-4.06 (m, 2H), 3.42-3.39 (m, 1H), 1.74-1.72 (m, 2H), 1.59-1.24 (m, 9H), 1.17-1.13 (m, 3H).

Example 53. Ethyl 2-{[(2-cyano-6-methylphenyl)carbamoyl]oxy}-3-(1H-pyrazol-1-yl)propanoate

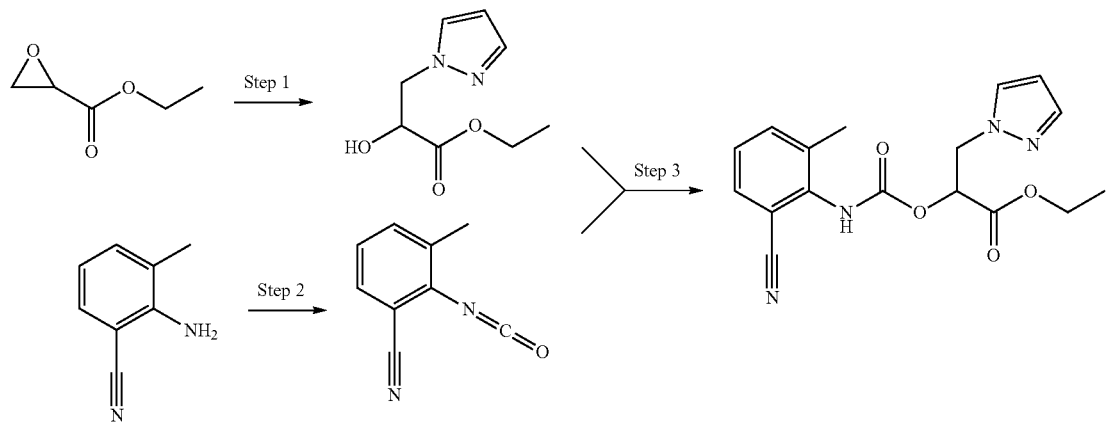

Step 1: ethyl 2-hydroxy-3-(1H-pyrazol-1-yl)propanoate. To a solution of ethyl-2,3-epoxy propanoate (11 g, 94.7 mmol) in dry EtOH (190 ml) was added pyrazole (16.1 g, 236 mmol). The RM was heated at 90° C. in a sealed reactor for 3 days. The RM was evaporated. The crude was purified by FCC (0-100% DCM in hexane, then 0-30% EtOAc in DCM) followed by evaporation (55° C., <4 mbar) to give the title compound as a yellow oil. Y=31%. $^1$H NMR (300 MHz, DMSO-$d_6$) δ 7.66 (dd, J=2, 1 Hz, 1H), 7.43 (dd, J=2, 1 Hz, 1H), 6.21 (t, J=2 Hz, 1H), 5.82 (d, J=6 Hz, 1H), 4.45-4.20 (m, 3H), 4.10 (q, J=7 Hz, 2H), 1.18 (t, J=7 Hz, 3H).

Step 2: 2-isocyanato-3-methylbenzonitrile. To a solution of 2-amino-3-methylbenzonitrile (0.85 g, 6.4 mmol) in THF (17 ml) was added triethylamine (0.99 ml, 7.1 mmol) followed by phosgene (20% in toluene, 3.41 ml, 6.4 mmol). The RM was heated at reflux for 4 h then allowed to cool to RT. The THF was evaporated in vacuo and the residue precipitated with cold pentane. The resulting mixture was filtered and the filtrate evaporated to give the title compound as a yellow oil. Y=74%. MS ES$^+$: 232.0 (compound analysed in diethylamine to generate diethyl urea).

Step 3: ethyl 2-{[(2-cyano-6-methylphenyl)carbamoyl]oxy}-3-(1H-pyrazol-1-yl)propanoate. The title compound was prepared according to the General procedure A using ethyl 2-hydroxy-3-(1H-pyrazol-1-yl)propanoate and 2-isocyanato-3-methylbenzonitrile as starting materials. The crude product was purified by FCC (0 to 60% EtOAc in hexane) followed by prep HPLC. Y=14%. MS ES$^+$: 343. $^1$H NMR (300 MHz, chloroform-d) δ 7.58-7.46 (m, 4H), 7.33 (d, J=8 Hz, 1H), 6.93 (s, 1H), 6.28 (s, 1H), 5.53-5.45 (m, 1H), 4.69 (s, 2H), 4.28 (q, J=7 Hz, 2H), 2.32 (s, 3H), 1.31 (t, J=7 Hz, 3H).

Example 54. Ethyl 2-{[(2-cyano-6-ethylphenyl)carbamoyl]oxy}-3-(1H-pyrazol-1-yl)propanoate

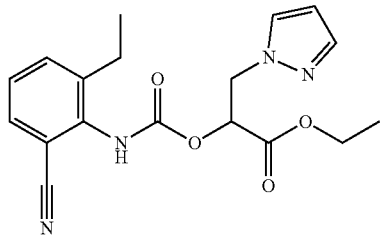 [SMILES: CCOC(=O)C(Cn1cccn1)OC(=O)Nc1c(C#N)cccc1CC]

Synthesised using a synthetic route analogous to Example 53. MS ES$^+$: 357

Example 55. Ethyl 2-{[(2-chloro-6-cyanophenyl)carbamoyl]oxy}-3-(1H-pyrazol-1-yl)propanoate

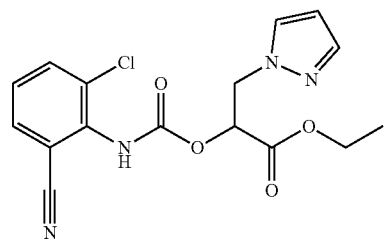 [SMILES: CCOC(=O)C(Cn1cccn1)OC(=O)Nc1c(Cl)cccc1C#N]

Synthesised using a synthetic route analogous to Example 53. MS ES$^+$: 363.0. $^1$H NMR (300 MHz, chloroform-d) δ 7.69 (dd, J=8, 1 Hz, 1H), 7.64 (dd, J=8, 1 Hz, 1H), 7.55 (d, J=2 Hz, 1H), 7.49-7.45 (m 1H), 7.34 (t, J=8 Hz, 1H), 7.08 (s, 1H), 6.31-6.24 (m, 1H), 5.52 (dd, J=6, 5 Hz, 1H), 4.76-4.71 (m, 2H), 4.36-4.19 (m, 2H), 1.73 (s, 1H), 1.30 (t, J=7 Hz, 3H).

Example 56. Ethyl 2-{[(1,2,3,5,6,7-hexahydro-s-indacen-4-yl)carbamoyl]oxy}-3-(pyrazin-2-yl)propanoate

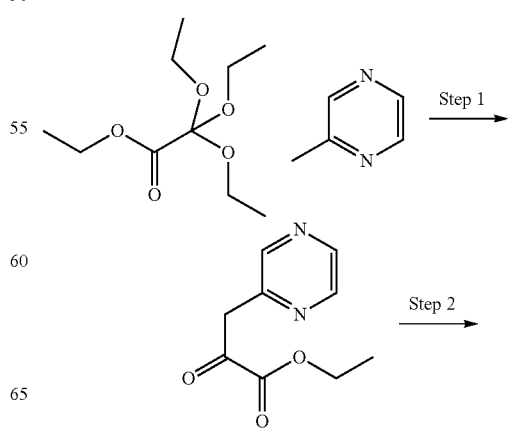

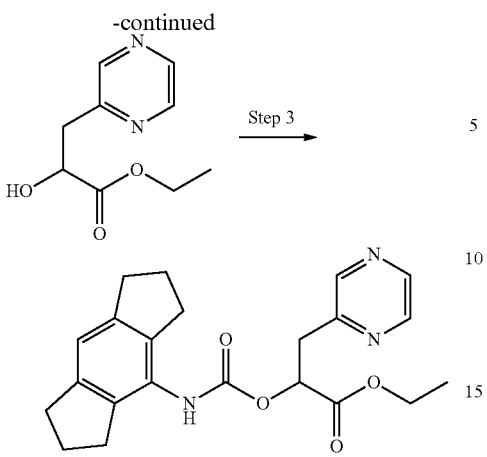

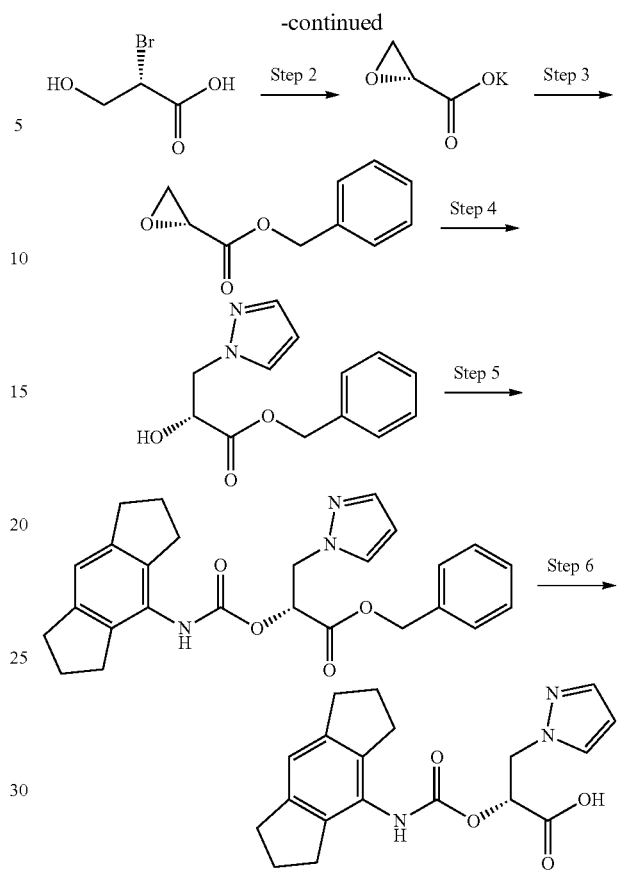

Step 1: ethyl 2-oxo-3-(pyrazin-2-yl)propanoate. To a solution of 2M LDA in THF/hexane/ethylbenzene (4.3 ml, 8.60 mmol) in dry THF (5 ml) cooled to −78° C. under inert atmosphere was added methylpyrazine (0.40 g, 4.25 mmol). The RM was stirred for 15 min then ethyl 2,2,2-triethoxy-acetate (1.03 ml, 4.68 mmol) was added. The solution was allowed to warm to RT and stirred for 16 h. The RM was poured into 1M HCl and stirred for 1 h. The mixture was neutralized with NaHCO$_3$ solution and extracted three times with DCM. The combined organics were washed with brine, dried over Na$_2$SO$_4$, filtered and evaporated. The crude was purified by FCC (0-90% EtOAc in DCM) to give the title compound as an orange solid. Y=87%. $^1$H NMR (300 MHz, chloroform-d) δ 13.01 (s, 1H), 8.60 (d, J=2 Hz, 1H), 8.49 (d, J=3 Hz, 1H), 8.45-8.41 (m, 1H), 6.66 (s, 1H), 4.40 (q, J=7 Hz, 2H), 1.42 (t, J=7 Hz, 3H)

Step 2: ethyl 2-hydroxy-3-(pyrazin-2-yl)propanoate. A solution of ethyl 2-oxo-3-(pyrazin-2-yl)propanoate (0.20 g, 1.03 mmol) in EtOH (40 ml) was cooled to −78° C. and treated with NaBH4 (0.16 g, 4.1 mmol). The RM was stirred for 1 h at −78° C. then allowed to warm to RT and stirred for a further 1 h. The RM was poured onto ice, acidified to pH 2 with 1M HCl and extracted with DCM. The organic phase was dried over Na$_2$SO$_4$, filtered and concentrated in vacuo. The crude was purified by FCC (EtOAc in hexane) to give the title compound as a yellow oil. Y=30%. MS ES$^+$: 197.

Step 3: ethyl 2-{[(1,2,3,5,6,7-hexahydro-s-indacen-4-yl)carbamoyl]oxy}-3-(pyrazin-2-yl)propanoate. The title compound was prepared according to the General procedure A using ethyl 2-hydroxy-3-(pyrazin-2-yl)propanoate and Intermediate A as starting materials. The crude product was purified by FCC (0 to 60% EtOAc in hexane) followed by prep HPLC. Y=7%. MS ES$^+$: 396.1. $^1$H NMR (300 MHz, acetonitrile-d$_3$) δ 8.60-8.48 (m, 3H), 7.00 (s, 1H), 5.36 (dd, J=8, 5 Hz, 1H), 4.20 (q, J=7 Hz, 2H), 3.40-3.30 (br. s, 2H), 2.87 (t, J=7 Hz, 4H), 2.74-2.63 (m 4H), 2.09-2.01 (m, 4H), 1.24 (t, J=7 Hz, 3H).

Example 57. (2R)-2-{[(1,2,3,5,6,7-hexahydro-s-indacen-4-yl)carbamoyl]oxy}-3-(1H-pyrazol-1-yl) propanoic acid

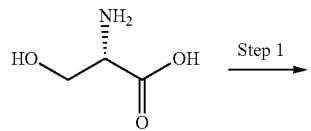

Step 1: (2S)-2-bromo-3-hydroxypropanoic acid. L-serine (52.5 g, 0.50 mol) and potassium bromide (202 g, 1.70 mol) were dissolved in water (400 ml). Hydrobromic acid (48%, 123 ml, 1.0 mol) was added and the RM cooled to −13° C. under Ar atmosphere. Sodium nitrite (43 g, 0.63 mol) was added slowly portionwise (ca. 5 g every 15 min). After each addition the RM turned brown and then the colour slowly faded, but the solution did not decolourise entirely. After complete addition (approximately 2.5 h) the solution was warmed to 0° C., the Ar purge was stopped and the RM stirred for 6 h. Excess nitrogen oxides were removed by bubbling Ar through the mixture for 1 h. The solution was extracted with diethyl ether (6×300 ml). The combined organics were concentrated to 0.5 l under vacuum, dried over anhydrous MgSO$_4$, filtered and evaporated to dryness to give the title compound as a pale yellow oil, used without further purification. Y=88%. $^1$H NMR (400 MHz, DMSO-d$_6$) δ 4.25-4.22, (dd, J=8, 6 Hz, 1H), 3.82-3.76 (m, 1H), 3.70-3.64 (dd, J=11, 6 Hz, 1H).

Step 2: potassium (2R)-oxirane-2-carboxylate. (2S)-2-bromo-3-hydroxypropanoic acid (74.5 g, 0.45 mol) was dissolved in absolute ethanol (300 ml) and cooled to −20° C. under nitrogen. A filtered solution of KOH (50 g, 0.89 mol) in absolute ethanol (300 ml) was slowly added. After 2 h the mixture was allowed to warm to 0° C. and stirred at this temperature for 14 h. The solution was filtered and the filtrate further concentrated to ca. half volume. The mixture was filtered again. The combined filtered solids were dried under vacuum to give the title compound as a white solid. Y=95%. $^1$H NMR (400 MHz, D$_2$O) δ 3.34-3.33 (dd, J=5, 3 Hz, 1H), 2.93-2.90 (dd, J=6, 5 Hz, 1H), 2.76-2.74 (dd, J=6, 3 Hz, 1H).

Step 3: benzyl (2R)-oxirane-2-carboxylate. A suspension of potassium (2R)-oxirane-2-carboxylate (4.0 g, 32 mmol), benzyltriethylammonium chloride (7.3 g, 32 mmol) and benzyl bromide (11.4 ml, 96 mmol) in dichloromethane (230 ml) was heated at reflux for 16 h. The solvent was removed in vacuo. The resulting solid was triturated three times with diethyl ether. The combined ether extracts were filtered, dried (MgSO₄) and evaporated under vacuum. The crude was purified by FCC (10-50% EtOAc/pet. ether) to give the title compound as a colourless oil. Y=46%. $^1$H NMR (400 MHz, CDCl₃) δ 7.43-7.32 (m, 5H), 5.28-5.18 (m, 2H), 3.49-3.48 (dd, J=4, 2 Hz, 1H), 3.02-2.92 (m, 2H).

Step 4: benzyl (2R)-2-hydroxy-3-(1H-pyrazol-1-yl)propanoate. Benzyl (2R)-oxirane-2-carboxylate (3.00 g, 16.8 mmol) was dissolved in absolute ethanol (32 ml) and the resulting solution treated with pyrazole (2.87 g, 42 mmol). The RM was stirred at 90° C. for 16 h then concentrated under vacuum. The crude was purified by FCC (0-70% EtOAc/hexane) then dried under high vacuum (<3 mbar, 63° C.) to remove residual pyrazole. The title compound was obtained as a yellow oil. Y=60%. $^1$H NMR (400 MHz, DMSO-d₆) δ 7.65 (d, J=2 Hz, 1H), 7.46-7.42 (m, 1H), 7.39-7.32 (m, 5H), 6.21 (d, J=2 Hz, 1H), 5.92 (d, J=6 Hz, 1H), 5.17-5.10 (m, 2H), 4.51-4.46 (m, 1H), 4.43-4.39 (m, 1H), 4.34-4.28 (m, 1H).

Step 5: benzyl (2R)-2-{[(1,2,3,5,6,7-hexahydro-s-indacen-4-yl)carbamoyl]oxy}-3-(1H-pyrazol-1-yl)propanoate. The title compound was prepared according to the General procedure A using benzyl (2R)-2-hydroxy-3-(1H-pyrazol-1-yl)propanoate and Intermediate A as starting materials. The crude product was purified by FCC (0 to 50% EtOAc in hexane). Y=78%. $^1$H NMR (300 MHz, DMSO-d₆) δ 9.17 (s, 1H), 7.78 (s, 1H), 7.48 (s, 1H), 7.35 (s, 5H), 6.93 (s, 1H), 6.28 (s, 1H), 5.38 (s, 1H), 5.19-5.10 (m, 2H), 4.66 (s, 2H), 2.78 (t, J=7 Hz, 4H), 2.66-2.52 (m, 4H), 2.01-1.84 (m, 4H).

Step 6: (2R)-2-{[(1,2,3,5,6,7-hexahydro-s-indacen-4-yl)carbamoyl]oxy}-3-(1H-pyrazol-1-yl)propanoic acid. A mixture of benzyl (2R)-2-{[(1,2,3,5,6,7-hexahydro-s-indacen-4-yl)carbamoyl]oxy}-3-(1H-pyrazol-1-yl)propanoate (1.4 g, 3.14 mmol), 10% Pd/C (163 mg, 0.14 mmol) and THF (3 ml) was purged and then stirred under hydrogen atmosphere for 16 h. The solution was filtered through a Quadrasil plug. The filtered solids were extracted with sequential acetonitrile, ethanol and hexane washes. The combined filtrates were evaporated to give the title compound as a white solid. Y=99%. MS ES⁺: 356.2. $^1$H NMR (400 MHz, DMSO-d₆) δ 9.10 (s, 1H), 7.77 (s, 1H), 7.46 (s, 1H), 6.93 (s, 1H), 6.27 (s, 1H), 5.22 (s, 1H), 4.59 (s, 2H), 2.79 (t, J=7 Hz, 4H), 2.65 (d, 4H), 1.97-1.90 (m, 4H).

Example 58. Ethyl 2-{[(1,2,3,5,6,7-hexahydro-s-indacen-4-yl)carbamoyl]oxy}-3-(pyridazin-3-yl)propanoate

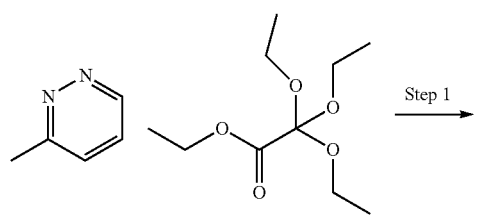

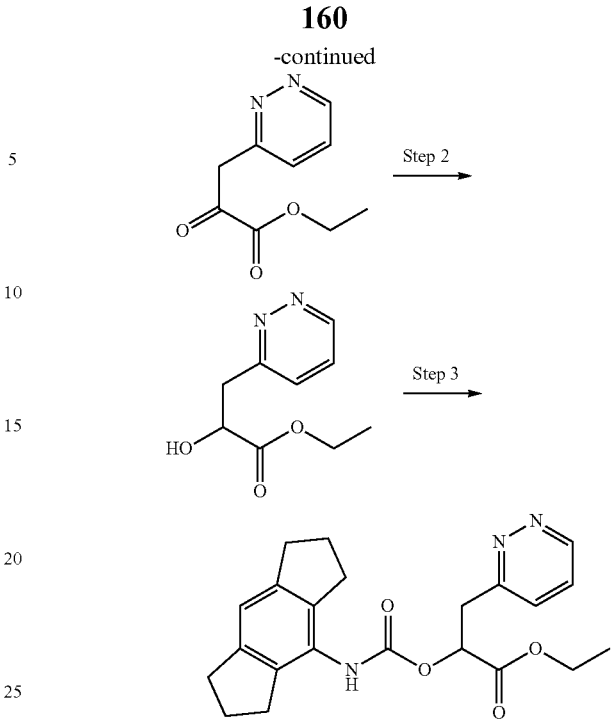

Step 1: ethyl 2-oxo-3-(pyridazin-3-yl)propanoate. To a solution of 2M LDA in THF/hexane/ethylbenzene (2.2 ml, 4.4 mmol) in dry THF (2.5 ml) cooled to −78° C. under inert atmosphere was added 2-methylpyridazine (0.20 g, 2.1 mmol). The RM was stirred for 15 min then ethyl 2,2,2-triethoxyacetate (0.51 ml, 2.3 mmol) was added. The solution was allowed to warm to RT and stirred for 16 h. The RM was poured into 1M HCl and stirred for 1 h. The mixture was neutralized with NaHCO₃ solution and extracted three times with DCM. The combined organics were washed with brine, dried over Na₂SO₄, filtered and evaporated. The crude was purified by FCC (0-90% EtOAc in DCM) to give the title compound as a green solid. Y=51%. $^1$H NMR (300 MHz, chloroform-d) δ 15.03 (s, 1H), 8.60 (dd, J=4, 2 Hz, 1H), 7.42-7.31 (m, 2H), 6.33 (s, 1H), 4.38 (q, J=7 Hz, 2H), 1.42 (t, J=7 Hz, 3H).

Step 2: ethyl 2-hydroxy-3-(pyridazin-3-yl)propanoate. A solution of ethyl 2-oxo-3-(pyridazin-3-yl)propanoate (0.22 g, 1.12 mmol) in EtOH (40 ml) was cooled to −78° C. and treated with NaBH₄ (0.17 g, 4.48 mmol). The RM was stirred for 1 h at −78° C. then allowed to warm to RT and stirred for a further 1.5 h. The RM was poured onto ice, acidified to pH 2 with 1M HCl and extracted with DCM. The organic phase was dried over Na₂SO₄, filtered and concentrated in vacuo. The crude was purified by FCC (MeOH in DCM) to give the title compound as a yellow oil. Y=11%. MS ES⁺: 197

Step 3: ethyl 2-{[(1,2,3,5,6,7-hexahydro-s-indacen-4-yl)carbamoyl]oxy}-3-(pyridazin-3-yl)propanoate. The title compound was prepared according to the General procedure A using ethyl 2-hydroxy-3-(pyridazin-3-yl)propanoate and Intermediate A as starting materials. The crude product was purified by prep HPLC. Y=10%. MS ES⁺: 396.1. $^1$H NMR (300 MHz, chloroform-d) δ 9.13 (s, 1H), 7.59-7.36 (m, 1H), 7.02 (s, 1H), 6.54-6.19 (m, 1H), 5.65-5.47 (m, 1H), 4.26 (q, J=7 Hz, 2H), 3.79-3.46 (m, 2H), 2.89 (t, J=7 Hz, 4H), 2.80-2.66 (m, 4H), 2.11-2.00 (m, 4H), 1.29 (t, J=7 Hz, 3H).

Example 59. Ethyl 3-(1H-pyrazol-1-yl)-2-{[(2,3,6-trifluorophenyl)carbamoyl]oxy}-propanoate

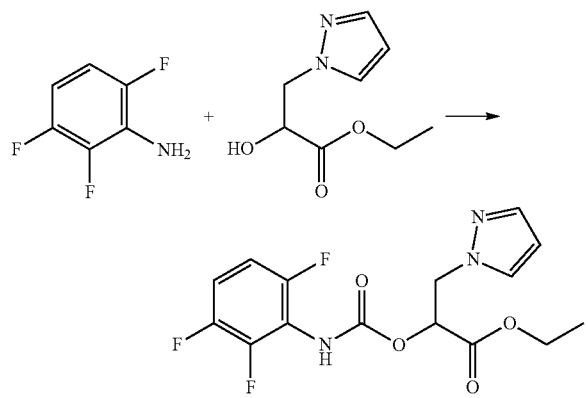

2,3-6-trifluorophenylaniline (0.072 ml, 0.68 mmol) and ethyl 2-hydroxy-3-(1H-pyrazol-1-yl)propanoate (0.15 g, 0.82 mmol) (for synthesis refer to Example 49) were dissolved in THF (8 ml) and treated with triethylamine (0.11 ml, 0.82 mmol). The solution was treated with triphosgene and the resulting mixture stirred at 60° C. for 4 h. The RM was evaporated, then coevaporated with DCM three times. The crude was purified by FCC (0-5% MeOH in DCM) followed by prep HPLC to give the title compound as a white solid. Y=24%. MS ES⁺: 358.4 ¹H NMR (400 MHz, DMSO-d₆) δ 9.78 (s, 1H), 7.85-7.62 (m, 1H), 7.53-7.38 (m, 2H), 7.28-7.16 (m, 1H), 6.26 (s, 1H), 5.31 (t, J=6 Hz, 1H), 4.62 (d, J=4 Hz, 2H), 4.17-4.09 (m, 2H), 1.18 (t, J=7 Hz, 3H).

Example 60. Benzyl (2R)-2-{[(1,2,3,5,6,7-hexahydro-s-indacen-4-yl)carbamoyl]oxy}-3-(1H-pyrazol-1-yl)propanoate

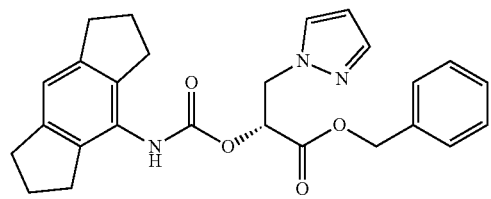 [SMILES: O=C(Nc1c2c(cc3c1CCC3)CCC2)O[C@H](Cn1cccn1)C(=O)OCc1ccccc1]

The title compound is synthesised following the procedures described in Example 57.

Example 61. Ethyl (2R)-2-{[(1,2,3,5,6,7-hexahydro-s-indacen-4-yl)carbamoyl]oxy}-3-(1H-pyrazol-1-yl)propanoate

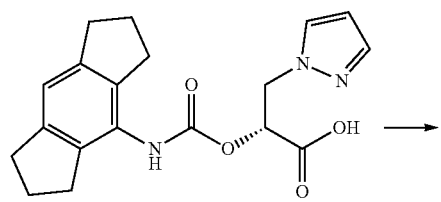

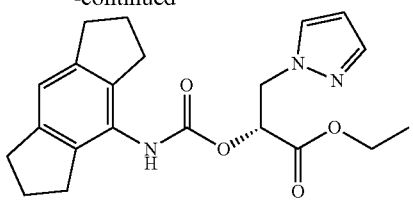

(2R)-2-{[(1,2,3,5,6,7-hexahydro-s-indacen-4-yl)carbamoyl]oxy}-3-(1H-pyrazol-1-yl)propanoic acid (0.20 g, 0.56 mmol) (for synthesis refer to Example 57) was dissolved in EtOH (5 ml) and cooled to 0° C. Thionyl chloride (82 μl, 1.13 mmol) was added and the RM stirred at RT for 16 h. The RM was concentrated in vacuo and the resulting residue diluted with sat. NaHCO₃ solution and extracted with DCM. The organic phase was dried over Na₂SO₄ and concentrated in vacuo. The resulting solid was suspended in hexane, filtered, washed thoroughly with hexane and dried under vacuum to give the title compound as a white solid. Y=66%. MS ES⁺: 384.3. ¹H NMR (300 MHz, chloroform-d) δ 7.55 (s, 1H), 7.49 (s, 1H), 7.03 (s, 1H), 6.43 (s, 1H), 6.28 (s, 1H), 5.45 (s, 1H), 4.66 (s, 2H), 4.24 (q, J=7 Hz, 2H), 2.90 (t, J=8 Hz, 4H), 2.79 (t, J=7 Hz, 4H), 2.18-1.98 (m, 4H), 1.31 (t, J=7 Hz, 3H)

Example 62. Ethyl 2-{[(2-ethyl-6-fluorophenyl)carbamoyl]oxy}-3-(1H-pyrazol-1-yl)propanoate

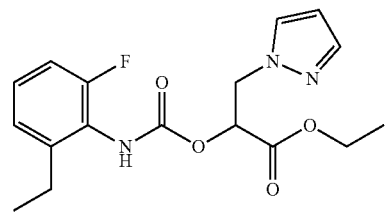 [SMILES: CCOC(=O)C(Cn1cccn1)OC(=O)Nc1c(F)cccc1CC]

Synthesised using a synthetic route analogous to Example 53.

Y=63%

MS ES⁺: 350

¹H NMR (400 MHz, DMSO-d₆) δ 9.19 (s, 1H), 7.78 (s, 1H), 7.48 (s, 1H), 7.32-7.20 (m, 1H), 7.13-7.06 (m, 2H), 6.29 (s, 1H), 5.35-5.25 (m, 1H), 4.69-4.57 (m, 2H), 4.17-4.06 (m, 2H), 2.62-2.52 (m, 2H), 1.17 (t, J=7 Hz, 3H), 1.09 (t, J=7 Hz, 3H).

Example 63. Ethyl (2R)-2-{[(1,2,3,5,6,7-hexahydro-s-indacen-4-yl)carbamoyl]oxy}-3-(1H-imidazol-1-yl)propanoate

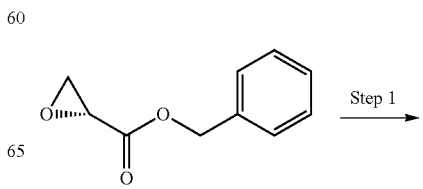

Step 1

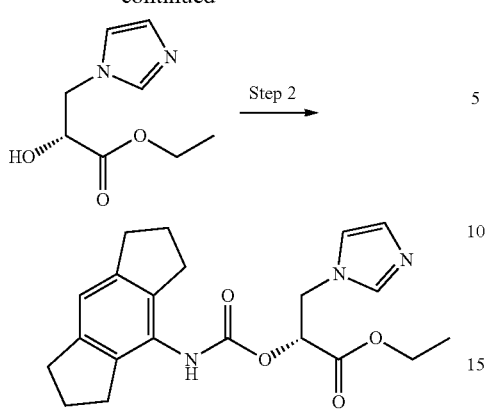

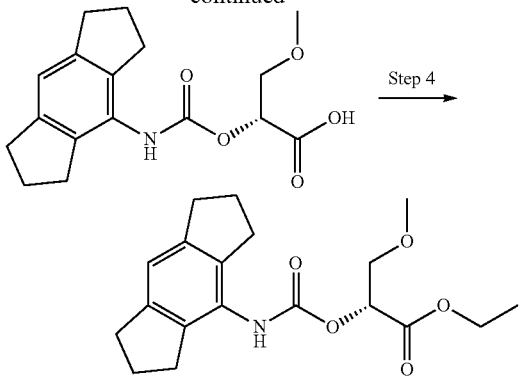

Step 1: ethyl (2R)-2-hydroxy-3-(1H-imidazol-1-yl)propanoate. A mixture of benzyl (2R)-oxirane-2-carboxylate (3.00 g, 16.8 mmol) (for synthesis refer to example 5AJ), imidazole (2.87 g, 42.1 mmol) and ethanol (32 ml) was heated at 90° C. for 16 h. The RM was concentrated in vacuo and purified by FCC (0-10% MeOH in DCM) to give the title compound as a yellow oil. Y=31%. MS ES+: 185.

Step 2: ethyl (2R)-2-{[(1,2,3,5,6,7-hexahydro-s-indacen-4-yl)carbamoyl]oxy}-3-(1H-imidazol-1-yl)propanoate. The title compound was prepared according to the General procedure A using ethyl (2R)-2-hydroxy-3-(1H-imidazol-1-yl)propanoate and Intermediate A as starting materials. The crude product was purified by FCC (0 to 100% (95:5 EtOAc/EtOH) in hexane). Y=32%. MS ES+: 384.3. $^1$H NMR (300 MHz, chloroform-d) δ 7.55 (s, 1H), 7.22-6.85 (m, 3H), 6.57 (s, 1H), 5.35 (s, 1H), 4.47 (s, 2H), 4.25 (q, J=7 Hz, 2H), 2.91 (t, J=7 Hz, 4H), 2.81 (t, J=7 Hz, 4H), 2.16-2.02 (m, 4H), 1.29 (t, J=7 Hz, 3H)

Example 64. Ethyl (2R)-2-{[(1,2,3,5,6,7-hexahydro-s-indacen-4-yl)carbamoyl]oxy}-3-methoxypropanoate

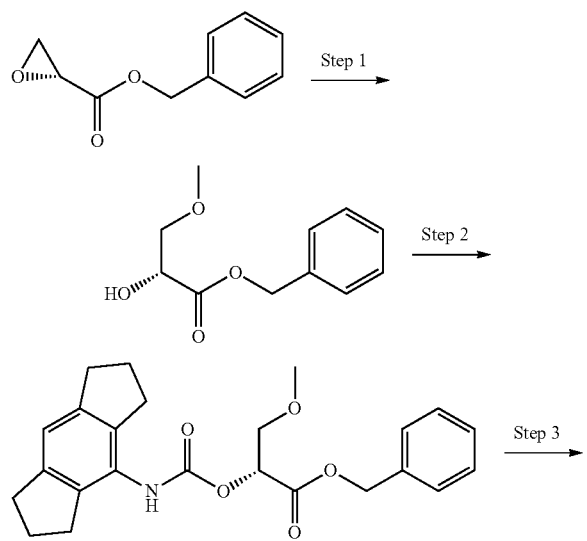

Step 1: benzyl (2R)-2-hydroxy-3-methoxypropanoate. A mixture of benzyl (2R)-oxirane-2-carboxylate (1.36 g, 7.6 mmol) (for synthesis refer to example 5AJ), magnesium perchlorate (0.43 g, 1.9 mmol) and methanol (0.37 ml, 9.2 mmol) were stirred at −10° C. for 10 min, then heated at 45° C. for 20 h. The RM was purified by FCC (20-50% EtOAc in hexane) to give the title compound as a colourless oil. Y=60%. $^1$H NMR (300 MHz, chloroform-d) δ 7.43-7.35 (m, 5H), 5.36-5.21 (m, 2H), 4.41-4.33 (m, 1H), 3.72 (dd, J=3, 2 Hz, 2H), 3.38 (s, 3H), 3.06 (d, J=3, 2 Hz, 1H)

Step 2: benzyl (2R)-2-{[(1,2,3,5,6,7-hexahydro-s-indacen-4-yl)carbamoyl]oxy}-3-methoxypropanoate. The title compound was prepared according to the General procedure B using benzyl (2R)-2-hydroxy-3-methoxypropanoate and Intermediate A as starting materials. The crude product was purified by FCC (0 to 20% EtOAc in hexane). Y=64%. MS ES+: 410.1.

Step 3: (2R)-2-{[(1,2,3,5,6,7-hexahydro-s-indacen-4-yl)carbamoyl]oxy}-3-methoxypropanoic acid. A mixture of benzyl (2R)-2-{[(1,2,3,5,6,7-hexahydro-s-indacen-4-yl)carbamoyl]oxy}-3-methoxypropanoate (0.89 g, 2.17 mmol), 10% Pd/C (0.1 g) and THF (50 ml) was purged and then stirred under hydrogen atmosphere for 16 h. The solution was filtered through Celite and concentrated. The crude was diluted with EtOAc and extracted with 1M NaOH. The aqueous phase was acidified to pH 5 and extracted with EtOAc. The organic phase was dried over Na$_2$SO$_4$, filtered and evaporated to give the title compound. Y=63%. MS ES+: 342.1 [M+Na]+.

Step 4: ethyl (2R)-2-{[(1,2,3,5,6,7-hexahydro-s-indacen-4-yl)carbamoyl]oxy}-3-methoxypropanoate. The title compound was prepared according to the General procedure E using (2R)-2-{[(1,2,3,5,6,7-hexahydro-s-indacen-4-yl)carbamoyl]oxy}-3-methoxypropanoic acid and ethanol as starting materials. The crude product was purified by FCC (0 to 20% EtOAc in hexane). Y=71%. MS ES+: 348.2. $^1$H NMR (300 MHz, chloroform-d) δ 7.03 (s, 1H), 6.46 (s, 1H), 5.32-5.27 (m, 1H), 4.35-4.23 (m, 2H), 3.97-3.88 (m, 1H), 3.87-3.77 (m, 1H), 3.45 (s, 3H), 2.94-2.82 (m, 8H), 2.15-2.03 (m, 4H), 1.33 (t, J=7 Hz, 3H)

Example 65. (2R)-2-{[(1,2,3,5,6,7-hexahydro-s-indacen-4-yl)carbamoyl]oxy}-3-methoxypropanoic acid

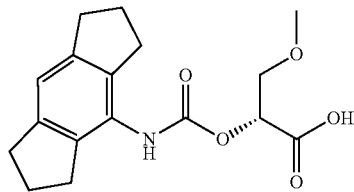 [SMILES: COC[C@@H](OC(=O)Nc1c2c(cc3c1CCC3)CCC2)C(=O)O]

The title compound is synthesized following the procedures described in Example 64.

Example 66. Ethyl 2-({[2-chloro-3-(trifluoromethyl)phenyl]carbamoyl}oxy)-3-(1H-pyrazol-1-yl)propanoate

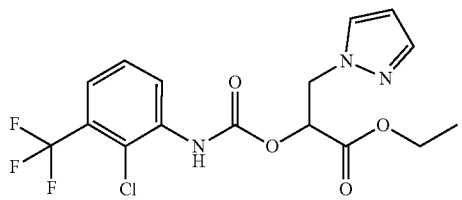 [SMILES: CCOC(=O)C(Cn1cccn1)OC(=O)Nc1cccc(C(F)(F)F)c1Cl]

Synthesised using a synthetic route analogous to Example 59. Y=45%. MS ES+: 406.0. $^1$H NMR (300 MHz, DMSO-d$_6$) δ 9.75 (s, 1H), 7.79-7.68 (m, 3H), 7.58-7.50 (m, 1H), 7.49-7.46 (m, 1H), 6.27 (t, J=2 Hz, 1H), 5.35 (t, J=5 Hz, 1H), 4.63 (d, J=5 Hz, 2H), 4.14 (q, J=7 Hz, 2H), 1.19 (t, J=7 Hz, 3H).

Example 67. Ethyl 2-{[(1,2,3,5,6,7-hexahydro-s-indacen-4-yl)carbamoyl]oxy}-3-(1H-1,2,4-triazol-1-yl)propanoate

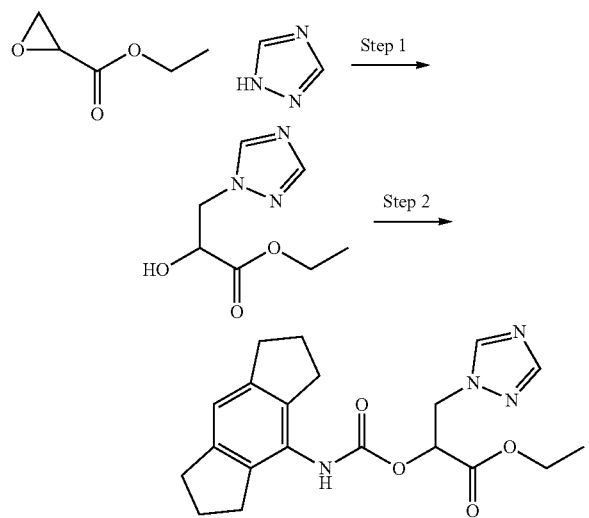

Step 1: ethyl 2-hydroxy-3-(1H-1,2,4-triazol-1-yl)propanoate. A solution of 1,2,4-triazole (0.10 g, 1.45 mmol) in dry DMF (1 ml) was treated with NaH (60% in mineral oil, 58 mg, 1.45 mmol). To this was added a solution of ethyl oxirane-2-carboxylate in DMF (1 ml). The RM was stirred at 60° C. for 4 h. The resulting mixture was diluted with EtOAc to give a solution, washed with sat. NH$_4$C$_1$ solution, dried over Na$_2$SO$_4$, filtered and evaporated to dryness. The crude was purified by FCC (0-5% MeOH in DCM) to give the title compound as an orange oil. Y=30%. MS ES+: 185.8. $^1$H NMR (300 MHz, DMSO-d$_6$) δ 8.44 (s, 1H), 7.96 (s, 1H), 5.97-5.92 (m, 1H), 4.49-4.35 (m, 3H), 4.12 (q, J=7 Hz, 2H), 1.20 (t, J=7 Hz, 3H)

Step 2: ethyl 2-{[(1,2,3,5,6,7-hexahydro-s-indacen-4-yl)carbamoyl]oxy}-3-(1H-1,2,4-triazol-1-yl)propanoate. The title compound was prepared according to the General procedure B using ethyl 2-hydroxy-3-(1H-1,2,4-triazol-1-yl)propanoate and Intermediate A as starting materials. The crude product was purified by prep HPLC. Y=41%. MS ES+: 385.2. $^1$H NMR (300 MHz, DMSO-d$_6$) δ 9.19 (s, 1H), 8.57 (s, 1H), 8.00 (s, 1H), 6.95 (s, 1H), 5.32 (s, 1H), 4.73 (s, 2H), 4.14 (q, J=7 Hz, 2H), 2.80 (t, J=7 Hz, 4H), 2.71-2.59 (m, 4H), 1.90-1.80 (m, 4H), 1.19 (t, J=7 Hz, 3H).

Example 68. Ethyl 2-{[(1,2,3,5,6,7-hexahydro-s-indacen-4-yl)carbamoyl]oxy}-3-(3-methyl-1H-pyrazol-1-yl)propanoate

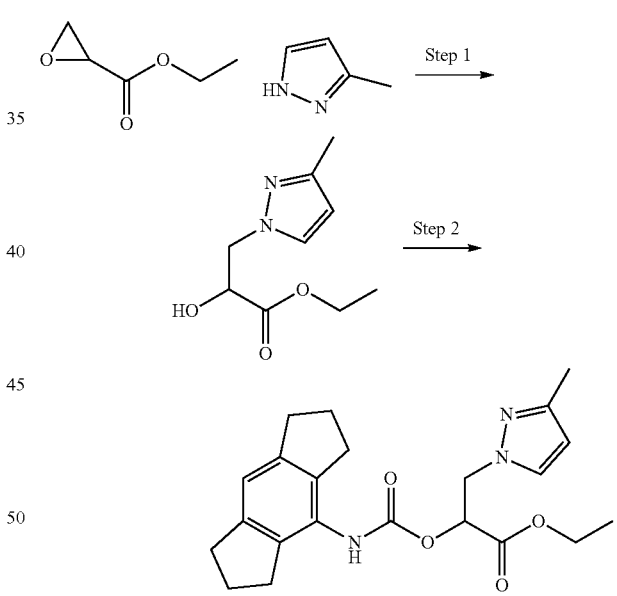

Step 1: ethyl 2-hydroxy-3-(3-methyl-1H-pyrazol-1-yl)propanoate. A sealed tube was charged with 3-methyl-1H-pyrazole (0.50 g, 6.09 mmol), ethyl oxirane-2-carboxylate (1.41 g, 12.2 mmol) and anhydrous ethanol (6 ml). The RM was heated at 90° C. for 16 h, then concentrated in vacuo. The crude was purified by FCC (0-100% DCM in hexane) to give the desired product in a 2:1 ratio with ethyl 2-hydroxy-3-(5-methyl-1H-pyrazol-1-yl)propanoate. This was used in the next step without further purification. Y=98%. MS ES+: 199.4

Step 2: ethyl 2-{[(1,2,3,5,6,7-hexahydro-s-indacen-4-yl)carbamoyl]oxy}-3-(3-methyl-1H-pyrazol-1-yl)propanoate. The title compound was prepared according to the General procedure B using ethyl 2-hydroxy-3-(3-methyl-1H-pyrazol-1-yl)propanoate and Intermediate A as starting materials. The crude product was purified by prep HPLC followed by crystallisation (hexane and diethyl ether). Y=13%. MS ES⁺: 398.1. ¹H NMR (300 MHz, chloroform-d) δ 7.03 (s, 1H), 6.40 (s, 1H), 6.03 (s, 1H), 5.42 (s, 1H), 4.68-4.42 (m, 2H), 4.33-4.20 (m, 2H), 2.90 (t, J=8 Hz, 4H), 2.79 (t, J=7 Hz, 4H), 2.28 (s, 3H), 2.15-2.00 (m, 4H), 1.36-1.26 (m, 3H)

Example 69. Ethyl 3-(1H-pyrazol-1-yl)-2-{[(2,4,6-trifluorophenyl)carbamoyl]oxy}-propanoate

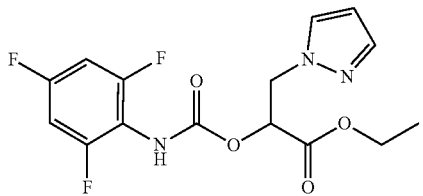 [SMILES: CCOC(=O)C(Cn1cccn1)OC(=O)Nc1c(F)cc(F)cc1F]

The title compound was prepared according to the General procedure B using ethyl 2-hydroxy-3-(1H-pyrazol-1-yl)propanoate and 1,3,5-trifluoro-2-isocyanatobenzene as starting materials. The crude product was purified by FCC (0-5% MeOH in DCM) followed by prep HPLC. Y=2%. MS ES⁺: 358.1. ¹H NMR (300 MHz, DMSO-d₆) δ 9.52 (s, 1H), 7.77 (s, 1H), 7.46 (s, 1H), 7.34-7.24 (m, 2H), 6.28 (s, 1H), 5.30 (s, 1H), 4.67-4.57 (m, 2H), 4.12 (q, J=7 Hz, 2H), 1.17 (t, J=7 Hz, 3H).

Example 70. Ethyl 2-({[2-methyl-6-(propan-2-yl)phenyl]carbamoyl}oxy)-3-(1H-pyrazol-1-yl)propanoate

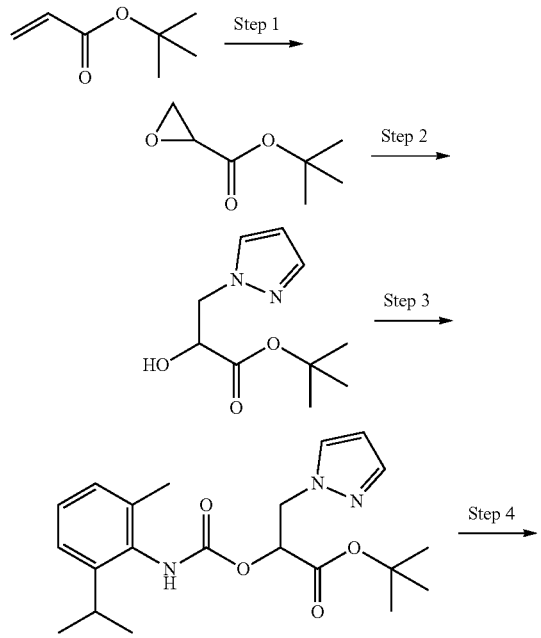

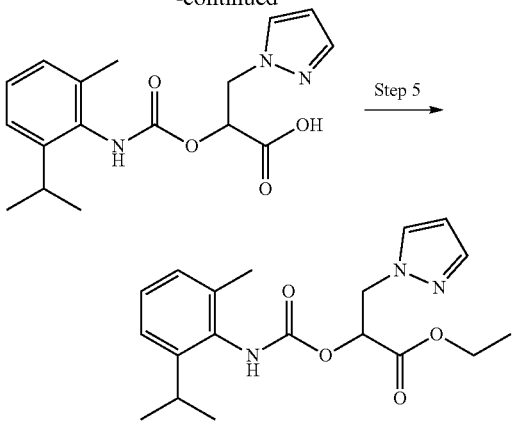

Step 1: tert-butyl oxirane-2-carboxylate. Tert-butyl acrylate (34.3 ml, 234 mmol) was dissolved in DCM (300 ml). A solution of mCPBA (50.5 g, 293 mmol) in DCM (420 ml) was added and the RM heated at reflux for 2 days. More mCPBA (67 g, 375 mmol) was added and the RM heated at reflux for a further 4 days. The RM was filtered and the filtrate cooled to 0° C. Sat. Na₂S₂O₃ was added dropwise then the layers were separated. The organic phase was filtered, washed with sat. sodium bicarbonate, filtered, washed with brine, filtered, dried over anhydrous sodium sulfate and concentrated under vacuum. The residue was triturated with cold hexanes, filtered and the filtrate evaporated to dryness to give the title compound as a yellow oil. Y=47%. ¹H NMR (300 MHz, chloroform-d) δ 3.34 (dd, J=4, 3 Hz, 1H), 2.95-2.87 (m, 2H), 1.52 (s, 9H).

Step 2: tert-butyl 2-hydroxy-3-(1H-pyrazol-1-yl)propanoate. To a solution of tert-butyl oxirane-2-carboxylate (4.80 g, 33 mmol) in absolute EtOH (100 ml) was added pyrazole (5.67 g, 83 mmol). The RM was heated at 80° C. for 18 h, concentrated and co-evaporated with toluene. The crude was purified by FCC (0-30% EtOAc in hexane) followed by reverse phase FCC (5-40% MeCN in H₂O) to give the title compound as a white solid. Y=64%. ¹H NMR (300 MHz, DMSO-d₆) δ 7.66 (dd, J=2, 1 Hz, 1H), 7.43 (dd, J=2, 1 Hz, 1H), 6.21 (t, J=2 Hz, 1H), 5.72-5.61 (m, 1H), 4.37-4.16 (m, 3H), 1.39 (s, 9H)

Step 3: tert-butyl 2-({[2-methyl-6-(propan-2-yl)phenyl]carbamoyl}oxy)-3-(1H-pyrazol-1-yl)propanoate. The title compound was prepared according to the General procedure A using tert-butyl 2-hydroxy-3-(1H-pyrazol-1-yl)propanoate and 2-isocyanato-1-methyl-3-(propan-2-yl)benzene as starting materials. The crude product was purified by FCC (0 to 50% EtOAc in hexane). Y=78%. MS ES⁺: 388.3

Step 4: 2-({[2-methyl-6-(propan-2-yl)phenyl]carbamoyl}oxy)-3-(1H-pyrazol-1-yl)propanoic acid. tert-butyl 2-({[2-methyl-6-(propan-2-yl)phenyl]carbamoyl}oxy)-3-(1H-pyrazol-1-yl)propanoate (0.36 g, 0.92 mmol) was dissolved in 1:4 TFA/DCM (10 ml) and stirred at rt for 18 h. The RM was concentrated and co-evaporated with hexane. The crude product was suspended in water, basified with NaHCO₃ and washed with EtOAc. The aqueous phase was acidified to pH 5 with 1M HCl and extracted with EtOAc. The organic phase was dried over sodium sulfate and evaporated. The crude was purified by FCC (0-20% EtOAc in (hexane+1% AcOH)) followed by prep HPLC to give the title compound as a white solid. Y=23%. MS ES⁺: 332.3

Step 5: ethyl 2-({[2-methyl-6-(propan-2-yl)phenyl]carbamoyl}oxy)-3-(1H-pyrazol-1-yl)propanoate. The title compound was prepared according to the General procedure E using 2-({[2-methyl-6-(propan-2-yl)phenyl]carbamoyl}oxy)-3-(1H-pyrazol-1-yl)propanoic acid and ethanol as starting materials. The crude product was purified by prep HPLC. Y=18%. MS ES+: 360.0. $^1$H NMR (400 MHz, chloroform-d) δ 7.54 (s, 1H), 7.40 (s, 1H), 7.27-7.18 (m, 2H), 7.14-7.02 (m, 1H), 6.53 (s, 1H), 6.26 (s, 1H), 5.40-5.30 (m, 1H), 4.72-4.56 (m, 2H), 1.47 (s, 9H)

Example 71. Ethyl 2-{[(3-chloro-2,6-difluorophenyl)carbamoyl]oxy}-3-(1H-pyrazol-1-yl)propanoate

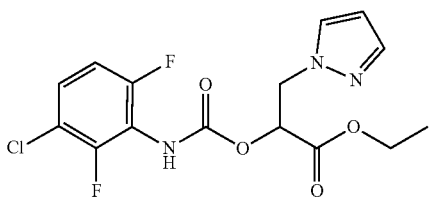 [SMILES: CCOC(=O)C(Cn1cccn1)OC(=O)Nc1c(F)ccc(Cl)c1F]

Synthesised using a synthetic route analogous to Example 59. Y=2%. MS ES+: 373.9 $^1$H NMR (300 MHz, methanol-d$_4$) δ 7.77-7.66 (m, 1H), 7.57-7.51 (m, 1H), 7.49-7.39 (m, 1H), 7.12-7.03 (m, 1H), 6.38-6.28 (m, 1H), 5.38 (t, J=5 Hz, 1H), 4.69 (d, J=5 Hz, 2H), 4.22 (q, J=7 Hz, 2H), 1.27 (t, J=7 Hz, 3H).

Example 72. Ethyl (2R)-3-(4-cyano-1H-pyrazol-1-yl)-2-{[(1,2,3,5,6,7-hexahydro-s-indacen-4-yl)carbamoyl]oxy}propanoate

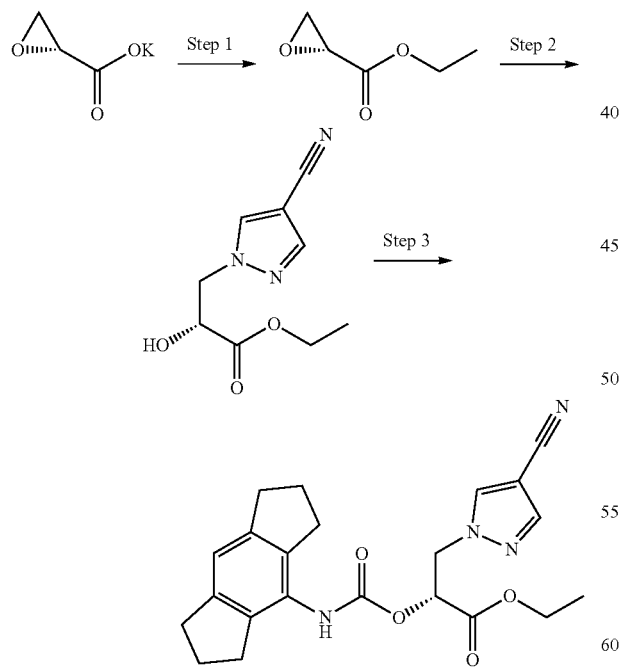

Step 1: ethyl (2R)-oxirane-2-carboxylate. To a mixture of potassium (2R)-oxirane-2-carboxylate (50.0 g, 396 mmol) (for synthesis refer to example 5AJ) in dichloromethane (250 ml) was added bromoethane (172 g, 1.59 mol) and benzyl(triethyl)ammonium chloride (90.2 g, 396 mmol) in one portion at 25° C. under N$_2$. The mixture was stirred at 45° C. for 16 h. The mixture was cooled to rt. The residue was poured into H$_2$O (300 ml) and stirred for 5 min. The aqueous phase was extracted with dichloromethane (150 ml). The combined organic phase was washed with brine (100 ml), dried with anhydrous Na$_2$SO$_4$, filtered and concentrated in vacuo. The crude was purified by FCC (0-50% EtOAc in petroleum ether) to give the title compound as a yellow oil. Y=9%. $^1$H NMR (400 MHz, chloroform-d) δ 4.23-4.28 (m, 2H), 3.42-3.44 (m, 1H), 2.93-2.98 (m, 2H), 1.31 (t, J=7 Hz, 3H)

Step 2: ethyl (2R)-3-(4-cyano-1H-pyrazol-1-yl)-2-hydroxypropanoate. In a sealed tube 1H-pyrazole-4-carbonitrile (2.00 g, 21.5 mmol) and ethyl (2R)-oxirane-2-carboxylate (1.00 g, 8.61 mmol) were dissolved in EtOH (7 ml). The RM was heated using microwave irradiation at 100° C. for 180 min. The RM was concentrated under reduced pressure and purified by prep HPLC (column: Phenomenex Luna C18 250*50 mm*10 μm; mobile phase: [water (0.1% TFA)-ACN]; B %: 10%-40%, 20 min) to the title compound as yellow oil. Y=42%. $^1$H NMR (400 MHz, chloroform-d) δ 7.95 (s, 1H), 7.79 (s, 1H), 4.50-4.54 (m, 3H), 4.25-4.30 (m, 2H), 1.31 (t, J=7 Hz, 3H)

Step 3: ethyl (2R)-3-(4-cyano-1H-pyrazol-1-yl)-2-{[(1,2,3,5,6,7-hexahydro-s-indacen-4-yl)carbamoyl]oxy}propanoate. The title compound was prepared according to the General procedure A using ethyl (2R)-3-(4-cyano-1H-pyrazol-1-yl)-2-hydroxypropanoate and Intermediate A as starting materials. The crude product was purified by prep HPLC (column: Phenomenex Luna C18 250*50 mm*10 μm; mobile phase: [water (0.1% TFA)-ACN]; B %: 50-80%, 20 min) to give the title compound as a white solid. Y=18%. MS ES+: 409.2. $^1$H NMR (400 MHz, DMSO-d$_6$) δ 9.17 (s, 1H), 8.61 (s, 1H), 8.10 (s, 1H), 6.95 (s, 1H), 5.34 (s, 1H), 4.71 (s, 2H), 4.05-4.16 (m, 2H), 2.65-2.80 (m, 8H), 1.94-1.99 (m, 4H), 1.18 (t, J=7 Hz, 3H).

Example 73. Benzyl (2R)-3-(4-cyano-1H-pyrazol-1-yl)-2-{[(1,2,3,5,6,7-hexahydro-s-indacen-4-yl)carbamoyl]oxy}propanoate

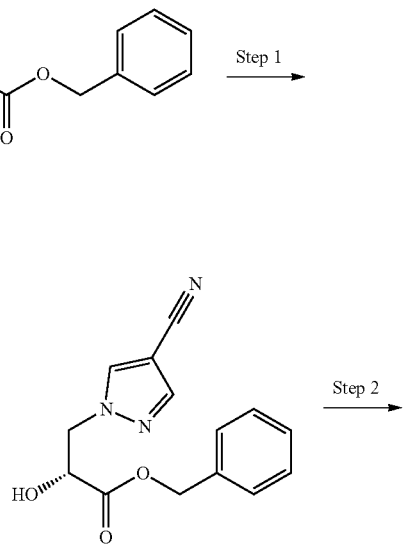

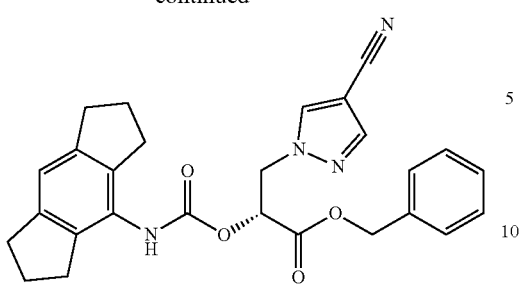

Step 1: benzyl (2R)-3-(4-cyano-1H-pyrazol-1-yl)-2-hydroxypropanoate. In a sealed tube a mixture of benzyl (2R)-oxirane-2-carboxylate (0.50 g, 2.81 mmol) and 4-cyanopyrazole (0.52 g, 5.62 mmol) in EtOH (1 ml) was heated under microwave irradiation at 120° C. for 1 h. The RM was concentrated and purified by FCC (EtOAc in hexane) to give the title compound. Y=20%. MS ES⁺: 272.2

Step 2: benzyl (2R)-3-(4-cyano-1H-pyrazol-1-yl)-2-{[(1,2,3,5,6,7-hexahydro-s-indacen-4-yl)carbamoyl]oxy}propanoate. The title compound was prepared according to the General procedure B using benzyl (2R)-3-(4-cyano-1H-pyrazol-1-yl)-2-hydroxypropanoate and Intermediate A as starting materials. The crude product was purified by FCC to give the title compound as a white solid. Y=50%. MS ES⁺: 471. ¹H NMR (300 MHz, chloroform-d) δ 7.78 (s, 2H), 7.44-7.33 (m, 5H), 7.06 (s, 1H), 6.37 (s, 1H), 5.55 (s, 1H), 5.30-5.16 (m, 2H), 4.69 (s, 2H), 2.99-2.86 (m, 4H), 2.80-2.68 (m, 4H), 2.12-2.02 (m, 4H)

Example 74. Ethyl 2-{[(2,6-dimethylphenyl)carbamoyl]oxy}-3-(pyrimidin-2-yl)propanoate

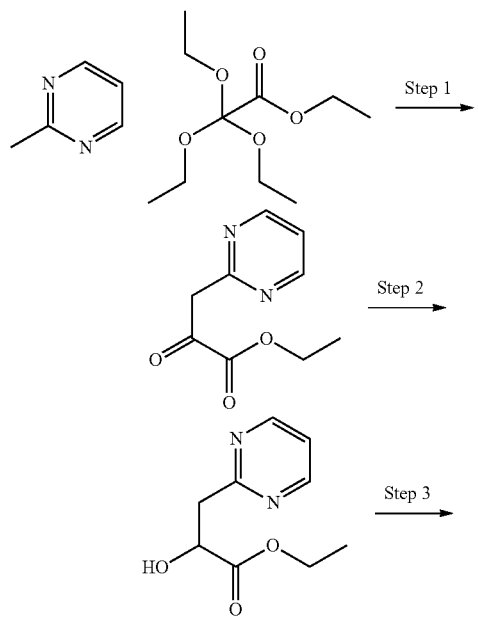

Step 1: ethyl 2-oxo-3-(pyrimidin-2-yl)propanoate. To a solution of 2M LDA in THF/hexane/ethylbenzene (6.4 ml, 12.8 mmol) in dry THF (15 ml) cooled to −78° C. under inert atmosphere was added 2-methylpyrimidine (0.60 g, 6.4 mmol). The RM was stirred for 1 h then ethyl 2,2,2-triethoxyacetate (1.31 ml, 7.0 mmol) was added. The solution was allowed to warm to RT and stirred for 3 days. The RM was poured into 1M HCl and stirred for 1 h. The mixture was neutralised with NaHCO₃ solution and extracted three times with EtOAc. The combined organics were washed with brine, dried over Na₂SO₄, filtered and evaporated. The crude was purified by FCC (0-50% EtOAc in hexane) to give the title compound as a yellow solid. Y=35%. ¹H NMR (300 MHz, DMSO-d₆) δ 13.63 (s, 1H), 8.89 (d, J=5 Hz, 2H), 7.43 (t, J=5 Hz, 1H), 6.52 (s, 1H), 4.29 (q, J=7 Hz, 2H), 1.30 (t, J=7 Hz, 3H).

Step 2: ethyl 2-hydroxy-3-(pyrimidin-2-yl)propanoate. A solution of ethyl 2-oxo-3-(pyrimidin-2-yl)propanoate (0.42 g, 2.16 mmol) in EtOH (20 ml) was cooled to −78° C. and treated with NaBH₄ (0.33 g, 8.65 mmol). The RM was stirred for 1 h at −78° C. then allowed to warm to RT and stirred for a further 1.5 h. The RM was poured onto ice, acidified to pH 2 with 1M HCl and extracted sequentially with EtOAc, nBuOH and 4:1 iPrOH/DCM. The combined organic phases were dried over Na₂SO₄, filtered and concentrated in vacuo to give the title compound as a yellow oil. Y=41%. MS ES⁻¹: 197.0

Step 3: ethyl 2-{[(2,6-dimethylphenyl)carbamoyl]oxy}-3-(pyrimidin-2-yl)propanoate. The title compound was prepared according to the General procedure B using ethyl 2-hydroxy-3-(pyrimidin-2-yl)propanoate and 2,6-dimethylphenyl isocyanate as starting materials. The crude product was purified by FCC (0-20% MeOH in DCM) to give the title compound as a colourless oil. Y=2%. MS ES⁻¹: 344.0. ¹H NMR (300 MHz, methanol-d₄) δ 8.78 (d, J=5 Hz, 2H), 8.74-8.61 (m, 1H), 7.41 (t, J=5 Hz, 1H), 7.13-7.01 (m, 3H), 5.73-5.63 (m, 1H), 4.24 (q, J=7 Hz, 2H), 3.63-3.44 (m, 2H), 2.20 (s, 6H), 1.28 (t, J=7 Hz, 3H)

Example 75. (2R)-2-{[(1,2,3,5,6,7-hexahydro-s-indacen-4-yl)carbamoyl]oxy}-3-(1H-imidazol-1-yl)propanoic acid

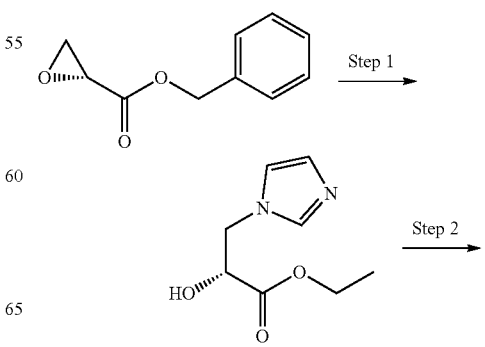

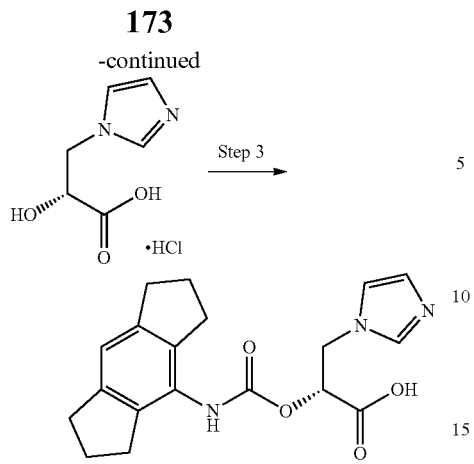

Step 1: ethyl (2R)-2-hydroxy-3-(1H-imidazol-1-yl)propanoate. Benzyl (2R)-oxirane-2-carboxylate (3.00 g, 16.8 mmol) (for synthesis refer to example 5AJ) was dissolved in EtOH (32 ml). Imidazole (2.87 g, 42.1 mmol) was added and the RM heated in a sealed tube at 90° C. for 16 h. The RM was concentrated and purified by FCC (0-10% MeOH/DCM) to give the title compound as a yellow oil. Y=31%. $^1$H NMR (300 MHz, DMSO-$d_6$) δ 7.56 (d, J=1 Hz, 1H), 7.12 (t, J=1 Hz, 1H), 6.85 (t, J=1 Hz, 1H), 5.96 (d, J=5 Hz, 1H), 4.40-4.30 (m, 1H), 4.29-4.05 (m, 4H), 1.19 (t, J=7 Hz, 3H).

Step 2: (2R)-2-hydroxy-3-(1H-imidazol-1-yl)propanoic acid hydrochloride. Ethyl (2R)-2-hydroxy-3-(1H-imidazol-1-yl)propanoate (0.97 g, 5.3 mmol) was dissolved in 1:1 THF/water (20 ml) and cooled to 0° C. Lithium hydroxide monohydrate (0.23 g, 5.5 mmol) was added and the RM stirred at 0° C. for 30 min, then at rt for 1 h. The THF was removed in vacuo and the RM acidified to pH ~3 with 2M HCl. The solution was washed with EtOAc and then lyophilised to give the title compound as a white solid. Y=93%. MS ES$^+$: 157.

Step 3: (2R)-2-{[(1,2,3,5,6,7-hexahydro-s-indacen-4-yl)carbamoyl]oxy}-3-(1H-imidazol-1-yl)propanoic acid. A solution of (2R)-2-hydroxy-3-(1H-imidazol-1-yl)propanoic acid hydrochloride (96 mg, 0.50 mmol), triethylamine (0.154 ml, 0.11 mmol) and DMSO (3 ml) was treated with Intermediate A (0.10 g, 0.50 mmol) and stirred for 16 h. The crude was purified by prep HPLC to give the title compound as a white solid. Y=17%. MS ES$^+$: 356. $^1$H NMR (300 MHz, DMSO-$d_6$) δ 13.38 (s, 1H), 9.14 (s, 1H), 7.70 (s, 1H), 7.24 (s, 1H), 6.96 (s, 1H), 6.91 (s, 1H), 5.22-5.12 (m, 1H), 4.56-4.35 (m, 2H), 2.81 (t, J=7 Hz, 4H), 2.69 (t, J=8 Hz, 4H), 2.02-1.89 (m, 4H).

Example 76. Ethyl 3-(4-fluoro-1H-pyrazol-1-yl)-2-{[(1,2,3,5,6,7-hexahydro-s-indacen-4-yl)carbamoyl]oxy}propanoate

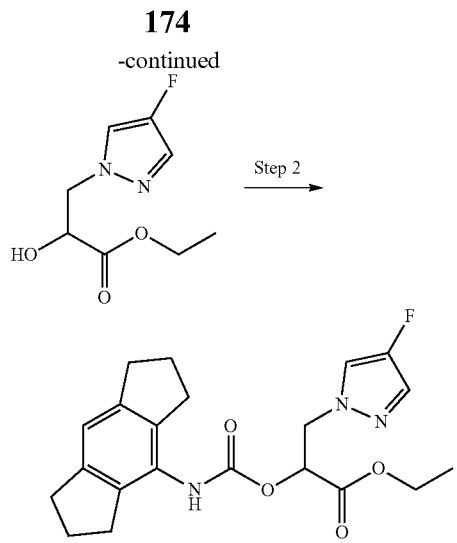

Step 1: ethyl 3-(4-fluoro-1H-pyrazol-1-yl)-2-hydroxypropanoate. Ethyl oxirane-2-carboxylate (0.15 g, 1.3 mmol) was dissolved in EtOH (3 ml). Pyrazole (0.28 g, 3.2 mmol) was added and the RM heated in a sealed tube at 90° C. for 16 h. The RM was evaporated at low pressure to remove excess pyrazole and give the title compound. MS ES$^+$: 203.1.

Step 2: ethyl 3-(4-fluoro-1H-pyrazol-1-yl)-2-{[(1,2,3,5,6,7-hexahydro-s-indacen-4-yl)carbamoyl]oxy}propanoate. The title compound was prepared according to the General procedure B using ethyl 3-(4-fluoro-1H-pyrazol-1-yl)-2-hydroxypropanoate and Intermediate A as starting materials. The crude product was purified by prep HPLC to give the title compound as a white solid. Y=34%. MS ES$^+$: 402. $^1$H NMR (300 MHz, DMSO-$d_6$) δ 9.19 (s, 1H) 7.94 (s, 1H), 7.56-7.45 (m, 1H), 6.96 (s, 1H), 5.32-5.21 (m, 1H), 4.54 (s, 2H), 4.13 (q, J=7 Hz, 2H), 2.81 (t, J=7 Hz, 4H), 2.73-2.59 (m, 4H), 2.01-1.91 (m, 4H), 1.19 (t, J=7 Hz, 3H).

Example 77. Ethyl 2-{[(1,2,3,5,6,7-hexahydro-s-indacen-4-yl)carbamoyl]oxy}-3-(5-methyl-1H-imidazol-1-yl)propanoate

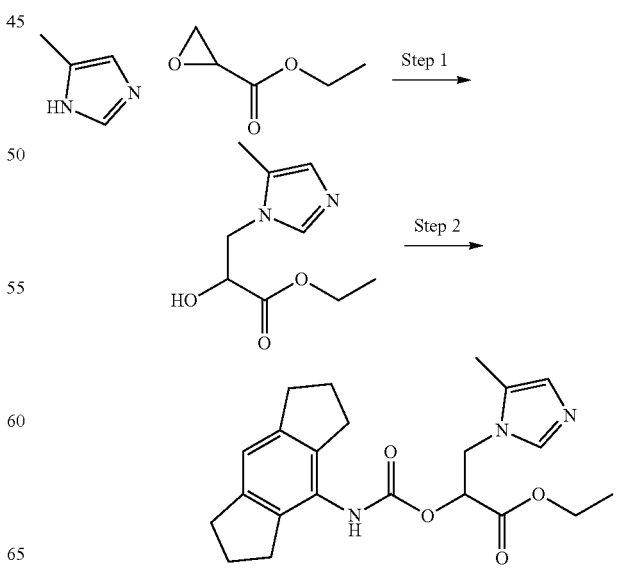

Step 1: ethyl 2-hydroxy-3-(5-methyl-1H-imidazol-1-yl) propanoate. Ethyl oxirane-2-carboxylate (0.10 g, 0.86 mmol) was dissolved in EtOH (1 ml). 5-methyl-1H-imidazole (71 mg, 0.86 mmol) was added and the RM heated in a microwave reactor at 120° C. for 1 h. The RM was evaporated to dryness and partitioned between EtOAc and water. The organic phase was dried over anhydrous sodium sulfate and evaporated. The crude was purified by FCC (0-7% MeOH in DCM) to give the title compound as a colourless oil. Y=52%. MS ES+: 199.

Step 2: ethyl 2-{[(1,2,3,5,6,7-hexahydro-s-indacen-4-yl) carbamoyl]oxy}-3-(5-methyl-1H-imidazol-1-yl)propanoate. The title compound was prepared according to the General procedure A using ethyl 2-hydroxy-3-(5-methyl-1H-imidazol-1-yl)propanoate and Intermediate A as starting materials. The crude product was purified by FCC (0-7% MeOH in DCM) to give the title compound as a white solid. Y=23%. MS ES+: 398.1. $^1$H NMR (300 MHz, DMSO-$d_6$) δ 9.22 (s, 1H) 7.08 (s, 1H), 6.96 (s, 1H), 6.79-6.63 (m, 1H), 5.33-5.13 (m, 1H), 4.38 (s, 2H), 4.18-4.09 (m, 2H), 2.81 (t, J=6 Hz, 4H), 2.75-2.59 (m, 4H), 2.33 (s, 3H), 2.01-1.91 (m, 4H), 1.19 (t, J=7 Hz, 3H).

Example 78. (2R)-3-(4-cyano-1H-pyrazol-1-yl)-2-{[(1,2,3,5,6,7-hexahydro-s-indacen-4-yl)carbamoyl]oxy}propanoic acid

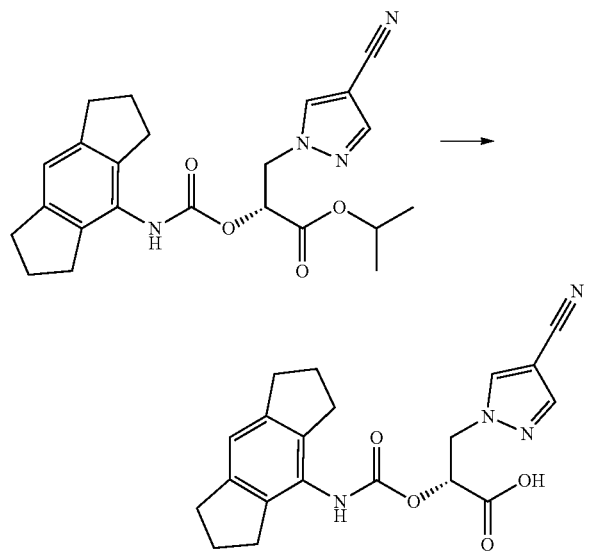

To a mixture of propan-2-yl(2R)-3-(4-cyano-1H-pyrazol-1-yl)-2-{[(1,2,3,5,6,7-hexahydro-s-indacen-4-yl)carbamoyl]oxy}propanoate (400 mg, 0.95 mmol) (for synthesis refer to example 5CI) in dioxane (5 ml) was added 6 M HCl (5 ml) in one portion at 20° C. The mixture was stirred at 20° C. for 48 h. The RM was concentrated under reduced pressure and the resulting residue purified by prep HPLC: (column: Phenomenex Luna C18 250*50 mm*10 μm; mobile phase: [water (0.1% TFA)-ACN]; B %: 45%-80%, 20 min) to give the title compound as white solid. Y=28%. MS ES+: 381.0. $^1$H NMR (400 MHz, DMSO-$d_6$) δ 13.40 (s, 1H), 9.09 (s, 1H), 8.60 (s, 1H), 8.10 (s, 1H), 6.95 (s, 1H), 5.28 (s, 1H), 4.69 (s, 2H), 2.80-2.64 (m, 8H), 1.98-1.91 (m, 4H).

Example 79. Ethyl (2R)-2-{[(1,2,3,5,6,7-hexahydro-s-indacen-4-yl)carbamoyl]oxy}-3-(1H-1,2,4-triazol-1-yl)propanoate

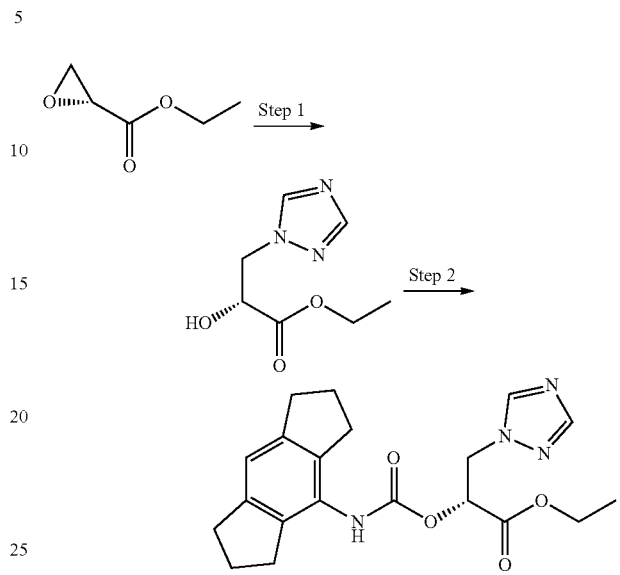

Step 1: ethyl (2R)-2-hydroxy-3-(1H-1,2,4-triazol-1-yl) propanoate. In a sealed tube ethyl (2R)-oxirane-2-carboxylate (1.00 g, 8.61 mmol) (for synthesis refer to example 5AY) and 1,2,4-triazole (1.49 g, 21.5 mmol) were dissolved in EtOH (10 ml). The RM was heated in a microwave reactor at 100° C. for 3 h. The RM was concentrated in vacuo and purified by prep HPLC (column: Agela Innoval ODS-2 250*80 mm; mobile phase: [water (0.1% TFA)-ACN]; B %: 0%-20%, 20 min) to give the title compound as a yellow oil. Y=27%. MS ES+: 186.1.

$^1$H NMR (400 MHz, methanol-$d_4$) δ 8.66 (s, 1H), 8.11 (s, 1H), 4.62-4.54 (m, 3H), 4.25-4.20 (m, 2H), 1.28 (t, J=7 Hz, 3H).

Step 2: ethyl (2R)-2-{[(1,2,3,5,6,7-hexahydro-s-indacen-4-yl)carbamoyl]oxy}-3-(1H-1,2,4-triazol-1-yl)propanoate. The title compound was prepared according to the General procedure A using ethyl (2R)-2-hydroxy-3-(1H-1,2,4-triazol-1-yl)propanoate and Intermediate A as starting materials. The crude product was purified by prep HPLC (column: Phenomenex Luna C18 250*50 mm*10 μm; mobile phase: [water (0.225% TFA)-ACN]; B %: 25-55%, 20 min) to give the title compound as a white solid. Y=26%. MS ES+: 385.3. $^1$H NMR (400 MHz, methanol-$d_4$) δ 8.66 (s, 1H), 8.08 (s, 1H), 6.96 (s, 1H), 5.42 (s, 1H), 4.86-4.81 (m, 2H), 4.26-4.21 (m, 2H), 2.87-2.72 (m, 8H), 2.07-1.99 (m, 4H), 1.28 (t, J=7 Hz, 3H).

Example 80. Ethyl 2-{[(1,2,3,5,6,7-hexahydro-s-indacen-4-yl)carbamoyl]oxy}-3-(2-methyl-1H-imidazol-1-yl)propanoate

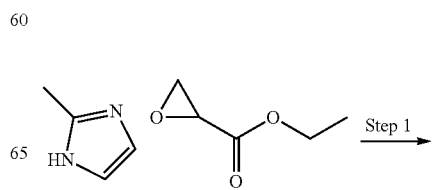

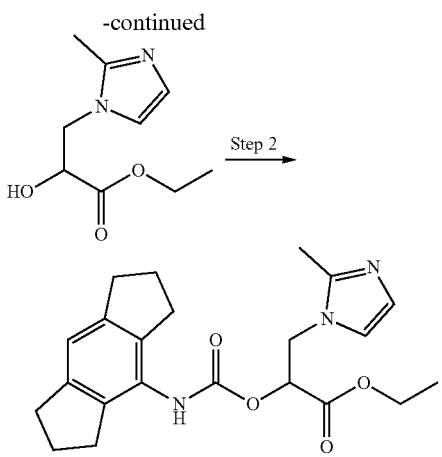

Step 1: ethyl 2-hydroxy-3-(2-methyl-1H-imidazol-1-yl) propanoate. In a sealed tube ethyl ethyl oxirane-2-carboxylate (212 mg, 1.83 mmol) and 2-methylimidazole (150 mg, 1.83 mmol) were dissolved in EtOH (1 ml). The RM was heated in a microwave reactor at 120° C. for 1 h. The RM was concentrated in vacuo and purified by FCC (0-10% MeOH in DCM) to give the title compound as an orange oil. Y=58%. MS ES+: 199.2.

Step 2: ethyl 2-{[(1,2,3,5,6,7-hexahydro-s-indacen-4-yl) carbamoyl]oxy}-3-(2-methyl-1H-imidazol-1-yl)propanoate. The title compound was prepared according to the General procedure B using ethyl 2-hydroxy-3-(2-methyl-1H-imidazol-1-yl)propanoate and Intermediate A as starting materials. The crude product was purified by FCC (0-10% MeOH in DCM) then further purified by prep HPLC to give the title compound as a white solid. MS ES+: 398.6. $^1$H NMR (300 MHz, DMSO-$d_6$) δ 9.21 (s, 1H), 7.08 (s, 1H), 6.97 (s, 1H), 6.74 (s, 1H), 5.34-5.21 (m, 1H), 4.49-4.26 (m, 2H), 4.19-4.10 (m, 2H), 2.81 (t, J=7 Hz, 4H), 2.75-2.55 (m, 4H), 2.33 (s, 3H), 2.01-1.91 (m, 4H), 1.19 (t, J=7 Hz, 3H).

Example 81. Ethyl 2-{[(2-chloro-6-ethylphenyl) carbamoyl]oxy}-3-(1H-pyrazol-1-yl)propanoate

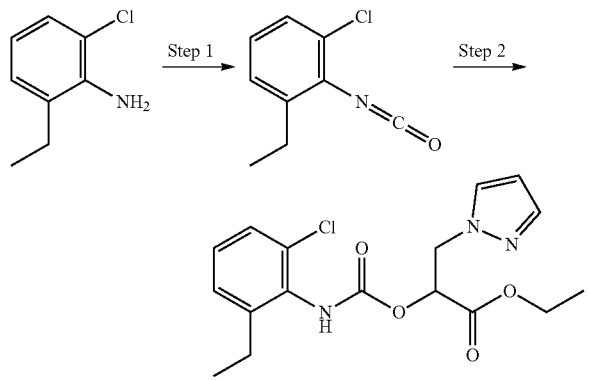

Step 1: 1-chloro-3-ethyl-2-isocyanatobenzene. To a solution of 2-chloro-6-ethylaniline (0.25 g, 1.61 mmol) in THF (10 ml) was added triethylamine (0.246 ml, 1.77 mmol) followed by phosgene (20% in toluene, 0.85 ml, 1.61 mmol). The RM was heated at 60° C. for 4 h then allowed to cool to RT. The THF was evaporated in vacuo and the residue precipitated with cold pentane. The resulting mixture was filtered and the filtrate evaporated to give the title compound as a red oil. Y=93%. MS ES+: 227 (compound analysed in diethylamine to generate diethyl urea)

Step 2: ethyl 2-{[(2-chloro-6-ethylphenyl)carbamoyl] oxy}-3-(1H-pyrazol-1-yl)propanoate. The title compound was prepared according to the General procedure B using ethyl 2-hydroxy-3-(1H-pyrazol-1-yl)propanoate (for synthesis refer to Example 49) and 1-chloro-3-ethyl-2-isocyanatobenzene as starting materials. The crude product was purified by FCC (0-10% MeOH in DCM) then further purified by prep TLC to give the title compound as an off-white solid. MS ES+: 366. $^1$H NMR (400 MHz, DMSO-$d_6$) δ 9.33 (s, 1H), 7.79 (d, J=2 Hz, 1H), 7.48 (d, J=2 Hz, 1H), 7.36-7.33 (m, 1H), 7.29-7.21 (m, 2H), 6.29 (t, J=2 Hz, 1H), 5.31 (t, J=6 Hz, 1H), 4.66-4.62 (m, 2H), 4.17-4.05 (m, 2H), 2.58-2.52 (m, 2H), 1.18 (t, J=7 Hz, 3H), 1.09 (t, J=8 Hz, 3H).

Example 82. Ethyl 2-{[(2-methylnaphthalen-1-yl) carbamoyl]oxy}-3-(1H-pyrazol-1-yl)propanoate

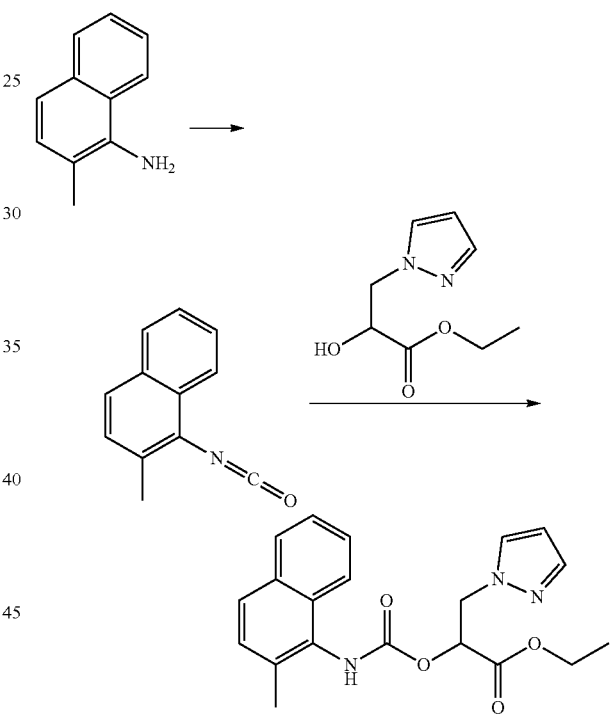

Step 1: 1-isocyanato-2-methylnaphthalene. To a mixture of 1-amino-2-methyl naphthalene (0.5 g, 3.18 mmol) and triethylamine (0.353 g, 3.49 mmol) in THF (6 ml) was added dropwise triphosgene (0.47 g, 1.59 mmol) at rt. The mixture was heated to reflux for 4 h. The reaction mixture was allowed to cool to rt, evaporated to dryness and the resultant residue filtered and washed with pentane (25 ml). The filtrate was evaporated in vacuo to give the title compound as a yellow liquid. This material was used directly without any further purification. Y=89%. $^1$H NMR (400 MHz, DMSO-$d_6$) δ 8.08 (d, J=8 Hz, 1H) 7.83 (d, J=8 Hz, 1H), 7.65 (d, J=8 Hz, 1H), 7.58-7.56 (m, 1H), 7.52-7.50 (m, 1H), 7.34 (d, J=8 Hz, 1H), 2.55 (s, 3H).

Step 2: ethyl 2-{[(2-methylnaphthalen-1-yl)carbamoyl] oxy}-3-(1H-pyrazol-1-yl)propanoate. The title compound was prepared according to the General procedure B using ethyl 2-hydroxy-3-(1H-pyrazol-1-yl)propanoate (for synthesis refer to Example 49) and 1-isocyanato-2-methylnaphthalene as starting materials. The crude product was purified by FCC (0-30% EtOAc in hexane) to give the title compound as a colourless oil. MS ES+: 368.2. ¹H NMR (400 MHz, DMSO-d₆) δ 9.53 (s, 1H), 7.91-7.78 (m, 4H), 7.52-7.40 (m, 4H), 6.34 (s, 1H), 5.35 (t, J=6 Hz, 1H), 4.69 (d, J=6 Hz, 2H), 4.16-4.14 (m, 2H), 2.46-2.31 (m, 3H), 1.22-1.18 (m, 3H).

Example 83. Ethyl 2-{[(2-methylcyclohexyl)carbamoyl]oxy}-3-(1H-pyrazol-1-yl)propanoate

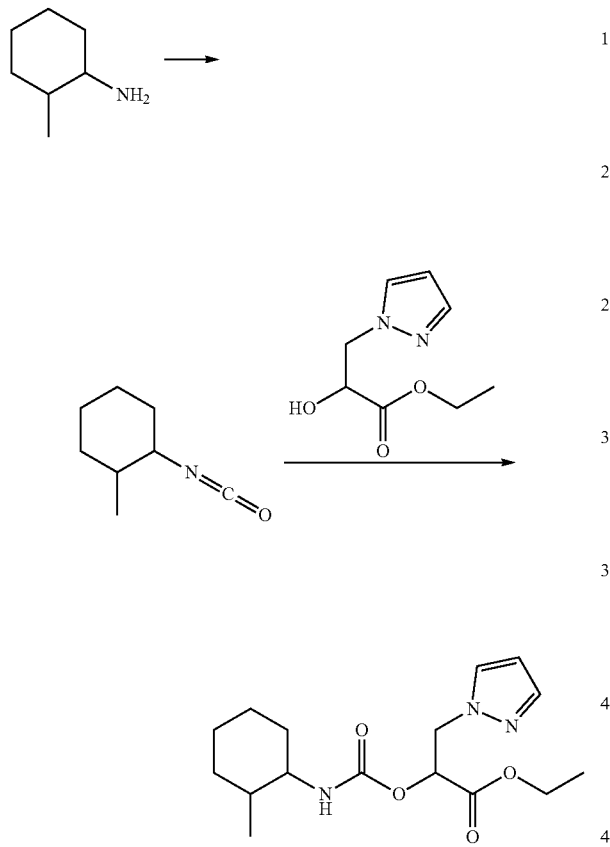

Step 1: 1-isocyanato-2-methylcyclohexane. To a solution of 2-methylcyclohexan-1-amine (0.2 g, 1.77 mmol) in toluene (3 ml) was added 20% phosgene in toluene (1 ml, 2.12 mmol) at 0° C. under N₂ atmosphere. The reaction mixture was heated at 80° C. for 4 h. The reaction mixture was concentrated under vacuum to give the title compound, which was used directly in the next step. Y=100%.

Step 2: ethyl 2-{[(2-methylcyclohexyl)carbamoyl]oxy}-3-(1H-pyrazol-1-yl)propanoate. The title compound was prepared according to the General procedure B using ethyl 2-hydroxy-3-(1H-pyrazol-1-yl)propanoate (for synthesis refer to Example 49) and 1-isocyanato-2-methylcyclohexane as starting materials. The crude product was purified by FCC (0-25% EtOAc in hexane) to give the title compound as a colourless oil. Y=10%. MS ES+: 324.1. ¹H NMR (400 MHz, DMSO-d₆) δ 7.72-7.71 (m, 1H), 7.45-7.43 (m, 1H), 7.35-7.31 (m, 1H), 6.26-6.24 (m, 1H), 5.18-5.15 (m, 1H), 4.54-4.56 (m, 2H), 4.11-4.05 (m, 2H), 2.92-2.80 (m, 1H), 1.67-1.55 (m, 4H), 1.45-1.09 (m, 8H), 0.98-0.81 (m, 3H).

Example 84. Ethyl (2R)-3-(4-chloro-1H-pyrazol-1-yl)-2-{[(1,2,3,5,6,7-hexahydro-s-indacen-4-yl)carbamoyl]oxy}propanoate

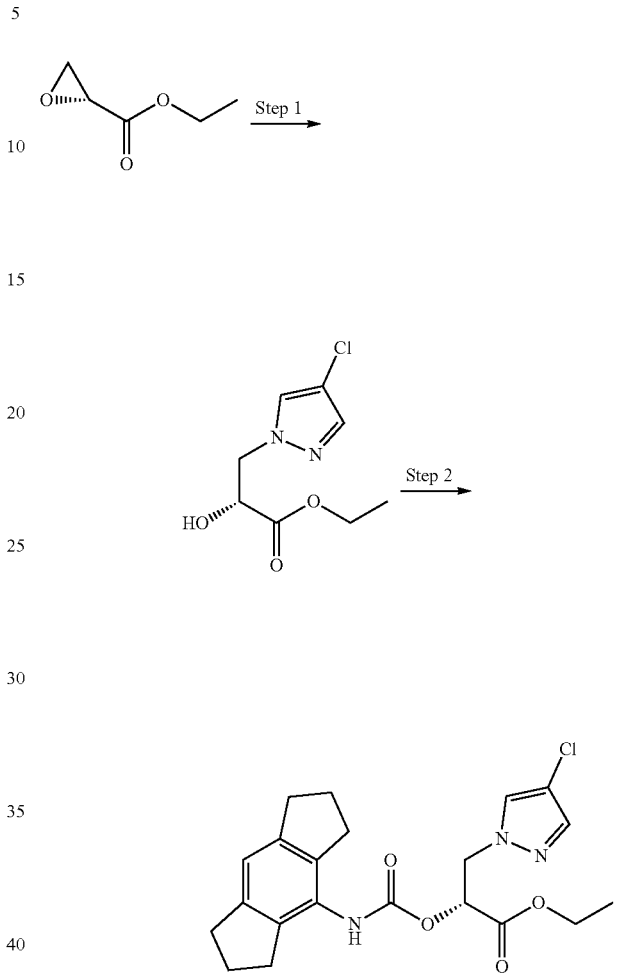

Step 1: ethyl (2R)-3-(4-chloro-1H-pyrazol-1-yl)-2-hydroxypropanoate. To a solution of ethyl (2R)-oxirane-2-carboxylate (0.5 g, 4.31 mmol) (for synthesis refer to example 5AY) in EtOH (5 ml) was added 4-chloro-1H-pyrazole (1.10 g, 10.77 mmol) in one portion at 80° C. under N₂. The mixture was stirred at 80° C. for 1 h, then filtered and concentrated under reduced pressure to give a residue. The residue was purified by FCC (30% EtOAc in petroleum ether) to give the title compound as a colourless oil. Y=21%. ¹H NMR (400 MHz, methanol-d₄) δ 7.71 (s, 1H), 7.69 (s, 1H), 7.49 (s, 1H), 4.51-4.43 (m, 1H), 4.41 (d, J=4 Hz, 1H), 4.36-4.28 (m, 1H), 4.22-4.15 (m, 2H), 1.28-1.22 (m, 3H).

Step 2: ethyl (2R)-3-(4-chloro-1H-pyrazol-1-yl)-2-{[(1,2,3,5,6,7-hexahydro-s-indacen-4-yl)carbamoyl]oxy}propanoate. The title compound was prepared according to the General procedure B using ethyl (2R)-3-(4-chloro-1H-pyrazol-1-yl)-2-hydroxypropanoate and Intermediate A as starting materials. The crude product was purified by prep TLC (1:2 EtOAc/hexane) to give the title compound as a white solid. Y=18%. MS ES+: 418.1. ¹H NMR (400 MHz, chloroform-d) δ 7.52-7.38 (m, 1H), 7.02 (s, 1H), 6.41 (s, 1H), 5.43 (br. s, 1H), 4.58 (s, 2H), 4.25 (q, J=7 Hz, 2H), 2.99-2.65 (m, 8H), 2.10-2.03 (m, 4H), 1.29 (t, J=7 Hz, 3H).

Example 85. Ethyl (2R)-3-(4-cyano-1H-imidazol-1-yl)-2-{[(1,2,3,5,6,7-hexahydro-s-indacen-4-yl)carbamoyl]oxy}propanoate and ethyl (2R)-3-(5-cyano-1H-imidazol-1-yl)-2-{[(1,2,3,5,6,7-hexahydro-s-indacen-4-yl)carbamoyl]oxy}propanoate

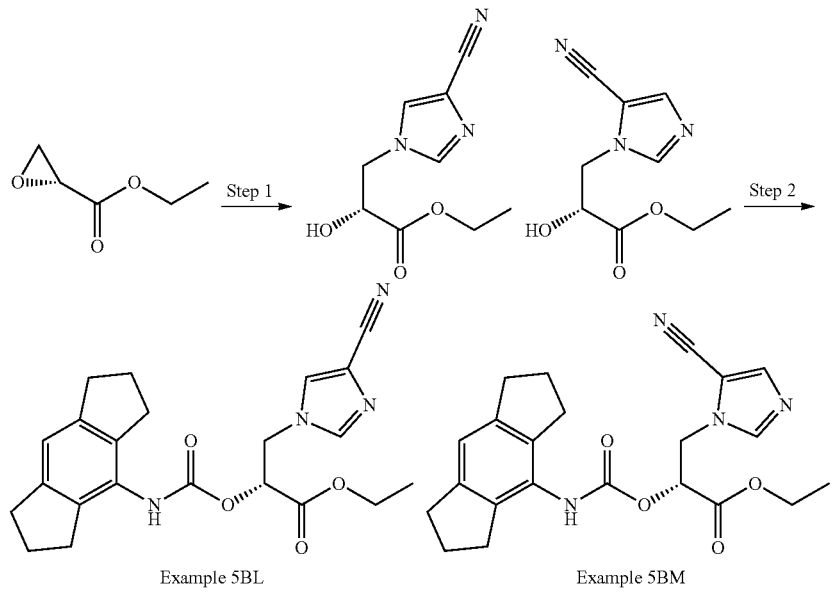

Example 5BL                Example 5BM

Step 1: mixture of ethyl (2R)-3-(4-cyano-1H-imidazol-1-yl)-2-hydroxypropanoate and ethyl (2R)-3-(5-cyano-1H-imidazol-1-yl)-2-hydroxypropanoate. To a solution of 4H-imidazole-5-carbonitrile (2.00 g, 21.53 mmol) in EtOH (10 ml) was added ethyl (2R)-oxirane-2-carboxylate (1 g, 8.61 mmol) (for synthesis refer to example 5AY) portionwise under $N_2$. The mixture was stirred at 95° C. for 0.5 h then concentrated under reduced pressure to give a residue. The residue was purified by FCC (1:2 EtOAc/petroleum ether) to give a mixture of (R)-ethyl 3-(4-cyano-1H-imidazol-1-yl)-2-hydroxypropanoate (28% yield) and (R)-ethyl 3-(5-cyano-1H-imidazol-1-yl)-2-hydroxypropanoate (28% yield) as a yellow oil.

Step 2: ethyl (2R)-3-(4-cyano-1H-imidazol-1-yl)-2-{[(1,2,3,5,6,7-hexahydro-s-indacen-4-yl)carbamoyl]oxy}propanoate and ethyl (2R)-3-(5-cyano-1H-imidazol-1-yl)-2-{[(1,2,3,5,6,7-hexahydro-s-indacen-4-yl)carbamoyl]oxy}propanoate. The mixture of ethyl (2S)-3-(4-cyanoimidazol-1-yl)-2-hydroxy-propanoate and ethyl (2R)-3-(5-cyanoimidazol-1-yl)-2-hydroxy-propanoate (200 mg, 0.96 mmol) was dissolved in anhydrous THF (2 ml) and cooled to 0° C. CuCl (47 mg, 478 μmop was added and the mixture stirred for 30 min, followed by slow addition of 4-isocyanato-1,2,3,5,6,7-hexahydro-s-indacene (200 mg, 1.00 mmol). The reaction mixture was allowed to warm to rt and stirring continued for 10 h. The reaction mixture was diluted with $H_2O$ (5 ml) and extracted with EtOAc (3×5 ml). The combined organic layers were washed with brine (10 ml), dried over $Na_2SO_4$, filtered and concentrated under reduced pressure to give a residue. The residue was purified by prep TLC (1:2 EtOAc/petroleum ether) to give the desired products as a white solid. This mixture was further separated by SFC (column: OD (250 mm*30 mm, 5 um); mobile phase: EtOH; B %: 35%, 12 min). Compound ethyl (2R)-3-(5-cyanoimidazol-1-yl)-2-(1,2,3,5,6,7-hexahydro-s-indacen-4-ylcarbamoyloxy)propanoate (5 mg, 2% yield) and ethyl (2R)-3-(4-cyanoimidazol-1-yl)-2-(1,2,3,5,6,7-hexahydro-s-indacen-4-ylcarbamoyloxy)propanoate (5 mg, 2% yield) were obtained as white solids. Ethyl (2R)-3-(4-cyano-1H-imidazol-1-yl)-2-{[(1,2,3,5,6,7-hexahydro-s-indacen-4-yl)carbamoyl]oxy}propanoate analysis: MS ES$^+$: 409.1. $^1$H NMR (400 MHz, acetonitrile-d$_3$) δ 7.81 (s, 1H), 7.67 (s, 1H), 7.53 (s, 1H), 7.00 (s, 1H), 5.30 (s, 1H), 4.51 (s, 2H), 4.20-4.15 (m, 2H), 2.87 (s, 4H), 2.73 (s, 4H), 2.04-1.93 (m, 4H), 1.22 (t, J=7 Hz, 3H). Ethyl (2R)-3-(5-cyano-1H-imidazol-1-yl)-2-{[(1,2,3,5,6,7-hexahydro-s-indacen-4-yl)carbamoyl]oxy}propanoate analysis: MS ES$^+$: 409.1. $^1$H NMR (400 MHz, acetonitrile-d$_3$) δ 7.85 (s, 1H), 7.66 (s, 1H), 7.46 (s, 1H), 7.00 (s, 1H), 5.32 (s, 1H), 4.59 (s, 2H), 4.25-4.18 (m, 2H), 2.86 (s, 4H), 2.72 (s, 4H), 2.06-1.98 (m, 4H), 1.25 (t, J=7 Hz, 3H).

Example 86. Ethyl 2-({[2,6-dimethyl-4-(trifluoromethyl)phenyl]carbamoyl}oxy)-3-(1H-pyrazol-1-yl)propanoate

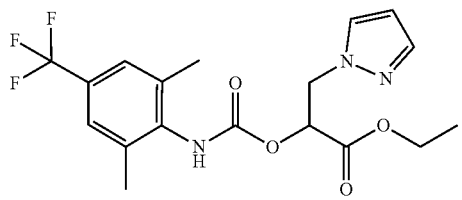

Synthesised using a synthetic route analogous to Example 59 using 2,6-dimethyl-4-(trifluoromethyl)aniline and ethyl 2-hydroxy-3-(1H-pyrazol-1-yl)propanoate (for synthesis refer to Example 49). Y=26%. MS ES$^+$: 400.0. $^1$H NMR (300 MHz, DMSO-d$_6$) δ 9.33 (s, 1H), 7.80 (s, 1H), 7.52-7.31 (m, 3H), 6.29 (s, 1H), 5.38-5.15 (m, 1H), 4.70-4.32 (m, 2H), 4.14 (q, J=7 Hz, 2H), 2.27-2.03 (m, 6H), 1.18 (t, J=7 Hz, 3H).

Example 87. Ethyl 2-{[(1,2,3,5,6,7-hexahydro-s-indacen-4-yl)carbamoyl]oxy}-3-(4-methoxy-1H-pyrazol-1-yl)propanoate

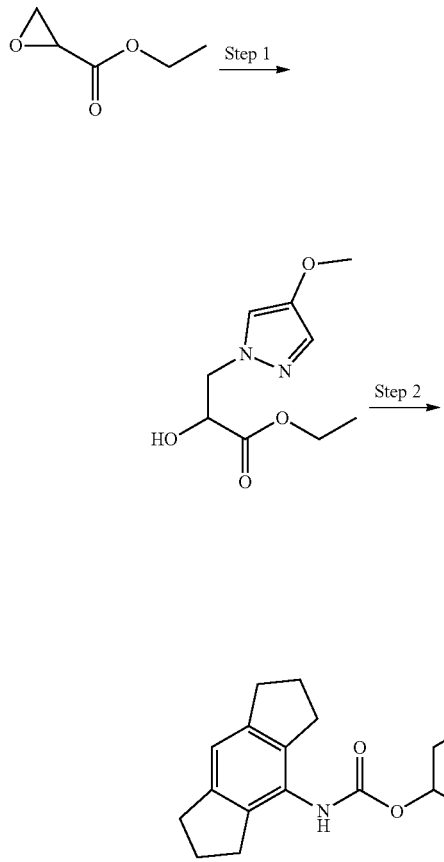

Step 1: ethyl 2-hydroxy-3-(4-methoxy-1H-pyrazol-1-yl) propanoate. In a sealed tube a mixture of 4-methoxy-1H-pyrazole (0.150 g, 1.53 mmol) and ethyl oxirane-2-carboxylate (0.178 g, 1.53 mmol) in EtOH (1 ml) was heated in a microwave reactor at 120° C. for 1 h. A further equivalent ethyl oxirane-2-carboxylate (0.178 g, 1.53 mmol) was added and the RM heated in a microwave reactor at 120° C. for 1 h. The RM was evaporated to dryness and purified by FCC (0-10% MeOH in DCM) to give the title compound as a yellow oil. Y=96%. $^1$H NMR (300 MHz, DMSO-$d_6$) δ 7.41 (d, J=1 Hz, 1H), 7.19 (d, J=1 Hz, 1H), 5.82 (d, J=6 Hz, 1H), 4.40-4.33 (m, 1H), 4.18-4.05 (m, 4H), 3.64 (s, 3H), 1.18 (t, J=7 Hz, 3H).

Step 2: ethyl 2-{[(1,2,3,5,6,7-hexahydro-s-indacen-4-yl) carbamoyl]oxy}-3-(4-methoxy-1H-pyrazol-1-yl)propanoate. The title compound was prepared according to the General procedure B using ethyl 2-hydroxy-3-(4-methoxy-1H-pyrazol-1-yl)propanoate and Intermediate A as starting materials. The crude product was purified by FCC (EtOAc/hexane) then further purified by prep HPLC to give the title compound. Y=1%. MS ES$^+$: 414.5. $^1$H NMR (300 MHz, chloroform-d) δ 7.14 (s, 1H), 7.03 (s, 1H), 6.42 (s, 1H), 5.43 (s, 1H), 4.53 (s, 2H), 4.27 (q, J=7 Hz, 2H), 3.74 (s, 3H), 2.90 (t, J=7 Hz, 4H), 2.81 (t, J=7 Hz, 4H), 2.14-2.04 (m, 4H), 1.31 (t, J=7 Hz, 3H).

Example 88. Ethyl (2R)-2-{[(1,2,3,5,6,7-hexahydro-s-indacen-4-yl)carbamoyl]oxy}-3-(pyrimidin-2-yl)propanoate

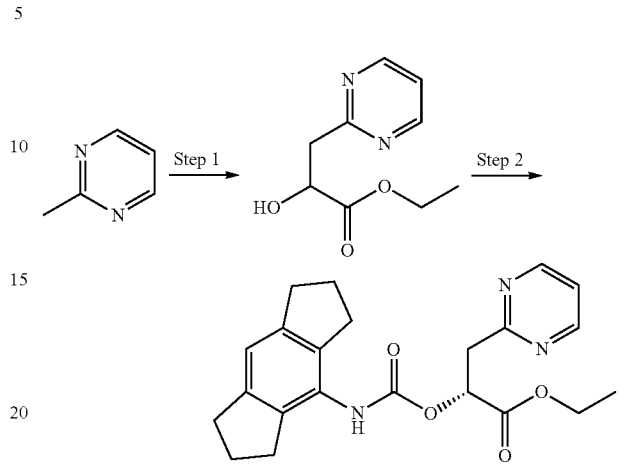

Step 1: ethyl 2-hydroxy-3-(pyrimidin-2-yl)propanoate. To a solution of 2-methylpyrimidine (42.0 g, 446 mmol) and ethyl 2-oxoacetate (118 g, 580 mmol) in 1,4-dioxane (290 ml) was added diacetoxyiron (3.88 g, 22 mmol) in one portion at 10 to 20° C. The mixture was warmed to 101° C. and stirred for 48 h. The RM was filtered and concentrated in vacuo. The resulting residue was purified by FCC (0-50% EtOAc/Petroleum ether) to give the title compound as a yellow solid. Y=74%. $^1$H NMR (400 MHz, chloroform-d) δ 8.70 (d, J=5 Hz, 2H), 7.22 (t, J=5 Hz, 1H), 5.77-5.44 (m, 1H), 4.80-4.69 (m, 1H), 4.26 (q, J=7 Hz, 2H), 3.47-3.56 (m, 1H), 3.36-3.46 (m, 1H), 1.24 (t, J=7 Hz, 3H).

Step 2: ethyl (2R)-2-{[(1,2,3,5,6,7-hexahydro-s-indacen-4-yl)carbamoyl]oxy}-3-(pyrimidin-2-yl)propanoate. The title compound was prepared according to the General procedure B using ethyl 2-hydroxy-3-(pyrimidin-2-yl)propanoate and Intermediate A as starting materials. The crude product was purified by FCC (0-60% EtOAc/hexane) to give the racemic product as a white solid. This was separated by chiral SFC (column: DAICEL CHIRALPAK IC (250 mm*30 mm, 5 μm); mobile phase: EtOH; B %: 22%, 3.9 min). Peak 1 contains the title compound. Y=9%. MS ES$^+$: 396.1. $^1$H NMR (400 MHz, chloroform-d) δ 8.70 (d, J=5 Hz, 2H), 7.21-7.17 (m, 1H), 6.98 (s, 1H), 6.27 (br. s, 1H), 5.80-5.75 (m, 1H), 4.26 (q, J=7 Hz, 2H), 3.65-3.49 (m, 2H), 2.89-2.83 (m, 4H), 2.79-2.74 (m, 4H), 2.09-1.99 (m, 4H), 1.28 (t, J=7 Hz, 3H).

Example 89. Ethyl (2R)-2-{[(1,2,3,5,6,7-hexahydro-s-indacen-4-yl)carbamoyl]oxy}-3-(pyrazin-2-yl)propanoate

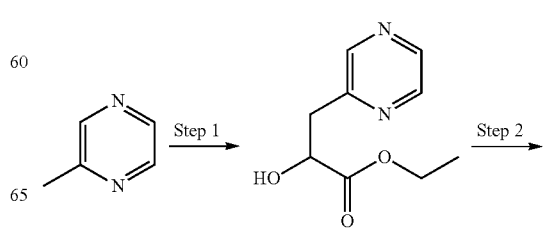

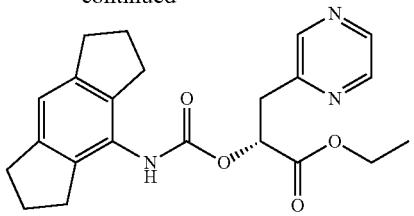

Step 1: ethyl 2-hydroxy-3-(pyrazin-2-yl)propanoate. To a solution of 2-methylpyrazine (20.0 g, 212 mmol) in 1,4-dioxane (140 ml) was added ethyl 2-oxoacetate (56.4 g, 276 mmol) and diacetoxyiron (0.99 g, 6.4 mmol) under $N_2$. The reaction was heated at 140° C. for 48 h. The mixture was concentrated under reduced pressure. The residue was purified by FCC (0-10% EtOAc/petroleum ether) to give the title compound. Y=30%. $^1$H NMR (400 MHz, chloroform-d) δ 8.54-8.48 (m, 3H), 4.70-4.64 (m, 1H), 4.26 (q, J=8 Hz, 2H), 3.38-3.33 (m, 1H), 3.25-3.19 (m, 1H), 1.26 (t, J=7 Hz, 3H).

Step 2: ethyl (2R)-2-{[(1,2,3,5,6,7-hexahydro-s-indacen-4-yl)carbamoyl]oxy}-3-(pyrazin-2-yl)propanoate. The title compound (as a racemic mixture) was prepared according to the General procedure B using ethyl 2-hydroxy-3-(pyrazin-2-yl)propanoate and Intermediate A as starting materials. The crude mixture was purified by FCC (0-50% EtOAc/hexane) to give the racemic product as a white solid. This was separated by chiral SFC (column: Daicel Chiralpak AD-H (250 mm*30 mm, 5 μm); mobile phase: EtOH; B %: 24%, 5.5 min). Peak 2 contains the title compound. Y=34%. MS ES$^+$: 396.1. $^1$H NMR (400 MHz, DMSO-d$_6$) δ 9.22-9.15 (br. s, 1H), 8.68-8.55 (m, 3H), 6.93 (s, 1H), 5.40-5.32 (m, 1H), 4.13 (q, J=7 Hz, 2H), 3.41-3.29 (m, 2H), 2.82-2.74 (m, 4H), 2.69-2.55 (m, 4H), 1.98-1.88 (m, 4H), 1.16 (t, J=7 Hz, 3H).

Example 90. Ethyl (2R)-3-ethoxy-2-{[(1,2,3,5,6,7-hexahydro-s-indacen-4-yl)carbamoyl]oxy}propanoate

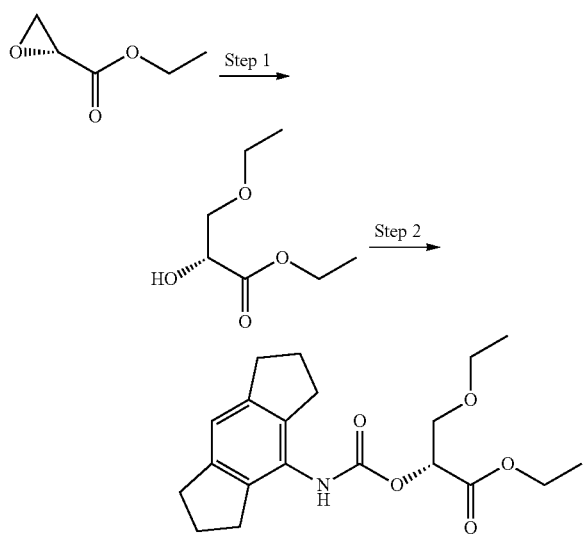

Step 1: ethyl (2R)-3-ethoxy-2-hydroxypropanoate. To a solution of ethyl (2R)-oxirane-2-carboxylate (100 mg, 0.86 mmol) (for synthesis refer to example 5AY) in EtOAc (1 ml) was added ethanol (0.35 ml, 6.0 mmol), then magnesium trifluoromethanesulfonate (444 mg, 1.38 mmol). The mixture was stirred at 60° C. for 24 h. The residue was purified by FCC (5-20% EtOAc in petroleum ether) to give the title compound as a colourless oil. Y=72%. $^1$H NMR (400 MHz, chloroform-d) δ 4.36-4.20 (m, 3H), 3.73 (d, J=4 Hz, 2H), 3.64-3.46 (m, 2H), 3.05 (d, J=6 Hz, 1H), 1.31 (t, J=7 Hz, 3H), 1.19 (t, J=7 Hz, 3H).

Step 2: ethyl (2R)-3-ethoxy-2-{[(1,2,3,5,6,7-hexahydro-s-indacen-4-yl)carbamoyl]oxy}propanoate. The title compound was prepared according to the General procedure B using ethyl (2R)-3-ethoxy-2-hydroxypropanoate and Intermediate A as starting materials. The crude mixture was purified by prep TLC (25% EtOAc/hexane) to give the title compound as a white solid. Y=10%. MS ES$^+$: 362.1. $^1$H NMR (400 MHz, chloroform-d) δ 7.01 (s, 1H), 6.48 (s, 1H), 5.28 (s, 1H), 4.43-4.13 (m, 2H), 4.01-3.84 (m, 2H), 3.70-3.45 (m, 2H), 3.01-2.76 (m, 8H), 2.17-1.98 (m, 4H), 1.31 (t, J=7 Hz, 3H), 1.27-1.19 (m, 3H).

Example 91. Ethyl (2R)-3-(3-cyano-1H-pyrazol-1-yl)-2-{[(1,2,3,5,6,7-hexahydro-s-indacen-4-yl)carbamoyl]oxy}propanoate

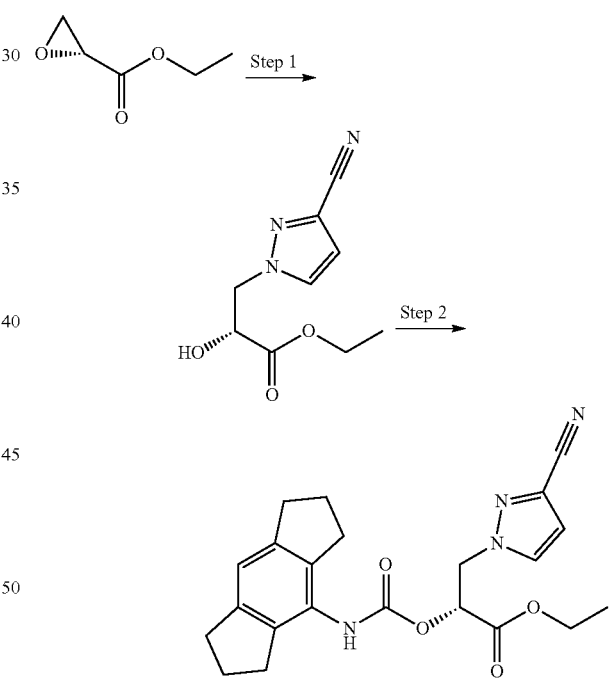

Step 1: ethyl (2R)-3-(3-cyano-1H-pyrazol-1-yl)-2-hydroxypropanoate. To a solution of 1H-pyrazole-3-carbonitrile (2.00 g, 21.5 mmol) in EtOH (3 ml) was added ethyl (2R)-oxirane-2-carboxylate (1.0 g, 8.61 mmol) (for synthesis refer to example 5AY) portionwise. Then the mixture was stirred at 90° C. for 0.5 h. The reaction mixture was concentrated under reduced pressure to give a residue. The residue was purified by FCC (1:2 EtOAc/petrol) to give the title compound as a colourless oil. Y=14%. $^1$H NMR (400 MHz, chloroform-d) δ 7.59 (d, J=3 Hz, 1H), 6.65 (d, J=3 Hz, 1H), 4.56-4.47 (m, 3H), 4.33-4.25 (m, 2H), 1.35-1.29 (m, 3H).

Step 2: ethyl (2R)-3-(3-cyano-1H-pyrazol-1-yl)-2-{[(1,2,3,5,6,7-hexahydro-s-indacen-4-yl)carbamoyl]oxy}propanoate. The title compound was prepared according to the General procedure B using ethyl (2R)-3-(3-cyano-1H-pyrazol-1-yl)-2-hydroxypropanoate and Intermediate A as starting materials. The crude mixture was purified by prep TLC (33% EtOAc/hexane) to give the title compound as a white solid. Y=10%. MS ES+: 409.2 $^1$H NMR (400 MHz, DMSO-d$_6$) δ 9.19 (s, 1H), 8.11 (s, 1H), 7.04 (s, 1H), 6.96 (s, 1H), 5.38 (s, 1H), 4.77 (s, 2H), 4.18-4.12 (m, 2H), 2.87-2.74 (m, 4H), 2.73-2.62 (m, 4H), 2.02-1.89 (m, 4H), 1.19 (t, J=7 Hz, 3H).

Example 92. Ethyl (2R)-2-{[(1,2,3,5,6,7-hexahydro-s-indacen-4-yl)carbamoyl]oxy}-3-[4-(trifluoromethyl)-1H-pyrazol-1-yl]propanoate

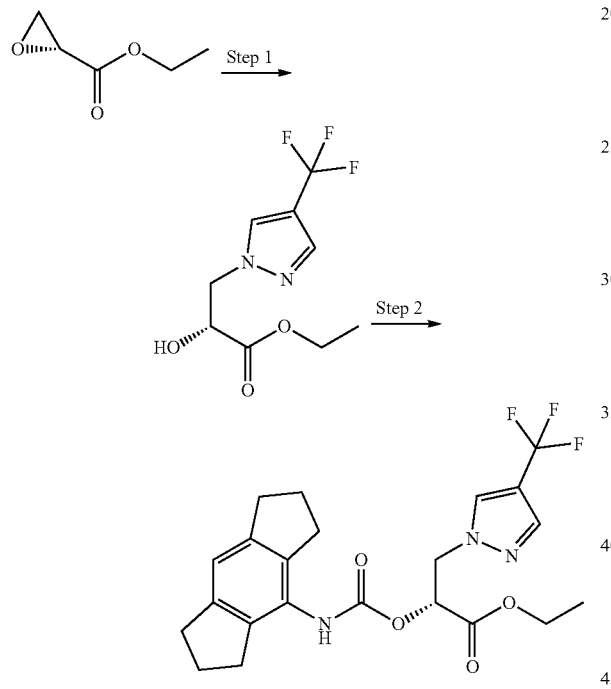

Step 1: ethyl (2R)-2-hydroxy-3-[4-(trifluoromethyl)-1H-pyrazol-1-yl]propanoate. To a solution of ethyl (2R)-oxirane-2-carboxylate (0.20 g, 1.72 mmol) (for synthesis refer to example 5AY) in EtOH (2 ml) was added 4-trifluoromethylpyrazole (586 mg, 4.31 mmol). The solution was stirred at 90° C. for 16 h. The reaction mixture was concentrated, diluted with H$_2$O (20 ml) and extracted with EtOAc (3×15 ml). The combined organic layers were washed with brine (10 ml), dried over Na$_2$SO$_4$, filtered and concentrated under reduced pressure to give a residue. The residue was purified by FCC (0-9% MeOH in DCM) to give the title compound as a yellow oil. Y=58%. $^1$H NMR (400 MHz, DMSO-d$_6$) δ 13.65-13.55 (br. s, 1H), 8.39 (s, 1H), 7.90 (s, 1H), 5.94 (d, J=6 Hz, 1H), 4.46-4.40 (m, 2H), 4.13-4.08 (m, 2H), 1.17 (t, J=7 Hz, 3H).

Step 2: ethyl (2R)-2-{[(1,2,3,5,6,7-hexahydro-s-indacen-4-yl)carbamoyl]oxy}-3-[4-(trifluoromethyl)-1H-pyrazol-1-yl]propanoate. The title compound was prepared according to the General procedure B using ethyl (2R)-2-hydroxy-3-[4-(trifluoromethyl)-1H-pyrazol-1-yl]propanoate and Intermediate A as starting materials. The crude mixture was purified by prep TLC (33% EtOAc/hexane) to give the title compound as a white solid. Y=12%. MS ES+: 452.2. $^1$H NMR (400 MHz, chloroform-d) δ 7.80-7.70 (m, 2H), 7.00 (s, 1H), 6.42 (s, 1H), 5.48 (s, 1H), 4.72-4.62 (m, 2H), 4.29-4.18 (m, 2H), 2.93-2.85 (m, 4H), 2.82-2.72 (m, 4H), 2.11-2.03 (m, 4H), 1.30 (m, 3H).

Example 93. (2R)-3-{4-[(dimethylamino)methyl]-1H-pyrazol-1-yl}-2-{[(1,2,3,5,6,7-hexahydro-s-indacen-4-yl)carbamoyl]oxy}propanoic acid hydrochloride

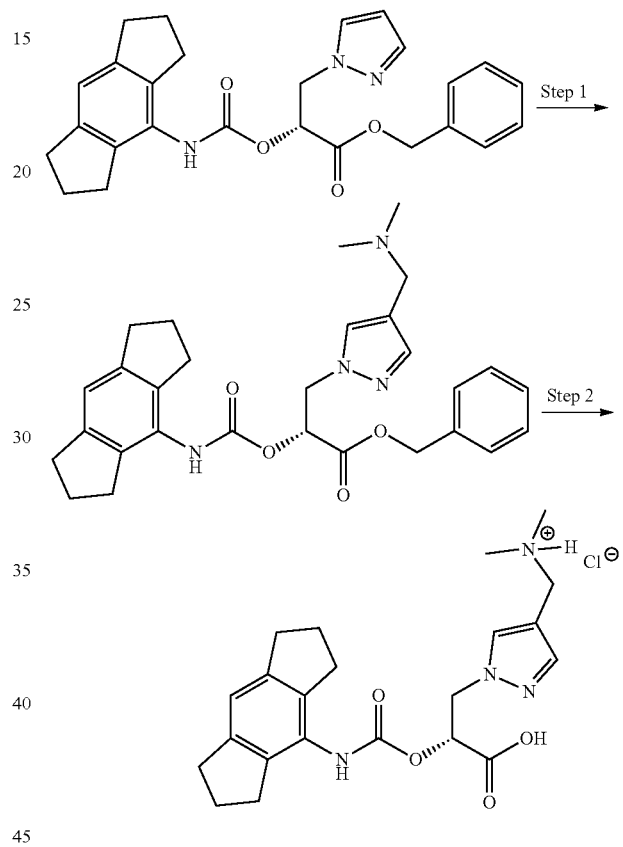

Step 1: benzyl (2R)-3-{4-[(dimethylamino)methyl]-1H-pyrazol-1-yl}-2-{[(1,2,3,5,6,7-hexahydro-s-indacen-4-yl)carbamoyl]oxy}propanoate. To a solution of benzyl (2R)-2-{[(1,2,3,5,6,7-hexahydro-s-indacen-4-yl)carbamoyl]oxy}-3-(1H-pyrazol-1-yl)propanoate (0.20 g, 0.45 mmol) (for synthesis refer to example SAM) in acetonitrile (2 ml) and DMF (1 ml) was added N,N-dimethylmethylideneammonium iodide (0.33 g, 1.80 mmol). The RM was purged with argon and sealed in a tube. The RM was heated at 90° C. for 16 h then concentrated in vacuo. The residue was purified by FCC (40% EtOAc in hexane, then 0-10% MeOH in DCM) to give the title compound as a green solid. Y=20%. MS ES+: 504.

Step 2: (2R)-3-{4-[(dimethylamino)methyl]-1H-pyrazol-1-yl}-2-{[(1,2,3,5,6,7-hexahydro-s-indacen-4-yl)carbamoyl]oxy}propanoic acid hydrochloride. Benzyl (2R)-3-{4-[(dimethylamino)methyl]-1H-pyrazol-1-yl}-2-{[(1,2,3,5,6,7-hexahydro-s-indacen-4-yl)carbamoyl]oxy}propanoate (31 mg, 0.06 mmol was dissolved in MeOH (5 ml) in a Parr reactor. 1,1,2-trichloroethane (6 µl, 0.07 mmol) and palladium on carbon (10%, 0.05 g) were added. The RM was stirred under hydrogen atmosphere for 16 h. The RM was filtered through Celite, washed with MeOH and the filtrate concentrated in vacuo. The resulting residue was dissolved in the minimum volume MeOH, precipitated with diethyl ether and the resulting solid filtered off to give the title compound as a yellow solid. MS ES⁺: 413. ¹H NMR (300 MHz, DMSO-d₆) δ 8.88 (s, 1H), 8.20 (s, 1H), 7.76-7.70 (m, 1H), 7.38 (s, 1H), 6.91 (s, 1H), 5.11-5.05 (m, 1H), 4.65-4.55 (m, 1H), 4.42-4.32 (m, 1H), 2.87-2.76 (m, 4H), 2.74-2.62 (m, 4H), 2.24 (s, 6H), 2.00-1.86 (m, 4H).

Example 94. Ethyl 2-{[(2,4-dimethylthiophen-3-yl)carbamoyl]oxy}-3-(1H-pyrazol-1-yl)propanoate

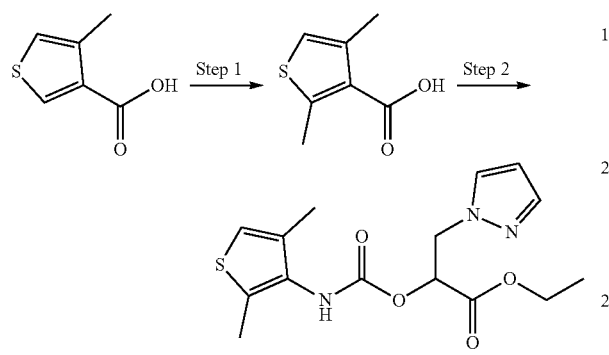

Step 1: 2,4-dimethylthiophene-3-carboxylic acid. To a solution of 4-methylthiophene-3-carboxylic acid (0.5 g, 3.5 mmol) in THF (20 ml) was added n-butyllithium (1.6 M in hexanes, 5 ml, 8.0 mmol) dropwise at −78° C. under N₂ atmosphere. The resulting reaction mixture was stirred at −78° C. for 30 min. A solution of iodomethane (0.24 ml, 3.8 mmol) in THF (20 ml) was added dropwise to the reaction mixture. The resulting reaction mixture was stirred at −78° C. for 30 min then allowed to warm to room temperature. The reaction mixture was poured into saturated ammonium chloride (50 ml) and the resulting solution/suspension concentrated under vacuum. The aqueous was extracted with DCM (70 ml) and filtered under reduced pressure. The filtrate was concentrated under vacuum. The crude was purified by trituration using diethyl ether (2×20 ml) then concentrated under vacuum to give the title compound as an off-white solid. Y=74%. ¹H NMR (400 MHz, DMSO-d₆) δ 12.64 (s, 1H), 6.93 (d, J=1 Hz, 1H), 2.58 (s, 3H), 2.28 (s, 3H).

Step 2: ethyl 2-{[(2,4-dimethylthiophen-3-yl)carbamoyl]oxy}-3-(1H-pyrazol-1-yl)propanoate. To a solution of 2,4-dimethylthiophene-3-carboxylic acid (0.2 g, 1.28 mmol) in toluene (10 ml) was added diphenylphosphoryl azide (0.38 g, 1.41 mmol) followed by N,N-diisopropylethylamine (0.20 g, 1.53 mmol) at 0° C. under N2 atmosphere. The RM was stirred at rt for 1 h. The reaction mixture was cooled to 0° C. and ethyl 2-hydroxy-3-(1H-pyrazol-1-yl)propanoate (0.20 g, 1.28 mmol) (for synthesis refer to Example 49) in toluene (5 ml) was added. 1-(isocyanatomethyl)-2-methylbenzene (0.94 g, 5.12 mmol) was added at 0° C. and the RM heated at 120° C. for 5 h then allowed to cool to rt. The RM was concentrated under vacuum, triturated with diethyl ether (2×20 ml) and the resulting solid filtered. This was further purified by prep-HPLC to give the title compound as a yellow solid. Y=9%. MS ES⁺: 338.1. ¹H NMR (400 MHz, DMSO-d₆) δ 8.98 (s, 1H), 7.78 (d, J=2 Hz, 1H), 7.47 (s, 1H), 6.86 (s, 1H), 6.28 (s, 1H), 5.32-5.24 (m, 1H), 4.62 (d, J=6 Hz, 2H), 4.11 (t, J=7 Hz, 2H), 2.12 (s, 3H), 1.96 (s, 3H), 1.15 (t, J=7 Hz, 3H).

Example 95. Ethyl 2-[({4,10-dioxatricyclo[7.3.0.0³,⁷]dodeca-1(9),2,7-trien-2-yl}-carbamoyl)oxy]-3-(1H-pyrazol-1-yl)propanoate

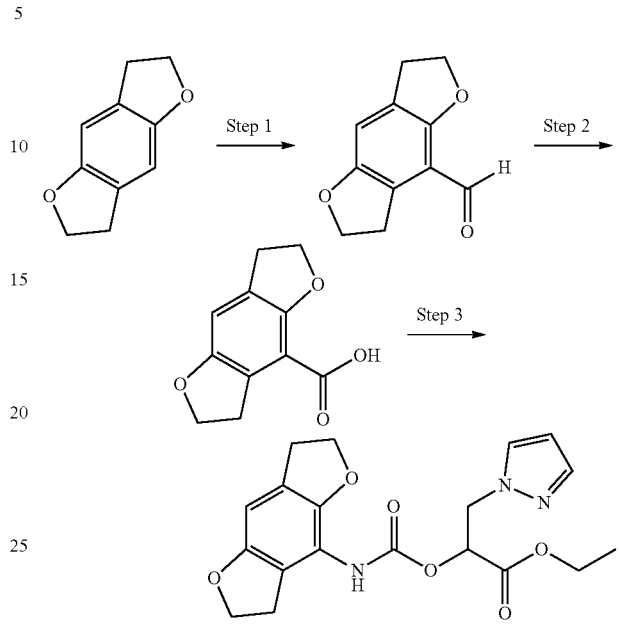

Step 1: 4,10-dioxatricyclo[7.3.0.0³,⁷]dodeca-1(9),2,7-triene-2-carbaldehyde. To a stirred solution of 4,10-dioxatricyclo[7.3.0.0³,⁷]dodeca-1,3(7),8-triene (0.55 g, 3.39 mmol) in dry DCM (11.5 ml) was added tin (IV) chloride (1.11 g, 4.27 mmol) and the RM stirred for 5 min. Dichloromethyl methyl ether (0.39 g, 3.39 mmol) in DCM (0.6 ml) was added under N₂ atmosphere at 0° C. The RM was stirred for 15 min at 0° C., then poured into water (25 ml). The aqueous was extracted with DCM (2×30 ml) and the combined organics washed with 3M HCl (15 ml). The organic phase was dried over anhydrous Na₂SO₄, filtered and evaporated under reduced pressure. The crude product was purified by FCC (0.5% ethyl acetate in hexane) to give the title compound as a yellow solid. Y=49%. ¹H NMR (400 MHz, chloroform-d) δ 10.31 (s, 1H), 6.89 (s, 1H), 4.70 (t, J=9 Hz, 2H), 4.61 (t, J=9 Hz, 2H), 3.50-3.45 (m, 2H), 3.22-3.17 (m, 2H).

Step 2: 4,10-dioxatricyclo[7.3.0.0³,⁷]dodeca-1(9),2,7-triene-2-carboxylic acid. To a stirred solution of 4,10-dioxatricyclo[7.3.0.03,7]dodeca-1(9),2,7-triene-2-carbaldehyde (0.32 g, 1.68 mmol) in acetone (3 ml) at 0° C. was added sulfamic acid (0.245 g, 2.52 mmol). A solution of sodium chlorite (0.196 g, 2.17 mmol) in water (0.5 ml) was added dropwise and RM stirred at 0° C. for 30 min. The RM was poured into cold water (20 ml) and extracted with ethyl acetate (3×30 ml). The combined organic layers were dried over anhydrous Na₂SO₄, filtered and concentrated under reduced. The resulting crude product was triturated with pentane (3×30 ml), filtered and dried under vacuum to give the title compound as a brown solid. Y=77%. MS ES⁺: 207.0.

Step 3: ethyl 2-[({4,10-dioxatricyclo[7.3.0.0³,⁷]dodeca-1(9),2,7-trien-2-yl}carbamoyl)oxy]-3-(1H-pyrazol-1-yl)propanoate. To a stirred solution of 4,10-dioxatricyclo[7.3.0.03,7]dodeca-1(9),2,7-triene-2-carboxylic acid (0.280 g, 1.35 mmol) in toluene (5 ml) was added triethylamine (0.50 ml, 4.07 mmol) and ethyl 2-hydroxy-3-(1H-pyrazol-1-yl)propanoate (0.250 g, 1.35 mmol) (for synthesis refer to Example 49). After stirring for 5 min, diphenyl phosphorylazide (1.11 g, 4.07 mmol) was added and RM heated in a microwave reactor at 100° C. for. The reaction was cooled to room temperature, poured into cold water (25 ml) and extracted with ethyl acetate (3×30 ml). The combined organic layers were dried over anhydrous $Na_2SO_4$, filtered and concentrated under vacuum. The crude was purified by FCC (50% ethyl acetate in hexane) and further purified by prep HPLC to give the title compound as an off-white solid. Y=2%. MS ES$^+$: 388.2. $^1$H NMR (400 MHz, DMSO-$d_6$) δ 7.88-7.82 (m, 1H), 7.45 (s, 1H), 7.26 (s, 1H), 7.14-7.13 (m, 1H), 6.27 (s, 1H), 5.21 (s, 1H), 4.58 (s, 2H), 4.48-4.41 (m, 2H), 4.11-4.09 (m, 2H), 3.14-3.06 (m, 2H), 2.95-2.86 (m, 2H), 1.23-1.15 (m, 3H). 2H obscured by solvent peak.

Example 96. Ethyl (2R)-2-{[(1,2,3,5,6,7-hexahydro-s-indacen-4-yl)carbamoyl]oxy}-3-(2-methoxyethoxy)propanoate

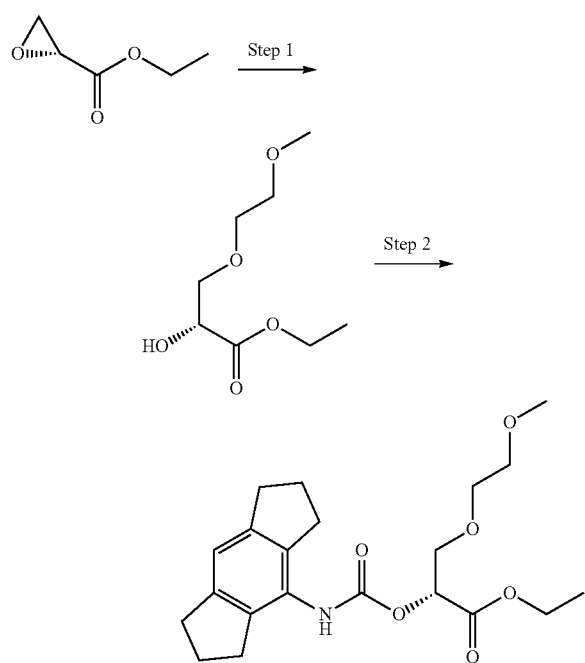

Step 1: ethyl (2R)-2-hydroxy-3-(2-methoxyethoxy)propanoate. To a solution of ethyl (2R)-oxirane-2-carboxylate (100 mg, 0.86 mmol) (for synthesis refer to example 5AY) in EtOAc (1 ml) was added 2-methoxyethanol (475 μl, 6.0 mmol) and magnesium trifluoromethane-sulfonate (444 mg, 1.38 mmol). The mixture was stirred at 60° C. for 12 h. The residue was purified by FCC (9-25% EtOAc in petrol) to give the title compound as a colourless oil. Y=42%. $^1$H NMR (400 MHz, chloroform-d) δ 4.32 (t, J=4 Hz, 1H), 4.27 (t, J=7 Hz, 2H), 3.82 (d, J=4 Hz, 2H), 3.73-3.66 (m, 2H), 3.58-3.51 (m, 2H), 3.38 (s, 3H), 1.31 (t, J=7 Hz, 3H).

Step 2: ethyl (2R)-2-{[(1,2,3,5,6,7-hexahydro-s-indacen-4-yl)carbamoyl]oxy}-3-(2-methoxyethoxy)propanoate. The title compound was prepared according to the General procedure B using ethyl (2R)-2-hydroxy-3-(2-methoxyethoxy)propanoate and Intermediate A as starting materials. The crude mixture was purified by prep TLC (33% EtOAc/hexane) to give the title compound as a white solid. Y=17%. MS ES$^+$: 392.1. $^1$H NMR (400 MHz, chloroform-d) δ 7.01 (s, 1H), 6.50-6.42 (br. s, 1H), 5.28 (s, 1H), 4.34-4.20 (m, 2H), 4.06-3.89 (m, 2H), 3.78-3.51 (m, 4H), 3.38 (s, 3H), 2.95-2.81 (m, 8H), 2.08 (m, 4H), 1.31 (t, J=7 Hz, 3H).

Example 97. Ethyl (2R)-2-{[(1,2,3,5,6,7-hexahydro-s-indacen-4-yl)carbamoyl]oxy}-3-(oxan-4-yloxy)propanoate

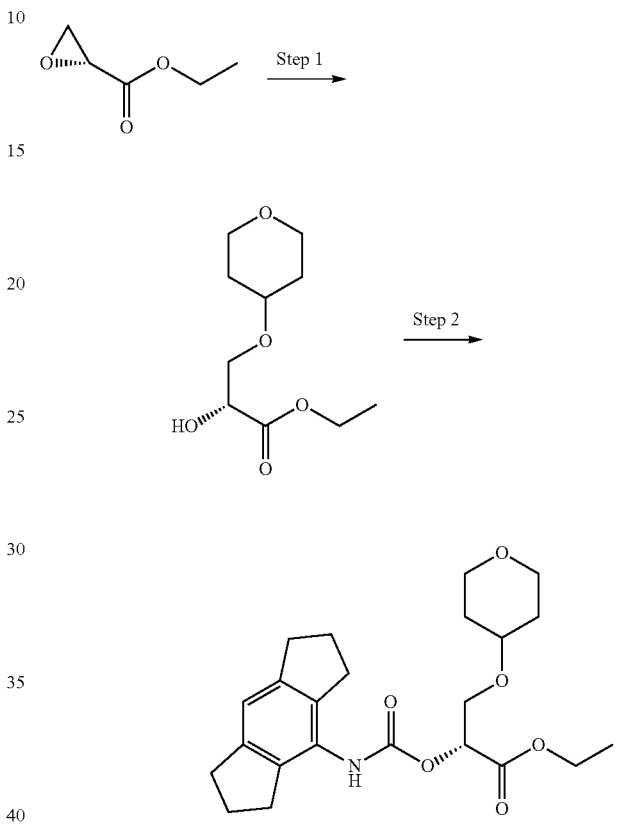

Step 1: ethyl (2R)-2-hydroxy-3-(oxan-4-yloxy)propanoate. To a solution of ethyl (2R)-oxirane-2-carboxylate (150 mg, 1.29 mmol) (for synthesis refer to example 5AY) in EtOAc (1 ml) was added tetrahydropyran-4-ol (155 μl, 1.55 mmol) and magnesium trifluoromethane-sulfonate (666 mg, 2.07 mmol). The mixture was stirred at 60° C. for 36 h. The residue was purified by FCC (5-10% EtOAc in petrol) to give the title compound as a colourless oil. Y=14%. $^1$H NMR (400 MHz, chloroform-d) δ 4.34-4.18 (m, 3H), 3.96-3.83 (m, 2H), 3.81-3.71 (m, 2H), 3.59-3.49 (m, 1H), 3.48-3.37 (m, 2H), 3.05 (d, J=7 Hz, 1H), 1.93-1.81 (m, 2H), 1.62-1.52 (m, 2H), 1.30 (t, J=7 Hz, 3H).

Step 2: ethyl (2R)-2-{[(1,2,3,5,6,7-hexahydro-s-indacen-4-yl)carbamoyl]oxy}-3-(oxan-4-yloxy)propanoate. The title compound was prepared according to the General procedure B using ethyl (2R)-2-hydroxy-3-(oxan-4-yloxy)propanoate and Intermediate A as starting materials. The crude mixture was purified by prep TLC (50% EtOAc/hexane) to give the title compound as a white solid. Y=10%. MS ES$^+$: 418.3. $^1$H NMR (400 MHz, chloroform-d) δ 7.01 (s, 1H), 6.50-6.46 (br. s, 1H), 5.28 (s, 1H), 4.32-4.20 (m, 2H), 4.02-3.83 (m, 4H), 3.65-3.33 (m, 3H), 2.93-2.80 (m, 8H), 2.13-2.02 (m, 4H), 1.93-1.75 (m, 2H), 1.70-1.50 (m, 2H), 1.31 (t, J=7 Hz, 3H).

Example 98. Ethyl (2R)-2-{[(1,2,3,5,6,7-hexahydro-s-indacen-4-yl)carbamoyl]oxy}-3-(5-methyl-1H-1,2,4-triazol-1-yl)propanoate and Ethyl (2R)-2-{[(1,2,3,5,6,7-hexahydro-s-indacen-4-yl)carbamoyl]oxy}-3-(3-methyl-1H-1,2,4-triazol-1-yl)propanoate

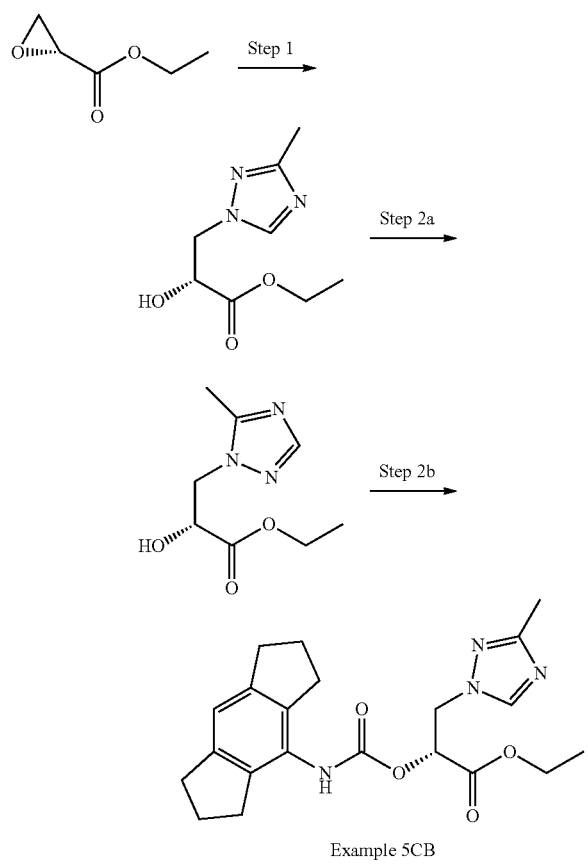

Example 5CB

Example 5BZ

Step 1: ethyl (2R)-2-hydroxy-3-(3-methyl-1H-1,2,4-triazol-1-yl)propanoate and ethyl (2R)-2-hydroxy-3-(5-methyl-1H-1,2,4-triazol-1-yl)propanoate. To a solution of ethyl (2R)-oxirane-2-carboxylate (1.50 g, 12.9 mmol) (for synthesis refer to example 5AY) in EtOH (15 ml) was added 5-methyl-1H-1,2,4-triazole (2.68 g, 32.3 mmol) and DIPEA (5.40 ml, 31.00 mmol). The mixture was stirred at rt for 3 h then concentrated. The crude was purified by prep-HPLC (column: Phenomenex Luna C18 250*50 mm*10 um; liquid phase: [A-TFA/H$_2$O=0.075% v/v; B-ACN] B %: 1%-20%, 20 min) to give ethyl (2R)-2-hydroxy-3-(3-methyl-1H-1,2,4-triazol-1-yl)propanoate (12% yield) as a yellow oil and ethyl (2R)-2-hydroxy-3-(5-methyl-1H-1,2,4-triazol-1-yl) propanoate (10% yield) as a yellow oil. Ethyl (2R)-2-hydroxy-3-(3-methyl-1H-1,2,4-triazol-1-yl)propanoate analysis: $^1$H NMR (400 MHz, DMSO-d$_6$) δ 8.57 (s, 1H), 5.70-5.30 (br. s, 1H), 4.43-4.31 (m, 3H), 4.13 (q, J=7 Hz, 2H), 2.27 (s, 3H), 1.19 (t, J=7 Hz, 3H). Ethyl (2R)-2-hydroxy-3-(5-methyl-1H-1,2,4-triazol-1-yl)propanoate analysis: $^1$H NMR (400 MHz, DMSO-d$_6$) δ 8.11 (s, 1H), 6.45-6.10 (br. s, 1H), 4.45-4.31 (m, 3H), 4.11 (q, J=7 Hz, 2H), 2.46 (s, 3H), 1.19 (t, J=7 Hz, 3H).

Step 2a: ethyl (2R)-2-{[(1,2,3,5,6,7-hexahydro-s-indacen-4-yl)carbamoyl]oxy}-3-(3-methyl-1H-1,2,4-triazol-1-yl)propanoate. The title compound was prepared according to the General procedure B using ethyl (2R)-2-hydroxy-3-(3-methyl-1H-1,2,4-triazol-1-yl)propanoate and Intermediate A as starting materials. The crude mixture was purified by FCC (0-17% EtOAc/hexane) followed by prep HPLC (column: Agela Durashell C18 150*25, 5 μm; liquid phase: [A-10 mM NH$_4$HCO$_3$ in H$_2$O; B-ACN] B %: 39%-69%, 10 min) to give the title compound as a white solid. Y=1%. MS ES$^+$: 399.2. $^1$H NMR (400 MHz, chloroform-d) δ 8.26 (s, 1H), 7.03 (s, 1H), 6.47 (s, 1H), 5.46 (s, 1H), 4.65 (s, 2H), 4.28 (q, J=7 Hz, 2H), 2.93-2.85 (m, 4H), 2.83-2.74 (m, 4H), 2.43 (s, 3H), 2.11-2.04 (m, 4H), 1.32 (t, J=7 Hz, 3H).

Step 2b: ethyl (2R)-2-{[(1,2,3,5,6,7-hexahydro-s-indacen-4-yl)carbamoyl]oxy}-3-(5-methyl-1H-1,2,4-triazol-1-yl)propanoate. The title compound was prepared according to the General procedure B using ethyl (2R)-2-hydroxy-3-(5-methyl-1H-1,2,4-triazol-1-yl)propanoate and Intermediate A as starting materials. The crude mixture was purified by prep TLC (9% MeOH/DCM) to give the title compound as a pale yellow solid. Y=1%. MS ES$^+$: 399.2. $^1$H NMR (400 MHz, chloroform-d) δ 7.73 (s, 1H), 6.95 (s, 1H), 6.33 (s, 1H), 5.41 (s, 1H), 4.53 (s, 2H), 4.19-4.12 (m, 2H), 2.86-2.75 (m, 4H), 2.73-2.63 (br. s, 4H), 2.02-1.95 (m, 4H), 1.51 (s, 3H), 1.25 (t, J=7 Hz, 3H).

Example 99. Ethyl (2R)-2-{[(1,2,3,5,6,7-hexahydro-s-indacen-4-yl)carbamoyl]oxy}-3-(propan-2-yloxy)propanoate

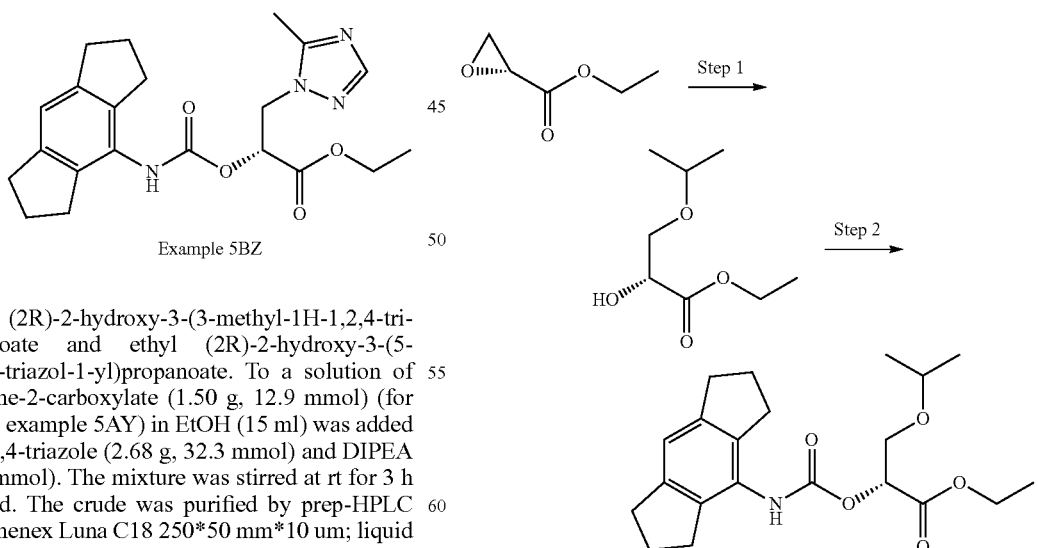

Step 1: ethyl (2R)-2-hydroxy-3-(propan-2-yloxy)propanoate. To a solution of ethyl (2R)-oxirane-2-carboxylate (100 mg, 0.86 mmol) (for synthesis refer to example 5AY) in EtOAc (1 ml) was added propan-2-ol (462 μl, 6.03 mmol)

and magnesium trifluoromethanesulfonate (444 mg, 1.38 mmol). The mixture was stirred at 60° C. for 24 h. The residue was purified by FCC (5-17% EtOAc in petrol) to give the title compound as a colourless oil. Y=69%. $^1$H NMR (400 MHz, chloroform-d) δ 4.35-4.16 (m, 3H), 3.77-3.65 (m, 2H), 3.61-3.57 (m, 1H), 1.29 (t, J=7 Hz, 3H), 1.18-1.06 (m, 6H).

Step 2: ethyl (2R)-2-{[(1,2,3,5,6,7-hexahydro-s-indacen-4-yl)carbamoyl]oxy}-3-(propan-2-yloxy)propanoate. The title compound was prepared according to the General procedure B using ethyl (2R)-2-hydroxy-3-(propan-2-yloxy)propanoate and Intermediate A as starting materials. The crude mixture was purified by prep TLC (25% EtOAc in petrol) to give the title compound as a white solid. Y=10%. MS ES$^+$: 376.3. $^1$H NMR (400 MHz, chloroform-d) δ 7.00 (s, 1H), 6.50-6.42 (br. s, 1H), 5.26 (s, 1H), 4.34-4.16 (m, 2H), 3.87 (s, 2H), 3.65 (s, 1H), 2.91-2.81 (m, 8H), 2.12-2.01 (m, 4H), 1.31 (t, J=7 Hz, 3H), 1.21-1.12 (br. s, 6H).

Example 100. (2R)-2-{[(1,2,3,5,6,7-hexahydro-s-indacen-4-yl)carbamoyl]oxy}-3-(pyrimidin-2-yl)propanoic acid

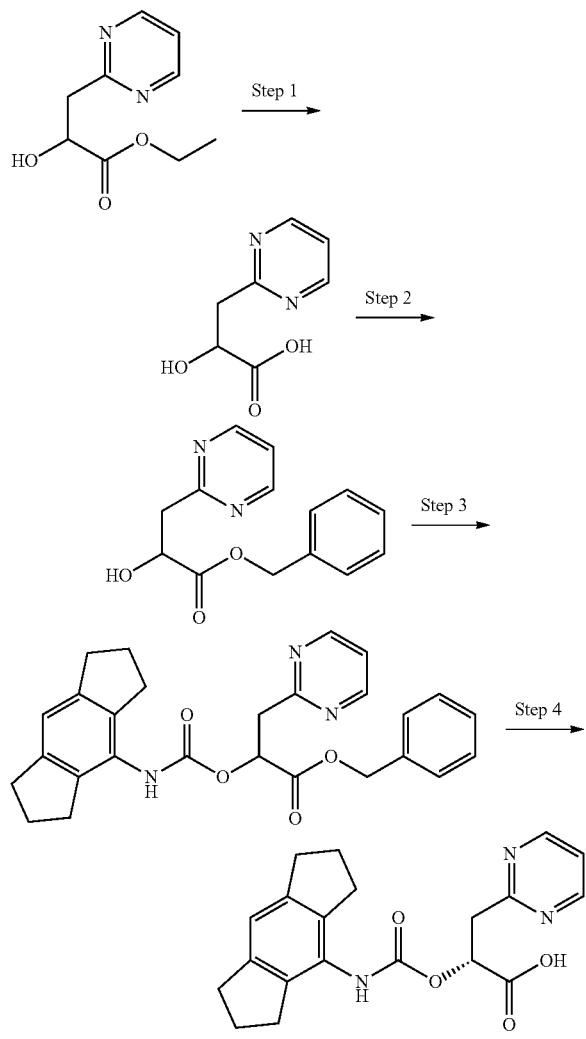

Step 1: 2-hydroxy-3-(pyrimidin-2-yl)propanoic acid. To a mixture of ethyl 2-hydroxy-3-(pyrimidin-2-yl)propanoate (26.0 g, 133 mmol) (for synthesis refer to example SBP) in THF (180 ml) and H$_2$O (180 ml) was added LiOH.H$_2$O (7.31 g, 174 mmol) in one portion at 10 to 20° C. The RM was stirred at between 10 and 20° C. for 16 h. The mixture was concentrated in vacuo to remove THF and give an aqueous solution. This was washed with EtOAc (3×40 ml). The aqueous was acidified to pH ~3 with 1M HCl then concentrated in vacuo to give the title compound as a yellow solid. Y=quantitative. $^1$H NMR (400 MHz, DMSO-d$_6$) δ 8.70 (d, J=6 Hz, 2H), 7.32 (t, J=5 Hz, 1H), 4.44-4.35 (m, 1H), 3.31 (dd, J=14, 4 Hz, 1H), 2.90 (dd, J=14, 10 Hz, 1H). Exchangeable protons not seen.

Step 2: benzyl 2-hydroxy-3-(pyrimidin-2-yl)propanoate. To a mixture of 2-hydroxy-3-(pyrimidin-2-yl)propanoic acid (10.0 g, 59 mmol) and benzyl alcohol (70 ml) was added H$_2$SO$_4$ (317 μl, 5.9 mmol) in one portion at between 10 and 20° C. The RM was warmed to 45° C. and stirred for 16 h. The mixture was concentrated and purified by FCC (0-60% ethyl acetate in petroleum ether) to give the title compound as a white solid. Y=19%. $^1$H NMR (400 MHz, chloroform-d) δ 8.62 (d, J=5 Hz, 2H), 7.36-7.28 (m, 4H), 7.15 (t, J=5 Hz, 1H), 5.20 (s, 2H), 4.83-4.76 (m, 1H), 4.42 (s, 1H), 3.58-3.51 (m, 1H), 3.50-3.43 (m, 1H).

Step 3: benzyl 2-{[(1,2,3,5,6,7-hexahydro-s-indacen-4-yl)carbamoyl]oxy}-3-(pyrimidin-2-yl)propanoate. The title compound was prepared according to the General procedure B using benzyl 2-hydroxy-3-(pyrimidin-2-yl)propanoate and Intermediate A as starting materials. The crude mixture was purified by FCC (0-60% EtOAc in petrol) to give the title compound as a white solid. Y=27%. MS ES$^+$: 458.1. $^1$H NMR (400 MHz, chloroform-d) δ 8.64 (d, J=4 Hz, 2H), 7.34 (s, 4H), 7.15 (t, J=5 Hz, 1H), 6.98 (s, 1H), 6.25 (s, 1H), 5.85 (t, J=6 Hz, 1H), 5.30-5.17 (m, 2H), 3.63-3.55 (m, 2H), 2.90-2.81 (m, 4H), 2.75-2.65 (m, 4H), 2.11-1.93 (m, 4H).

Step 4: (2R)-2-{[(1,2,3,5,6,7-hexahydro-s-indacen-4-yl)carbamoyl]oxy}-3-(pyrimidin-2-yl)propanoic acid. To a solution of benzyl 2-{[(1,2,3,5,6,7-hexahydro-s-indacen-4-yl)carbamoyl]oxy}-3-(pyrimidin-2-yl)propanoate (790 mg, 1.73 mmol) in MeOH (20 ml) was added 10% Pd/C (1.73 mmol) under N$_2$. The mixture was stirred under H$_2$ (15 psi) at 15° C. for 2 h. The mixture was filtered through Celite and concentrated in vacuo to give a residue. The residue was purified by reverse-phase chromatography (column: Waters Xbridge 150*25, 5 μm; mobile phase: [water (10 mM NH$_4$HCO$_3$)-ACN]; B %: 14%-44%, 12 min) to give the racemic product. This was separated by chiral SFC (column: Daicel Chiralpak IC (250 mm*30 mm, 5 μm); mobile phase: [0.1% NH$_3$.H$_2$O in EtOH]; B %: 45%, 6 min) to give the title compound as a white solid. The desired (R)-enantiomer is peak 1. Y=15%. MS ES$^+$: 368.1. $^1$H NMR (400 MHz, DMSO-d$_6$) δ 8.85 (s, 1H), 8.75 (d, J=5 Hz, 2H), 7.38 (t, J=5 Hz, 1H), 6.89 (s, 1H), 5.52-5.45 (m, 1H), 3.58-3.38 (m, 2H), 2.82-2.72 (m, 4H), 2.69-2.53 (m, 4H), 1.97-1.85 (m, 4H). CO$_2$H not seen.

Example 101. Propan-2-yl (2R)-2-{[(1,2,3,5,6,7-hexahydro-s-indacen-4-yl)carbamoyl]oxy}-3-(pyrimidin-2-yl)propanoate

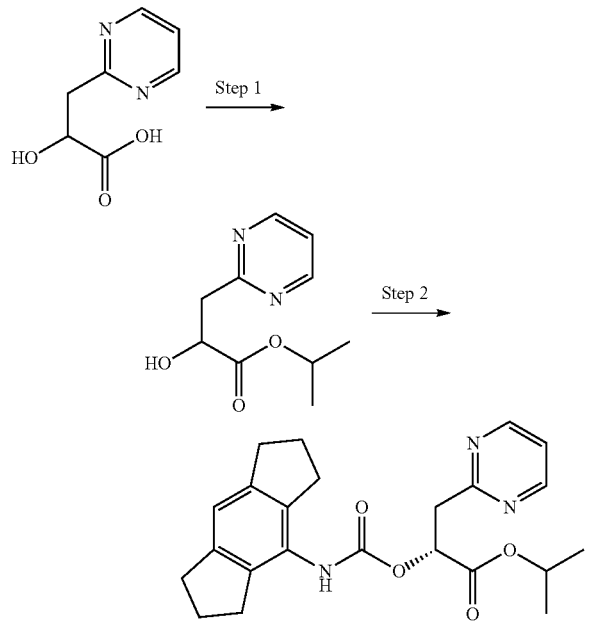

Step 1: propan-2-yl 2-hydroxy-3-(pyrimidin-2-yl)propanoate. To a mixture of 2-hydroxy-3-(pyrimidin-2-yl)propanoic acid (10.0 g, 59.5 mmol) (for synthesis refer to example SCC) in isopropanol (70 ml) was added H₂SO₄ (317 µl, 5.95 mmol) in one portion at between 10 and 20° C. The RM was heated at 45° C. for 16 h. The RM was basified to pH ~8 with aq. NaHCO₃ then concentrated under vacuum. The resulting aqueous solution/suspension was extracted with EtOAc (3×50 ml). The combined organic phases were concentrated under vacuum to give a residue. The residue was purified by FCC (0-50% EtOAc/petroleum ether) to give the title compound as a white solid. Y=23%. ¹H NMR (400 MHz, chloroform-d) 8.68 (d, J=5 Hz, 2H), 7.20 (t, J=5 Hz, 1H), 5.14-5.03 (m, 1H), 4.71 (br. s, 1H), 4.27 (br. s, 1H), 3.55-3.48 (m, 1H), 3.46-3.38 (m, 1H), 1.25 (d, J=6 Hz, 3H), 1.19 (d, J=6 Hz, 3H).

Step 2: propan-2-yl (2R)-2-{[(1,2,3,5,6,7-hexahydro-s-indacen-4-yl)carbamoyl]oxy}-3-(pyrimidin-2-yl)propanoate. The title compound was prepared according to the General procedure B using propan-2-yl 2-hydroxy-3-(pyrimidin-2-yl)propanoate and Intermediate A as starting materials. The crude mixture was purified by FCC (0-60% EtOAc in petrol) to give the racemic mixture of products as a white solid. The enantiomers were separated by chiral SFC (column: Daicel Chiralpak AY-H (250 mm*30 mm, 5 µm); mobile phase: EtOH; B %: 45%, 8 min) to give the title compound as a white solid. The desired (R)-enantiomer is peak 1. Y=8%. MS ES⁺: 410.2. ¹H NMR (400 MHz, chloroform-d) 8.70 (s, 2H), 7.19 (s, 1H), 6.98 (s, 1H), 6.26 (br. s, 1H), 5.78-5.70 (m, 1H), 5.18-5.06 (m, 1H), 3.56 (br. s, 2H), 2.91-2.81 (m, 4H), 2.80-2.70 (m, 4H), 2.10-1.98 (m, 4H), 1.27 (d, J=6 Hz, 3H), 1.24 (d, J=6 Hz, 3H).

Example 102. Cyclopentyl (2R)-2-{[(1,2,3,5,6,7-hexahydro-s-indacen-4-yl)carbamoyl]oxy}-3-(pyrimidin-2-yl)propanoate

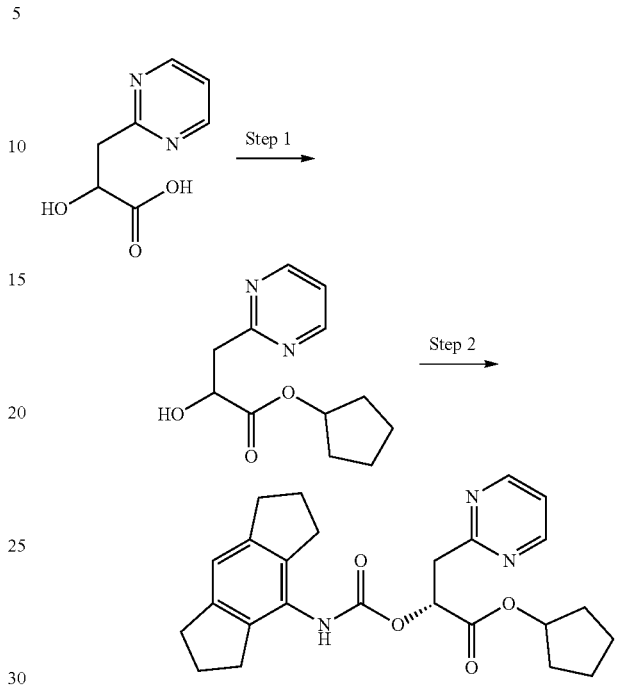

Step 1: cyclopentyl 2-hydroxy-3-(pyrimidin-2-yl)propanoate. To a mixture of 2-hydroxy-3-(pyrimidin-2-yl)propanoic acid (10.0 g, 59.5 mmol) (for synthesis refer to example SCC) in cyclopentanol (70 ml) was added H₂SO₄ (317 µl, 5.95 mmol) in one portion at between 10 and 20° C. The RM was heated at 45° C. for 16 h. The RM was basified to pH ~8 with aq. NaHCO₃ then concentrated under vacuum. The resulting aqueous solution/suspension was extracted with EtOAc (3×50 ml). The combined organic phases were concentrated under vacuum to give a residue. The residue was purified by FCC (0-60% EtOAc/petroleum ether) to give the title compound as a white solid. Y=15%. ¹H NMR (400 MHz, chloroform-d) 8.67 (d, J=5 Hz, 2H), 7.19 (t, J=5 Hz, 1H), 5.26-5.19 (m, 1H), 4.72-4.66 (m, 1H), 4.41-4.11 (m, 1H), 3.53-3.44 (m, 1H), 3.43-3.35 (m, 1H), 1.89-1.73 (m, 2H), 1.73-1.46 (m, 6H).

Step 2: cyclopentyl (2R)-2-{[(1,2,3,5,6,7-hexahydro-s-indacen-4-yl)carbamoyl]oxy}-3-(pyrimidin-2-yl)propanoate. The title compound was prepared according to the General procedure B using cyclopentyl 2-hydroxy-3-(pyrimidin-2-yl)propanoate and Intermediate A as starting materials. The crude mixture was purified by FCC (0-60% EtOAc in petrol) to give the racemic mixture of products as a white solid. The enantiomers were separated by chiral SFC (column: Daicel Chiralpak AY-H (250 mm*30 mm, 5 µm); mobile phase: IPA; B %: 45%, 20 min) to give the title compound as a white solid. The desired (R)-enantiomer is peak 1. Y=5%. MS ES⁺: 436.2. ¹H NMR (400 MHz, DMSO-d₆) δ 9.07 (br. s, 1H), 8.77 (d, J=4 Hz, 2H), 7.41 (t, J=5 Hz, 1H), 6.91 (s, 1H), 5.54-5.44 (m, 1H), 5.15-5.10 (m, 1H), 3.40 (br. s, 2H), 2.82-2.72 (m, 4H), 2.62 (br. s, 4H), 1.93 (br. s, 4H), 1.85-1.69 (m, 2H), 1.66-1.44 (m, 6H).

Example 103. (2R)-2-{[(1,2,3,5,6,7-hexahydro-s-indacen-4-yl)carbamoyl]oxy}-3-(pyrazin-2-yl)propanoic acid

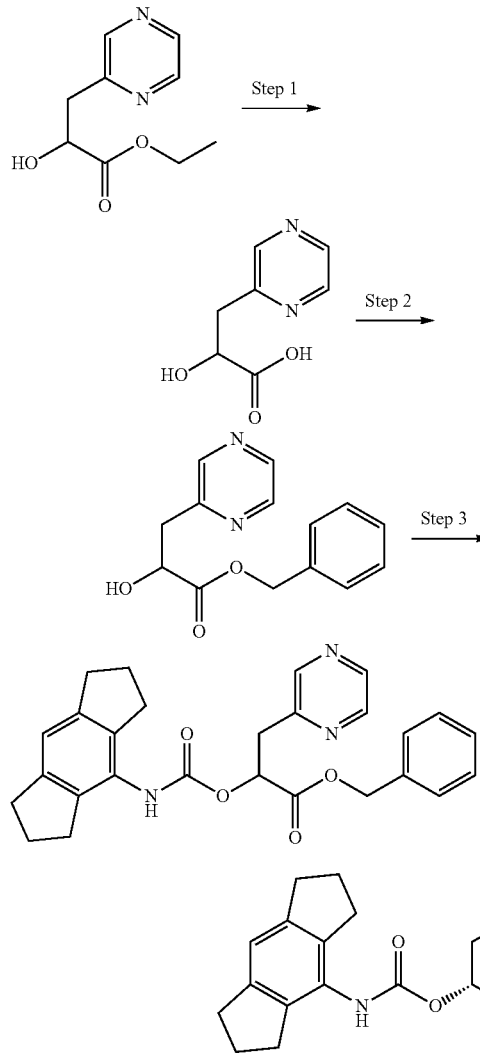

Step 1: 2-hydroxy-3-(pyrazin-2-yl)propanoic acid. To a solution of ethyl 2-hydroxy-3-(pyrazin-2-yl)propanoate (6.00 g, 30.5 mmol) (for synthesis refer to example 5BQ) in EtOH (42 ml) was added 2M NaOH (18.3 ml, 36.6 mmol) and the mixture stirred at rt for 1 h. The reaction was concentrated under vacuum to give an aqueous solution. This was washed with ethyl acetate (2×20 ml), the aqueous phase adjusted to pH ~2 and concentrated under vacuum to give the title compound as a brown solid, used without purification. Y=quantitative. $^1$H NMR (400 MHz, D$_2$O) δ 8.54-8.53 (m, 2H), 8.47 (d, J=2 Hz, 1H), 4.50-4.44 (m, 1H), 3.33-3.26 (m, 1H), 3.17-3.09 (m, 1H). Exchangeable protons not seen.

Step 2: benzyl 2-hydroxy-3-(pyrazin-2-yl)propanoate. To a mixture of 2-hydroxy-3-(pyrazin-2-yl)propanoic acid (10.0 g, 59 mmol) and benzyl alcohol (70 ml) was added H$_2$SO$_4$ (317 μl, 5.9 mmol) in one portion at between 10 and 20° C. The RM was warmed to 45° C. and stirred for 16 h. The mixture was concentrated and purified by FCC (0-60% ethyl acetate in petroleum ether) to give the title compound as a white solid.

Step 3: benzyl 2-{[(1,2,3,5,6,7-hexahydro-s-indacen-4-yl)carbamoyl]oxy}-3-(pyrazin-2-yl)propanoate. The title compound was prepared according to the General procedure B using benzyl 2-hydroxy-3-(pyrazin-2-yl)propanoate and Intermediate A as starting materials. The crude mixture was purified by FCC (0-50% EtOAc in petrol) to give the title compound as a white solid. Y=22%. MS ES$^+$: 458.1. $^1$H NMR (400 MHz, chloroform-d) δ 8.50-8.42 (m, 3H), 7.35 (s, 5H), 7.00 (s, 1H), 5.62 (br. s, 1H), 5.29-5.16 (m, 2H), 3.42 (br. s, 2H), 2.90-2.84 (m, 4H), 2.75-2.65 (m, 3H), 2.09-2.00 (m, 4H). NH not seen.

Step 4: (2R)-2-{[(1,2,3,5,6,7-hexahydro-s-indacen-4-yl)carbamoyl]oxy}-3-(pyrazin-2-yl)propanoic acid. To a solution of benzyl 2-{[(1,2,3,5,6,7-hexahydro-s-indacen-4-yl)carbamoyl]oxy}-3-(pyrazin-2-yl)propanoate (400 mg, 0.87 mmol) in MeOH (8 ml) was added 10% Pd/C (0.87 mmol) under N$_2$. The mixture was stirred under H$_2$ atmosphere at rt for 25 min. The mixture was filtered through Celite and concentrated in vacuo to give the racemic product. This was separated by chiral SFC (column: Daicel Chiralpak IC (250 mm*30 mm, 5 μm); mobile phase: [0.1% NH$_3$.H$_2$O in EtOH]; B %: 35%, 8 min) to give the title compound as a white solid. The desired (R)-enantiomer is peak 2. Y=45%. MS ES$^+$: 368.1. $^1$H NMR (400 MHz, DMSO-d$_6$) δ 8.88 (br. s, 1H), 8.65-8.50 (m, 3H), 6.89 (s, 1H), 5.27-5.19 (m, 1H), 3.34-3.21 (m, 2H), 2.81-2.73 (m, 4H), 2.65-2.52 (m, 4H), 1.97-1.82 (m, 4H).

Example 104. Propan-2-yl (2R)-2-{[(1,2,3,5,6,7-hexahydro-s-indacen-4-yl)carbamoyl]oxy}-3-(pyrazin-2-yl)propanoate

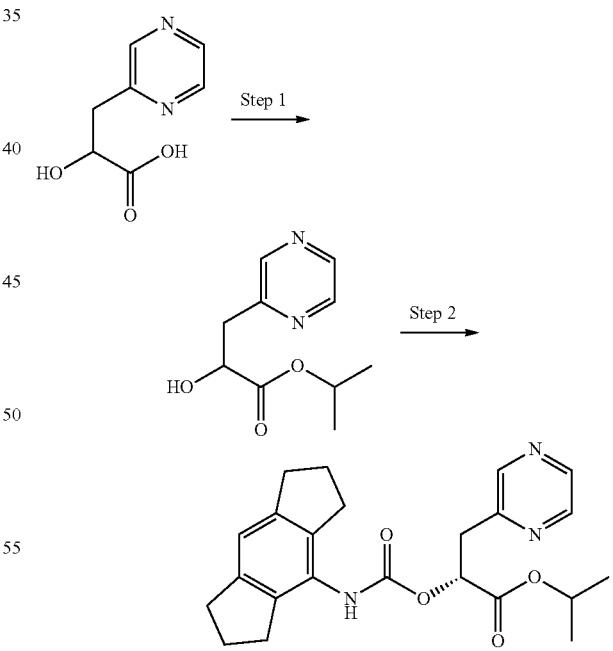

Step 1: propan-2-yl 2-hydroxy-3-(pyrazin-2-yl)propanoate. To a solution of 2-hydroxy-3-(pyrazin-2-yl)propanoic acid (4.00 g, 23.8 mmol, 1.0 eq) (for synthesis refer to example 5CF) in isopropanol (28 ml) was added 4-(dimethylamino)pyridine (290 mg, 2.38 mmol), followed by dropwise oxalyl chloride (2.29 ml, 26.2 mmol). The RM was stirred at rt for 12 h, then concentrated under reduced pressure. The residue was purified by FCC (0 to 15% EtOAc/petroleum ether) to give the title compound as a brown oil. Y=24%. $^1$H NMR (400 MHz, chloroform-d) δ 8.53-8.49 (m, 2H), 8.46 (d, J=2 Hz, 1H), 5.14-5.02 (m, 1H), 4.64-4.58 (m, 1H), 3.38-3.28 (m, 1H), 3.22-3.16 (m, 1H), 1.27-1.20 (m, 6H).

Step 2: propan-2-yl (2R)-2-{[(1,2,3,5,6,7-hexahydro-s-indacen-4-yl)carbamoyl]oxy}-3-(pyrazin-2-yl)propanoate. The title compound was prepared according to the General procedure B using propan-2-yl 2-hydroxy-3-(pyrazin-2-yl)propanoate and Intermediate A as starting materials. The crude mixture was purified by FCC (0-50% EtOAc in petrol) to give the racemic mixture of products as a white solid. The enantiomers were separated by chiral SFC (column: Daicel Chiralpak AD-H (250 mm*30 mm, 5 μm); mobile phase: EtOH; B %: 30%, 6 min) to give the title compound as a white solid. The desired (R)-enantiomer is peak 1. Y=31%. MS ES$^+$: 410.2. $^1$H NMR (400 MHz, DMSO-d$_6$) δ 9.12 (br. s, 1H), 8.72-8.51 (m, 3H), 6.92 (s, 1H), 5.34-5.26 (m, 1H), 4.98-4.85 (m, 1H), 3.33-3.30 (m, 2H), 2.82-2.74 (m, 4H), 2.69-2.56 (m, 4H), 1.98-1.88 (m, 4H), 1.16 (d, J=6 Hz, 3H), 1.12 (d, J=6 Hz, 3H).

Example 105. Cyclopentyl (2R)-2-{[(1,2,3,5,6,7-hexahydro-s-indacen-4-yl)carbamoyl]oxy}-3-(pyrazin-2-yl)propanoate

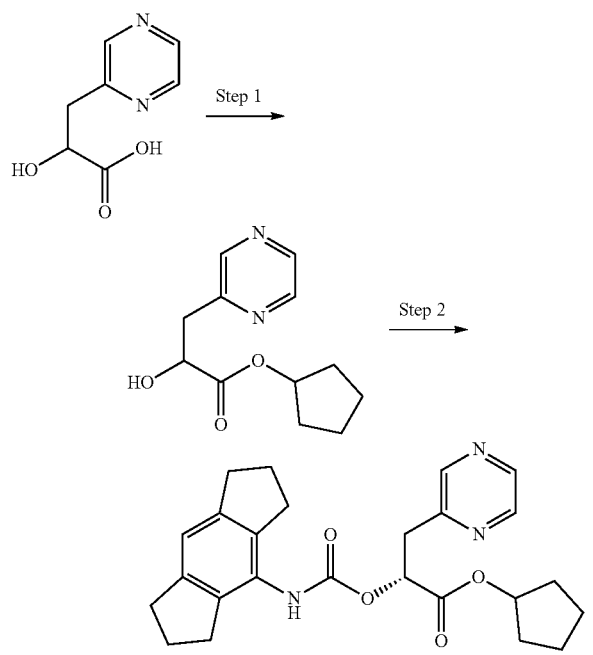

Step 1: cyclopentyl 2-hydroxy-3-(pyrazin-2-yl)propanoate. To a solution of 2-hydroxy-3-(pyrazin-2-yl)propanoic acid (4.00 g, 23.7 mmol) (for synthesis refer to example 5CF) in cyclopentanol (28 ml) was added DMAP (290 mg, 2.38 mmol), then oxalyl chloride (2.29 ml, 26.1 mmol) dropwise. The RM was stirred at rt for 12 h, then concentrated under reduced pressure. The residue was purified by FCC (0 to 15% EtOAc/petroleum ether) to give the title compound as a brown oil. Y=28%. $^1$H NMR (400 MHz, chloroform-d) δ 8.52-8.50 (m, 2H), 8.47 (d, J=2 Hz, 1H), 5.30-5.23 (m, 1H), 4.64-4.59 (m, 1H), 3.39-3.26 (m, 1H), 3.24-3.15 (m, 1H), 1.90-1.55 (m, 8H).

Step 2: cyclopentyl (2R)-2-{[(1,2,3,5,6,7-hexahydro-s-indacen-4-yl)carbamoyl]oxy}-3-(pyrazin-2-yl)propanoate. The title compound was prepared according to the General procedure B using cyclopentyl 2-hydroxy-3-(pyrazin-2-yl)propanoate and Intermediate A as starting materials. The crude mixture was purified by FCC (0-50% EtOAc in petrol) to give the racemic mixture of products as a white solid. The enantiomers were separated by chiral SFC (column: Daicel Chiralpak AD-H (250 mm*30 mm, 5 μm); mobile phase: [0.1% NH$_3$.H$_2$O/MeOH]; B %: 26%, 20 min) to give the title compound as a white solid. The desired (R)-enantiomer is peak 2. Y=35%. MS ES$^+$: 436.2. $^1$H NMR (400 MHz, DMSO-d$_6$) δ 9.14-9.06 (br. s, 1H), 8.73-8.66 (br. s, 1H), 8.59 (s, 1H), 8.54 (s, 1H), 6.92 (s, 1H), 5.34-5.26 (m, 1H), 5.14-5.05 (m, 1H), 3.40-3.28 (m, 2H), 2.82-2.76 (m, 4H), 2.66-2.59 (m, 4H), 2.00-1.88 (m, 4H), 1.86-1.71 (m, 2H), 1.58-1.51 (m, 6H).

Example 108. Propan-2-yl (2R)-3-(4-cyano-1H-pyrazol-1-yl)-2-{[(1,2,3,5,6,7-hexahydro-s-indacen-4-yl)carbamoyl]oxy}propanoate

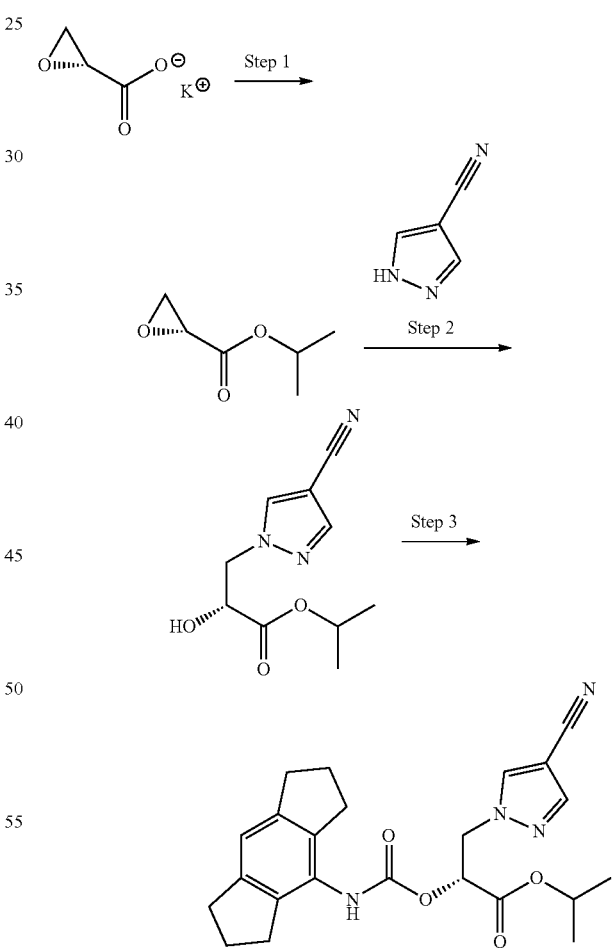

Step 1: propan-2-yl (2R)-oxirane-2-carboxylate. To a mixture of potassium (2R)-oxirane-2-carboxylate (30.0 g, 237 mmol) (for synthesis refer to example 5AJ) in DCM (150 ml) was added benzyltriethylammonium chloride (54.2 g, 238 mmol) and 2-bromopropane (117 g, 951 mmol) in one portion at rt under N$_2$. The mixture was stirred at 45° C. for 16 h. The RM was allowed to cool, poured into H₂O (500 ml) and stirred for 5 min. The aqueous phase was extracted with dichloromethane (100 ml). The organic phase was washed with brine (200 ml), dried with anhydrous Na₂SO₄, filtered and concentrated under vacuum. The residue was purified by FCC (0 to 50% EtOAc/petrol) to obtain the title compound as a yellow oil. ¹H NMR (400 MHz, chloroform-d) δ 5.16-5.04 (m, 1H), 3.39-3.37 (m, 1H), 2.96-2.89 (m, 2H), 1.30-1.24 (m, 6H).

Step 2: propan-2-yl (2R)-3-(4-cyano-1H-pyrazol-1-yl)-2-hydroxypropanoate. In a microwave tube propan-2-yl(2R)-oxirane-2-carboxylate (2.00 g, 15.4 mmol) and 4-cyanopyrazole (3.58 g, 38.4 mmol) were dissolved in isopropanol (10 ml). The RM was heated in a microwave reactor at 100° C. for 3 h. The RM was concentrated in vacuo, then purified by prep-HPLC: (column: Agela Innoval ODS-2 100 mm*350 mm; mobile phase: [water (0.1% TFA)-ACN]; B %: 5%-25%, 20 min) to obtain the title compound as a yellow oil. MS ES⁺: 224.2. ¹H NMR (400 MHz, chloroform-d) δ 7.94 (s, 1H), 7.78 (s, 1H), 5.13-5.06 (m, 1H), 4.51-4.48 (m, 2H), 3.72 (s, 1H), 1.32-1.26 (m, 6H).

Step 3: propan-2-yl (2R)-3-(4-cyano-1H-pyrazol-1-yl)-2-{[(1,2,3,5,6,7-hexahydro-s-indacen-4-yl)carbamoyl]oxy}propanoate. The title compound was prepared according to the General procedure A using propan-2-yl (2R)-3-(4-cyano-1H-pyrazol-1-yl)-2-hydroxypropanoate and Intermediate A as starting materials. The crude product was purified by prep HPLC (column: Phenomenex Luna C18 250*50 mm*10 μm; mobile phase: [water (0.1% TFA)-ACN]; B %: 50%-80%, 20 min) to give the title compound as a white solid. Y=26%. MS ES⁺: 423.3. ¹H NMR (400 MHz, DMSO-d₆) δ 9.16 (s, 1H), 8.61 (s, 1H), 8.10 (s, 1H), 6.95 (s, 1H), 5.29 (s, 1H), 4.98-4.88 (m, 2H), 4.70 (s, 2H), 2.85-2.77 (m, 4H), 2.74-2.60 (m, 4H), 1.99-1.92 (m, 4H), 1.23-1.16 (m, 6H).

Example 109. Cyclopentyl (2R)-3-(4-cyano-1H-pyrazol-1-yl)-2-{[(1,2,3,5,6,7-hexahydro-s-indacen-4-yl)carbamoyl]oxy}propanoate

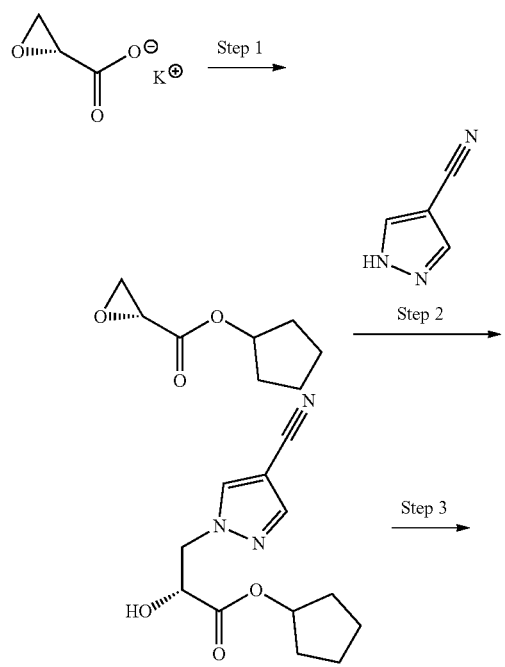

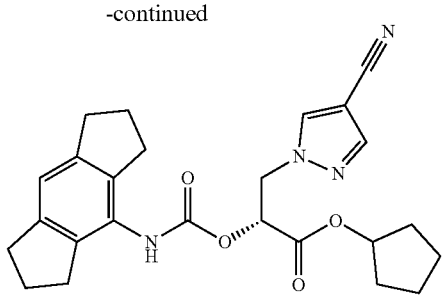

Step 1: cyclopentyl (2R)-oxirane-2-carboxylate. To a mixture of potassium (2R)-oxirane-2-carboxylate (50.0 g, 396 mmol) (for synthesis refer to example 5AJ) and cyclopropyl bromide (236 g, 1.59 mol) in dichloromethane (250 ml) was added benzyltriethylammonium chloride (90.3 g, 396 mmol) in one portion at rt under N₂. The mixture was stirred at 45° C. for 16 h. The mixture was allowed to cool, poured into water (1500 ml) and stirred for 5 min. The aqueous phase was extracted with dichloromethane (200 ml). The organic phase was washed with brine (200 ml), dried with anhydrous Na₂SO₄, filtered and concentrated in vacuo. The residue was purified by FCC (0 to 50% EtOAc/petrol) to obtain the title compound as a yellow oil. Y=22%. ¹H NMR (400 MHz, chloroform-d) δ 5.29-5.22 (m, 1H), 3.40-3.34 (m, 1H), 2.95-2.85 (m, 2H), 1.89-1.58 (m, 8H).

Step 2: cyclopentyl (2R)-3-(4-cyano-1H-pyrazol-1-yl)-2-hydroxypropanoate. In a microwave tube cyclopentyl (2R)-oxirane-2-carboxylate (1.50 g, 9.60 mmol) and 4-cyanopyrazole (2.24 g, 24.0 mmol) were dissolved in cyclopentanol (10 ml). The RM was heated in a microwave reactor at 100° C. for 2 h. The mixture was concentrated under reduced pressure and the resulting residue purified by prep-HPLC (column: Agela Innoval ODS-2 250*80 mm; mobile phase: [water (0.1% TFA)-ACN]; B %: 12%-42%, 30 min) to obtain the title compound as a yellow oil. MS ES⁺: 250.2. ¹H NMR (400 MHz, chloroform-d) δ 7.93 (s, 1H), 7.79 (s, 1H), 5.30-5.24 (m, 1H), 4.51-4.48 (m, 2H), 3.79-3.73 (m, 1H), 1.95-1.55 (m, 8H).

Step 3: cyclopentyl (2R)-3-(4-cyano-1H-pyrazol-1-yl)-2-{[(1,2,3,5,6,7-hexahydro-s-indacen-4-yl)carbamoyl]oxy}propanoate. The title compound was prepared according to the General procedure A using cyclopentyl (2R)-3-(4-cyano-1H-pyrazol-1-yl)-2-hydroxypropanoate and Intermediate A as starting materials. The crude product was purified by prep HPLC (column: Phenomenex Luna C18 250*50 mm*10 μm; mobile phase: [water (0.1% TFA)-ACN]; B %: 50%-80%, 20 min) to give the title compound as a white solid. Y=5%. MS ES⁺: 449.4. ¹H NMR (400 MHz, DMSO-d₆) δ 9.17 (s, 1H), 8.62 (s, 1H), 8.10 (s, 1H), 6.95 (s, 1H), 5.29 (s, 1H), 5.13-5.08 (m, 2H), 4.73-4.67 (m, 2H), 2.90-2.77 (m, 4H), 2.73-2.62 (m, 4H), 1.99-1.94 (m, 4H), 1.77-1.54 (m, 8H).

Example 110. (2R)-2-{[(1,2,3,5,6,7-hexahydro-s-indacen-4-yl)carbamoyl]oxy}-3-(1H-1,2,4-triazol-1-yl)propanoic acid and Propan-2-yl (2R)-2-{[(1,2,3,5,6,7-hexahydro-s-indacen-4-yl)carbamoyl]oxy}-3-(1H-1,2,4-triazol-1-yl)propanoate

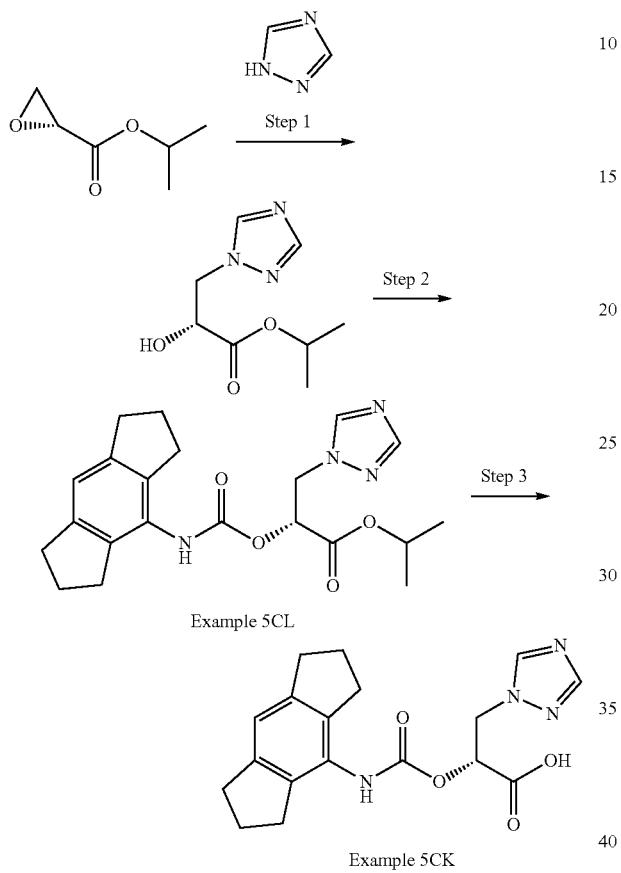

Example 5CL

Example 5CK

Step 1: propan-2-yl (2R)-2-hydroxy-3-(1H-1,2,4-triazol-1-yl)propanoate. In a microwave tube propan-2-yl(2R)-oxirane-2-carboxylate (2.00 g, 15.4 mmol) (for synthesis refer to example 5C₁) and 1H-1,2,4-triazole (2.65 g, 38.4 mmol) were dissolved in isopropanol (10 ml). The RM was heated in a microwave reactor at 100° C. for 3 h. The mixture was concentrated in vacuo and the resulting residue purified by prep-HPLC: (column: Agela Innoval ODS-2 250*80 mm; mobile phase: [water (0.1% TFA)-ACN]; B %: 0%-21%, 30 min) to give the title compound as a yellow oil. MS ES⁺: 200.1. ¹H NMR (400 MHz, chloroform-d) δ 8.58 (s, 1H), 8.04 (s, 1H), 5.10-5.05 (m, 1H), 4.62-4.51 (m, 3H), 1.29-1.23 (m, 6H).

Step 2: propan-2-yl (2R)-2-{[(1,2,3,5,6,7-hexahydro-s-indacen-4-yl)carbamoyl]oxy}-3-(1H-1,2,4-triazol-1-yl)propanoate. The title compound was prepared according to the General procedure A using propan-2-yl (2R)-2-hydroxy-3-(1H-1,2,4-triazol-1-yl)propanoate and Intermediate A as starting materials. The crude product was purified by prep HPLC (column: Phenomenex Luna C18 250*50 mm*10 µm; mobile phase: [water (0.1% TFA)-ACN]; B %: 45%-75%, 20 min) to give the title compound as a white solid. Y=25%. MS ES⁺: 399.3. ¹H NMR (400 MHz, DMSO-d₆) δ 9.19 (s, 1H), 8.60 (s, 1H), 8.02 (s, 1H), 6.95 (s, 1H), 5.32-5.24 (m, 1H), 4.99-4.90 (m, 1H), 4.72-4.66 (m, 2H), 2.85-2.80 (m, 4H), 2.70-2.61 (m, 4H), 2.00-1.90 (m, 4H), 1.24-1.17 (m, 6H).

Step 3: (2R)-2-{[(1,2,3,5,6,7-hexahydro-s-indacen-4-yl)carbamoyl]oxy}-3-(1H-1,2,4-triazol-1-yl)propanoic acid. To a mixture of propan-2-yl (2R)-2-{[(1,2,3,5,6,7-hexahydro-s-indacen-4-yl)carbamoyl]oxy}-3-(1H-1,2,4-triazol-1-yl)propanoate (400 mg, 1.00 mmol) in 1,4-dioxane (5 ml) was added 4M HCl (5 ml) in one portion at rt. The mixture was stirred at rt for 48 h. The RM was concentrated under reduced pressure and purified by prep-HPLC: (column: Phenomenex Luna C18 200*40 mm*10 µm; mobile phase: [water (0.1% TFA)-ACN]; B %: 20%-55%, 10 min) to give the title compound as a white solid. Y=28%. MS ES⁺: 357.0. ¹H NMR (400 MHz, DMSO-d₆) δ 13.46-13.28 (br. s, 1H), 9.11 (s, 1H), 8.56 (s, 1H), 7.99 (s, 1H), 6.94 (s, 1H), 5.26 (s, 1H), 4.74-4.66 (m, 2H), 2.90-2.84 (m, 4H), 2.82-2.78 (m, 4H), 1.98-1.92 (m, 4H).

Example 111. Cyclopentyl (2R)-2-{[(1,2,3,5,6,7-hexahydro-s-indacen-4-yl)carbamoyl]oxy}-3-(1H-1,2,4-triazol-1-yl)propanoate

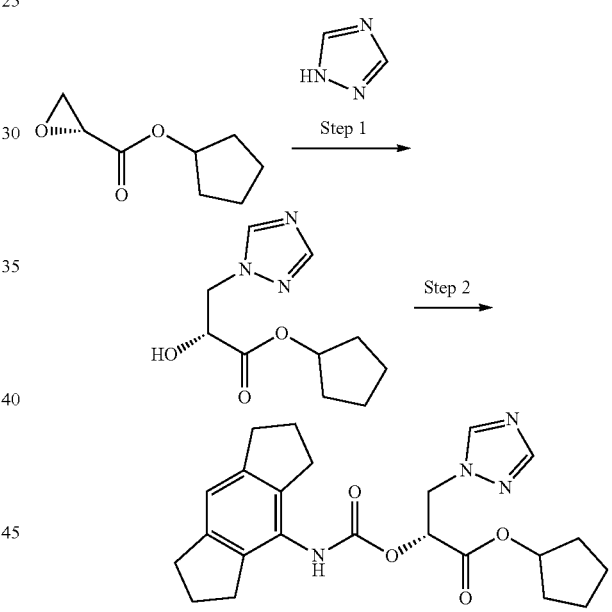

Step 1: cyclopentyl (2R)-2-hydroxy-3-(1H-1,2,4-triazol-1-yl)propanoate. In a microwave tube cyclopentyl (2R)-oxirane-2-carboxylate (1.00 g, 6.40 mmol) (for synthesis refer to example 5CJ) and 1H-1,2,4-triazole (1.11 g, 16.0 mmol) were dissolved in cyclopentanol (7 ml). The RM was heated in a microwave reactor at 100° C. for 3 h. The RM was concentrated under reduced pressure to give a residue. The residue was purified by prep-HPLC (column: Phenomenex Luna C18 250*50 mm*10 µm; mobile phase: [water (0.1% TFA)-ACN]; B %: 10%-40%, 20 min) to give the title compound as a colourless oil. Y=46%. ¹H NMR (400 MHz, methanol-d₄) δ 8.68 (s, 1H), 8.13 (s, 1H), 5.25-5.21 (m, 1H), 4.62-4.49 (m, 3H), 1.89-1.61 (m, 8H).

Step 2: cyclopentyl (2R)-2-{[(1,2,3,5,6,7-hexahydro-s-indacen-4-yl)carbamoyl]oxy}-3-(1H-1,2,4-triazol-1-yl)propanoate. The title compound was prepared according to the General procedure A using cyclopentyl (2R)-2-hydroxy-3-(1H-1,2,4-triazol-1-yl)propanoate and Intermediate A as starting materials. The crude product was purified by prep HPLC (column: Phenomenex Luna C18 250*50 mm*10 µm; mobile phase: [water (0.1% TFA)-ACN]; B %: 50%-80%, 20 min) to give the title compound as a white solid. Y=5%. MS ES⁺: 425.1. ¹H NMR (400 MHz, methanol-$d_4$) δ 8.62 (s, 1H), 8.05 (s, 1H), 6.96 (s, 1H), 5.36 (s, 1H), 5.25-5.20 (m, 1H), 4.83-4.75 (m, 2H), 2.90-2.82 (m, 4H), 2.80-2.71 (m, 4H), 2.06-2.00 (m, 4H), 1.87-1.61 (m, 8H).

Example 112. Propan-2-yl 2-{[(1,2,3,5,6,7-hexahydro-s-indacen-4-yl)carbamoyl]oxy}-3-(6-methylpyrazin-2-yl)propanoate

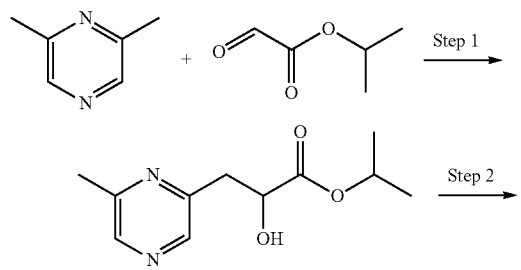

Step 1: propan-2-yl 2-hydroxy-3-(6-methylpyrazin-2-yl) propanoate. To a solution of isopropyl 2-oxoacetate (1.13 g, 9.71 mmol) in dioxane (8 ml) was added 2,6-dimethylpyrazine (1.0 g, 9.25 mmol) and diacetoxyiron (80 mg, 462 µmol) under N₂. The RM was heated at 120° C. for 42 h. The reaction was concentrated under vacuum and the resulting residue purified by FCC (0-10% MeOH/DCM) to give the title compound as a brown oil. Y=9%. ¹H NMR (400 MHz, chloroform-d) δ 8.34 (s, 1H), 8.31 (s, 1H), 5.18-4.99 (m, 1H), 4.67-4.52 (m, 1H), 3.82 (d, J=6 Hz, 1H), 3.33-3.23 (m, 1H), 3.20-3.11 (m, 1H), 2.54 (s, 3H), 1.27-1.24 (m, 6H).

Step 2: propan-2-yl 2-{[(1,2,3,5,6,7-hexahydro-s-indacen-4-yl)carbamoyl]oxy}-3-(6-methylpyrazin-2-yl)propanoate. The title compound was prepared according to the General procedure B using propan-2-yl 2-hydroxy-3-(6-methylpyrazin-2-yl)propanoate and Intermediate A as starting materials. The crude mixture was purified by prep TLC (50% EtOAc in petrol) to give the title compound as a white solid. Y=14%. MS ES⁺: 424.4. ¹H NMR (400 MHz, chloroform-d) δ 8.38-8.30 (br. s, 2H), 7.00 (s, 1H), 6.29-6.19 (br. s, 1H), 5.53-5.45 (m, 1H), 5.15-5.06 (m, 1H), 3.39-3.29 (m, 2H), 2.87 (t, J=7 Hz, 4H), 2.80-2.70 (t, J=7 Hz, 4H), 2.55 (s, 3H), 2.10-1.99 (m, 4H), 1.29-1.25 (m, 6H).

Example 113. Propan-2-yl 2-{[(3-methylcyclohexyl)carbamoyl]oxy}-3-(pyrimidin-2-yl)propanoate

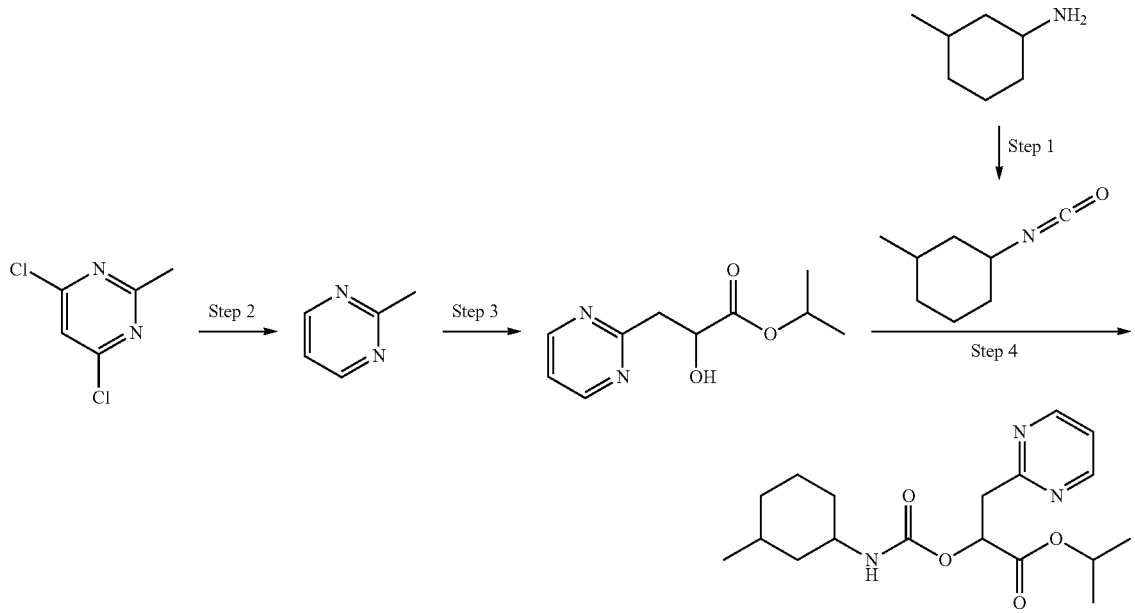

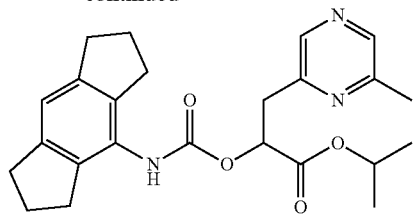

Step 1: 1-isocyanato-3-methylcyclohexane. To a solution of triphosgene (655 mg, 2.21 mmol) in DCM (3 ml) was added 3-methylcyclohexanamine (250 mg, 2.21 mmol) and triethylamine (655 µl, 4.64 mmol). The mixture was stirred at rt for 1 h, then concentrated to give the title compound as a yellow solid. This compound was used directly in the next step.

Step 2: 2-methylpyrimidine. To a solution of 4,6-dichloro-2-methyl-pyrimidine (240 g, 1.47 mol) in methanol (1.32 l) and H₂O (1.10 l) were added 10% Pd/C (240 g) and MgO (240 g, 5.95 mol). The RM was stirred at rt under H₂ atmosphere (30 psi) for 1 h. The mixture was filtered through Celite. The filtrate was extracted with DCM (4×1 l). The combined organic phases were distilled to remove DCM at 39° C. and methanol at 65° C. under 1 atm of pressure to give the title compound as a brown liquid. Y=28%. ¹H NMR (400 MHz, methanol-d₄) δ 8.66 (d, J=5 Hz, 2H), 7.29 (t, J=5 Hz, 1H), 2.65 (s, 3H).

Step 3: propan-2-yl 2-hydroxy-3-(pyrimidin-2-yl)propanoate. To a solution of 2-methylpyrimidine (10 g, 106 mmol) and isopropyl 2-oxoacetate (24.7 g, 212 mmol) in dioxane (100 ml) was added diacetoxyiron (924 mg, 5.3 mmol) in one portion at between 10 and 20° C. The mixture was heated at 140° C. for 48 h. The reaction mixture was concentrated in vacuo to give a residue. This was purified by FCC (10 to 50% EtOAc in petrol) to give the title compound as a yellow solid. Y=22%. ¹H NMR (400 MHz, chloroform-d) δ 8.70 (d, J=5 Hz, 2H), 7.22 (t, J=5 Hz, 1H) 5.20-5.07 (m, 1H), 4.73-4.71 (m, 1H), 3.55-3.40 (m, 2H), 1.26 (d, J=6 Hz, 3H), 1.21 (d, J=6 Hz, 3H).

Step 4: propan-2-yl 2-{[(3-methylcyclohexyl)carbamoyl]oxy}-3-(pyrimidin-2-yl)propanoate. The title compound was prepared according to the General procedure B using propan-2-yl 2-hydroxy-3-(pyrimidin-2-yl)propanoate and 1-isocyanato-3-methylcyclohexane as starting materials. The crude mixture was purified by prep-TLC (2:1 EtOAc/petrol, Rf=0.3) to give the title compound as a white solid. Y=52%. MS ES⁺: 350.2. ¹H NMR (400 MHz, chloroform-d) δ 8.69 (d, J=5 Hz, 2H), 7.17 (t, J=5 Hz, 1H) 5.68-5.58 (m, 1H), 5.14-5.07 (m, 1H), 4.69-4.63 (m, 1H), 3.51-3.37 (m, 2H), 2.06-1.83 (m, 2H), 1.78-1.63 (m, 2H), 1.55-1.31 (m, 2H), 1.27 (d, J=6 Hz, 3H), 1.22 (d, J=6 Hz, 3H), 0.94-0.89 (m, 1H), 0.88 (d, J=3 Hz, 3H), 0.87-0.69 (m, 2H)

Example 114. Propan-2-yl 3-(5-cyanopyrazin-2-yl)-2-{[(1,2,3,5,6,7-hexahydro-s-indacen-4-yl)carbamoyl]oxy}propanoate

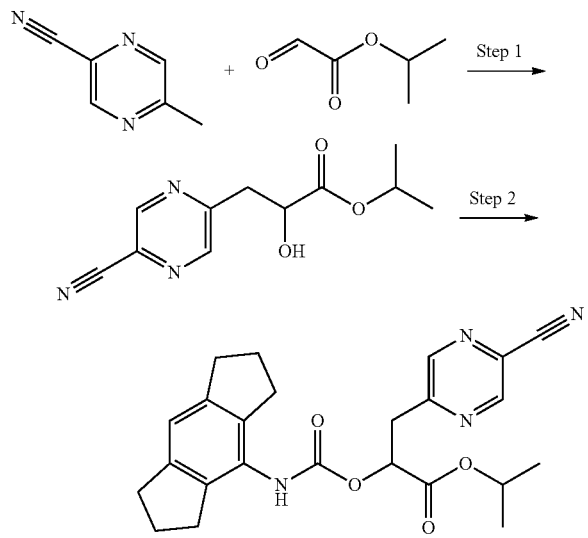

Step 1: propan-2-yl 3-(5-cyanopyrazin-2-yl)-2-hydroxypropanoate. To a solution of 5-methylpyrazine-2-carbonitrile (1.0 g, 8.39 mmol) in dioxane (7 ml) was added isopropyl 2-oxoacetate (1.17 g, 10.07 mmol) and diacetoxyiron (73 mg, 419 μmol) under N₂ atmosphere. The RM was heated at 120° C. for 48 h. The solvent was removed under reduced pressure. The residue was purified by prep-HPLC (column: Phenomenex Luna C18 250*50 mm*10 μm; mobile phase: [water (0.1% TFA)-ACN]; B %: 5-35, 20 min) to give the title compound as a light yellow oil. Y=23%. ¹H NMR (400 MHz, chloroform-d) δ 8.83 (s, 1H), 8.65 (s, 1H), 5.19-5.05 (m, 1H), 4.65-4.59 (m, 1H), 3.45-3.40 (m, 1H), 3.30-3.23 (m, 1H), 1.29 (t, J=6 Hz, 6H).

Step 2: propan-2-yl 3-(5-cyanopyrazin-2-yl)-2-{[(1,2,3,5,6,7-hexahydro-s-indacen-4-yl)carbamoyl]oxy}propanoate. The title compound was prepared according to the General procedure B using propan-2-yl 3-(5-cyanopyrazin-2-yl)-2-hydroxypropanoate and Intermediate A as starting materials. The crude mixture was purified by prep-HPLC (column: Nano-Micro Unisil 8-120 C18 Ultra Plus 250*50 mm; mobile phase: [water (10 mM NH₄HCO₃)-ACN]; B %: 47-70, 20 min) to give the title compound as a yellow solid. Y=8%. MS ES⁺: 435.3 ¹H NMR (400 MHz, methanol-d₄) δ 8.99 (s, 1H), 8.80 (s, 1H), 6.96 (s, 1H), 5.48-5.42 (m, 1H), 5.11-5.01 (m, 1H), 3.57-3.45 (m, 2H), 2.90-2.80 (m, 4H), 2.76-2.68 (m, 4H), 2.07-1.95 (m, 4H), 1.29-1.23 (m, 6H).

Example 115. Propan-2-yl 2-{[(1,2,3,5,6,7-hexahydro-s-indacen-4-yl)carbamoyl]oxy}-3-(2-methylpyrimidin-4-yl)propanoate

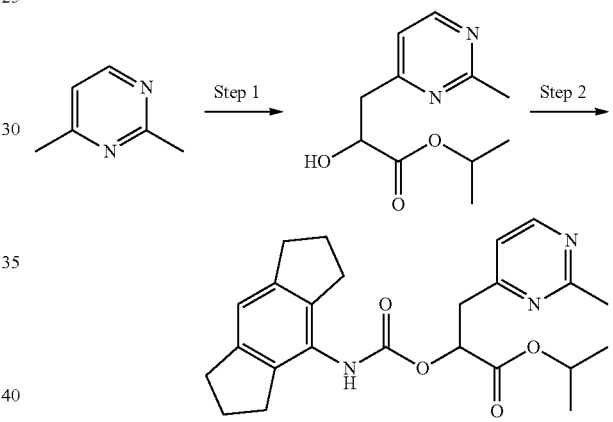

Step 1: propan-2-yl 2-hydroxy-3-(2-methylpyrimidin-4-yl)propanoate. To a solution of 2,4-dimethylpyrimidine (1.00 g, 9.25 mmol) in dioxane (7 ml) was added isopropyl 2-oxoacetate (1.18 g, 10.17 mmol) and diacetoxyiron (80 mg, 0.46 mmol) under nitrogen atmosphere. The mixture was stirred at 120° C. for 48 h under nitrogen. The solvent was removed under reduced pressure. The residue was purified by FCC (33-100% EtOAc/petrol) to give the title compound as a light brown oil. Y=14%. ¹H NMR (400 MHz, chloroform-d) δ ppm 8.53 (d, J=5 Hz, 1H), 7.04 (d, J=5 Hz, 1H), 5.14-5.01 (m, 1H), 4.62-4.57 (m, 1H), 3.27-3.04 (m, 2H), 2.70 (s, 3H), 1.26-1.20 (m, 6H).

Step 2: propan-2-yl 2-{[(1,2,3,5,6,7-hexahydro-s-indacen-4-yl)carbamoyl]oxy}-3-(2-methylpyrimidin-4-yl)propanoate. The title compound was prepared according to the General procedure B using propan-2-yl 2-hydroxy-3-(2-methylpyrimidin-4-yl)propanoate and Intermediate A as starting materials. The crude mixture was purified by prep-HPLC (column: Xtimate C18 10μ 250 mm*50 mm; mobile phase: [water (10 mM NH₄HCO₃)-ACN]; B %: 40-60, 25 min) to give the title compound as a white solid. Y=2%. MS ES⁺: 424.3. ¹H NMR (400 MHz, methanol-d₄) δ 8.58 (br. s, 1H), 7.32 (br. s, 1H), 6.90 (s, 1H), 5.45 (br. s, 1H), 5.10-5.00 (m, 1H), 2.88-2.82 (m, 4H), 2.77-2.61 (m, 9H), 2.09-1.95 (m, 4H), 1.27-1.23 (m, 6H).

Example 116. Propan-2-yl 2-{[(1,2,3,5,6,7-hexahydro-s-indacen-4-yl)carbamoyl]oxy}-3-(5-methylpyrazin-2-yl)propanoate

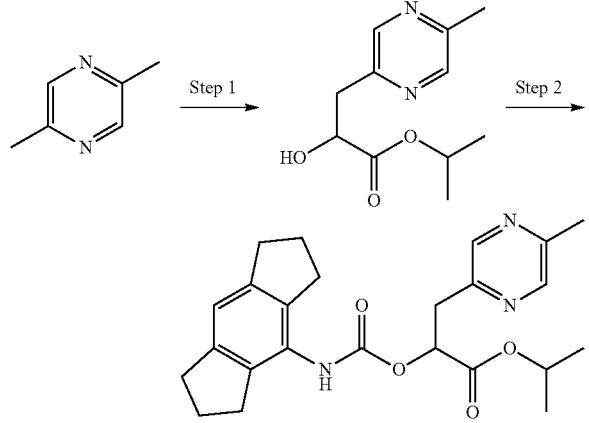

Step 1: propan-2-yl 2-hydroxy-3-(5-methylpyrazin-2-yl)propanoate. To a solution of isopropyl 2-oxoacetate (564 mg, 4.85 mmol) in dioxane (5 ml) was added 2,5-dimethylpyrazine (0.50 g, 4.62 mmol) and diacetoxyiron (24 mg, 0.14 mmol) under $N_2$. The reaction was stirred at 140° C. for 48 h. The reaction mixture was concentrated in vacuo, then purified by prep-HPLC followed by FCC (9% MeOH in DCM) give the title compound as a yellow oil. Y=17%. $^1$H NMR (400 MHz, chloroform-d) δ ppm 8.38 (s, 1H), 8.37 (s, 1H), 5.14-5.04 (m, 1H), 4.61-4.56 (m, 1H), 3.67 (d, J=6 Hz, 1H), 3.35-3.09 (m, 2H), 2.55 (s, 3H), 1.27-1.24 (m, 6H).

Step 2: propan-2-yl 2-{[(1,2,3,5,6,7-hexahydro-s-indacen-4-yl)carbamoyl]oxy}-3-(5-methylpyrazin-2-yl)propanoate. The title compound was prepared according to the General procedure B using propan-2-yl 2-hydroxy-3-(5-methylpyrazin-2-yl)propanoate and Intermediate A as starting materials. The crude mixture was purified by prep-TLC (1:1 EtOAc/petrol) to give the title compound as a white solid. Y=18%. MS ES$^+$: 424.2. $^1$H NMR (400 MHz, chloroform-d) δ ppm 8.43 (br. s, 2H), 7.00 (s, 1H), 6.27 (br. s, 1H) 5.50-5.42 (m, 1H), 5.15-5.06 (m, 1H), 3.40-3.25 (m, 2H), 2.91-2.83 (m, 4H), 2.75-2.62 (m, 4H), 2.57 (s, 3H), 2.14-1.94 (m, 4H), 1.28-1.24 (m, 6H).

Example 117. Propan-2-yl 2-{[(1-methylcyclohexyl)carbamoyl]oxy}-3-(pyrimidin-2-yl)propanoate

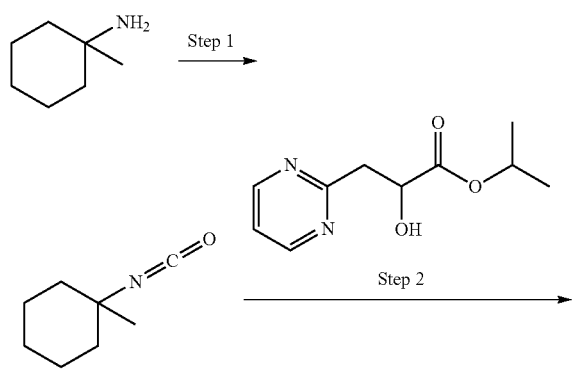

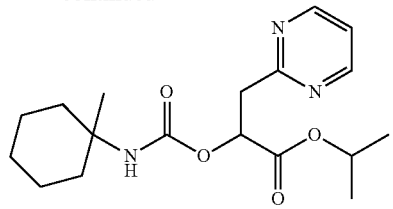

Step 1: 1-isocyanato-1-methylcyclohexane. To a mixture of triphosgene (393 mg, 1.33 mmol) in DCM (2 ml) cooled to 0° C. under nitrogen were added 1-methylcyclohexanamine (150 mg, 1.33 mmol) and triethylamine (369 μl, 2.65 mmol). The mixture was stirred at rt for 2 h. The solvent was removed under reduced pressure to give the title compound as a white solid, used in the next step directly. Y=100%.

Step 2: propan-2-yl 2-{[(1-methylcyclohexyl)carbamoyl]oxy}-3-(pyrimidin-2-yl)propanoate. The title compound was prepared according to the General procedure B using propan-2-yl 2-hydroxy-3-(pyrimidin-2-yl)propanoate (for synthesis refer to example 5C$_0$) and 1-isocyanato-1-methylcyclohexane as starting materials. The crude mixture was purified by prep-TLC (2:1 EtOAc/petrol) to give the title compound as a colourless gum. Y=9%. MS ES$^+$: 350.1. $^1$H NMR (400 MHz, chloroform-d) δ 8.69 (d, J=5 Hz, 2H), 7.17 (t, J=5 Hz, 1H), 5.63-5.57 (m, 1H), 5.14-5.07 (m, 1H), 4.68 (s, 1H), 3.49 (s, 2H), 1.95-1.78 (m, 2H), 1.52-1.33 (m, 8H), 1.29-1.25 (m, 6H), 1.22 (d, J=6 Hz, 3H).

Example 118. Propan-2-yl 2-{[(2-chloro-6-fluorophenyl)carbamoyl]oxy}-3-(pyrimidin-2-yl)propanoate

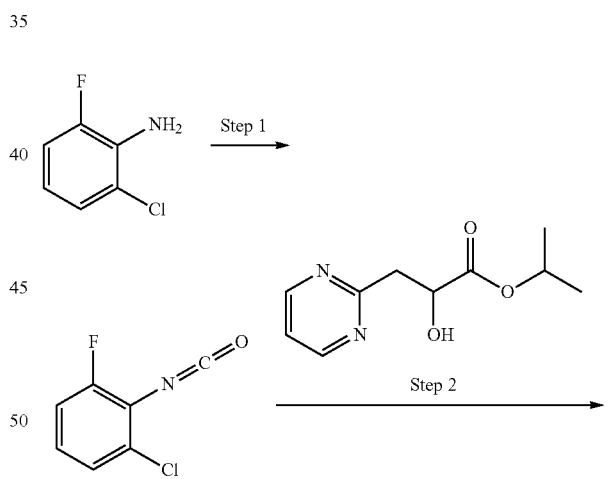

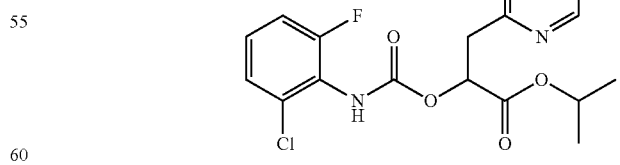

Step 1: 1-chloro-3-fluoro-2-isocyanatobenzene. To a solution of triphosgene (408 mg, 1.37 mmol) in DCM (3 ml) was added 2-chloro-6-fluoro-aniline (200 mg, 1.37 mmol). The RM was cooled to 0° C. and treated with triethylamine (402 μl, 2.89 mmol). The RM was stirred at rt for 1 h. The solvent was removed under reduced pressure to give the desired product as a white solid and it was used in the next step without further purification. MS ES+: 204.2 (in methanol).

Step 2: propan-2-yl 2-{[(2-chloro-6-fluorophenyl)carbamoyl]oxy}-3-(pyrimidin-2-yl)propanoate. The title compound was prepared according to the General procedure B using propan-2-yl 2-hydroxy-3-(pyrimidin-2-yl)propanoate (for synthesis refer to example 5C$_O$) and 1-chloro-3-fluoro-2-isocyanatobenzene as starting materials. The crude mixture was purified by prep-TLC (1:1 EtOAc/petrol, Rf=0.4) to give the title compound as a colourless gum. Y=28%. MS ES+: 382.1. $^1$H NMR (400 MHz, chloroform-d) δ 8.70 (d, J=5 Hz, 2H), 7.22-7.14 (m, 3H), 7.08-6.99 (m, 1H), 6.34 (s, 1H), 5.79-5.75 (m, 1H), 5.17-5.08 (m, 1H), 3.62-3.52 (m, 2H), 1.28 (d, J=6 Hz, 3H), 1.25 (d, J=6 Hz, 3H).

Example 119. Propan-2-yl 2-{[(2,6-difluorophenyl)carbamoyl]oxy}-3-(pyrimidin-2-yl)propanoate

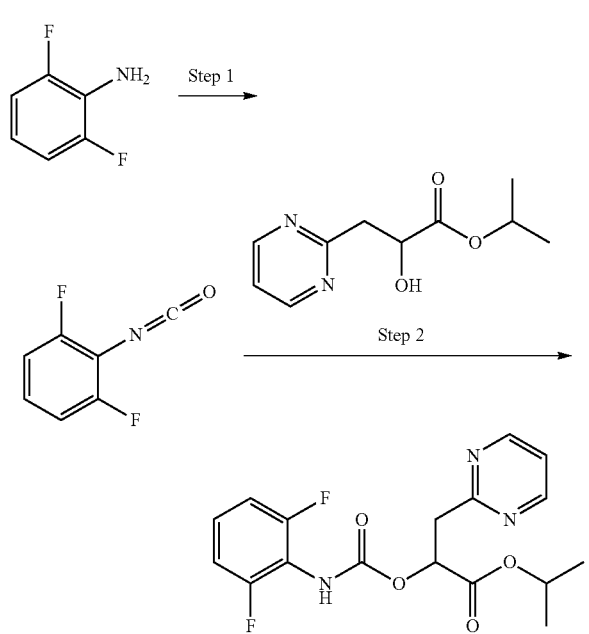

Step 1: 1,3-difluoro-2-isocyanatobenzene. To a solution of triphosgene (460 mg, 1.55 mmol) in DCM (3 ml) was added 2,6-difluoro-aniline (200 mg, 1.55 mmol). The RM was cooled to 0° C. and treated with triethylamine (453 µl, 3.25 mmol). The RM was stirred at rt for 1 h. The solvent was removed under reduced pressure to give the desired product as a white solid and it was used in the next step without further purification. MS ES+: 188.3 (in methanol).

Step 2: propan-2-yl 2-{[(2,6-difluorophenyl)carbamoyl]oxy}-3-(pyrimidin-2-yl)propanoate. The title compound was prepared according to the General procedure B using propan-2-yl 2-hydroxy-3-(pyrimidin-2-yl)propanoate (for synthesis refer to example 5CO) and 1,3-difluoro-2-isocyanatobenzene as starting materials. The crude mixture was purified by prep-TLC (1:1 EtOAc/petrol, Rf=0.4) to give the title compound as a colourless gum. Y=12%. MS ES+: 366.1. $^1$H NMR (400 MHz, chloroform-d) δ 8.70 (d, J=5 Hz, 2H), 7.23-7.12 (m, 2H), 6.97-6.86 (m, 2H), 6.24 (s, 1H), 5.78-5.72 (m, 1H), 5.17-5.07 (m, 1H), 3.62-3.49 (m, 2H), 1.28 (d, J=6 Hz, 3H), 1.25 (d, J=6 Hz, 3H).

Example 120. Propan-2-yl 2-{[(2,6-dichlorophenyl)carbamoyl]oxy}-3-(pyrimidin-2-yl)propanoate

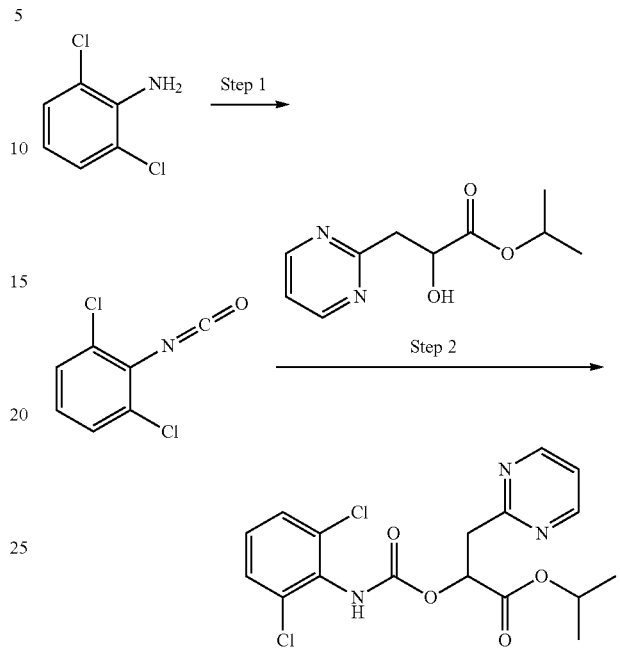

Step 1: 1,3-dichloro-2-isocyanatobenzene. To a solution of triphosgene (366 mg, 1.23 mmol) in DCM (3 ml) was added 2,6-dichloro-aniline (200 mg, 1.23 mmol). The RM was cooled to 0° C. and treated with triethylamine (361 µl, 2.59 mmol). The RM was stirred at rt for 1 h. The solvent was removed under reduced pressure to give the desired product as a white solid and it was used in the next step without further purification. MS ES+: 220.2 (in methanol).

Step 2: propan-2-yl 2-{[(2,6-dichlorophenyl)carbamoyl]oxy}-3-(pyrimidin-2-yl)propanoate. The title compound was prepared according to the General procedure B using propan-2-yl 2-hydroxy-3-(pyrimidin-2-yl)propanoate (for synthesis refer to example 5C$_O$) and 1,3-dichloro-2-isocyanatobenzene as starting materials. The crude mixture was purified by prep-TLC (1:1 EtOAc/petrol, Rf=0.4) to give the title compound as a colourless gum. Y=28%. MS ES+: 398.1. $^1$H NMR (400 MHz, chloroform-d) δ 8.70 (d, J=5 Hz, 2H), 7.34 (d, J=8 Hz, 2H), 7.22-7.11 (m, 2H), 6.48-6.35 (br. s, 1H), 5.82-5.76 (m, 1H), 5.18-5.07 (m, 1H), 3.70-3.43 (m, 2H), 1.28 (d, J=6 Hz, 3H), 1.25 (d, J=6 Hz, 3H).

Example 121. Propan-2-yl (2R)-3-(3-cyano-1H-1,2,4-triazol-1-yl)-2-{[(1,2,3,5,6,7-hexahydro-s-indacen-4-yl)carbamoyl]oxy}propanoate

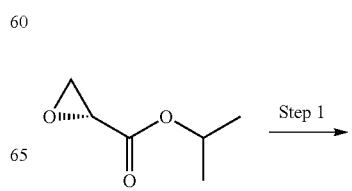

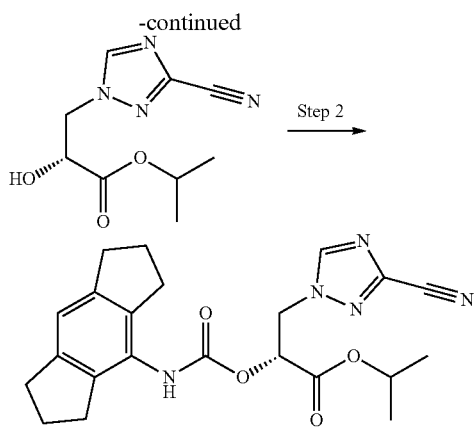

Step 1: propan-2-yl (2R)-3-(3-cyano-1H-1,2,4-triazol-1-yl)-2-hydroxypropanoate. To a solution of isopropyl (2R)-oxirane-2-carboxylate (0.4 g, 3.07 mmol) (for synthesis refer to example 5CI) in EtOH (10 ml) was added 1H-1,2,4-triazole-3-carbonitrile (723 mg, 7.68 mmol) and DIPEA (1.28 ml, 7.38 mmol). The mixture was stirred at rt for 16 h then concentrated in vacuo. The residue was purified by prep-HPLC (column: Phenomenex Luna C18 250*50 mm*10 μm; mobile phase: [water (0.1% TFA)-ACN]; B %: 5-35, 20 min) to give the title compound as a white solid. Y=27%. $^1$H NMR (400 MHz, methanol-d$_4$) δ 8.60 (s, 1H), 5.11-5.03 (m, 1H), 4.68-4.50 (m, 3H), 1.36-1.26 (m, 6H).

Step 2: propan-2-yl (2R)-3-(3-cyano-1H-1,2,4-triazol-1-yl)-2-{[(1,2,3,5,6,7-hexahydro-s-indacen-4-yl)carbamoyl]oxy}propanoate. The title compound was prepared according to the General procedure B using propan-2-yl (2R)-3-(3-cyano-1H-1,2,4-triazol-1-yl)-2-hydroxypropanoate and Intermediate A as starting materials. The crude product was purified by prep HPLC (column: Waters Xbridge 150*50 10 μm; mobile phase: [water (0.1% TFA)-ACN]; B %: 47-67, 12 min) to give the title compound as a white solid. Y=8%. MS ES$^+$: 424.1. $^1$H NMR (400 MHz, chloroform-d) δ 8.25 (s, 1H), 7.04 (s, 1H), 6.42 (s, 1H), 5.46 (s, 1H), 5.16-5.10 (m, 1H), 4.80 (s, 1H), 2.98-2.82 (m, 4H), 2.80-2.70 (m, 4H), 2.12-2.04 (m, 4H), 1.29 (t, J=6 Hz, 6H).

Example 122. Propan-2-yl 2-[({bicyclo[2.2.2]octan-1-yl}carbamoyl)oxy]-3-(pyrimidin-2-yl)propanoate

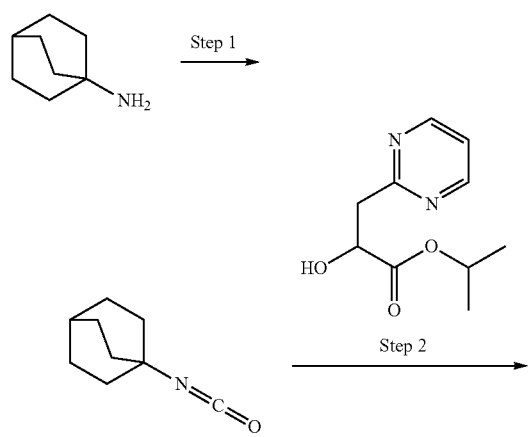

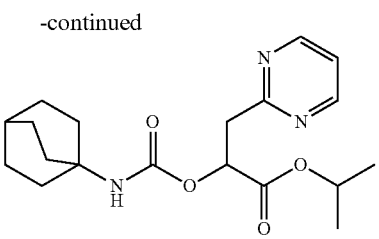

Step 1: 1-isocyanatobicyclo[2.2.2]octane. To a solution of triphosgene (119 mg, 399 μmop in DCM (2 ml) cooled to 0° C. was added bicyclo[2.2.2]octan-4-amine (50 mg, 399 μmop and then Et$_3$N (0.167 ml, 1.20 mmol). The mixture was stirred at rt for 1 h, then the solvent was removed under reduced pressure to give the title compound as a white solid. The product was used for the next step directly. Y=99%. MS ES$^+$: 184.1 (in methanol).

Step 2: propan-2-yl 2-[({bicyclo[2.2.2]octan-1-yl}carbamoyl)oxy]-3-(pyrimidin-2-yl)propanoate. The title compound was prepared according to the General procedure B using propan-2-yl 2-hydroxy-3-(pyrimidin-2-yl)propanoate (for synthesis refer to example 5C$_O$) and 1-isocyanatobicyclo[2.2.2]octane as starting materials. The crude mixture was purified by prep-TLC (1:1 EtOAc/petrol, Rf=0.35) to give the title compound as a white solid. Y=19%. MS ES$^+$: 362.2. $^1$H NMR (400 MHz, methanol-d$_4$+D$_2$O) δ 8.72 (d, J=5 Hz, 2H), 7.36 (t, J=5 Hz, 1H), 5.40-5.32 (m, 1H), 5.06-4.99 (m, 1H), 3.47-3.35 (m, 2H), 1.76-1.50 (m, 13H), 1.26-1.17 (m, 6H).

Example 123. Propan-2-yl 2-{[(1,2,3,5,6,7-hexahydro-s-indacen-4-yl)carbamoyl]oxy}-3-(pyridazin-4-yl)propanoate

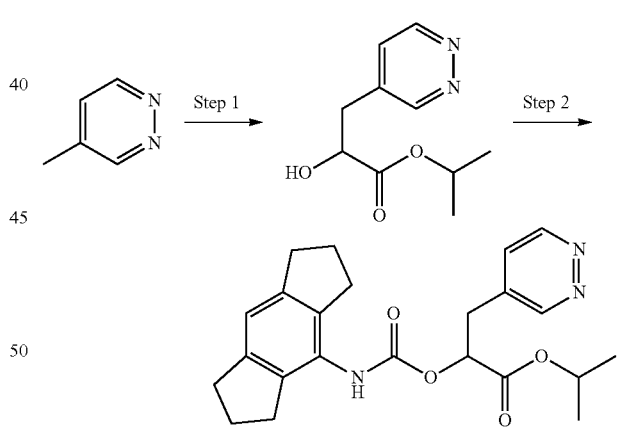

Step 1: propan-2-yl 2-hydroxy-3-(pyridazin-4-yl)propanoate. To a solution of 4-methylpyridazine (500 mg, 5.31 mmol) in dioxane (5 ml) was added isopropyl 2-oxoacetate (1.23 g, 10.62 mmol) and diacetoxyiron (46 mg, 0.27 mmol) under N$_2$ atmosphere. The reaction mixture was heated at 100° C. for 24 h. The reaction mixture was filtered and the filtrate was directly purified by pre-HPLC (column: Phenomenex Luna C18 250*50 mm*10 μm; mobile phase: [water (0.1% TFA)-ACN]; B %: 1-20, 20 min) to give the title compound as a pink oil. Y=38%. $^1$H NMR (400 MHz, chloroform-d) δ 9.28-9.20 (m, 2H), 7.78-7.72 (m, 1H), 5.16-5.06 (m, 1H), 4.49-4.46 (m, 1H), 3.30-3.24 (m, 1H), 3.09-3.01 (m, 1H), 1.31-1.28 (m, 6H).

Step 2: propan-2-yl 2-{[(1,2,3,5,6,7-hexahydro-s-indacen-4-yl)carbamoyl]oxy}-3-(pyridazin-4-yl)propanoate. The title compound was prepared according to the General procedure B using propan-2-yl 2-hydroxy-3-(pyridazin-4-yl)propanoate and Intermediate A as starting materials. The crude product was purified by prep HPLC (column: Nano-micro Kromasil C18 100*30 mm 5 μm; mobile phase: [water (0.1% TFA)-ACN]; B %: 40-55, 10 min) to give the title compound as a brown solid. Y=1%. MS ES+: 410.2. $^1$H NMR (400 MHz, chloroform-d) δ 9.24-9.12 (m, 2H), 7.47 (s, 1H), 7.05-6.95 (m, 1H), 6.34 (s, 1H), 5.40-5.30 (m, 1H), 5.08-5.02 (m, 1H), 3.35-3.10 (m, 2H), 2.95-2.48 (m, 8H), 2.07-2.00 (m, 4H), 1.95-1.12 (m, 6H).

Example 124. Propan-2-yl 2-{[(trans-2-methylcyclohexyl)carbamoyl]oxy}-3-(pyrimidin-2-yl)propanoate

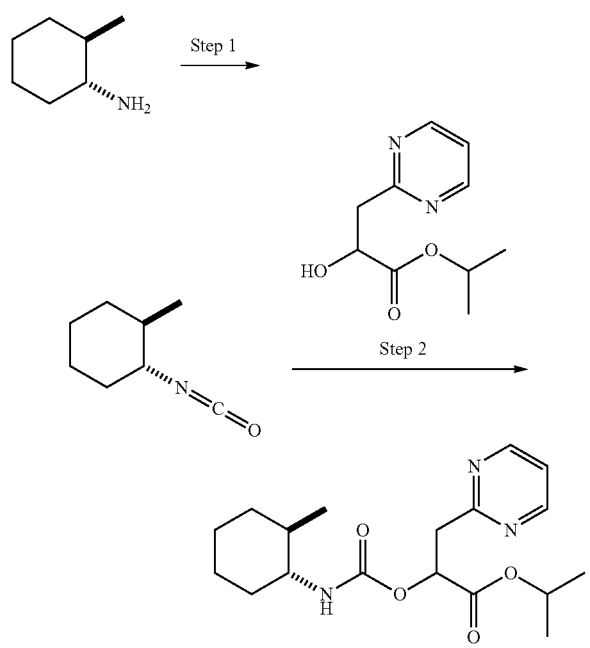

Step 1: trans-1-isocyanato-2-methylcyclohexane. To a mixture of triphosgene (131 mg, 0.44 mmol) in DCM (1 ml) were added trans-2-methylcyclohexanamine (50 mg, 0.44 mmol) and Et$_3$N (89 mg, 0.88 mmol) in portions at 0° C. under N$_2$ atmosphere. The mixture was stirred at rt for 2 h. The solvent was removed under reduced pressure to give the title compound as a white solid. Y=100%.

Step 2: propan-2-yl 2-{[(trans-2-methylcyclohexyl)carbamoyl]oxy}-3-(pyrimidin-2-yl)propanoate. The title compound was prepared according to the General procedure B using propan-2-yl 2-hydroxy-3-(pyrimidin-2-yl)propanoate (for synthesis refer to example 5CO) and trans-1-isocyanato-2-methylcyclohexane as starting materials. The crude mixture was purified by prep-HPLC (column: Waters Xbridge 150*50 mm, 10 μm; mobile phase: [water (0.1% TFA)-ACN]; B %: 30-60, 12 min) to give the title compound as a white solid. Y=5%. MS ES+: 350.2. $^1$H NMR (400 MHz, chloroform-d) δ 8.70 (d, J=5 Hz, 2H), 7.20-7.17 (m, 1H), 5.66-5.60 (m, 1H), 5.15-5.01 (m, 1H), 4.58 (d, J=9 Hz, 1H), 3.53-3.44 (m, 2H), 3.14-3.10 (m, 1H), 2.00-1.88 (m, 2H), 1.65-1.62 (m, 2H), 1.28-1.20 (m, 6H), 1.21-1.02 (m, 5H), 0.99-0.88 (m, 3H).

Example 125. Propan-2-yl 3-(5-cyanopyrimidin-2-yl)-2-{[(1,2,3,5,6,7-hexahydro-s-indacen-4-yl)carbamoyl]oxy}propanoate

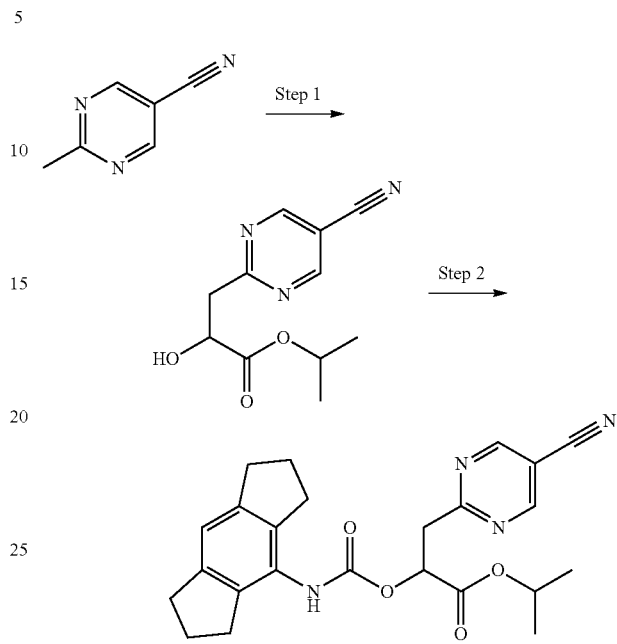

Step 1: propan-2-yl 3-(5-cyanopyrimidin-2-yl)-2-hydroxypropanoate. To a mixture of 2-methylpyrimidine-5-carbonitrile (200 mg, 1.68 mmol) and isopropyl 2-oxoacetate (585 mg, 5.04 mmol) in dioxane (3 ml) was added diacetoxyiron (29 mg, 0.17 mmol) in one portion under N$_2$. The mixture was stirred at 100° C. for 48 h. The mixture was poured into H$_2$O (25 ml) and the resulting mixture extracted with ethyl acetate (3×20 ml). The combined organic phases were washed with brine (10 ml), dried with anhydrous Na$_2$SO$_4$, filtered and concentrated in vacuo. The residue was purified by FCC (0-100% EtOAc in petrol) to give the title compound as a white solid. Y=30%. $^1$H NMR (400 MHz, DMSO-d$_6$) δ 9.24 (s, 1H), 5.66 (d, J=6 Hz, 1H), 4.95-4.85 (m, 1H), 4.64-4.55 (m, 1H), 3.38-3.32 (m, 1H), 3.29-3.20 (m, 1H), 1.21-1.10 (m, 6H).

Step 2: propan-2-yl 3-(5-cyanopyrimidin-2-yl)-2-{[(1,2,3,5,6,7-hexahydro-s-indacen-4-yl)carbamoyl]oxy}propanoate. The title compound was prepared according to the General procedure B using propan-2-yl 3-(5-cyanopyrimidin-2-yl)-2-hydroxypropanoate and Intermediate A as starting materials. The crude product was purified by prep TLC (SiO$_2$, 1:1 EtOAc/petrol) to give the title compound as a colourless oil. Y=34%. MS ES+: 435.2 $^1$H NMR (400 MHz, chloroform-d) δ 8.95 (s, 2H), 7.00 (s, 1H), 6.27-6.17 (br. s, 1H), 5.79-5.71 (m, 1H), 5.20-5.05 (m, 1H), 3.71-3.61 (m, 2H), 2.93-2.83 (m, 4H), 2.82-2.70 (m, 4H), 2.11-1.98 (m, 4H), 1.30-1.21 (m, 6H).

Example 126. Biological Activity of the Compounds of the Present Disclosure

The biological activity of the compounds of the present disclosure was determined utilising the assay described herein.
PBMC IC50 Determination Assay The compounds of the present disclosure were tested for their inhibitory activity against IL-1β release upon NLRP3 activation in peripheral blood mononuclear cells (PBMC).

PBMC were isolated from buffy coats by density gradient centrifugation on Histopaque-1077 (Sigma, cat no. 10771). Isolated cells were seeded into the wells of a 96-well plate and incubated for 3 h with lipopolysaccharide (LPS). Following medium exchange, the compounds of the present disclosure were added (a single compound per well) and the cells were incubated for 30 min. Next, the cells were stimulated either with ATP (5 mM) or nigericin (10 µM) for 1 h and the cell culture media from the wells were collected for further analysis.

The release of IL-1β into the media was determined by a quantitative detection of IL-1β in the media using an IL-1β enzyme-linked immunosorbent assay (ELISA) Ready-SET-Go!, eBioscience cat. No. 88-7261-88. Briefly, in a first step, high affinity binding plates (Corning, Costar 9018 or NUNC Maxisorp Cat No. 44-2404) were coated overnight at 4° C. with specific capture antibody included in the kit (anti-human IL-1β ref 14-7018-68). Subsequently, plates were blocked with blocking buffer for 1 h at room temperature (rt) and after washing with a buffer (PBS with 0.05% Tween-20) incubated with protein standard and culture media. After 2 h of incubation at rt, plates were washed and incubated with biotinylated detection antibody included in the kit (anti-human IL-1β Biotin ref 33-7110-68) for 1 h at rt. Plates were washed and incubated with HRP-streptavidin for 30 min at rt and washed again. The signal was developed after addition of 3,3,5,5-tetramethylbenzidine-peroxidase (TMB) until colour appeared and the reaction was stopped by 2 M $H_2SO_4$. A microplate spectrophotometer (BioTek) was used to detect signals with 450 nm. The detection range of IL-1β ELISA was 2-150 ng/ml.

The determination of the $IC_{50}$ values was performed using the Graph Pad Prism software and the measured $IC_{50}$ values of compounds of the present disclosure are shown in Table 2 below ("A" means $IC_{50}$<10 nM; "B" means $IC_{50}$ ranging between 10 nM and 100 nM; "C" means $IC_{50}$ ranging between 100 nM and 1 µM; "D" means $IC_{50}$ ranging between >1 µM and 10 µM; "E" means $IC_{50}$>10 µM). These results show that the compounds of the present disclosure are capable of inhibiting IL-1β release upon inflammasome activation.

TABLE 2

| Compound No. | PBMC $IC_{50}$ (µM) |
|---|---|
| 1 | C |
| 2 | D |
| 3 | C |
| 4 | D |
| 5 | E |
| 6 | B |
| 7 | D |
| 8 | C |
| 9 | C |
| 10 | D |
| 11 | D |
| 12 | B |
| 13 | D |
| 14 | D |
| 15 | D |
| 16 | C |
| 17 | C |
| 18 | C |
| 19 | D |
| 20 | C |
| 21 | C |
| 22 | C |
| 23 | C |
| 24 | C |
| 25 | C |
| 26 | C |
| 27 | D |
| 28 | D |
| 29 | D |
| 30 | C |
| 31 | B |
| 32 | C |
| 33 | C |
| 34 | D |
| 35 | E |
| 36 | D |
| 37 | C |
| 38 | D |
| 39 | D |
| 40 | C |
| 41 | B |
| 42 | C |
| 43 | C |
| 44 | C |
| 45 | E |
| 46 | C |
| 47 | C |
| 48 | C |
| 49 | C |
| 50 | C |
| 51 | D |
| 52 | D |
| 53 | D |
| 54 | D |
| 55 | A |
| 56 | E |
| 57 | E |
| 58 | D |
| 59 | E |
| 60 | B |
| 61 | C |
| 62 | C |
| 63 | C |
| 64 | C |
| 65 | C |
| 66 | C |
| 67 | C |
| 68 | D |
| 69 | C |
| 70 | D |
| 71 | B |
| 72 | B |
| 73 | C |
| 74 | C |
| 75 | C |
| 76 | A |
| 77 | B |
| 78 | C |
| 79 | D |
| 80 | B |
| 81 | D |
| 82 | B |
| 83 | A |
| 84 | D |
| 85 | B |
| 86 | B |
| 87 | D |
| 88 | B |
| 89 | C |
| 90 | D |
| 91 | D |
| 92 | C |
| 93 | A |
| 94 | A |
| 95 | C |
| 96 | C |
| 97 | C |
| 98 | D |
| 99 | C |
| 100 | D |
| 101 | C |

TABLE 2-continued

| Compound No. | PBMC IC$_{50}$ (μM) |
|---|---|
| 102 | C |
| 103 | B |
| 104 | D |
| 105 | B |
| 106 | C |
| 107 | A |
| 108 | A |
| 109 | C |
| 110 | A |
| 111 | A |
| 112 | A |
| 113 | A |
| 114 | C |
| 115 | A |
| 116 | A |
| 117 | A |
| 118 | D |
| 119 | A |
| 120 | B |
| 121 | B |
| 122 | E (60% inhibition) |
| 123 | C |
| 124 | C |
| 125 | D |
| 126 | B |
| 127 | D |
| 128 | C |
| 129 | D |
| 130 | B |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I):

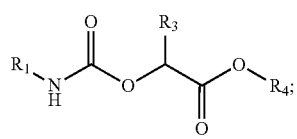

or a prodrug, hydrate, solvate, or pharmaceutically acceptable salt thereof, wherein:

$R_1$ is:
(a) $C_8$-$C_{16}$ polycyclic cycloalkyl optionally substituted by one or more $R_6$;
(b) benzofuranyl or dihydrobenzofuranyl, wherein the benzofuranyl or dihydrobenzofuranyl is optionally substituted by one or more $R_6$;
(c)

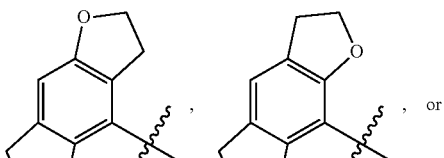

(d)

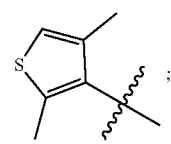 [SMILES: *c1c(C)csc1C]

or (e)

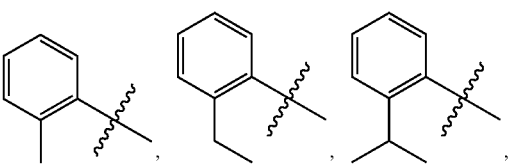

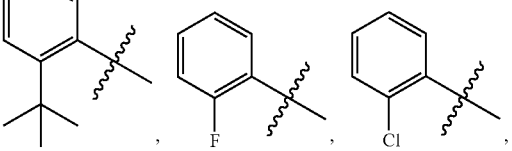

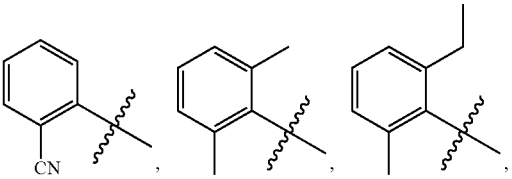

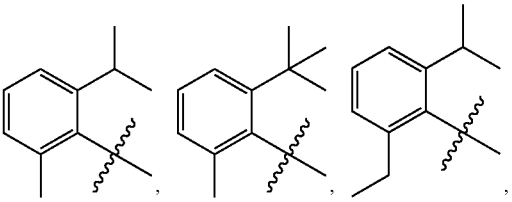

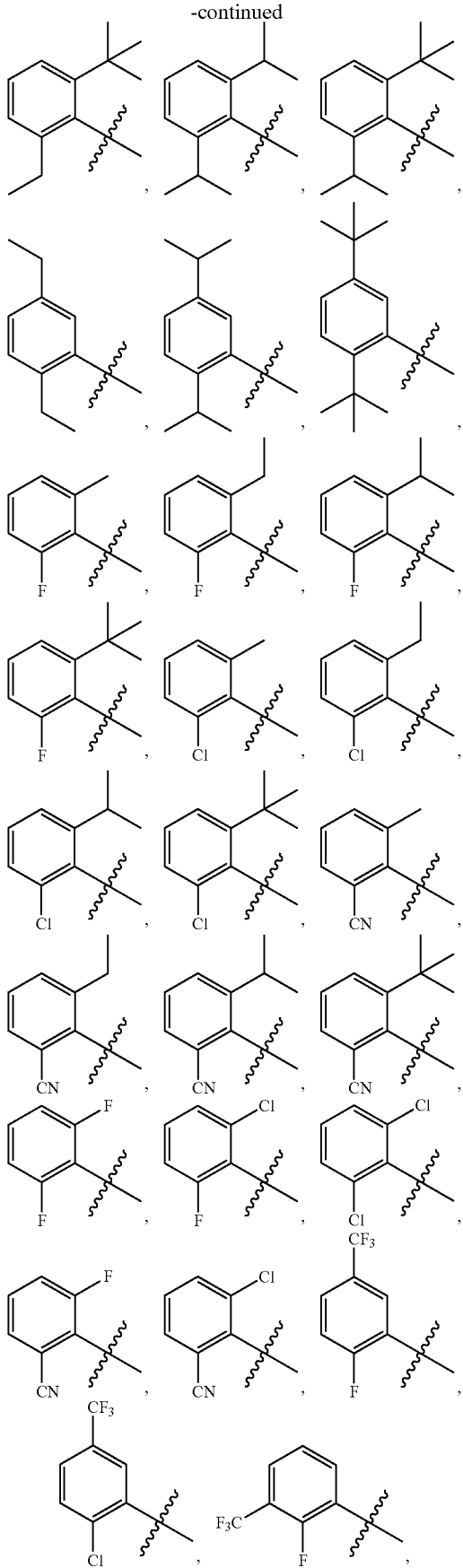

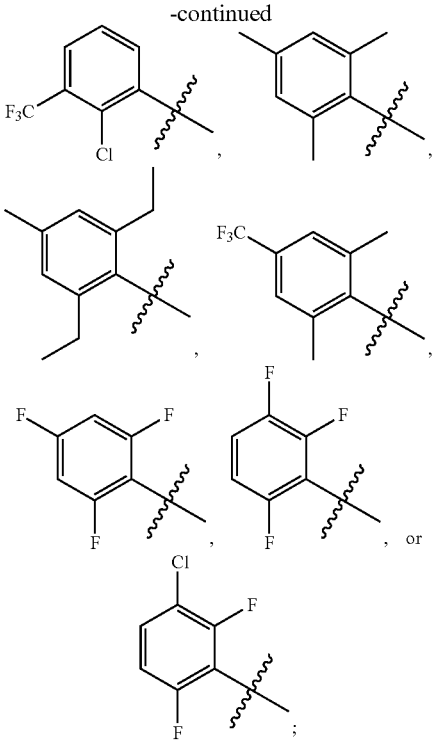

R₃ is H or $C_1$-$C_4$ alkyl substituted with one or more $R_7$;
R₄ is $C_1$-$C_6$ alkyl, -(CH$_2$)$_{0-3}$-($C_3$-$C_6$ cycloalkyl),

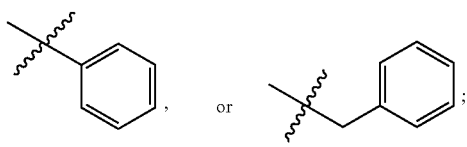 [SMILES: *c1ccccc1 ; *Cc1ccccc1]

R₆ is $C_1$-$C_6$ alkyl, $C_2$-$C_6$ alkenyl, $C_1$-$C_6$ alkoxy, $C_3$-$C_8$ cycloalkyl, halo, oxo, —OH, —CN, —NH$_2$, —NH($C_1$-$C_6$ alkyl), —N($C_1$-$C_6$ alkyl)$_2$, —CH$_2$F, —CHF$_2$, or —CF$_3$;

R₇ is —OR$_8$, $C_5$-$C_{10}$ aryl, or 5- to 10-membered heteroaryl, wherein the $C_5$-$C_{10}$ aryl or 5- to 10-membered heteroaryl is optionally substituted by one or more $R_{7S}$, wherein each $R_{7S}$ is independently $C_1$-$C_6$ alkyl, $C_1$-$C_6$ alkoxy, 5- to 10-membered heteroaryl, halo, —OH, —CN, —(CH$_2$)$_{0-3}$—NH$_2$, —(CH$_2$)$_{0-3}$—NH($C_1$-$C_6$ alkyl), —(CH$_2$)$_{0-3}$-N($C_1$-$C_6$ alkyl)$_2$, —CH$_2$F, —CHF$_2$, or —CF$_3$; and R₈ is $C_1$-$C_6$ alkyl or 5- to 7-membered heterocycloalkyl, wherein the $C_1$-$C_6$ alkyl or 5- to 7-membered heterocycloalkyl is optionally substituted by one or more $R_{7S}$.

2. The compound of claim 1, wherein $R_1$ is

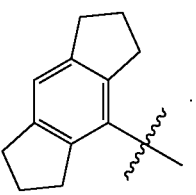 [SMILES: *c1c2c(cc3c1CCC3)CCC2]

3. The compound of claim 1, wherein $R_3$ is $C_1$-$C_4$ alkyl substituted with one or more —$OR_8$, $C_5$-$C_{10}$ aryl, or 5- to 10-membered heteroaryl.

4. The compound of claim 1, wherein $R_3$ is methyl substituted with one or more 5- to 10-membered heteroaryl, wherein the 5- to 10-membered heteroaryl is optionally substituted with one or more $C_1$-$C_6$ alkyl, $C_1$-$C_6$ alkoxy, halo, —CN, —$(CH_2)_{0-3}$—$N(C_1$-$C_6$ alkyl$)_2$, or —$CF_3$.

5. The compound of claim 1, wherein $R_3$ is

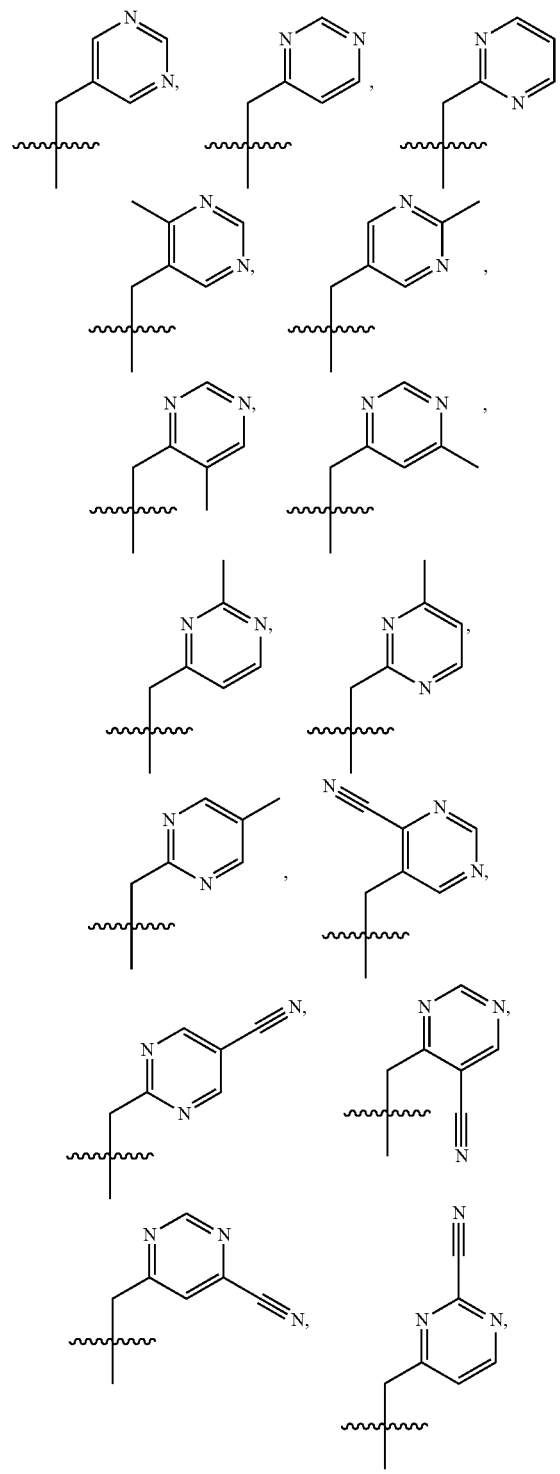

-continued

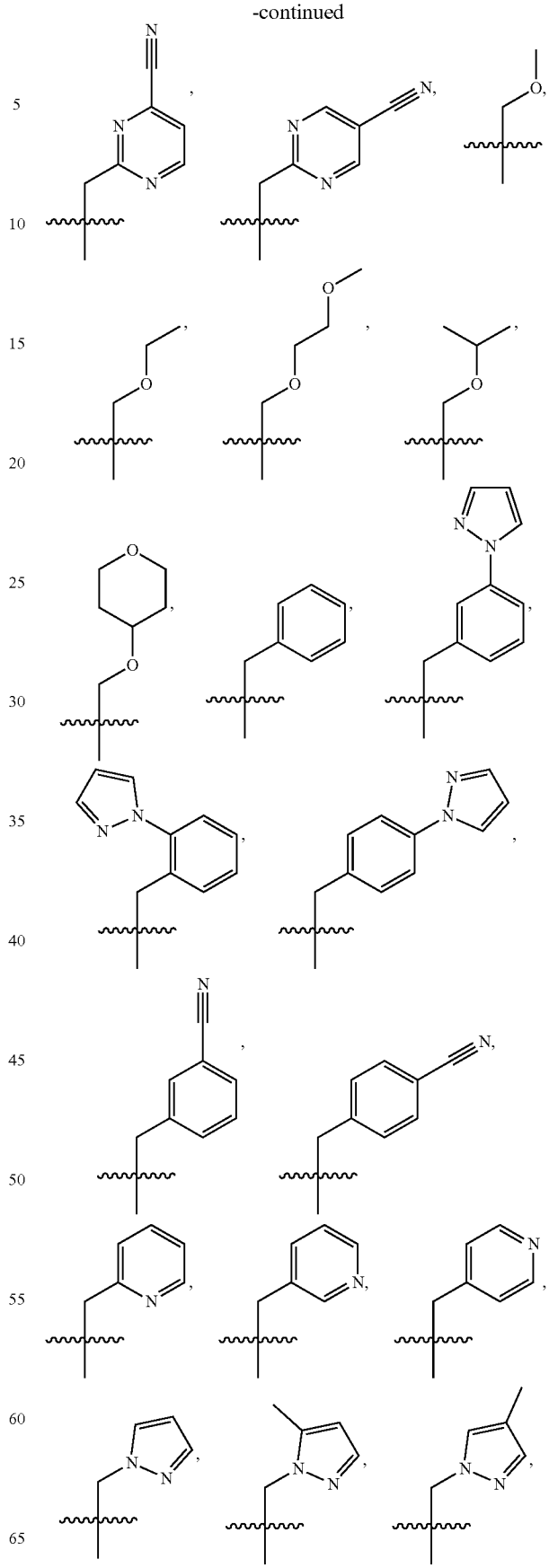

227
-continued
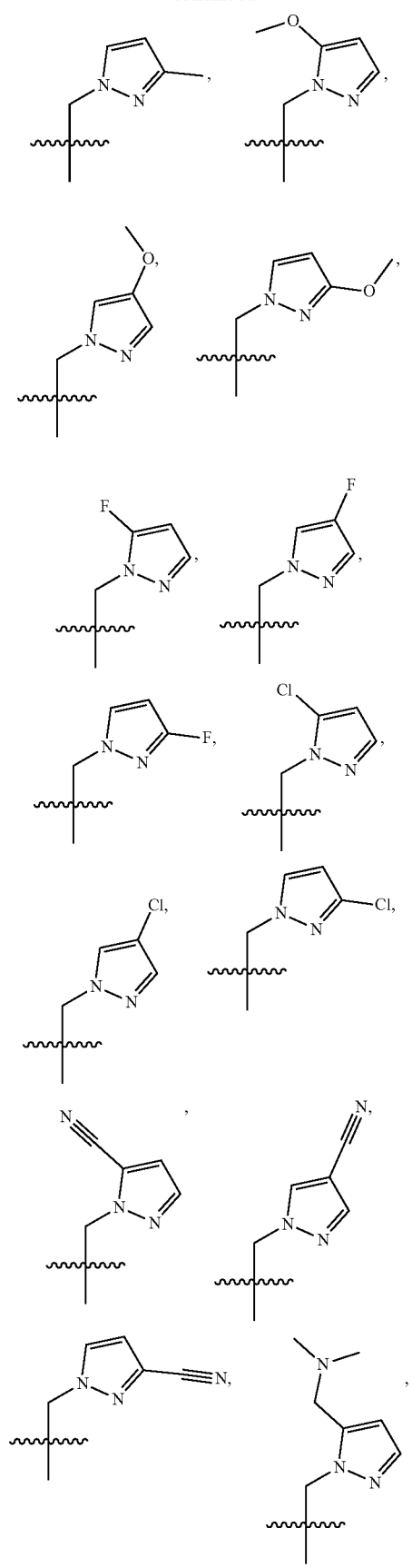
228
-continued
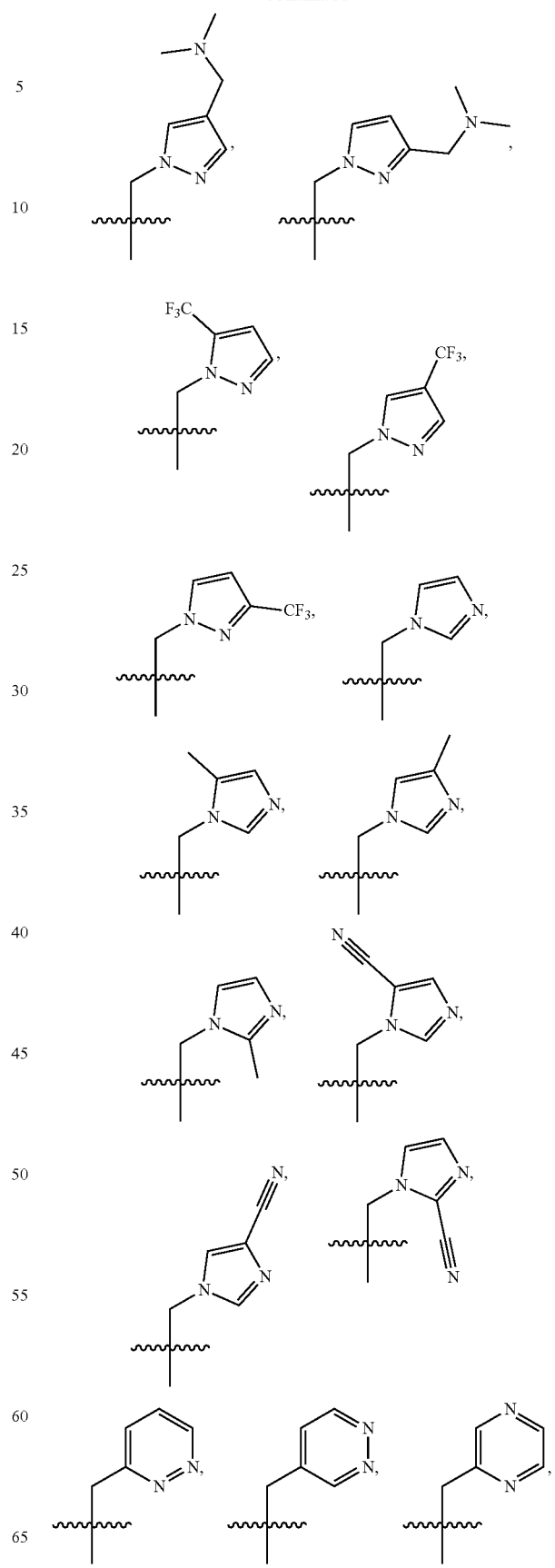

-continued

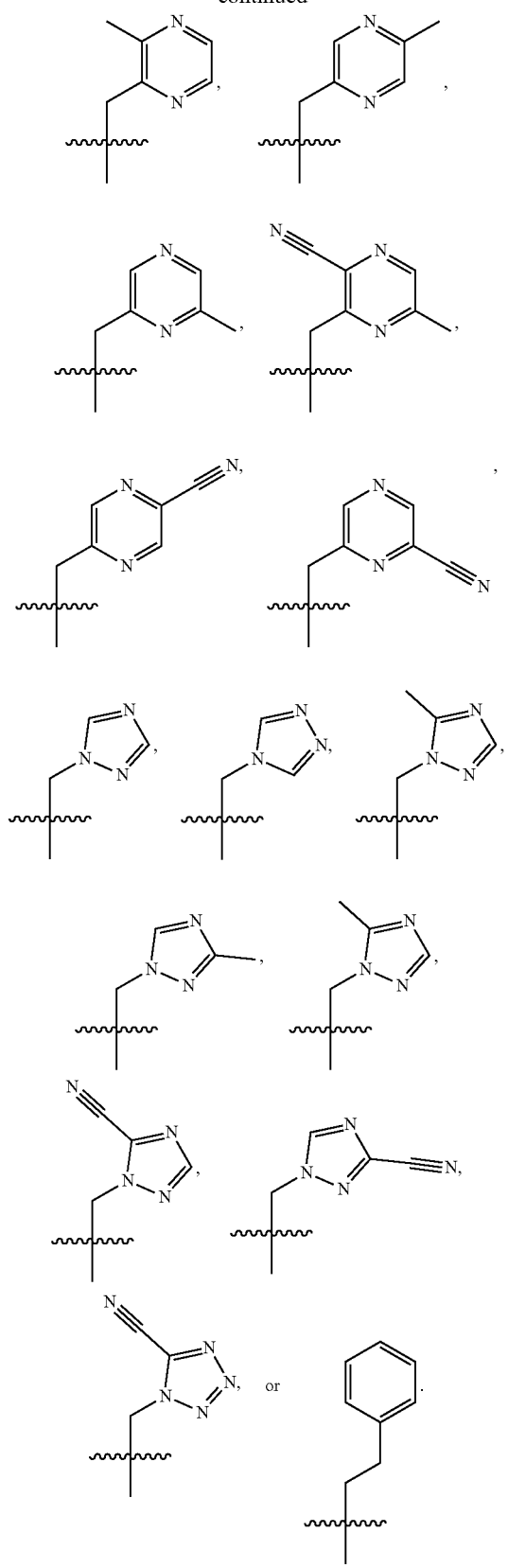

6. The compound of claim 1, wherein $R_4$ is $C_1$-$C_6$ alkyl, —$(CH_2)_{0-1}$—$(C_3$-$C_6$ cycloalkyl),

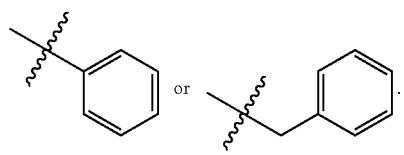 [SMILES: *c1ccccc1 ; *Cc1ccccc1]

7. The compound of claim 1, wherein $R_4$ is methyl, ethyl, propyl, butyl,

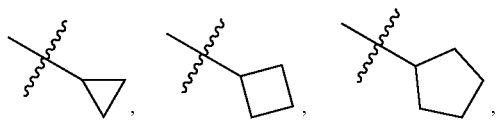

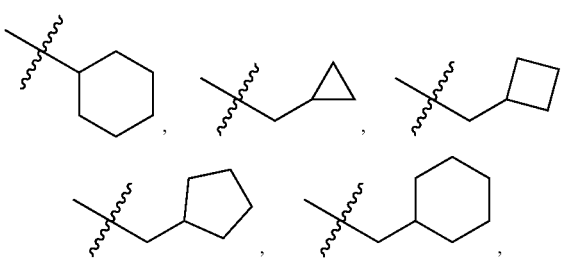

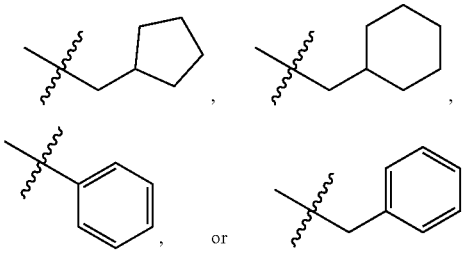

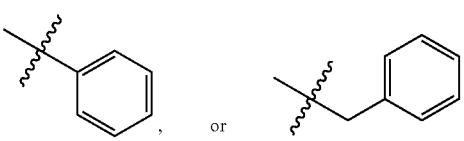

8. The compound of claim 1, wherein at least one $R_7$ is 5- to 10-membered heteroaryl optionally substituted by one or more halo, —OH, —CN, —$(CH_2)_{0-3}$—$NH_2$, —$(CH_2)_{0-3}$—$NH(C_1$-$C_6$ alkyl), —$(CH_2)_{0-3}$—$N(C_1$-$C_6$ alkyl)$_2$, —$CH_2F$, —$CHF_2$, or —$CF_3$.

9. The compound of claim 1, being of Formula (Ia), (Ib), (II), (IIa), (IIb), (III), (IIIa), (IIIb), (IV), (IVa), (Ivb), (V), (Va), (Vb), (VI), (Via), (Vib), VII), (VIIa), (VIIb), (VIII), (VIIIa), (VIIIb), (IX), (Ixa), (Ixb), (X), (Xa), or (Xb):

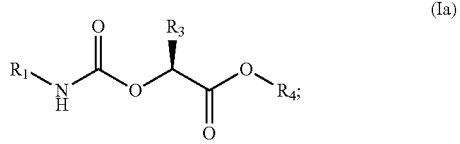

(Ia)

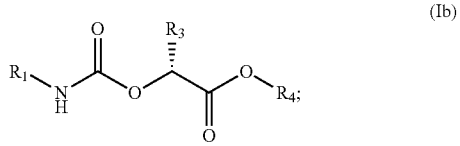

(Ib)

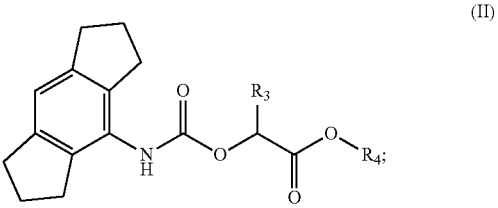

(II)

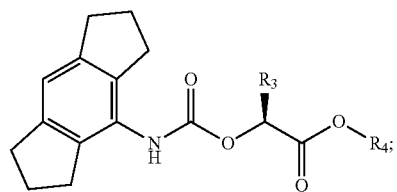
(IIa)
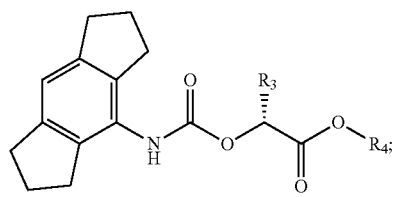
(IIb)
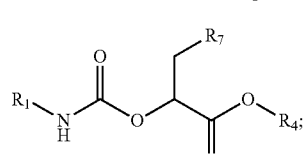
(III)
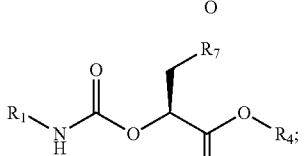
(IIIa)
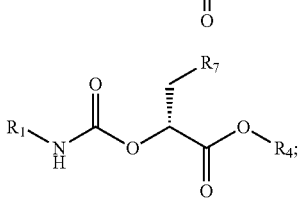
(IIIb)
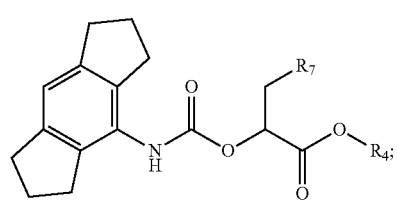
(IV)
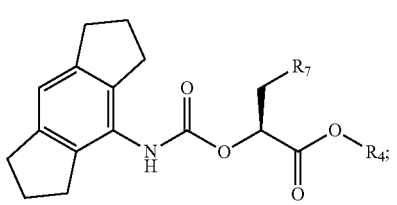
(IVa)
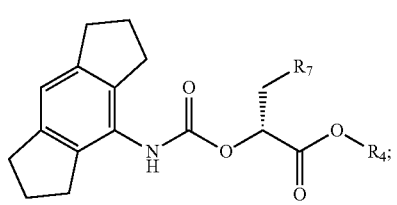
(IVb)
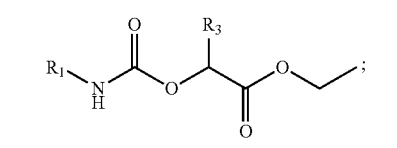
(V)
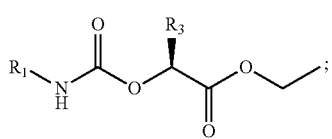
(Va)
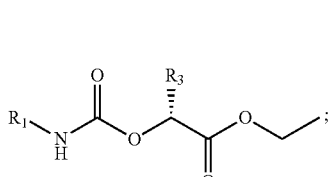
(Vb)
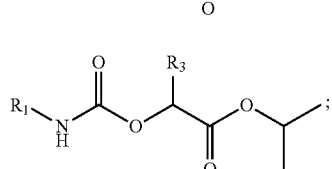
(VI)
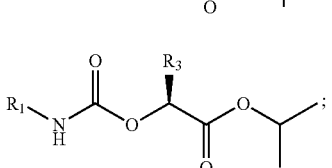
(VIa)
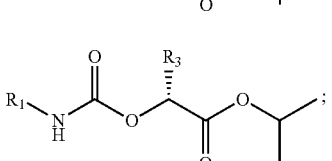
(VIb)
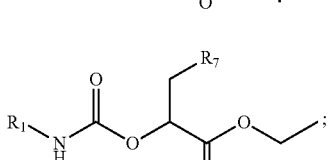
(VII)
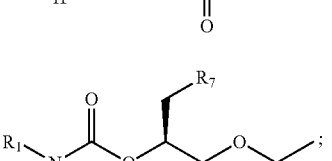
(VIIa)
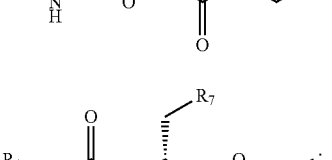
(VIIb)
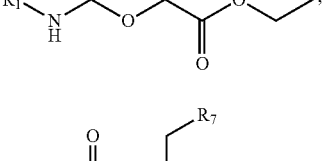
(VIII)
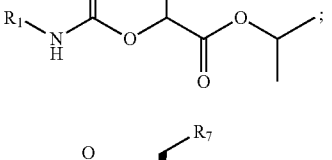
(VIIIa)

10. A compound selected from:

Ethyl 2-{[(1,2,3,5,6,7-hexahydro-s-indacen-4-yl)carbamoyl]oxy}acetate;

Ethyl 2-{[(2,6-difluorophenyl)carbamoyl]oxy}acetate;

Ethyl 2-{[(2,6-dichlorophenyl)carbamoyl]oxy}acetate;

Ethyl 2-{[(naphthalen-1-yl)carbamoyl]oxy}acetate;

Ethyl 2-{[(2,2-dimethyl-2,3-dihydro-1-benzofuran-7-yl)carbamoyl]oxy}acetate;

Ethyl 2-{[(1,2,3,5,6,7-hexahydro-s-indacen-4-yl)carbamoyl]oxy}-3-methoxypropanoate;

Ethyl 2-({[2-fluoro-5-(trifluoromethyl)phenyl]carbamoyl}oxy)acetate;

or a prodrug, hydrate, solvate, or pharmaceutically acceptable salt thereof.

-continued

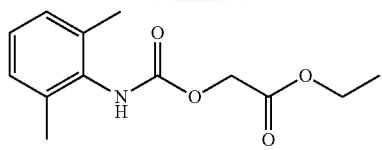

Ethyl 2-{[(2,6-dimethylphenyl)carbamoyl]oxy}acetate;

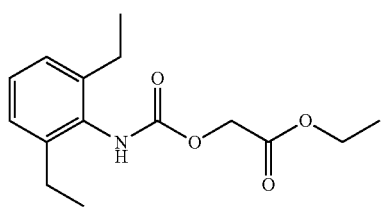

Ethyl 2-{[(2,6-diethylphenyl)carbamoyl]oxy}acetate;

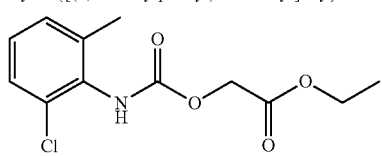

Ethyl 2-({[2-(chloro-6-methylphenyl)carbamoyl]oxy}acetate;

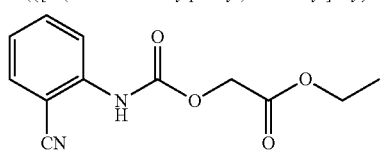

Ethyl 2-{[(2-cyanophenyl)carbamoyl]oxy}acetate;

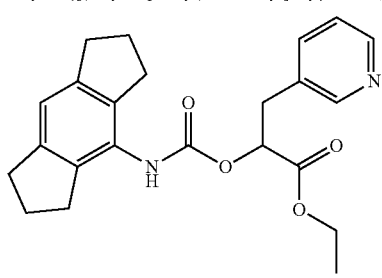

Ethyl 2-{[(1,2,3,5,6,7-hexahydro-s-indacen-4-yl)carbamoyl]oxy}-3-(pyridin-3-yl)propanoate;

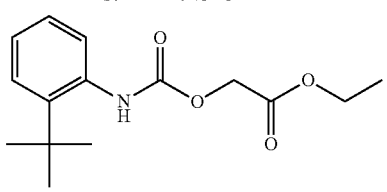

Ethyl 2-{[(2-tert-butylphenyl)carbamoyl]oxy}acetate;

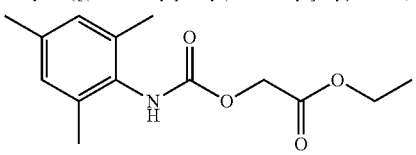

Ethyl 2-((mesitylcarbamoyl)oxy)acetate;

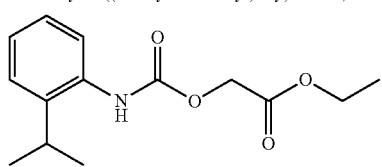

Ethyl 2-(((2-isopropylphenyl)carbamoyl)oxy)acetate;

-continued

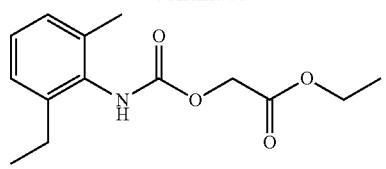

Ethyl 2-(((2-ethyl-6-methylphenyl)carbamoyl)oxy)acetate;

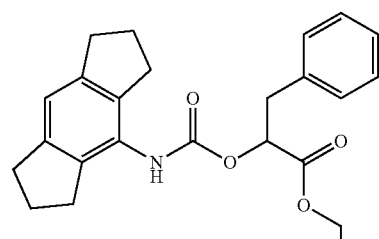

Ethyl 2-(((1,2,3,5,6,7-hexahydro-s-indacen-4-yl)carbamoyl)oxy)-3-phenylpropanoate;

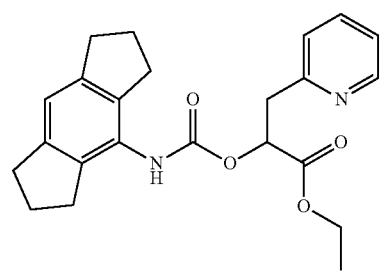

Ethyl 2-(((1,2,3,5,6,7-hexahydro-s-indacen-4-yl)carbamoyl)oxy)-3-(pyridin-2-yl)propanoate;

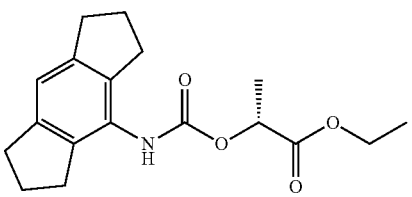

Ethyl (2R)-2-{[(1,2,3,5,6,7-hexahydro-s-indacen-4-yl)carbamoyl]oxy}propanoate;

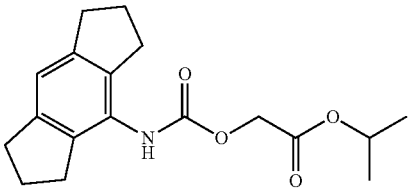

Propan-2-yl 2-{[(1,2,3,5,6,7-hexahydro-s-indacen-4-yl)carbamoyl]oxy}acetate;

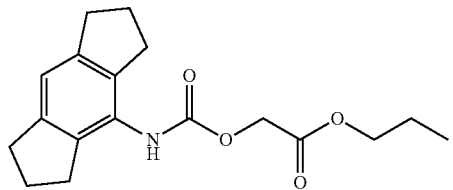

2-{[(1,2,3,5,6,7-Hexahydro-s-indacen-4-yl)carbamoyl]oxy}acetate;

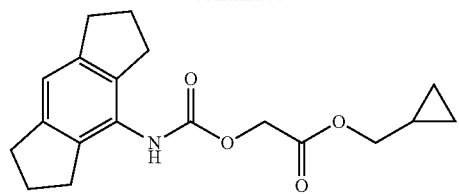

Cyclopropylmethyl 2-{[(1,2,3,5,6,7-hexahydro-s-indacen-4-yl)carbamoyl]oxy}acetate;

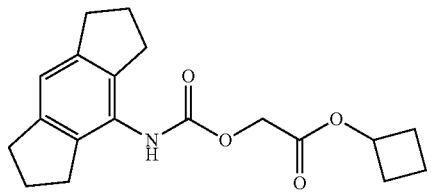

Cyclobutyl 2-{[(1,2,3,5,6,7-hexahydro-s-indacen-4-yl)carbamoyl]oxy}acetate;

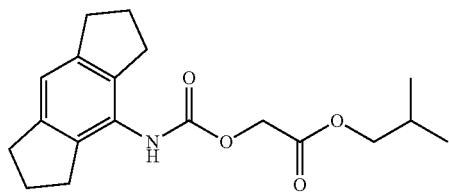

2-methylpropyl 2-{[(1,2,3,5,6,7-hexahydro-s-indacen-4-yl)carbamoyl]oxy}acetate;

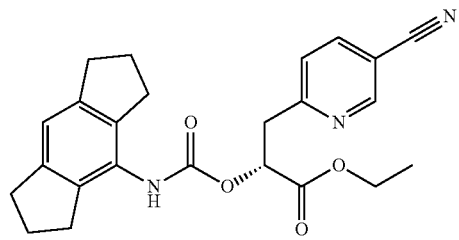

Ethyl 3-(4-cyanophenyl)-2-{[(1,2,3,5,6,7-hexahydro-s-indacen-4-yl)carbamoyl]oxy}propanoate;

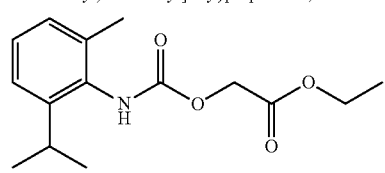

Ethyl 2-({[2-methyl-6-(propan-2-yl)phenyl]carbamoyl}oxy)acetate;

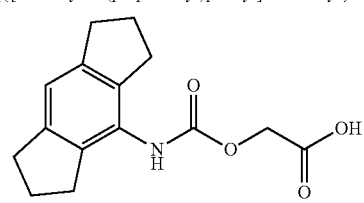

2-{[(1,2,3,5,6,7-Hexahydro-s-indacen-4-yl)carbamoyl]oxy}acetic acid;

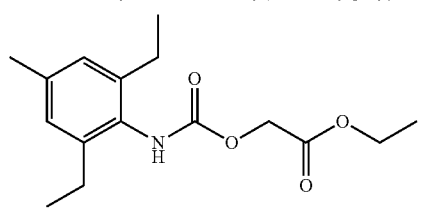

Ethyl 2-{[(2,6-diethyl-4-methylphenyl)carbamoyl]oxy}acetate;

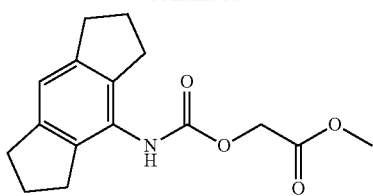

Methyl 2-{[(1,2,3,5,6,7-hexahydro-s-indacen-4-yl)carbamoyl]oxy}acetate;

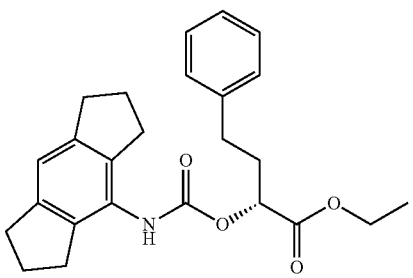

Ethyl (2R)-2-{[(1,2,3,5,6,7-hexahydro-s-indacen-4-yl)carbamoyl]oxy}-4-phenylbutanoate;

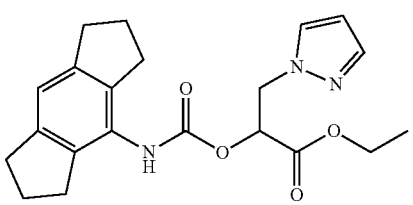

Ethyl 2-{[(1,2,3,5,6,7-hexahydro-s-indacen-4-yl)carbamoyl]oxy}-3-(1H-pyrazol-1-yl)propanoate;

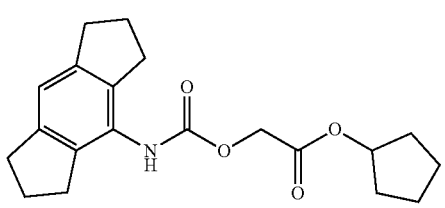

Cyclopentyl 2-{[(1,2,3,5,6,7-hexahydro-s-indacen-4-yl)carbamoyl]oxy}acetate;

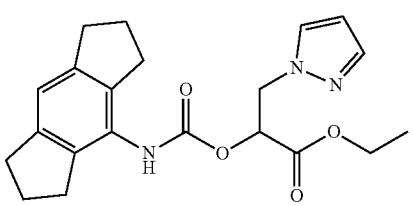

Ethyl 2-{[(1,2,3,5,6,7-hexahydro-s-indacen-4-yl)carbamoyl]oxy}-3-(1H-imidazol-1-yl)propanoate;

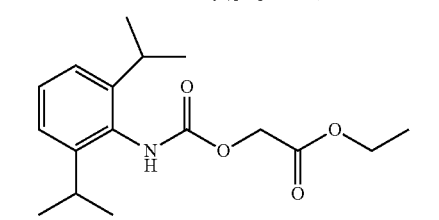

Ethyl 2-({[2,6-bis(propan-2-yl)phenyl]carbamoyl}oxy)acetate;

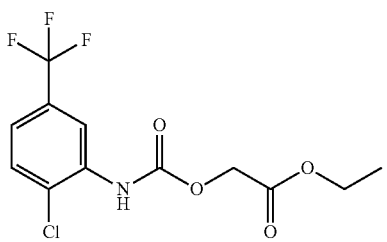

Ethyl 2-({[2-chloro-5-(trifluoromethyl)phenyl]carbamoyl}oxy)acetate;

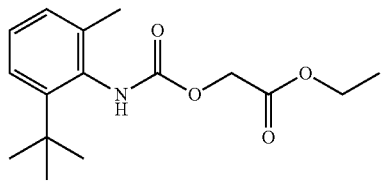

Ethyl 2-{[(2-tert-butyl-6-methylphenyl)carbamoyl]oxy}acetate;

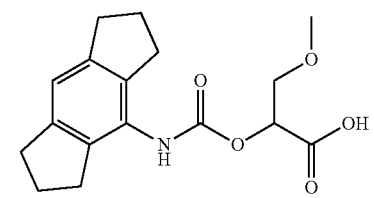

2-{[(1,2,3,5,6,7-hexahydro-s-indacen-4-yl)carbamoyl]oxy}-3-methoxypropanoic acid;

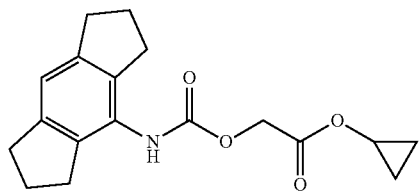

cyclopropyl 2-{[(1,2,3,5,6,7-hexahydro-s-indacen-4-yl)carbamoyl]oxy}acetate;

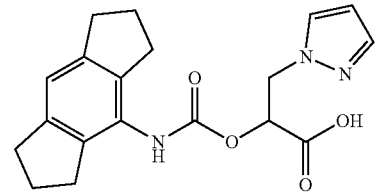

2-{[(1,2,3,5,6,7-hexahydro-s-indacen-4-yl)carbamoyl]oxy}-3-(1H-pyrazol-1-yl)propanoic acid;

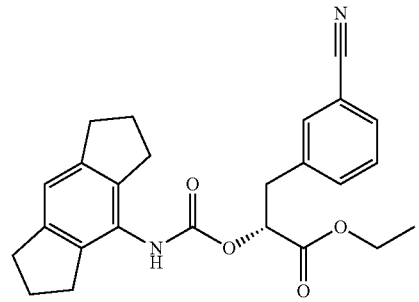

Ethyl (2R)-3-(3-cyanophenyl)-2-{[(1,2,3,5,6,7-hexahydro-s-indacen-4-yl)carbamoyl]oxy}propanoate;

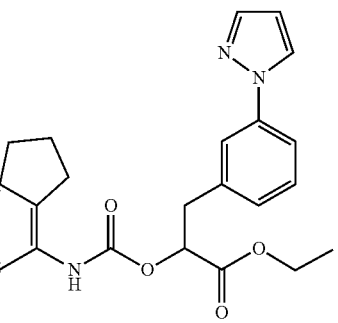

Ethyl 2-{[(1,2,3,5,6,7-hexahydro-s-indacen-4-yl)carbamoyl]oxy}-3-[3-(1H-pyrazol-1-yl)phenyl]propanoate;

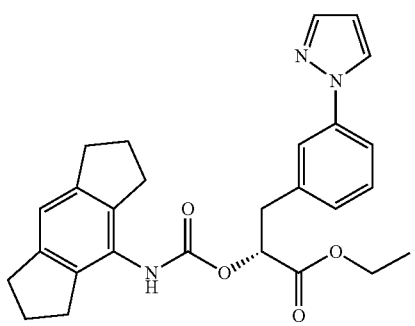

Ethyl (2R)-2-{[(1,2,3,5,6,7-hexahydro-s-indacen-4-yl)carbamoyl]oxy}-3-[3-(1H-pyrazol-1-yl)phenyl]propanoate;

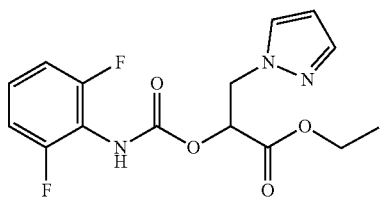

Ethyl 2-{[(2,6-difluorophenyl)carbamoyl]oxy}-3-1H-pyrazol-1-yl)propanoate;

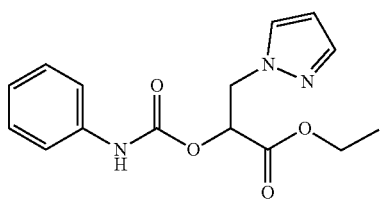

Ethyl 2-[(phenylcarbamoyl)oxy]-3-(1H-pyrazol-1-yl)propanoate;

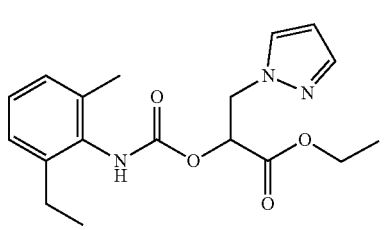

Ethyl 2-{[(2-ethyl-6-methylphenyl)carbamoyl]oxy}-3-(1H-pyrazol-1-yl)propanoate;

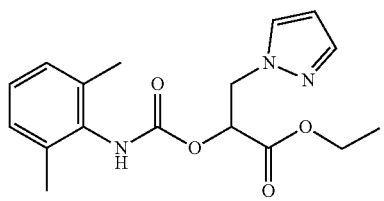

Ethyl 2-{[(2,6-dimethylphenyl)
carbamoyl]oxy}-3-(1H-pyrazol-1-yl)propanoate;

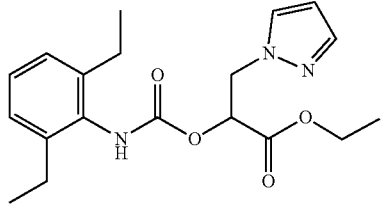

Ethyl 2-{[(2,6-diethylphenyl)
carbamoyl]oxy}-3-(1H-pyrazol-1-yl)propanoate;

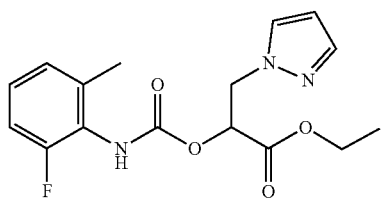

Ethyl 2-{[(2-fluoro-6-methylphenyl)
carbamoyl]oxy}-3-(1H-pyrazol-1-yl)propanoate;

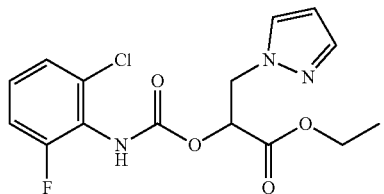

Ethyl 2-{[(2-chloro-6-fluorophenyl)
carbamoyl]oxy}-3-(1H-pyrazol-1-yl)propanoate;

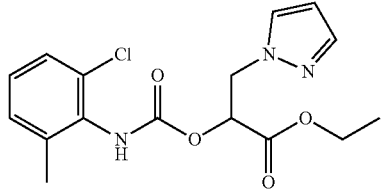

Ethyl 2-{[(2-chloro-6-methylphenyl)
carbamoyl]oxy}-3-(1H-pyrazol-1-yl)propanoate;

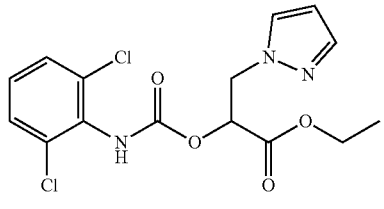

Ethyl 2-{[(2,6-dichlorophenyl)
carbamoyl]oxy}-3-(1H-pyrazol-1-yl)propanoate;

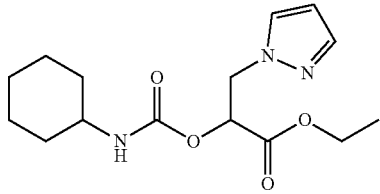

ethyl 2-[(cyclohexylcarbamoyl)
oxy]-3-(1H-pyrazol-1-yl)propanoate;

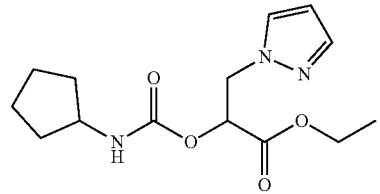

Ethyl 2-[(cyclopentylcarbamoyl)
oxy]-3-(1H-pyrazol-1-yl)propanoate;

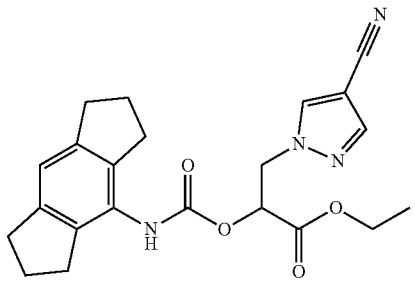

Ethyl 3-(4-cyano-1H-pyrazol-1-yl)-2-
{[(1,2,3,5,6,7-hexahydro-s-indacen-4-yl)carbamoyl]oxy}propanoate;

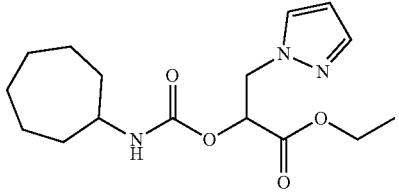

Ethyl 2-[(cycloheptylcarbamoyl)oxy]
-3-(1H-pyrazol-1-yl)propanoate;

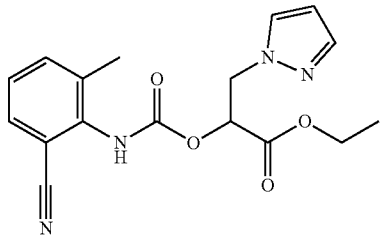

Ethyl 2-{[(2-cyano-6-methylphenyl)
carbamoyl]oxy}-3-(1H-pyrazol-1-yl)propanoate;

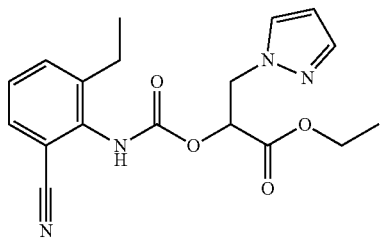

Ethyl 2-{[(2-cyano-6-ethylphenyl)
carbamoyl]oxy}-3-(1H-pyrazol-1-yl)propanoate;

-continued

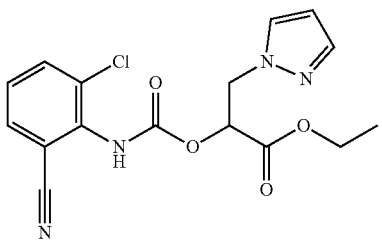

Ethyl 2-{[(2-chloro-6-cyanophenyl)
carbamoyl]oxy}-3-(1H-pyrazol-1-yl)propanoate;

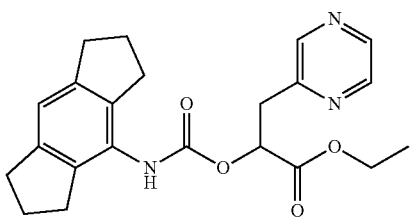

Ethyl 2-{[(1,2,3,5,6,7-hexahydro-s-indacen-4-yl)
carbamoyl]oxy}-3-(pyrazin-2-yl)propanoate;

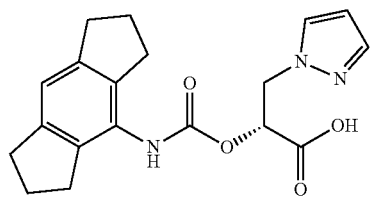

(2R)-2-{[(1,2,3,5,6,7-hexahydro-s-indacen-4-yl)
carbamoyl]oxy}-3-(1H-pyrazol-1-yl)propanoic acid;

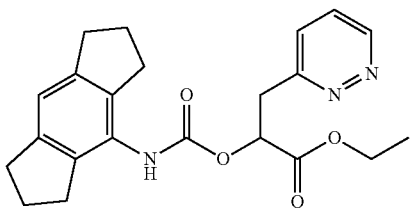

Ethyl 2-{[(1,2,3,5,6,7-hexahydro-s-indacen-4-yl)
carbamoyl]oxy}-3-(pyridazin-3-yl)propanoate;

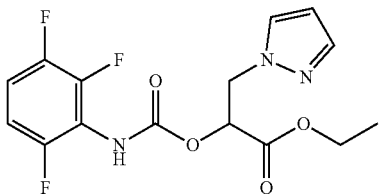

Ethyl 3-(1H-pyrazol-1-yl)-2-{[(2,3,6-trifluorophenyl)
carbamoyl]oxy}propanoate;

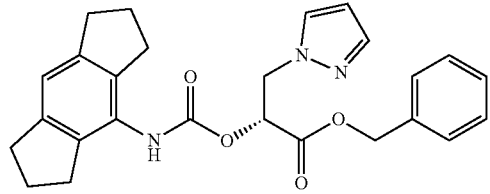

Benzyl (2R)-2-{[(1,2,3,5,6,7-hexahydro-s-indacen-4-yl)
carbamoyl]oxy}-3-(1H-pyrazol-1-yl)propanoate;

-continued

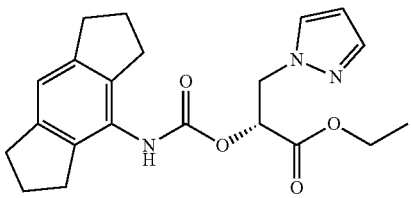

Ethyl (2R)-2-{[(1,2,3,5,6,7-hexahydro-s-indacen-4-yl)
carbamoyl]oxy}-3-(1H-pyrazol-1-yl)propanoate;

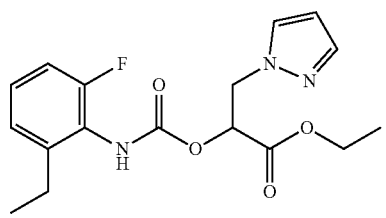

Ethyl 2-{[(2-ethyl-6-fluorophenyl)
carbamoyl]oxy}-3-(1H-pyrazol-1-yl)propanoate;

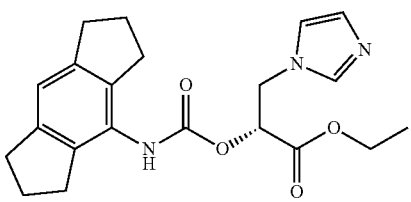

Ethyl (2R)-2-{[(1,2,3,5,6,7-hexahydro-s-indacen-4-yl)
carbamoyl]oxy}-3-(1H-imidazol-1-yl)propanoate;

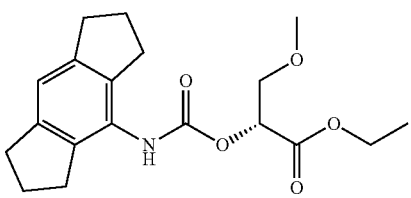

Ethyl (2R)-2-{[(1,2,3,5,6,7-hexahydro-s-indacen-4-yl)
carbamoyl]oxy}-3-methoxypropanoate;

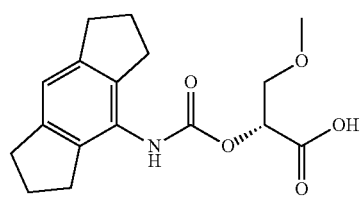

(2R)-2-{[(1,2,3,5,6,7-hexahydro-s-indacen-4-yl)
carbamoyl]oxy}-3-methoxypropanoic acid;

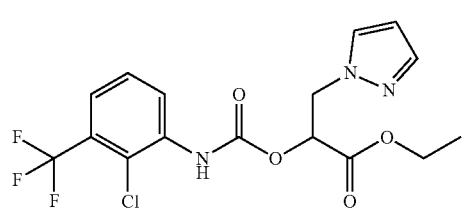

Ethyl 2-({[2-chloro-3-(trifluoromethyl)phenyl]
carbamoyl}oxy)-3-(1H-pyrazol-1-yl)propanoate;

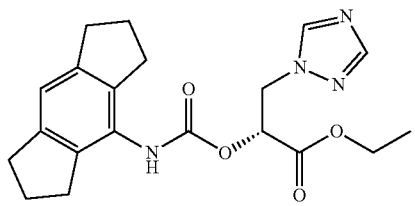

Ethyl 2-{[(1,2,3,5,6,7-hexahydro-s-indacen-4-yl)carbamoyl]oxy}-3-(1H-1,2,4-triazol-1-yl)propanoate;

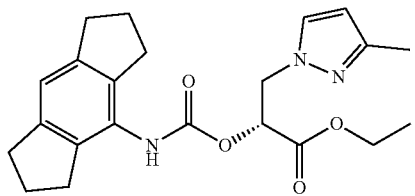

Ethyl 2-{[(1,2,3,5,6,7-hexahydro-s-indacen-4-yl)carbamoyl]oxy}-3-(3-methyl-1H-pyrazol-1-yl)propanoate;

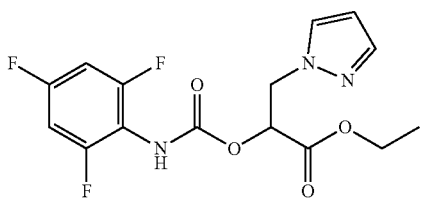

Ethyl 3-(1H-pyrazol-1-yl)-2-{[(2,4,6-trifluorophenyl)carbamoyl]oxy}propanoate;

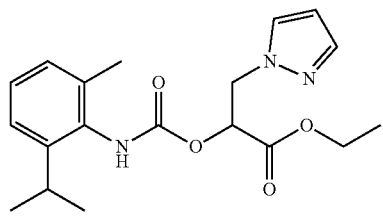

Ethyl 2-({[2-methyl-6-(propan-2-yl)phenyl]carbamoyl}oxy)-3-(1H-pyrazol-1-yl)propanoate;

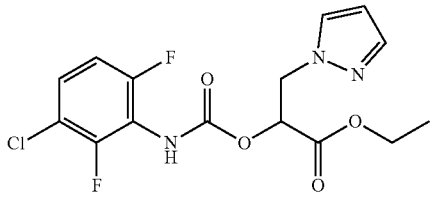

Ethyl 2-{[(3-chloro-2,6-difluorophenyl)carbamoyl]oxy}-3-(1H-pyrazol-1-yl)propanoate;

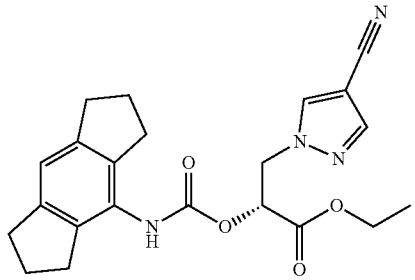

Ethyl (2R)-3-(4-cyano-1H-pyrazol-1-yl)-2-{[(1,2,3,5,6,7-hexahydro-s-indacen-4-yl)carbamoyl]oxy}propanoate;

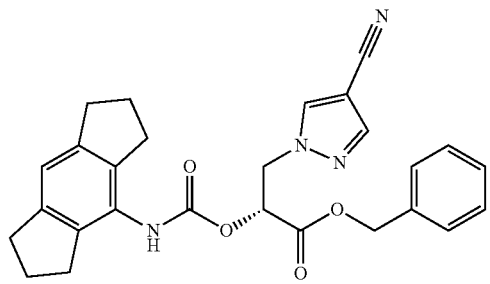

Benzyl (2R)-3-(4-cyano-1H-pyrazol-1-yl)-2-{[(1,2,3,5,6,7-hexahydro-s-indacen-4-yl)carbamoyl]oxy}propanoate;

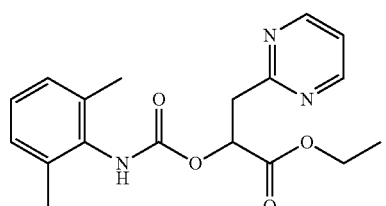

Ethyl 2-{[(2,6-dimethylphenyl)carbamoyl]oxy}-3-(pyrimidin-2-yl)propanoate;

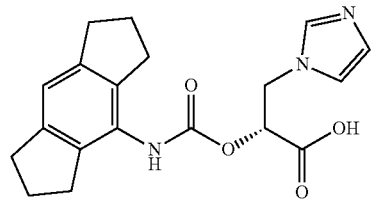

(2R)-2-{[(1,2,3,5,6,7-hexahydro-s-indacen-4-yl)carbamoyl]oxy}-3-(1H-imidazol-1-yl)propanoic aicd;

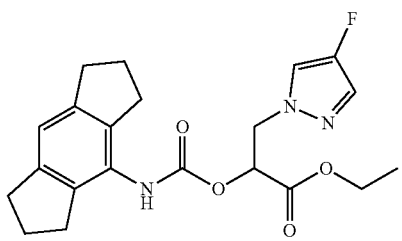

Ethyl 3-(4-fluoro-1H-pyrazol-1-yl)-2-{[(1,2,3,5,6,7-hexahydro-s-indacen-4-yl)carbamoyl]oxy}propanoate;

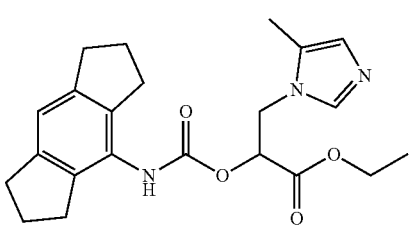

Ethyl 2-{[(1,2,3,5,6,7-hexahydro-s-indacen-4-yl)carbamoyl]oxy}-3-(5-methyl-1H-imidazol-1-yl)propanoate;

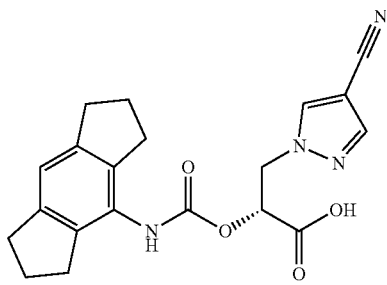

(2R)-3-(4-cyano-1H-pyrazol-1-yl)-2-{[(1,2,3,5,6,7-hexahydro-s-indacen-4-yl)carbamoyl]oxy}propanoic acid;

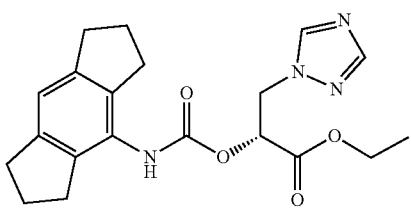

Ethyl (2R)-2-{[(1,2,3,5,6,7-hexahydro-s-indacen-4-yl)carbamoyl]oxy}-3-(1H-1,2,34-triazol-1-yl)propanoate;

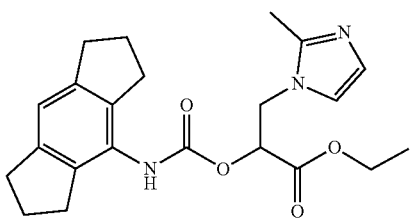

Ethyl 2-{[(1,2,3,5,6,7-hexahydro-s-indacen-4-yl)carbamoyl]oxy}-3-(2-methyl-1H-imidazol-1-yl)propanoate;

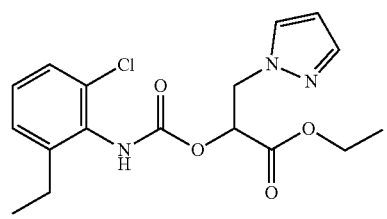

Ethyl 2-{[(2-chloro-6-ethylphenyl)carbamoyl]oxy}-3-(1H-pyrazol-1-yl)propanoate;

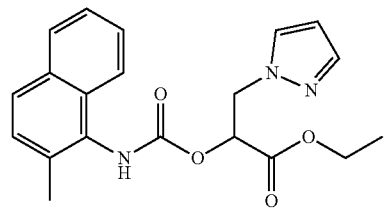

Ethyl 2-{[(2-methylnaphthalen-1-yl)carbamoyl]oxy}-3-(1H-pyrazol-1-yl)propanoate;

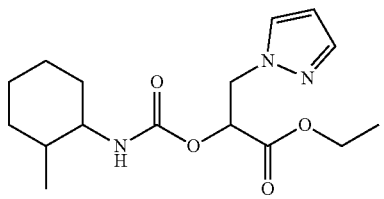

Ethyl 2-{[(2-methylcyclohexyl)carbamoyl]oxy}-3-(1H-pyrazol-1-yl)propanoate;

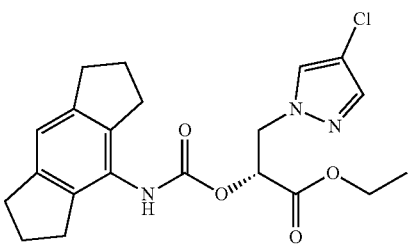

Ethyl (2R)-3-(4-chloro-1H-pyrazol-1-yl)-2-{[(1,2,3,5,6,7-hexahydro-s-indacen-4-yl)carbamoyl]oxy}propanoate;

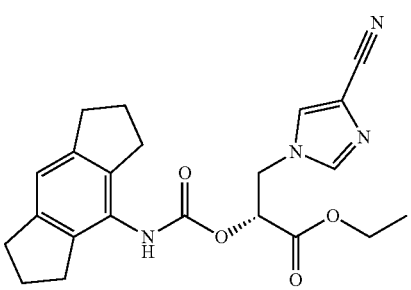

Ethyl (2R)-3-(4-cyano-1H-imidazol-1-yl)-2-{[(1,2,3,5,6,7-hexahydro-s-indacen-4-yl)carbamoyl]oxy}propanoate;

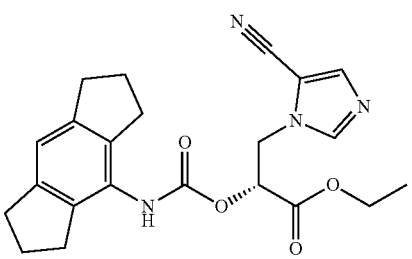

Ethyl (2R)-3-(5-cyano-1H-imidazol-1-yl)-2-{[(1,2,3,5,6,7-hexahydro-s-indacen-4-yl)carbamoyl]oxy}propanoate;

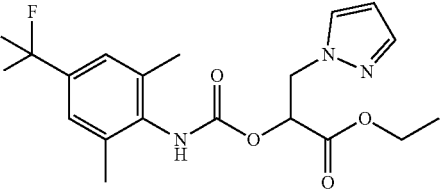

Ethyl 2-({[2,6-dimethyl-4-(trifluoromethyl)phenyl]carbamoyl}oxy)-3-(1H-pyrazol-1-yl)propanoate;

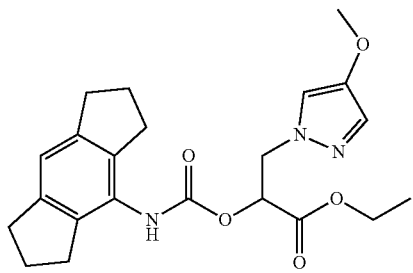

Ethyl 2-{[(1,2,3,5,6,7-hexahydro-s-indacen-4-yl)carbamoyl]oxy}-3-(4-methoxy-1H-pyrazol-1-yl)propanoate;

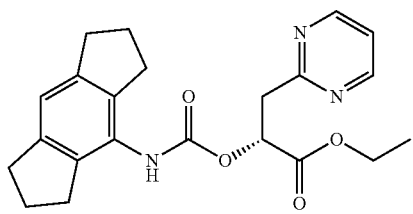

Ethyl (2R)-2-{[(1,2,3,5,6,7-hexahydro-s-indacen-4-yl)carbamoyl]oxy}-3-(pyrimidin-2-yl)propanoate;

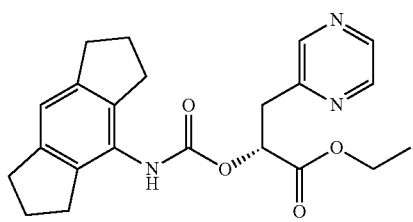

Ethyl (2R)-2-{[(1,2,3,5,6,7-hexahydro-s-indacen-4-yl)carbamoyl]oxy}-3-(pyrazin-2-yl)propanoate;

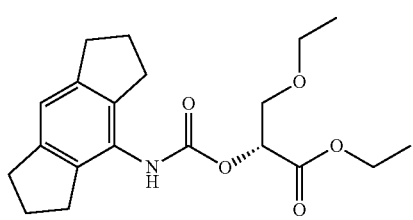

Ethyl (2R)-3-ethoxy-2-{[(1,2,3,5,6,7-hexahydro-s-indacen-4-yl)carbamoyl]oxy}propanoate;

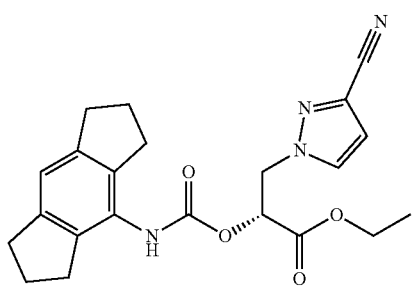

Ethyl (2R)-3-(3-cyano-1-1H-pyrazol-1-yl)-2-{[(1,2,3,5,6,7-hexahydro-s-indacen-4-yl)carbamoyl]oxy}propanoate;

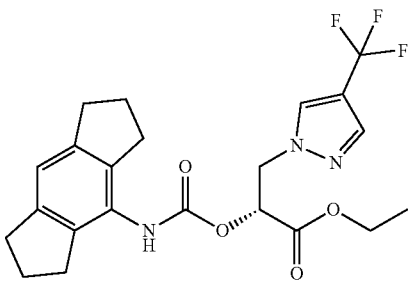

Ethyl (2R)-2-{[(1,2,3,5,6,7-hexahydro-s-indacen-4-yl)carbamoyl]oxy}-3-[4-(trifluoromethyl)-1H-pyrazol-1-yl]propanoate;

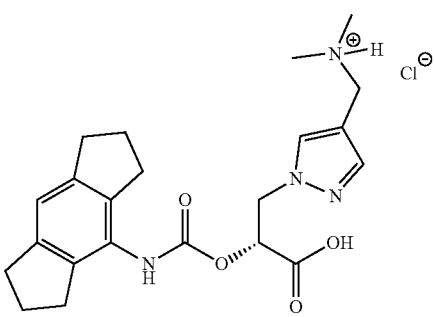

(2R)-3-{4-[(dimethylamino)methyl]-1H-pyrazol-1-yl}-2-{[(1,2,3,5,6,7-hexahydro-s-indacen-4-yl)carbamoyl]oxy}propanoic acid hydrochloride;

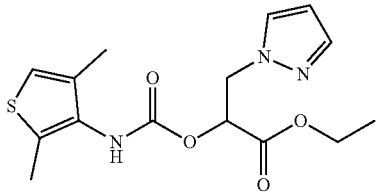

Ethyl 2-{[(2,4-dimethylthiophen-3-yl)carbamoyl]oxy}-3-(1H-pyrazol-1-yl)propanoate;

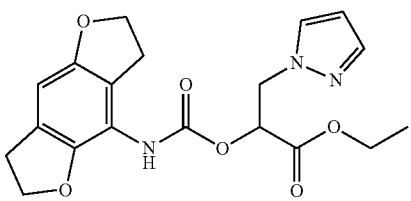

Ethyl 2-[({4,10-dioxatricyclo[7.3.0.0$^{3,7}$]dodeca-1,3(7),8-trien-2-yl}carbamoyl)oxy]-3-(1H-pyrazol-1-yl)propanoate;

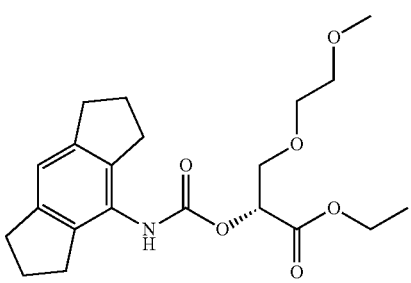

Ethyl (2R)-2-{[(1,2,3,5,6,7-hexahydro-s-indacen-4-yl)carbamoyl]oxy}-3-(2-methoxyethoxy)propanoate;

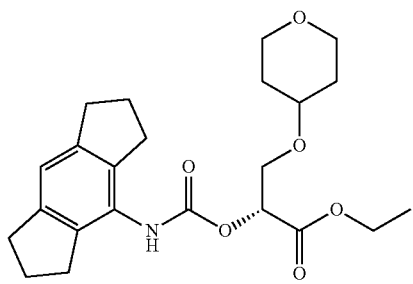

Ethyl (2R)-2-{[(1,2,3,5,6,7-hexahydro-s-indacen-4-yl)
carbamoyl]oxy}-3-(oxan-4-yloxy)propanoate;

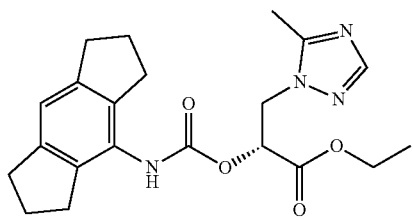

Ethyl (2R)-2-{[(1,2,3,5,6,7-hexahydro-s-inacen-4-yl)
carbamoyl]oxy}-3-(5-methyl-1H-1,2,4-triazol-1-yl)propanoate;

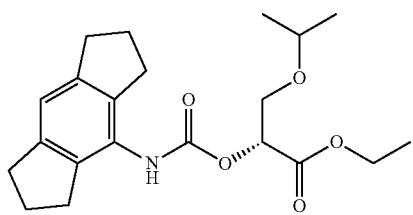

Ethyl (2R)-2-{[(1,2,3,5,6,7-hexahydro-s-indacen-4-yl)
carbamoyl]oxy}-3-(propan-2-yloxy)propanoate;

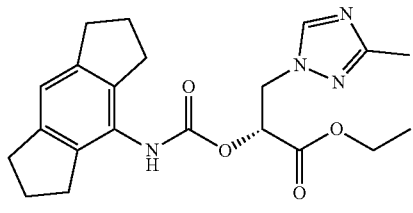

Ethyl (2R)-2-{[(1,2,3,5,6,7-hexahydro-s-indacen-4-yl)
carbamoyl]oxy}-3-(3-methyl-1H-1,2,4-triazol-1-yl)propanoate;

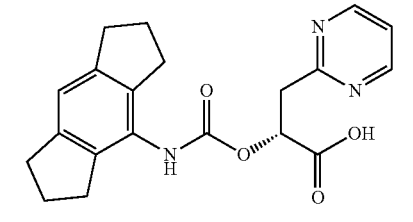

(2R)-2-{[(1,2,3,5,6,7-hexahydro-s-indacen-4-yl)
carbamoyl]oxy}-3-(pyrimidin-2-yl)propanoic acid;

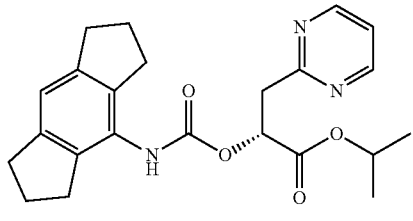

Propan-2-yl (2R)-2-{[(1,2,3,5,6,7-hexahydro-s-indacen-4-yl)
carbamoyl]oxy}-3-(pyrimidin-2-yl)propanoate;

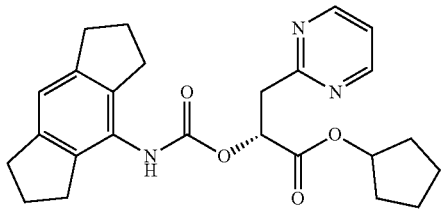

Cyclopentyl (2R)-2-{[(1,2,3,5,6,7-hexahydro-s-indacen-4-yl)
carbamoyl]oxy}-3-(pyrimidin-2-yl)propanoate;

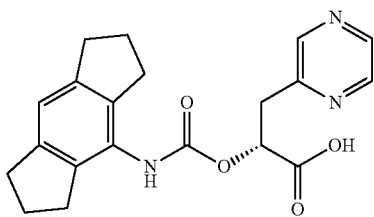

(2R)-2-{[(1,2,3,5,6,7-hexahydro-s-indacen-4-yl)
carbamoyl]oxy}-3-(pyrazin-2-yl)propanoic acid;

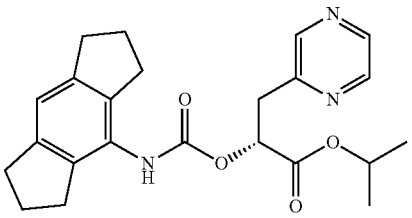

Propan-2-yl (2R)-2-{[(1,2,3,5,6,7-hexahydro-s-indacen-4-yl)
carbamoyl]oxy}-3-(pyrazin-2-yl)propanoate;

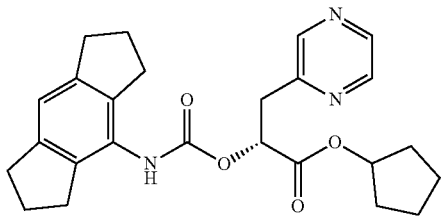

Cyclopentyl (2R)-2-{[(1,2,3,5,6,7-hexahydro-s-indacen-4-yl)
carbamoyl]oxy}-3-(pyrazin-2-yl)propanoate;

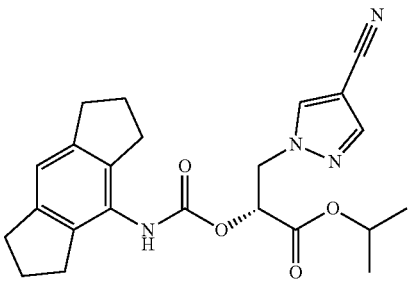

Propan-2-yl (2R)-3-(4-cyano-1H-pyrazol-1-yl)-2-{[(1,2,3,5,6,7-
hexahydro-s-indacen-4-yl)carbamoyl]oxy}propanoate;

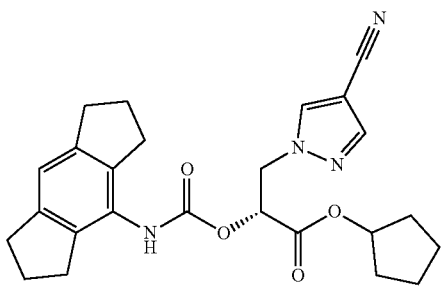

Cyclopentyl (2R)-3-(4-cyano-1H-pyrazol-1-yl)-2-{[(1,2,3,5,6,7-hexahydro-s-indacen-4-yl)carbamoyl]oxy}propanoate;

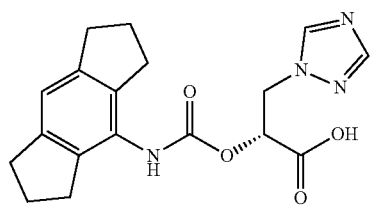

(2R)-2-{[(1,2,3,5,6,7,-hexahydro-s-indacen-4-yl)carbamoyl]oxy}-3-(1H-1,2,4-triazol-1-yl)propanoic acid;

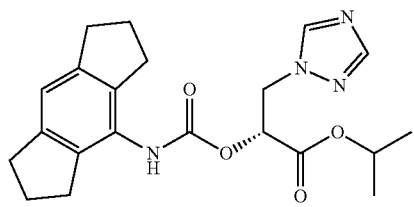

Propan-2-yl (2R)-2-{[(1,2,3,5,6,7-hexahydro-s-indacen-4-yl)carbamoyl]oxy}-3-(1H-1,2,4-triazol-1-yl)propanoate;

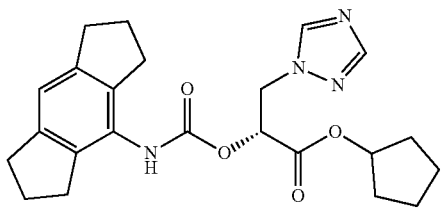

Cyclopentyl (2R)-2-{[(1,2,3,5,6,7-hexahydro-s-indacen-4-yl)carbamoyl]oxy}-3-(1H-1,2,4-triazol-1-yl)propanoate;

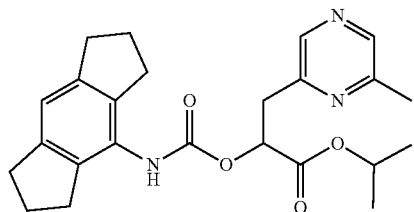

Propan-2-yl 2-{[(1,2,3,5,6,7-hexahydro-s-indacen-4-yl)carbamoyl]oxy}-3-(6-methylpyrazin-2-yl)propanoate;

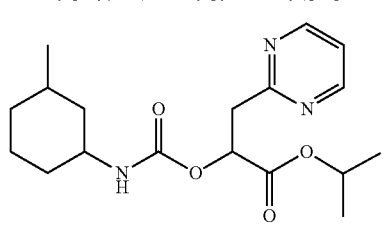

Propan-2-yl 2-{[(3-methylcyclohexyl)carbamoyl]oxy}-3-(pyrimidin-2-yl)propanoate;

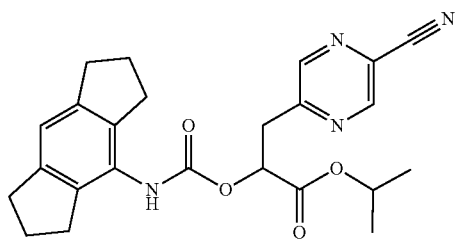

Propan-2-yl 3-(5-cyanopyrazin-2-yl)-2-{[(1,2,3,5,6,7-hexahydro-s-indacen-4-yl)carbamoyl]oxy}propanoate;

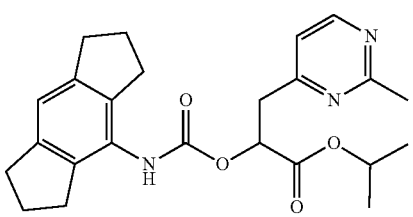

Propan-2-yl 2-{[(1,2,3,5,6,7-hexahydro-s-indacen-4-yl)carbamoyl]oxy}-3-(2-methylpyrimidin-4-yl)propanoate;

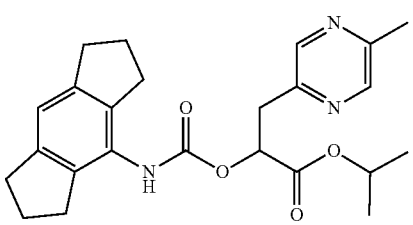

Propan-2-yl 2-{[(1,2,3,5,6,7-hexahydro-s-indacen-4-yl)carbamoyl]oxy}-3-(5-methylpyrazin-2-yl)propanoate;

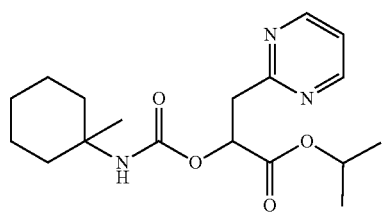

Propan-2-yl 2-{[(1-methylcyclohexyl)carbamoyl]oxy}-3-(pyrimidin-2-yl)propanoate;

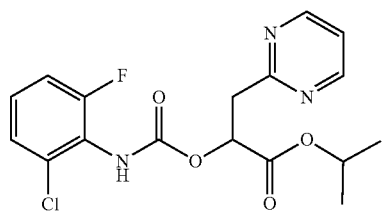

Propan-2-yl 2-{[(2-chloro-6-fluorophenyl)carbamoyloxy}-3-(pyrimidin-2-yl)propanoate;

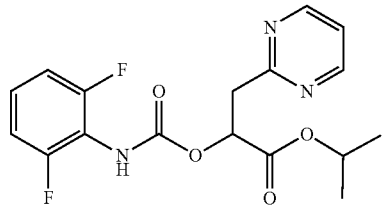

Propan-2-yl 2-{[(2,6-difluorophenyl)carbamoyl]oxy}-3-(pyrimidin-2-yl)propanoate;

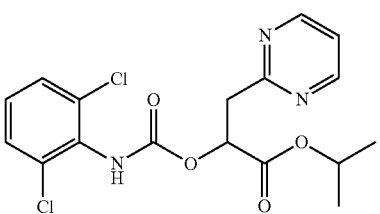

Propan-2-yl 2-{[(2,6-dichlorophenyl)carbamoyl]oxy}-3-(pyrimidin-2-yl)propanoate;

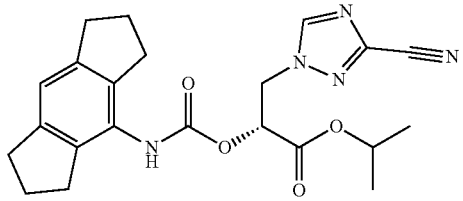

Propan-2-yl (2R)-3-(3-cyano-1H-1,2,4-triazol-1-yl)-2-{[(1,2,3,5,6,7-hexahydro-s-indacen-4-yl)carbamoyl]oxy}propanoate;

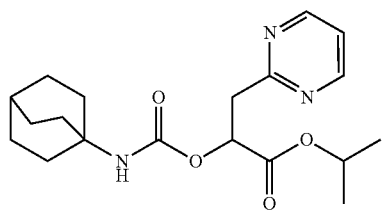

Propan-2-yl 2-[({bicyclo[2.2.2]octan-1-yl}carbamoyl)oxy]-3-(pyrimidin-2-yl)propanoate;

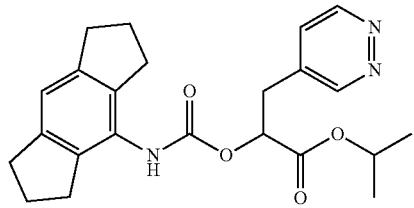

Propan-2-yl 2-{[(1,2,3,5,6,7-hexahydro-s-indacen-4-yl)carbamoyl]oxy}-3-(pyridazin-4-yl)propanoate;

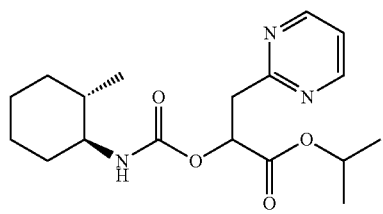

Propan-2-yl 2-{[(trans-2-methylcyclohexyl)carbamoyl]oxy}-3-(pyrimidin-2-yl)propanoate; and

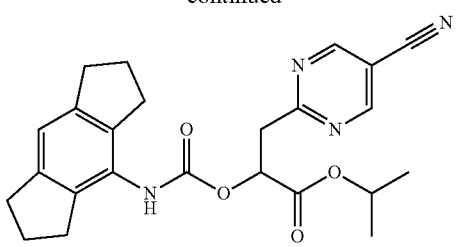

Propan-2-yl 3-(5-cyanopyrimidin-2-yl)-2-{[(1,2,3,5,6,7-hexahydro-s-indacen-4-yl)carbamoyl]oxy}propanoate, or a pharmaceutically acceptable salt thereof.

11. A compound of Formula (I):

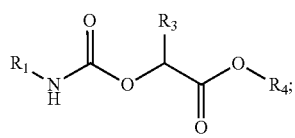

(I)

or a prodrug, hydrate, solvate, or pharmaceutically acceptable salt thereof, wherein:

$R_1$ is:

(a) $C_8$-$C_{16}$ polycyclic cycloalkyl optionally substituted by one or more $R_6$;

(b) benzofuranyl or dihydrobenzofuranyl, wherein the benzofuranyl or dihydrobenzofuranyl is optionally substituted by one or more $R_6$;

(c)

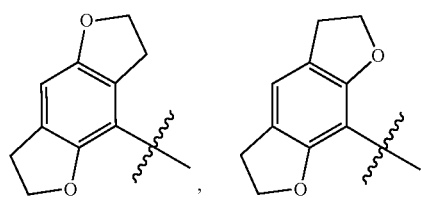

, or

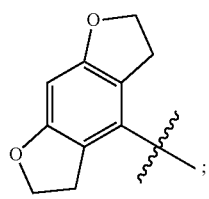

;

(d)

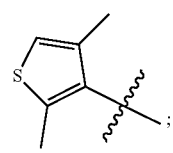

;

or
(e)
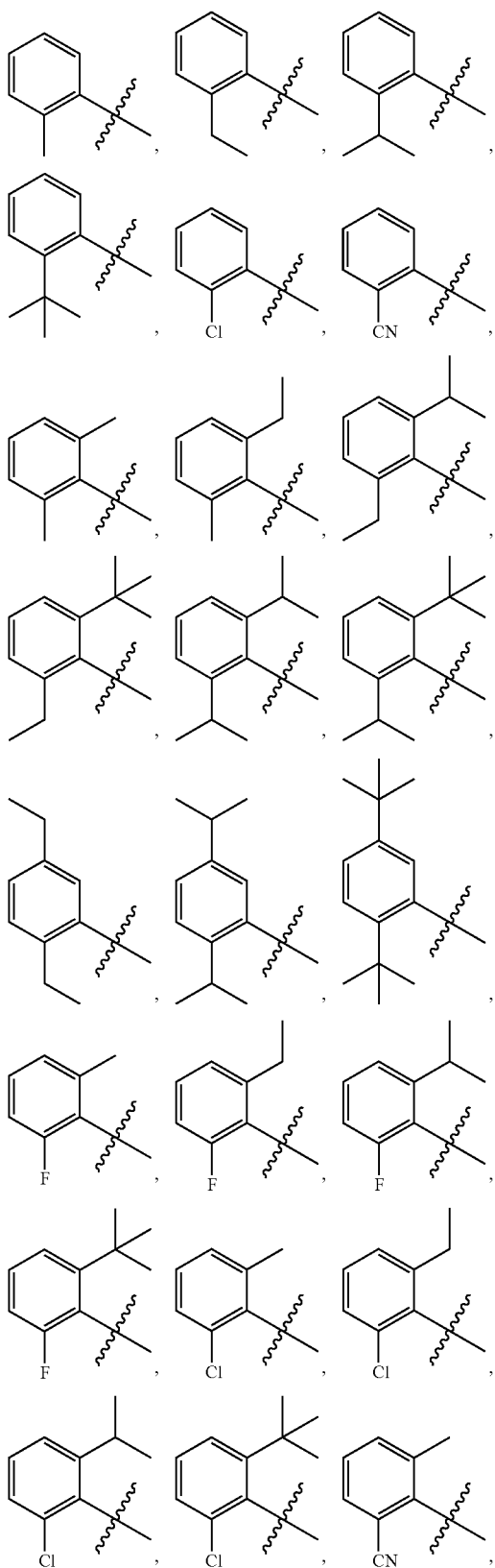
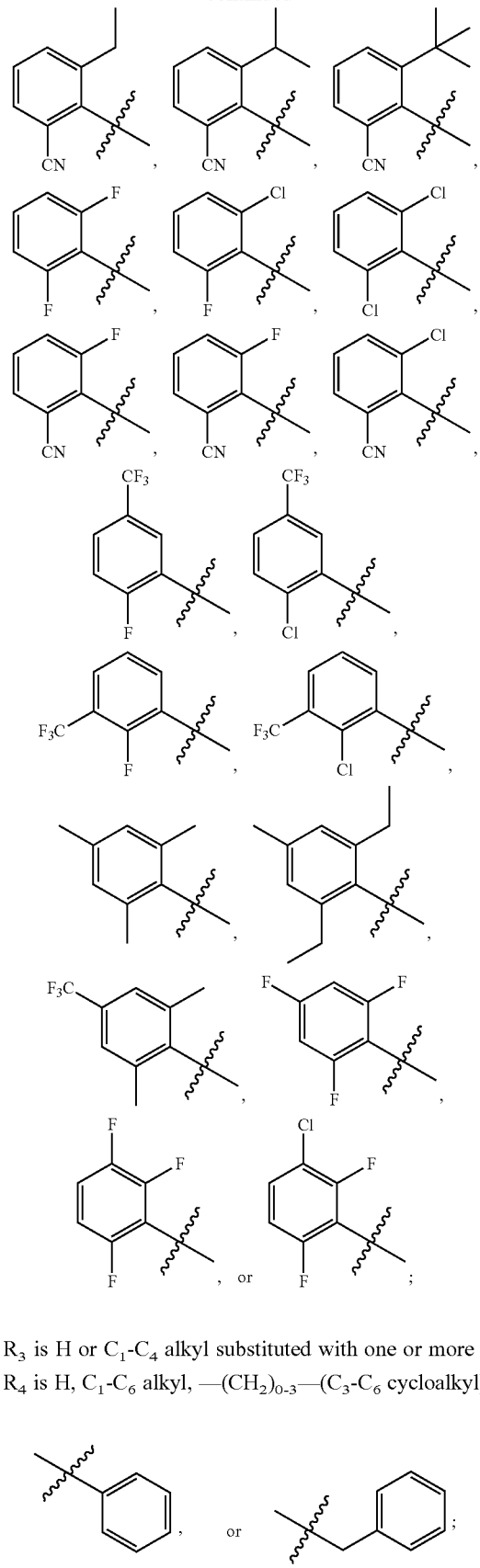
R$_3$ is H or C$_1$-C$_4$ alkyl substituted with one or more R$_7$;
R$_4$ is H, C$_1$-C$_6$ alkyl, —(CH$_2$)$_{0-3}$—(C$_3$-C$_6$ cycloalkyl), $R_6$ is $C_1$-$C_6$ alkyl, $C_2$-$C_6$ alkenyl, $C_1$-$C_6$ alkoxy, $C_3$-$C_8$ cycloalkyl, halo, oxo, —OH, —CN, —NH$_2$, —NH($C_1$-$C_6$ alkyl), —N($C_1$-$C_6$ alkyl)$_2$, —CH$_2$F, —CHF$_2$, or —CF$_3$;

$R_7$ is —OR$_8$, $C_5$-$C_{10}$ aryl, or 5- to 10-membered heteroaryl, wherein the $C_5$-$C_{10}$ aryl or 5- to 10-membered heteroaryl is optionally substituted by one or more $R_{7S}$, wherein each $R_{7S}$ is independently $C_1$-$C_6$ alkyl, $C_1$-$C_6$ alkoxy, 5- to 10-membered heteroaryl, halo, —OH, —CN, —(CH$_2$)$_{0-3}$—NH$_2$, —(CH$_2$)$_{0-3}$—NH($C_1$-$C_6$ alkyl), —(CH$_2$)$_{0-3}$—N($C_1$-$C_6$ alkyl)$_2$, —CH$_2$F, —CHF$_2$, or —CF$_3$; and $R_8$ is $C_1$-$C_6$ alkyl or 5- to 7-membered heterocycloalkyl, wherein the $C_1$-$C_6$ alkyl or 5- to 7-membered heterocycloalkyl is optionally substituted by one or more $R_{7S}$.

12. A pharmaceutical composition comprising the compound of claim 1 or a pharmaceutically acceptable salt thereof, and a pharmaceutically acceptable diluent or carrier.

13. A method of inhibiting inflammasome activity, comprising contacting a cell with an effective amount of the compound of claim 1 or a pharmaceutically acceptable salt thereof.

14. A method of treating a disease or disorder selected from a cryopyrin-associated autoinflammatory syndrome, familial Mediterranean fever, nonalcoholic fatty liver disease, non-alcoholic steatohepatitis, atherosclerosis, gout, rheumatoid arthritis, osteoarthritis, Inflammatory Bowel Disease, Crohn's disease, ulcerative colitis, chronic obstructive pulmonary disease, chronic kidney disease, fibrosis, obesity, type 2 diabetes, clonal hematopoiesis of indeterminate potential, and a neuroinflammation occurring in protein misfolding disease in a subject, comprising administering to the subject a compound of claim 1 or a pharmaceutically acceptable salt thereof.

15. The method of claim 14, wherein the cryopyrin-associate autoinflammatory syndrome is selected from familial cold autoinflammatory syndrome, Muckle-Wells syndrome, chronic infantile neurological cutaneous and articular syndrome, and neonatal-onset multisystem inflammatory disease.

16. The method of claim 14, wherein the neuroinflammation occurring in protein misfolding disease is Prion disease.

17. A method of treating a neurodegenerative disease selected from Parkinson's disease, Alzheimer's disease, multiple sclerosis, amyotrophic lateral sclerosis, and Huntington's disease in a subject, comprising administering to the subject a compound of claim 1 or a pharmaceutically acceptable salt thereof.

18. A method of treating a cancer selected from metastasising cancer, gastrointestinal cancer, skin cancer, non-small-cell lung carcinoma, brain cancer, and colorectal adenocarcinoma in a subject, comprising administering to the subject a compound of claim 1 or a pharmaceutically acceptable salt thereof.

\* \* \* \* \*